(12) United States Patent
Bahar et al.

(10) Patent No.: US 11,746,144 B2
(45) Date of Patent: Sep. 5, 2023

(54) COMPOSITIONS AND METHODS FOR TREATING A COVID-19 INFECTION

(71) Applicants: UNIVERSITY OF PITTSBURGH-OF THE COMMONWEALTH SYSTEM OF HIGHER EDUCATION, Pittsburgh, PA (US); CEDARS-SINAI MEDICAL CENTER, Los Angeles, CA (US)

(72) Inventors: Ivet Bahar, Wexford, PA (US); Hongying Cheng, Pittsburgh, PA (US); She Zhang, Pittsburgh, PA (US); Rebecca Porritt, Sherman Oaks, CA (US); Moshe Arditi, Encino, CA (US)

(73) Assignees: University of Pittsburgh—Of The Commonwealth System of Higher Education, Pittsburgh, PA (US); Cedars-Sinai Medical Center, Los Angeles, CA (US)

( * ) Notice: Subject to any disclaimer, the term of this patent is extended or adjusted under 35 U.S.C. 154(b) by 50 days.

(21) Appl. No.: 17/375,601

(22) Filed: Jul. 14, 2021

(65) Prior Publication Data
US 2022/0235119 A1 Jul. 28, 2022

Related U.S. Application Data

(60) Provisional application No. 63/051,481, filed on Jul. 14, 2020.

(51) Int. Cl.
*C07K 16/12* (2006.01)
*A61K 39/215* (2006.01)
*A61P 31/14* (2006.01)

(52) U.S. Cl.
CPC ........ *C07K 16/1271* (2013.01); *A61K 39/215* (2013.01); *A61P 31/14* (2018.01); *C07K 2317/24* (2013.01); *C07K 2317/56* (2013.01); *C07K 2317/565* (2013.01)

(58) Field of Classification Search
CPC .... C07K 16/1271; A61K 39/215; A61P 31/14
See application file for complete search history.

(56) References Cited

U.S. PATENT DOCUMENTS

| 2014/0234325 A1 | 4/2014 | Fries et al. |
| 2016/0039914 A1 | 2/2016 | McIntyre et al. |

OTHER PUBLICATIONS

A. Varshney, et al.,Generation, Characterization, and Epitope Mapping of Neutralizing and Protective Monoclonal Antibodies against Staphylococcal Enterotoxin B-induced Lethal Shock*, Journal of Biological Chemistry, vol. 286, Issue 11 (Year: 2011).*

T. Krakauer, Staphylococcal superantigens: pyrogenic toxins induce toxic shock. Toxins 11. 178 (Year: 2019).*

Lu, R Zhao, et al., Genomic characterisation and epidemiology of 2019 novel coronavirus: implications for virus origins and receptor binding. Lancet. Feb. 22, 2020;395(10224):565-574. doi: 10.1016/S0140-6736(20)30251-8. Epub Jan. 30, 2020. PMID: 32007145; PMCID: PMC7159086. (Year: 2020).*

G. Arad et al., Binding of superantigen toxins into the CD28 homodimer interface is essential for induction of cytokine genes that mediate lethal shock. PLoS Biol. 9, e1001149 (Year: 2011).*

A. C. Papageorgiou, H. S. Tranter, K. R. Acharya, Crystal structure of microbial superantigen staphylococcal enterotoxin B at 1.5 A resolution: implications for superantigen recognition by MHC class II molecules and T-cell receptors. J. Mol. Biol. 277, 61-79 (Year: 1998).*

J.P. Changeux, Z. Amoura, F. Rey, M. Miyara, A nicotinic hypothesis for Covid-19 with preventive and therapeutic implications. Qeios doi:10.32388/FXGQSB (Year: 2020).*

Moritz Anft, et al.,COVID-19 progression is potentially driven by T cell immunopathogenesis, medRxiv 2020.04.28.20083089; doi:https://doi.org/10.1101/2020.04.28.20083089 (Year: 2020).*

E Whittaker, MD, et al., COVID-19 progression is potentially driven by T cell immunopathogenesis, JAMA. 2020;324(3):259-269. doi:10.1001/jama.2020.10369 Published online Jun. 8, 2020. Corrected on Jun. 30, 2020. (Year: 2020).*

K Yu, et al., Thymosin alpha-1 Protected T Cells from Excessive Activation in Severe COVID-19, https://doi.org/10.21203/rs.3.rs-25869/v1, [preprint version 1—posted May 1, 2020) (Year: 2020).*

Andersen, K.G., Rambaut, A., Lipkin, W.I., Holmes, E.C., and Garry, R.F. (2020). The proximal origin of SARS-CoV-2. Nat Med 26, 450-452.

Andreano, E., Piccini, G., Licastro, D., Casalino, L., Johnson, N.V., Paciello, I., Monego, S.D., Pantano, E., Manganaro, N., Manenti, A., et al. (2020). SARS-CoV-2 escape in vitro from a highly neutralizing COVID-19 convalescent plasma. bioRxiv.

Arad et al., Binding of superantigen toxins into the CD28 homodimer interface is essential for induction of cytokine genes that mediate lethal shock. PLoS Biol. 9, e1001149 (2011).

Barnes, C.O., West, A.P., Huey-Tubman, K., Hoffmann, M.A., Sharaf, N.G., Hoffman, P.R., Koranda, N., Gristick, H.B., Gaebler, C., and Muecksch, F. (2020). Structures of human antibodies bound to SARS-CoV-2 spike reveal common epitopes and recurrent features of antibodies. Cell 182, 828-842.

Belhadjer, Z., Méot, M., Bajolle, F., Khraiche, D., Legendre, A., Abakka, S., Auriau, J., Grimaud, M., Oualha, M., Beghetti, M., et al. (2020). Acute heart failure in multisystem inflammatory syndrome in children (MIS-C) in the context of global SARS-CoV-2 pandemic. Circulation 142, 429-436.

(Continued)

*Primary Examiner* — Adam Weidner
*Assistant Examiner* — Ashley H. Gao
(74) *Attorney, Agent, or Firm* — Meunier Carlin & Curfman LLC

(57) ABSTRACT

Provided herein are methods of treating a COVID-19 infection in a subject, comprising administering to the subject an effective amount of a composition that reduces the superantigen character of SARS-CoV-2 Spike protein. In some embodiments, the compositions are mimetic peptides of the superantigen region. In some embodiments, the comp

(56) References Cited

OTHER PUBLICATIONS

Benton, D.J., Wrobel, A.G., Xu, P., Roustan, C., Martin, S.R., Rosenthal, P.B., Skehel, J.J., and Gamblin, S.J. (2020). Receptor binding and priming of the spike protein of SARS-CoV-2 for membrane fusion. Nature, in press.

Bestle, D., Heindl, M.R., Limburg, H., Van Lam van, T., Pilgram, O., Moulton, H., Stein, D.A., Hardes, K., Eickmann, M., Dolnik, O., et al. (2020). TMPRSS2 and furin are both essential for proteolytic activation of SARS-CoV-2 in human airway cells. Life Sci Alliance 3, e202000786.

Bracci, et al., Molecular mimicry between the rabies virus glycoprotein and human immunodeficiency virus-1 GP120: cross-reacting antibodies induced by rabies vaccination. Blood, Am. J. Hematol. 90, 3623-3628 (1997).

Cai, Y., Zhang, J., Xiao, T., Peng, H., Sterling, S.M., Walsh, R.M., Jr., Rawson, S., Rits-Volloch, S., and Chen, B. (2020). Distinct conformational states of SARS-CoV-2 spike protein. Science 369, 1586-1592.

Cantuti-Castelvetri, L., Ojha, R., Pedro, L.D., Djannatian, M., Franz, J., Kuivanen, S., van der Meer, F., Kallio, K., Kaya, T., and Anastasina, M. (2020). Neuropilin-1 facilitates SARS-CoV-2 cell entry and infectivity. Science 370, 856-860.

Cao, L., Goreshnik, I., Coventry, B., Case, J.B., Miller, L., Kozodoy, L., Chen, R.E., Carter, L., Walls, A.C., Park, Y.-J., et al. (2020a). De novo design of picomolar SARS-CoV-2 miniprotein inhibitors. Science 370, 426-431.

Cao, Y., Su, B., Guo, X., Sun, W., Deng, Y., Bao, L., Zhu, Q., Zhang, X., Zheng, Y., Geng, C., et al. (2020b). Potent neutralizing antibodies against SARS-CoV-2 identified by high-throughput single-cell sequencing of convalescent patients' B cells. Cell 182, 73-84. e16.

Casalino, L., Gaieb, Z., Goldsmith, J.A., Hjorth, C.K., Dommer, A.C., Harbison, A.M., Fogarty, C.A., Barros, E.P., Taylor, B.C., McLellan, J.S., et al. (2020). Beyond shielding: The roles of glycans in the SARS-CoV-2 Spike protein. ACS central science 6, 1722-1734.

Changeux, Z. Amoura, F. Rey, M. Miyara, A nicotinic hypothesis for Covid-19 with preventive and therapeutic implications. Qeios doi:10. 32388/FXGQSB. (2020).

Cheng, M.H., Zhang, S., Porritt, R.A., Arditi, M., and Bahar, I. (2020). Superantigenic character of an insert unique to SARS-CoV-2 spike supported by skewed TCR repertoire in patients with hyperinflammation. Proc Natl Acad Sci USA 117, 25254-25262.

Cheung, E.W., Zachariah, P., Gorelik, M., Boneparth, A., Kernie, S.G., Orange, J.S., and Milner, J.D. (2020). Multisystem inflammatory syndrome related to COVID-19 in previously healthy children and adolescents in New York city. JAMA 324, 294-296.

Chi et al., A potent neutralizing human antibody reveals the N-terminal domain of the Spike protein of SARS-CoV-2 as a site of vulnerability. bioRxiv, 2020.2005.2008.083964 (2020).

Chi, X., Yan, R., Zhang, J., Zhang, G., Zhang, Y., Hao, M., Zhang, Z., Fan, P., Dong, Y., Yang, Y., et al. (2020). A neutralizing human antibody binds to the N-terminal domain of the Spike protein of SARS-CoV-2. Science 369, 650-655.

Choi et al., Interaction of *Staphylococcus aureus* toxin "superantigens" with human T cells. Proc. Natl. Acad. Sci. U.S.A. 86, 8941-8945 (1989).

Cook, et al., Manifestations of Toxic Shock Syndrome in Children, Columbus, Ohio, USA, 2010-2017. Emerg. Infect. Dis. 26, 1077-1083 (2020).

Coutard, B., Valle, C., de Lamballerie, X., Canard, B., Seidah, N.G., and Decroly, E. (2020). The spike glycoprotein of the new coronavirus 2019-nCoV contains a furin-like cleavage site absent in CoV of the same clade. Antiviral Res 176, 104742.

Cristiani et al., Will children reveal their secret? The coronavirus dilemma. Eur. Respir. J., in press (2020).

Cui, J., Li, F., and Shi, Z.-L. (2019). Origin and evolution of pathogenic coronaviruses. Nat Rev Microbiol 17, 181-192.

Dahms, S.O., Creemers, J.W., Schaub, Y., Bourenkov, G.P., Zogg, T., Brandstetter, H., and Than, M.E. (2016). The structure of a furin-antibody complex explains non-competitive inhibition by steric exclusion of substrate conformers. Sci Rep 6, 34303.

Daly, J.L., Simonetti, B., Klein, K., Chen, K.-E., Williamson, M.K., Antón-Plágaro, C., Shoemark, D.K., Simón-Gracia, L., Bauer, M., Hollandi, R., et al. (2020). Neuropilin-1 is a host factor for SARS-CoV-2 infection. Science 370, 861-865.

Dutta, K., Varshney, A.K., Franklin, M.C., Goger, M., Wang, X., and Fries, B.C. (2015). Mechanisms mediating enhanced neutralization efficacy of staphylococcal enterotoxin B by combinations of monoclonal antibodies. J Biol Chem 290, 6715-6730.

Eastman, P. et al. OpenMM 7: Rapid development of high performance algorithms for molecular dynamics. PLoS computational biology 13, e1005659 (2017).

Forni, D., Cagliani, R., Clerici, M., and Sironi, M. (2017). Molecular evolution of human coronavirus genomes. Trends Microbiol 25, 35-48.

Fraser, T. Proft, The bacterial superantigen and superantigen-like proteins. Immunol. Rev. 225, 226-243 (2008).

Garcia, G., Sharma, A., Ramaiah, A., Sen, C., Kohn, D., Gomperts, B., Svendsen, C.N., Damoiseaux, R.D., and Arumugaswami, V. (2020). Antiviral Drug Screen of Kinase inhibitors Identifies Cellular Signaling Pathways Critical for SARS-CoV-2 Replication. bioRxiv, 2020.2006.2024.150326.

Graham, B.S., Gilman, M.S.A., and McLellan, J.S. (2019). Structure-Based Vaccine Antigen Design. Annu Rev Med 70, 91-104.

Greaney, A.J., Starr, T.N., Gilchuk, P., Zost, S.J., Binshtein, E., Loes, A.N., Hilton, S.K., Huddleston, J., Eguia, R., Crawford, K.H.D., et al. (2021). Complete Mapping of Mutations to the SARS-CoV-2 Spike Receptor-Binding Domain that Escape Antibody Recognition. Cell Host Microbe 29, 44-57.e49.

Grifoni, A., Weiskopf, D., Ramirez, S.I., Mateus, J., Dan, J.M., Moderbacher, C.R., Rawlings, S.A., Sutherland, A., Premkumar, L., Jadi, R.S., et al. (2020). Targets of T cell responses to SARS-CoV-2 coronavirus in humans with COVID-19 disease and unexposed individuals. Cell 181, 1489-1501 e1415.

Gupta, A., Madhavan, M.V., Sehgal, K., Nair, N., Mahajan, S., Sehrawat, T.S., Bikdeli, B., Ahluwalia, N., Ausiello, J.C., Wan, E.Y., et al. (2020). Extrapulmonary manifestations of COVID-19. Nat Med 26, 1017-1032.

Hansen, J., Baum, A., Pascal, K.E., Russo, V., Giordano, S., Wloga, E., Fulton, B.O., Yan, Y., Koon, K., Patel, K., et al. (2020). Studies in humanized mice and convalescent humans yield a SARS-CoV-2 antibody cocktail. Science 369, 1010-1014.

Hoare HL, et al. (2006) Structural basis for a major histocompatibility complex class Ib-restricted T cell response. Nature Immunology 7(3):256-264.

Hoffmann et al., SARS-CoV-2 Cell Entry Depends on ACE2 and TMPRSS2 and is Blocked by a Clinically Proven Protease Inhibitor. Cell 181, 271-280 (2020).

Holland CJ, et al. (2018) In Silico and Structural Analyses Demonstrate That Intrinsic Protein Motions Guide T Cell Receptor Complementarity Determining Region Loop Flexibility. Frontiers in immunology 9:674.

Huang, A.T., Garcia-Carreras, B., Hitchings, M.D.T., Yang, B., Katzelnick, L.C., Rattigan, S.M., Borgert, B.A., Moreno, C.A., Solomon, B.D., Trimmer-Smith, L., et al. (2020). A systematic review of antibody mediated immunity to coronaviruses kinetics, correlates of protection, and association with severity. Nat Commun 11, 4704.

Jaimes, J.A., André, N.M., Chappie, J.S., Millet, J.K., and Whittaker, G.R. (2020). Phylogenetic analysis and structural modeling of SARS-CoV-2 spike protein reveals an evolutionary distinct and proteolytically sensitive activation loop. J Mol Biol 432, 3309-3325.

Johnson, B.A., Xie, X., Bailey, A.L., Kalveram, B., Lokugamage, K.G., Muruato, A., Zou, J., Zhang, X., Juelich, T., Smith, J.K., et al. (2021). Loss of furin cleavage site attenuates SARS-CoV-2 pathogenesis. Nature.

(56) References Cited

OTHER PUBLICATIONS

Kemp, S., Collier, D., Datir, R., Gayed, S., Jahun, A., Hosmillo, M., Ferreira, I., Rees-Spear, C., Mlcochova, P., Lumb, I.U., et al. (2020). Neutralising antibodies drive Spike mediated SARS-CoV-2 evasion. medRxiv, 2020.2012.2005.20241927.

Korber et al., Spike mutation pipeline reveals the emergence of a more transmissible form of SARS-CoV-2. bioRxiv, 2020.2004.2029.069054 (2020).

Kozakov et al., The ClusPro web server for protein-protein docking. Nat. Protoc. 12, 255 (2017).

Krakauer, M. Buckley, H. J. Issaq, S. D. Fox, Rapamycin protects mice from staphylococcal enterotoxin B-induced toxic shock and blocks cytokine release in vitro and in vivo. Antimicrob. Agents Chemother. 54, 1125-1131 (2010).

Krakauer, Staphylococcal superantigens: pyrogenic toxins induce toxic shock. Toxins 11, 178 (2019).

Larkin, B. G. Stiles, R. G. Ulrich, Inhibition of toxic shock by human monoclonal antibodies against staphylococcal enterotoxin B. PLoS One 5, e13253 (2010).

Lemmin, T., Kalbermatter, D., Harder, D., Plattet, P., and Fotiadis, D. (2020). Structures and dynamics of the novel S1/S2 protease cleavage site loop of the SARS-CoV-2 spike glycoprotein. J Struct Biol: X 4, 100038.

Li et al., Structure-based preliminary analysis of immunity and virulence of SARS coronavirus. Viral Immunol. 17, 528-534 (2004).

Li, A. Llera, E. L. Malchiodi, R. A. Mariuzza, The structural basis of T cell activation by superantigens. Annu. Rev. Immunol. 17, 435-466 (1999).

Li, W., Schäfer, A., Kulkarni, S.S., Liu, X., Martinez, D.R., Chen, C., Sun, Z., Leist, S.R., Drelich, A., Zhang, L., et al. (2020). High potency of a bivalent human VH domain in SARS-CoV-2 animal models. Cell 183, 429-441.e416.

Liu, L., Wang, P., Nair, M.S., Yu, J., Rapp, M., Wang, Q., Luo, Y., Chan, J.F., Sahi, V., Figueroa, A., et al. (2020). Potent neutralizing antibodies directed to multiple epitopes on SARS-CoV-2 spike. Nature 584, 450-456.

Low, Toxic shock syndrome: major advances in pathogenesis, but not treatment. Crit. Care Clin. 29, 651-675 (2013).

Lv, H., Wu, N.C., Tsang, O.T., Yuan, M., Perera, R., Leung, W.S., So, R.T.Y., Chan, J.M.C., Yip, G.K., Chik, T.S.H., et al. (2020a). Cross-reactive Antibody Response between SARS-CoV-2 and SARS-CoV Infections. Cell Rep 31, 107725.

Lv, Z., Deng, Y.-Q., Ye, Q., Cao, L., Sun, C.-Y., Fan, C., Huang, W., Sun, S., Sun, Y., Zhu, L., et al. (2020b). Structural basis for neutralization of SARS-CoV-2 and SARS-CoV by a potent therapeutic antibody. Science 369, 1505-1509.

Maier et al., ff14SB: Improving the Accuracy of Protein Side Chain and Backbone Parameters from ff99SB. J. Chem. Theory Comput. 11, 3696-3713 (2015).

Mateus, J., Grifoni, A., Tarke, A., Sidney, J., Ramirez, S.I., Dan, J.M., Burger, Z.C., Rawlings, S.A., Smith, D.M., Phillips, E., et al. (2020). Selective and cross-reactive SARS-CoV-2 T cell epitopes in unexposed humans. Science 370, 89-94.

Matsuda et al., Early and definitive diagnosis of toxic shock syndrome by detection of marked expansion of T-cell-receptor Vβ2-positive T cells. Emerg. Infect. Dis. 9, 387 (2003).

Matsuyama, S., Nao, N., Shirato, K., Kawase, M., Saito, S., Takayama, I., Nagata, N., Sekizuka, T., Katoh, H., Kato, F., et al. (2020). Enhanced isolation of SARS-CoV-2 by TMPRSS2-expressing cells. Proc Natl Acad Sci USA 117, 7001-7003.

McCarthy, K.R., Rennick, L.J., Nambulli, S., Robinson-McCarthy, L.R., Bain, W.G., Haidar, G., and Duprex, W.P. (2020). Natural deletions in the SARS-CoV-2 spike glycoprotein drive antibody escape. bioRxiv, 2020.2011.2019.389916.

Nguyen et al., Human leukocyte antigen susceptibility map for SARS-CoV-2. J. Virol., JVI.00510-00520 (2020).

Nishi et al., B cell epitope mapping of the bacterial superantigen staphylococcal enterotoxin B: the dominant epitope region recognized by intravenous IgG. J. Immunol. 158, 247-254 (1997).

Noval Rivas, M., Porritt, R.A., Cheng, M.H., Bahar, I., and Arditi, M. (2020). COVID-19-associated multisystem inflammatory syndrome in children (MIS-C): A novel disease that mimics toxic shock syndrome—the superantigen hypothesis. J Allergy Clin Immunol, S0091-6749(0020)31414-31417.

Papageorgiou, et al., Crystal structure of microbial superantigen staphylococcal enterotoxin B at 1.5 A resolution: implications for superantigen recognition by MHC class II molecules and T-cell receptors. J. Mol. Biol. 277, 61-79 (1998).

Pinto, D., Park, Y.-J., Beltramello, M., Walls, A.C., Tortorici, M.A., Bianchi, S., Jaconi, S., Culap, K., Zatta, F., De Marco, A., et al. (2020). Cross-neutralization of SARS-CoV-2 by a human monoclonal SARS-CoV antibody. Nature 583, 290-295.

Popugailo, et al., Staphylococcal and streptococcal superantigens trigger B7/CD28 costimulatory receptor engagement to hyperinduce inflammatory cytokines. Front Immunol. 10, 942 (2019).

Porritt, R.A., Paschold, L., Rivas, M.N., Cheng, M.H., Yonker, L.M., Chandnani, H., Lopez, M., Simnica, D., Schultheiß, C., Santiskulvong, C., et al. (2020). HLA Class I-associated expansion of TRBV11-2 T cells via a CDR3-independent mechanism in Multisystem Inflammatory Syndrome in Children (MIS-C). J Clin Invest, in press.

Renn, A., Fu, Y., Hu, X., Hall, M.D., and Simeonov, A. (2020). Fruitful neutralizing antibody pipeline brings hope to defeat SARS-Cov-2. Trends Pharmacol Sci 41, 815-829.

Riphagen, S., Gomez, X., Gonzalez-Martinez, C., Wilkinson, N., and Theocharis, P. (2020). Hyperinflammatory shock in children during COVID-19 pandemic. Lancet 395, 1607-1608.

Saline et al., The structure of superantigen complexed with TCR and MHC reveals novel insights into superantigenic T cell activation. Nat. Commun. 1, 119 (2010).

Scherer, L. Ignatowicz, G. M. Winslow, J. W. Kappler, P. Marrack, Superantigens: bacterial and viral proteins that manipulate the immune system. Annu. Rev. Cell Biol. 9, 101-128 (1993).

Schultheiss C, et al. (2020) Next-Generation Sequencing of T and B Cell Receptor Repertoires from COVID-19 Patients Showed Signatures Associated with Severity of Disease. Immunity 53:442-455.

Shajahan, A., Supekar, N.T., Gleinich, A.S., and Azadi, P. (2020). Deducing the N- and O-glycosylation profile of the spike protein of novel coronavirus SARS-CoV-2. Glycobiology.

Shang, J., Wan, Y., Luo, C., Ye, G., Geng, Q., Auerbach, A., and Li, F. (2020). Cell entry mechanisms of SARS-CoV-2. Proc Natl Acad Sci U S A 117, 11727-11734.

Shi, R., Shan, C., Duan, X., Chen, Z., Liu, P., Song, J., Song, T., Bi, X., Han, C., Wu, L., et al. (2020). A human neutralizing antibody targets the receptor-binding site of SARS-CoV-2. Nature 584, 120-124.

Sievers F, et al. (2011) Fast, scalable generation of high-quality protein multiple sequence alignments using Clustal Omega. Mol Syst Biol 7(1):539.

Sim MJW, et al. (2020) High-affinity oligoclonal TCRs define effective adoptive T cell therapy targeting mutant KRAS-G12D. Proceedings of the National Academy of Sciences of the United States of America 117(23):12826-12835.

Simnica D, et al. (2019) High-Throughput Immunogenetics Reveals a Lack of Physiological T Cell Clusters in Patients With Autoimmune Cytopenias. Frontiers in Immunology 10(1897).

Simnica D, et al. (2019) T cell receptor next-generation sequencing reveals cancer-associated repertoire metrics and reconstitution after chemotherapy in patients with hematological and solid tumors. Oncoimmunology 8(11):e1644110.

Song, et al., Cryo-EM structure of the SARS coronavirus spike glycoprotein in complex with its host cell receptor ACE2. PLoS Pathog. 14, e1007236 (2018).

Steinhauer, D.A. (1999). Role of hemagglutinin cleavage for the pathogenicity of influenza virus. Virology 258, 1-20.

Tay, M.Z., Poh, C.M., Rénia, L., MacAry, P.A., and Ng, L.F.P. (2020). The trinity of COVID-19: immunity, inflammation and intervention. Nat Rev Immunol 20, 363-374.

Thomas, G. (2002). Furin at the cutting edge: from protein traffic to embryogenesis and disease. Nat Rev Mol Cell Biol 3, 753-766.

(56) References Cited

OTHER PUBLICATIONS

Tian, S., Huajun, W., and Wu, J. (2012). Computational prediction of furin cleavage sites by a hybrid method and understanding mechanism underlying diseases. Sci Rep 2, 261-261.

Tirado, K.-J. Yoon, Antibody-dependent enhancement of virus infection and disease. Viral Immunol. 16, 69-86 (2003).

Tortorici, M.A., Walls, A.C., Lang, Y., Wang, C., Li, Z., Koerhuis, D., Boons, G.J., Bosch, B.J., Rey, F.A., de Groot, R.J., et al. (2019). Structural basis for human coronavirus attachment to sialic acid receptors. Nature structural & molecular biology 26, 481-489.

Vabret, et al., 2020. Immunology of COVID-19: current state of the science. Immunity 52, 910-941.

Van Zundert, G., Rodrigues, J., Trellet, M., Schmitz, C., Kastritis, P., Karaca, E., Melquiond, A., van Dijk, M., De Vries, S., and Bonvin, A. (2016). The HADDOCK2. 2 web server: user-friendly integrative modeling of biomolecular complexes. J Mol Biol 428, 720-725.

Vangone, A. & Bonvin, A. M. Contacts-based prediction of binding affinity in protein-protein complexes, elife 4, e07454 (2015).

Varshney, A.K., Wang, X., Cook, E., Dutta, K., Scharff, M.D., Goger, M.J., and Fries, B.C. (2011). Generation, characterization, and epitope mapping of neutralizing and protective monoclonal antibodies against staphylococcal enterotoxin B-induced lethal shock. J Biol Chem 286, 9737-9747.

Verdoni, L., Mazza, A., Gervasoni, A., Martelli, L., Ruggeri, M., Ciuffreda, M., Bonanomi, E., and D'Antiga, L. (2020). An outbreak of severe Kawasaki-like disease at the Italian epicentre of the SARS-CoV-2 epidemic: an observational cohort study. Lancet 395, 1771-1778.

Walls et al., Structure, Function, and Antigenicity of the SARS-CoV-2 Spike Glycoprotein. Cell 180, 281-292 (2020).

Watanabe, Y., Allen, J.D., Wrapp, D., McLellan, J.S., and Crispin, M. (2020). Site-specific glycan analysis of the SARS-CoV-2 spike. Science 369, 330-333.

Waterhouse et al., Swiss-Model: homology modelling of protein structures and complexes. Nucleic Acids Res 46, W296-W303 (2018).

Whitfield et al., Interference of the T cell and antigen-presenting cell costimulatory pathway using CTLA4-Ig (abatacept) prevents Staphylococcal enterotoxin B pathology. J. Immunol. 198, 3989-3998 (2017).

Woo, H., Park, S.-J., Choi, Y.K., Park, T., Tanveer, M., Cao, Y., Kern, N.R., Lee, J., Yeom, M.S., Croll, T.I., et al. (2020). Developing a fully glycosylated full-Length SARS-CoV-2 spike protein model in a viral membrane. J Phys Chem B 124, 7128-7137.

Wrapp et al., Cryo-EM structure of the 2019-nCoV spike in the prefusion conformation. Science 367, 1260-1263 (2020).

Xu et al., Characteristics of pediatric SARS-CoV-2 infection and potential evidence for persistent fecal viral shedding. Nat. Med. 26, 502-505 (2020).

Xue, et al., Prodigy: a web server for predicting the binding affinity of protein-protein complexes. Bioinformatics 32, 3676-3678 (2016).

Yan, R., Zhang, Y., Li, Y., Xia, L., Guo, Y., and Zhou, Q. (2020). Structural basis for the recognition of SARS-CoV-2 by full-length human ACE2. Science 367, 1444-1448.

Young, Thornton, Toxic shock syndrome in burns: diagnosis and management. Arch. Dis. Child. Educ. Pract. 92, ep97-ep100 (2007).

Yuan et al., A highly conserved cryptic epitope in the receptor binding domains of SARS-CoV-2 and SARS-CoV. Science 368, 630-633 (2020).

Yuan et al., Cryo-EM structures of MERS-CoV and SARS-CoV spike glycoproteins reveal the dynamic receptor binding domains. Nature communications 8, 15092 (2017).

Zhan, et al., SARS-CoV-2 is well adapted for humans. What does this mean for re-emergence? bioRxiv, 2020.2005.2001.073262 (2020).

Zhou, D., Duyvesteyn, H.M., Chen, C.-P., Huang, C.-G., Chen, T.-H., Shih, S.-R., Lin, Y.-C., Cheng, C.-Y., Cheng, S.-H., Huang, Y.-C., et al. (2020a). Structural basis for the neutralization of SARS-CoV-2 by an antibody from a convalescent patient. Nat Struct Mol Biol 27, 950-958.

Zhou, H., Chen, X., Hu, T., Li, J., Song, H., Liu, Y., Wang, P., Liu, D., Yang, J., and Holmes, E.C. (2020b). A novel bat coronavirus closely related to SARS-CoV-2 contains natural insertions at the S1/S2 cleavage site of the spike protein. Curr Biol 30, 2196-2203.

Zost, S.J., Gilchuk, P., Case, J.B., Binshtein, E., Chen, R.E., Nkolola, J.P., Schafer, A., Reidy, J.X., Trivette, A., Nargi, R.S., et al. (2020). Potently neutralizing and protective human antibodies against SARS-CoV-2. Nature 584, 443-449.

Whittaker E, et al. (2020) Clinical Characteristics of 58 Children With a Pediatric Inflammatory Multisystem Syndrome Temporally Associated With SARS-CoV-2. JAMA 324(3):259-269.

Weisberg SP, et al. (2020) Antibody responses to SARS-CoV2 are distinct in children with MIS-C compared to adults with COVID-19. medRxiv.

Ho M (2020) Perspectives on the development of neutralizing antibodies against SARS-CoV-2. Antib Ther 3(2):109-114.

\* cited by examiner

| | | | | | | | | | | | |
|---|---|---|---|---|---|---|---|---|---|---|---|
| SARS-CoV-2 Protein (674-685) | Y | Q | T | Q | T | N | S | P | R | R | A | R |
| a-cobratoxin (Naja naja) | C | D | G | F | C | S | S | . | R | G | K | R |
| a-bungarotoxin | C | D | A | F | C | S | S | . | R | G | K | V |
| Rabies Virus G Protein (189-199) | C | D | I | F | T | N | S | . | R | G | K | R |
| a-cobratoxin (Naja kaouthia) | C | D | A | F | C | S | I | . | R | G | K | R |
| HIV-1 gp120 (164-174) | F | N | I | S | T | S | I | . | R | G | K | V |

```
SEB SAG:       (150)YN-KKKATVQELD(161)      Inverted SAG:(161)DLE--------QVTAKKKNY(150)
SARS-CoV-2:    (678)TNSPRRARSVASQ(690)      SARS-CoV2:   (661)ECDIPIGAGICASYQTQTNSPRRAR(685)
SARS-CoV:      (664)SLL----RSTSQK(672)      SARS-CoV:    (647)ECDIPIGAGICASYHTVSLL----R(667)
```

FIG. 3A

Superantigen in SEB

FIG. 3B

SARS-CoV-2 spike proposed superantigen

FIG. 3C

SARS-CoV homologous region

FIG. 3D

TCRA
TCRB
CD28

PRRARS motif
Spike interacting subunit
Other spike subunits

FIG. 3E

TCR binding to PRRA motif region

PRRA insert region

TCRα

TCRβ

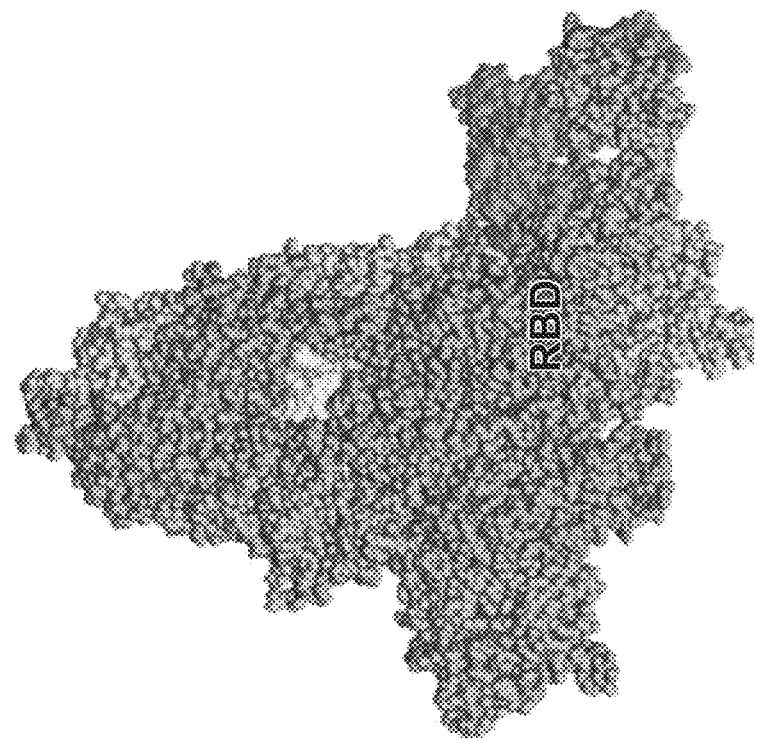
FIG. 5H
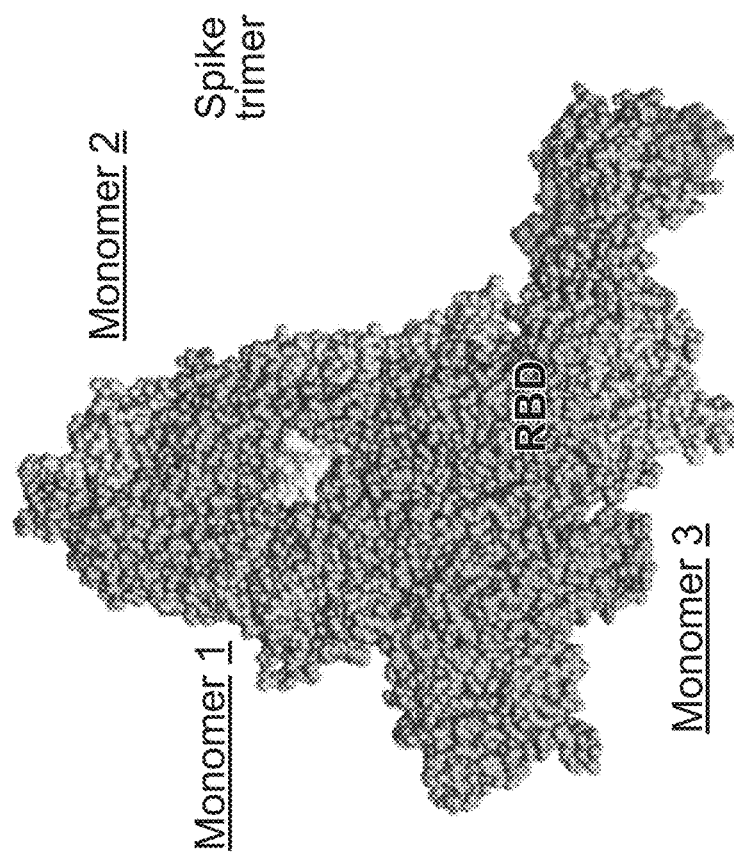
FIG. 5G

| | Bioactive (SAg/toxic/ICAM-like) sequences of SARS-Cov S protein (1st row) and corresponding homologous sequences in SARS-CoV-2 spike (2nd row) | Residues | Seq id |
|---|---|---|---|
| 1 | VIPFKDGIYFAATEKSNVVRGWVFGSTM | 80-107 | 68% |
|   | VIPFKDGVYFASTEKSNIIRGWIFGTTL | 83-110 | |
| 2 | QTHTMIFDNAFNCTFEYISDAFSLDVS | 147-173 | 37% |
|   | ESEFRVYSSANNCTFEYVSQPFLMDLE | 154-180 | |
| 3 | NITNFRAILT---AF-SPAQDI----WGTSA | 227-249 | 30% |
|   | NITRFQTLLALHRSYLTPG-DSSSGWTAGA | 234-262 | |
| 4 | YDENGTITDAVDCSQNPLAELKC | 266-288 | 74% |
|   | YNENGTITDAVDCALDPLSETKC | 279-301 | |
| 5 | LKCSVKSFEIDKGIYQTSNFRVVPSGDVVRFPNITNLCPFGEVFNATKFPSVY | 286-338 | 75% |
|   | TKCTLKSFTVEKGIYQTSNFRVQPTESIVRFPNITNLCPFGEVFNATRFASVY | 299-351 | |
| 6 | GCLIGAEHVDTSYECDIPIG | 634-653 | 90% |
|   | GCLIGAEHVNNSYECDIPIG | 648-667 | |
| 7 | NTREVFAQVKQMYKTPTLKYFGGFNFSQILP | 759-789 | 84% |
|   | NTQEVFAQVKQIYKTPPIKDFGGFNFSQILP | 777-807 | |
| 8 | EAEVQIDRLITGRLQSLQTYVTQQLIRAAEIRASANLAATKMSECVLGQSKRVDFCGKGYHLMS FPQAAPHGVVFLHVTYVPS | 970-1052 | 98% |
|   | EAEVQIDRLITGRLQSLQTYVTQQLIRAAEIRASANLAATKMSECVLGQSKRVDFCGKGYHLMS FPQSAPHGVVFLHVTYVPA | 988-1070 | |
| 9 | LQPELDSFKEELDKYFKNHTSPDVDLGDISGINASVVNIQKEIDRLNEVAKNLNESLIDLQ | 1123-1188 | 100% |
|   | LQPELDSFKEELDKYFKNHTSPDVDLGDISGINASVVNIQKEIDRLNEVAKNLNESLIDLQ | 1141-1201 | |

FIG. 6A

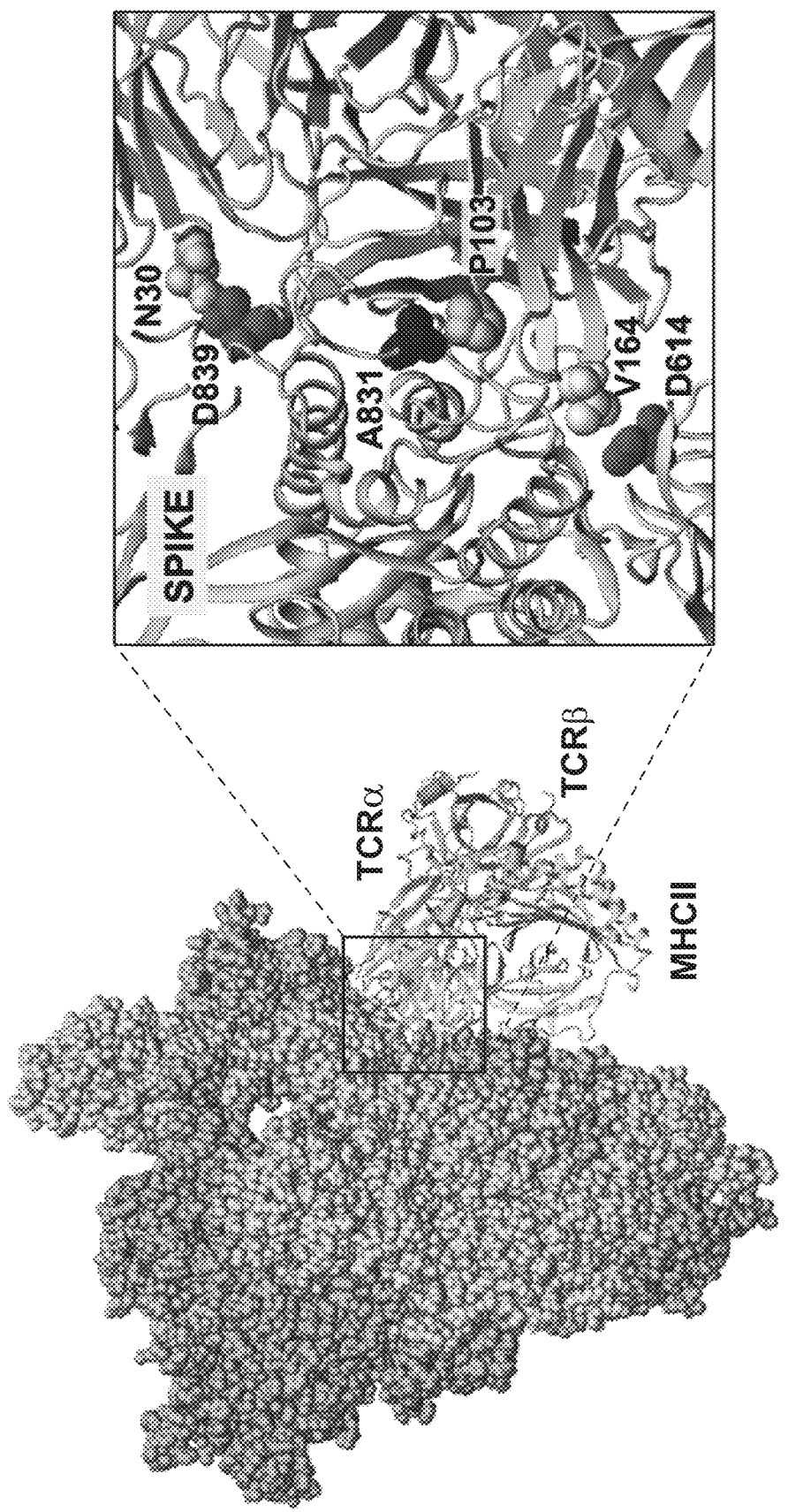

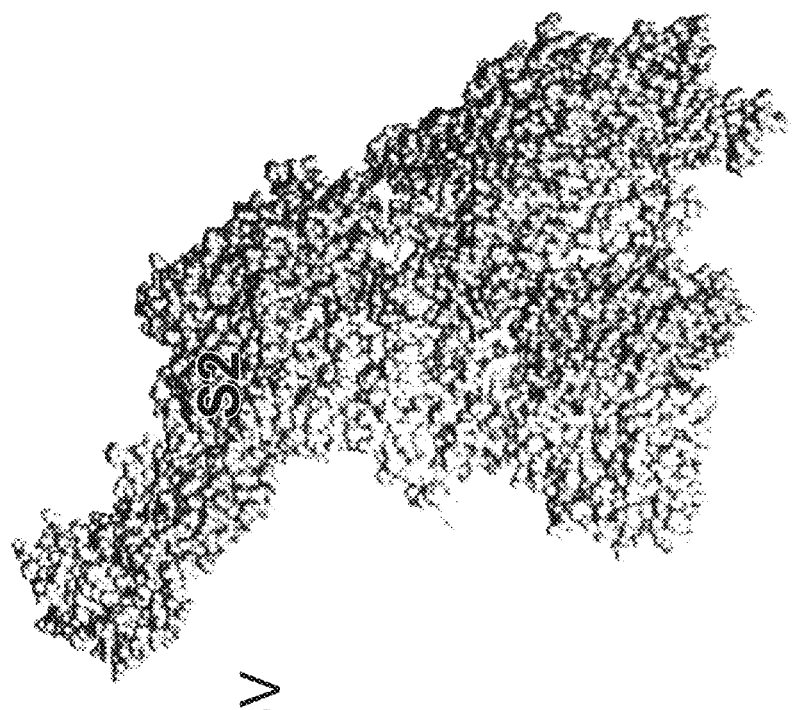
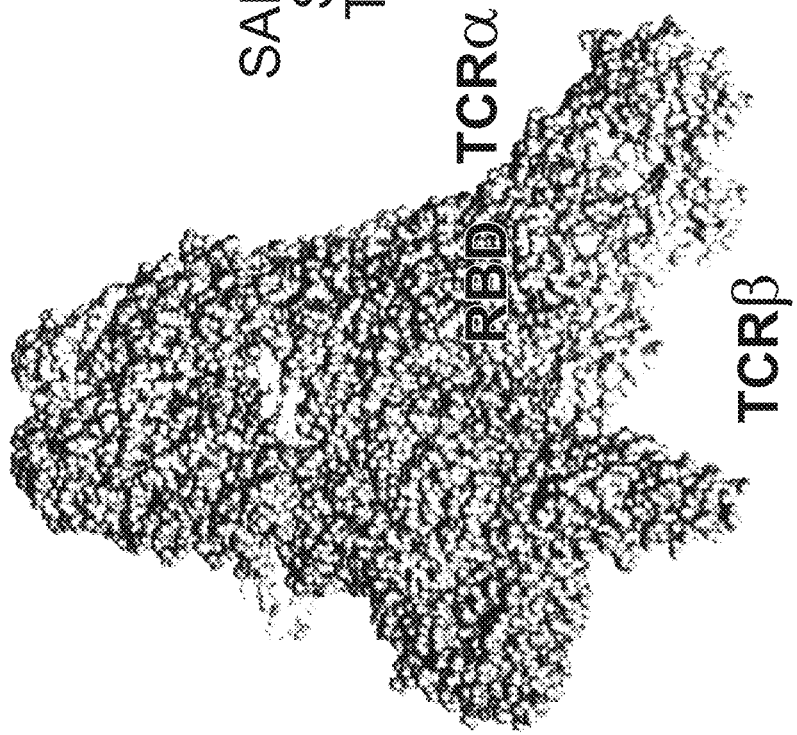
FIG. 9B
FIG. 9A

| Neurotoxin- or ICAM-1-like and bioactive sequences in SARS1 and SARS-CoV-2 S | | | Sequence identity % |
|---|---|---|---|
| 1 | SARS1 | 80-107 | 68% |
| | SARS-CoV-2 | 83-110 | |
| 2 | SARS1 | 147-173 | 37% |
| | SARS-CoV-2 | 154-180 | |
| 3 | SARS1 | 227-249 | 30% |
| | SARS-CoV-2 | 234-262 | |
| 4 | SARS1 | 266-288 | 74% |
| | SARS-CoV-2 | 279-301 | |
| 5 | SARS1 | 286-338 | 75% |
| | SARS-CoV-2 | 299-351 | |
| 6 | SARS1 | 364-653 | 90% |
| | SARS-CoV-2 | 648-667 | |
| 7 | SARS1 | 759-789 | 84% |
| | SARS-CoV-2 | 777-807 | |
| 8 | SARS1 | 970-1052 | 98% |
| | SARS-CoV-2 | 988-1070 | |
| 9 | SARS1 | 1123-1183 | 100% |
| | SARS-CoV-2 | 1141-1207 | |

FIG. 10A

ICAM-1-like sequence

PRRA region

Neurotoxin like sequence motif

FIG. 10B

SARS-CoV-2 spike - TCR complex

Neurotoxin-like motif T299-Y351

TCRβ

TCRα

SARS-CoV- (SARS1) spike - TCR complex

Neurotoxin-like motif L286-Y338

FIG. 10C

Neurotoxin-like segment 299-351 and corresponding epitopes with high T cell reactivity

299 TKCTLKSFTVEKGIYQTSNFRVQPTESIVRFPNITNLCPFGEVFNATRFASVY 351

FIG. 13

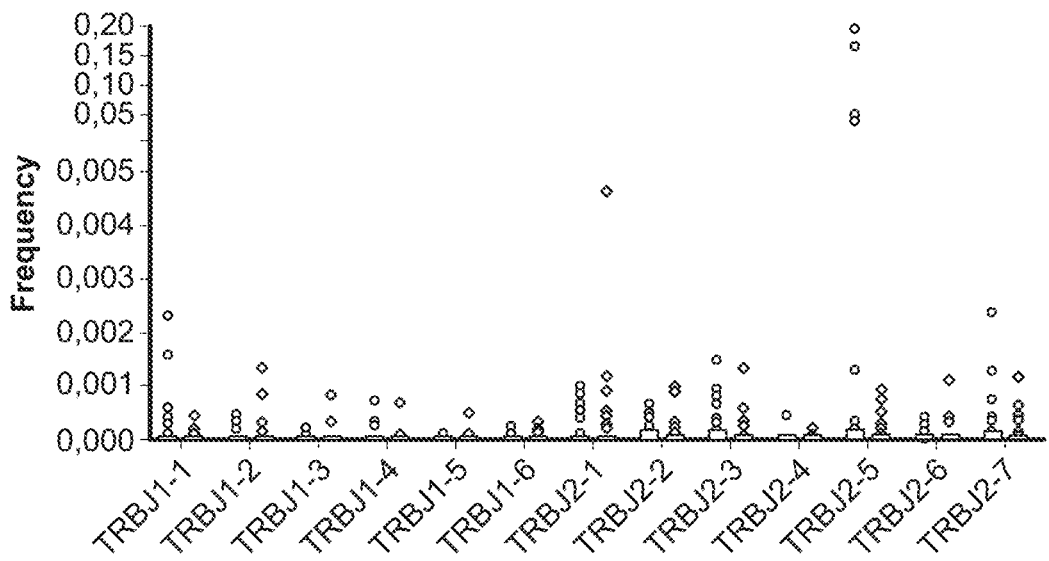
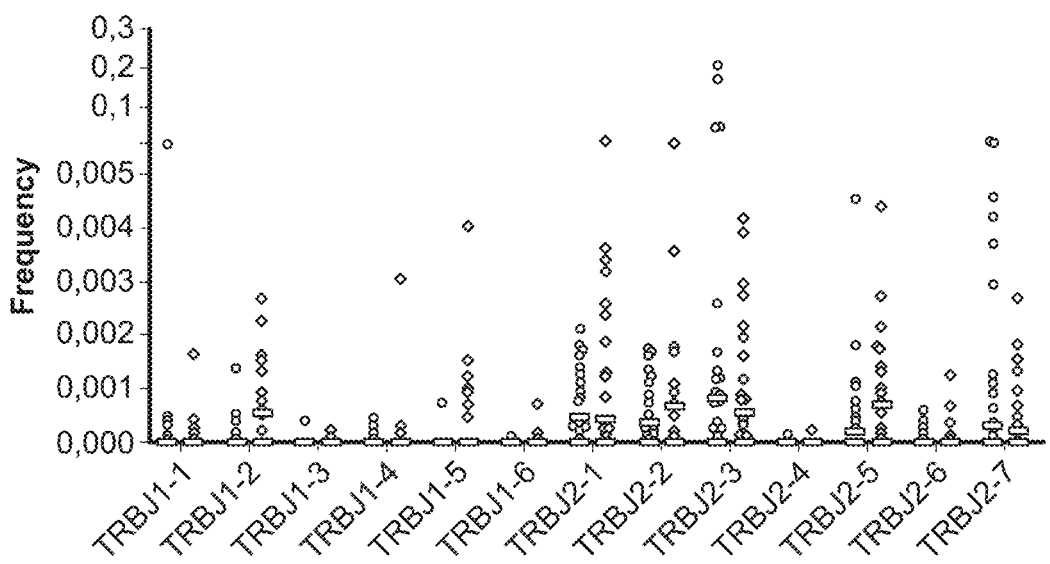
FIG. 14 Continued

In silico models for TCR-Spike binary complexes

| PDB ID | βTCR | | |
|---|---|---|---|
| 2XN9 | TCRB | MVDGGITQSPKYLFRKEGQNVTLSCEQNLNHDAMYWYRQDPGQGLRLIYSQIVNDFQKG | 60 |
| 6ULR | TRBV5-6 | --MAGVTQSPTHLIKTRGQQVTLRCSPKSGHDTVSWYQQALGQGPQFIFQYYEEEERQRG | 58 |
| 2ESV | TRBV14 | --EAGVTQFPSHSVIEKGQTVTLRCDPISGHDNLYWYRVMGKEIKFLLHFVKESKQDES | 58 |
| 6EH6 | TRBV24-1 | ---ADVTQTPRNRITKTGKRIMLECSQTKGHDRMYWYRQDPGLGLRLIYYSFDVKDINKG | 57 |
| | | ..: *  . . *:  :  *.*:: *  *:: |

CDR1                    CDR2

| 2XN9 | TCRB | DIA-EGYSVSREKKESFPLTVTSAQKNPTAFYLCASSSRS--SYEQYFGPGTRLTVEDL | 117 |
|---|---|---|---|
| 6ULR | TRBV5-6 | NFP-DRFSGHQFPNYSSELNVNALLLGDSALYLCASSLGEGRVDGYTFGSGTRLTVEDL | 117 |
| 2ESV | TRBV14 | GMPNNRFLAERTGGTYSTLKVQPAELEDSGVYFCASSQDR--DTQYFGPGTRLTVLEDL | 115 |
| 6EH6 | TRBV24-1 | EIS-DGYSVSRQAQAKFSLSLESAIPNQTALYFCATSD-E--SYGYTFGSSTRLTVVEDL | 113 |
| | | : . .  . . : :    .* : *..:. :    ** ****** *** |

CDR3

TCRβ   TRBV5-6   TRBV14   TRBV24-1

FIG. 15D

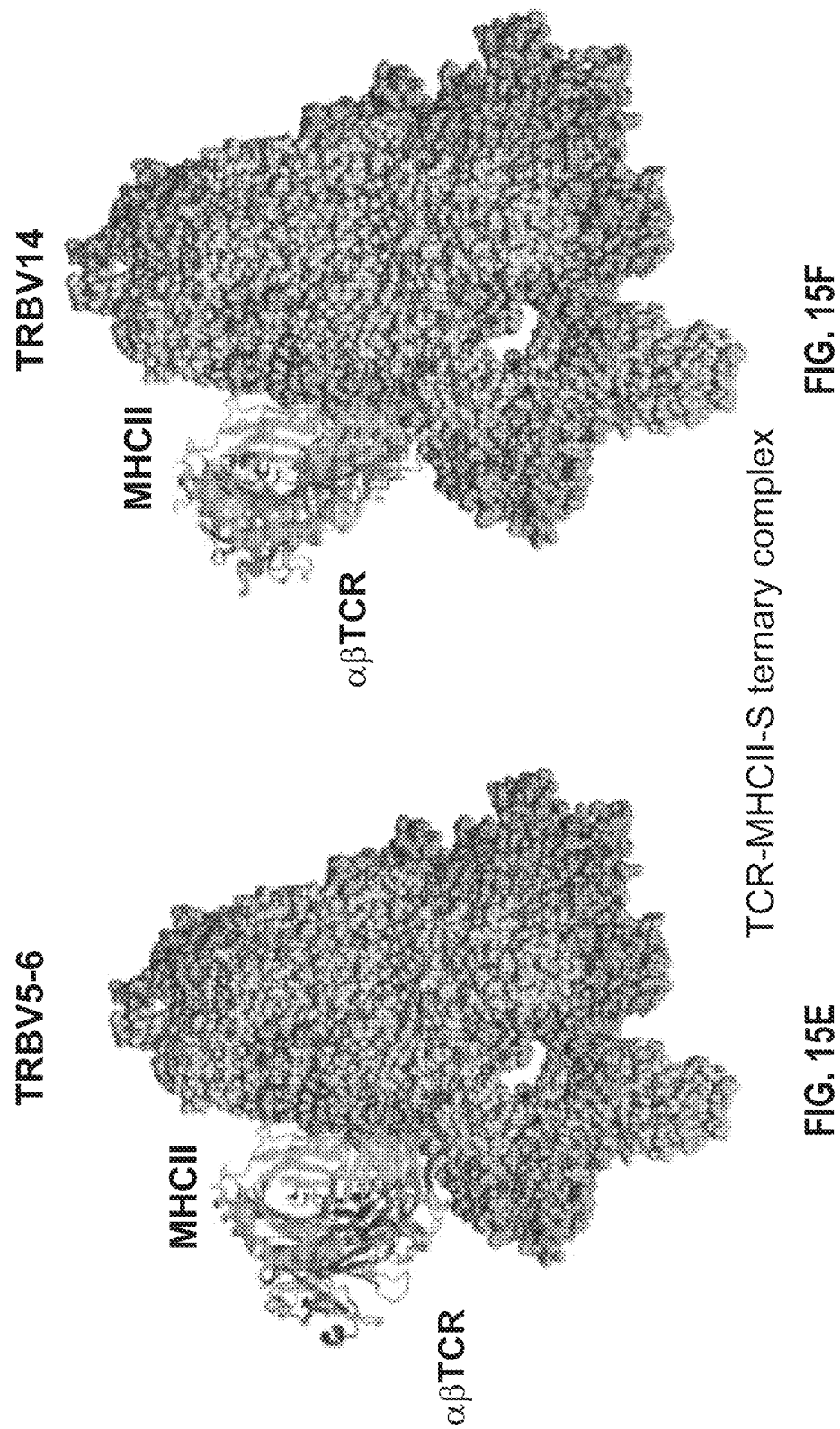
FIG. 15E TCR-MHCII-S ternary complex FIG. 15F

| | S1/S2 cleavage site → S2 | | |
|---|---|---|---|
| | SAg-like motif $E_{661}$-$R_{685}$ | polybasic insert | |
| SARS-CoV-2 (671-692) | C A S Y Q T Q T - N S | P R R A R | S V A S Q S I |
| Bat SARS-like CoV RaTG13 | C A S Y Q T Q T - N S | - - - - - | R S V A S Q S I |
| Bat SARS-like CoV WIV16 | C A S Y H T V S - L L | - - - - - | R S V S W K S I |
| Pangolin CoV (A0A6M3G9R1) | C A S Y H T Q T - N S | - - - - - | R S V S W K S I |
| BAT SARS-like RmYN02 | C A S Y H T V S - N S P - A A R - | - - - - - | V G Y N S I |
| BAT SARS-like RmYN01 | C A S Y H T A S - L L | - - - - - | R N T G Q K S I |
| BAT SARS-like CoV ZC45 | C A S Y H T A S - L L | - - - - - | R S T S Q K A I |
| BAT SARS-like CoV ZXC21 | C A S Y H T A S - L L | - - - - - | R S T G Q K A I |
| HCoV-SARS (P59594) | C A S Y H T V S - S L | - - - - - | R S T S Q K S I |
| HCoV-HKU1 (Q0ZME7) | C I D Y A T P S - - | S R R K R | R G I S S P Y R |
| HCoV-OC43 (P36334) | C V D Y S K - - - - | N R R S R | G A I T T G Y |
| HCoV-MERS (A0A140AYZ5) | C A L P G T P S T L T | P R S V R | S V P G F M R |
| HCoV-229E (P15423) | C A D G S T I A V Q P | - - - - - | R N V S Y D S V |
| HCoV-NL63 (Q6Q1S2) | C A D G S L I P V R P | - - - - - | R N S S D N G I |

Furin-cleavage site

FIG. 16B

Red: dsRNA, Blue: DAPI

Red: SARS-CoV-2 spike, Blue: DAPI

FIG. 24

```
                                                              CDR1                                                    CDR2
6D3|4RNG    QVQLQQSGAELVKPGASVKLSCKASGYTFTSHWMHWVKQRPGQGLEWIGEIDPSDSYINY  60
4A8|7C2L    EVQLVESGAEVKKPGASVKVSCKVSGYTLTELSMHWVRQAPGKGLEWMGGFDPEDGETMY  60
S309|6Z2PS  QVQLVQSGAEVKKPGASVKVSCKASGYPFTSYGISWVRQAPGQGLEWMGWISTYNGNTNY  60
C105|6XCN   QVQLVESGGGLIQPGGSLRLSCAASGFTVSSNYMSWVRQAPGKGLEWVSVI-YSGGSTYY  59
2-4|6XEY    QVQLVQSGAEVKKPGASVKVSCKASGYTFTGYYMHWVRQAPGQGLEWMGWINPNSGGTNY  60
Ab23|7BYR   QVQLVQSGSELKKPGASVKVSCKASGYTFTSYAMNWVRQAPGQGLEWMGWINTNTGNPTY  60
EY6A|6ZDH   EVQLVESGGGVVQPGRSLRLSCAASAFTFSSYDMHWVRQAPGKGLEWVAVISYDGSNKYY  60
H014|7CAI   EVQLVQSGAEVKKPGATVKISCKVSGYSFSNYYIHWVKQAPGKSLEWIGYIDPFNGGTSD  60
20B1|4RGM   QIQLVQSGPELKKPGETVRISCKASGYIFTIAGIQWVQKMPGRGLRWIGWINTHSGVPEY  60
14G8|4RGO   EVNLIESGGDLVKPGGSLKLSCATSGFTFSAYGLSWVRQTPERRLEWVASIS-GGGSVYY  59
               :::  * .*      .    :       :.  *    .*  *   *      .

6D3|4RNG    NQIFEGKATLTVDKSSTTAYLQLSSLTSEDSAVYYCARTAGL------LAPMDYWGQ    111
4A8|7C2L    AQKFQGRVTMTEDTSTDTAYMELSSLRSEDTVVYCATSTAVAGTPDLFDYYYGMDVWGQ  120
S309|6Z2PS  AQKFQGRVTMTEDTSTDTGYMELRRLRSDDTAVYYCARDYTRGAW--E----GWELPYDYWGQ  119
C105|6XCN   ADSVKGRFTISRDNSKNTLYLQMNSLRAEDTAVYYCARG--E------GWELPYDYWGQ  110
2-4|6XEY    TQMFQGRVTMTRDTSISTAYMEVSRLRSDDTAVYYCARDRSWAVV------YYYMDVWGK  114
Ab23|7BYR   AWGFTGRFVFSLDTSVSTAYLQISSLKAEDTAVYYCARPQGGSSW--YRDYYYGMDVWGQ  118
EY6A|6ZDH   ADSVKGRFTISRDNSKNTLYLQMNSLRAEDTAVYYCAKDGGK------LWVYFDYWGQ   113
H014|7CAI   NLKFKGAATLTADTSTDTAYMELSSLRSEDTAVYYCARSE------YDPYYVMDYWGQ  112
20B1|4RGM   AEEFKGRFAFSLETSARTAYLQISNLKDEDTATYFCARIVYG------NNGGVMDYWGQ  113
14G8|4RGO   PDSVKGRFTISRDTAGDILFLQMNSLRSEDSAIYYCVRDLYG------DYVGRYAYWGQ  112
             .    .:*:. :: :      .*    .:  :.*  :       *           *
                                                  CDR3
```

FIG. 25A

SARS-CoV-2 S protein
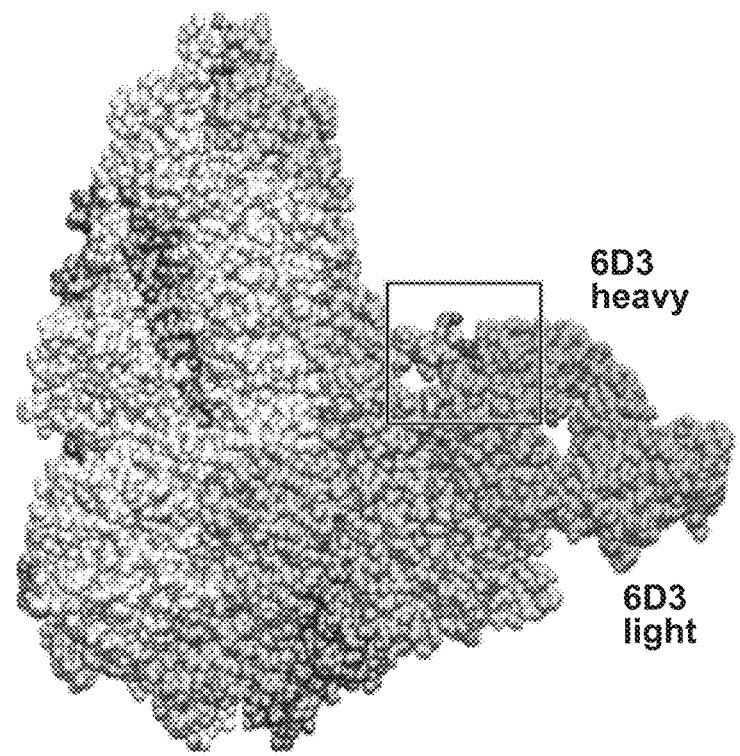
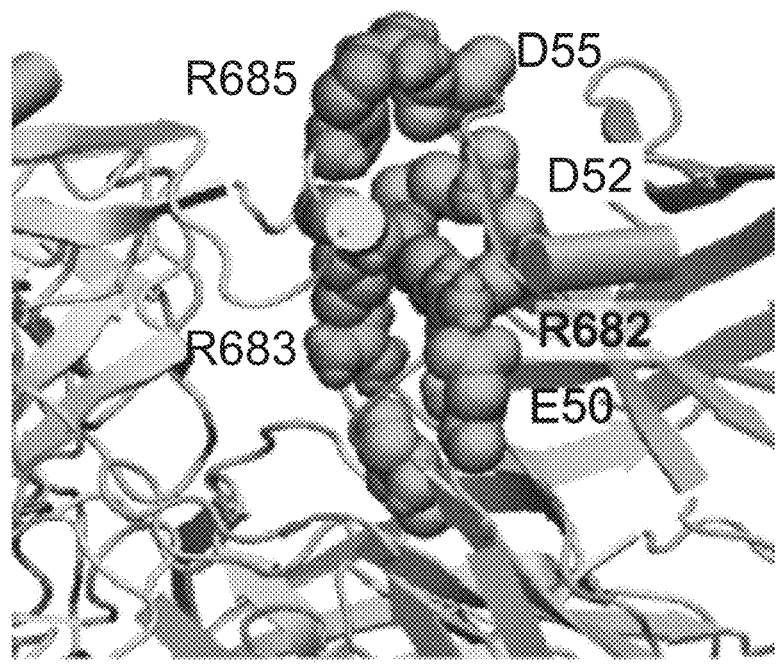
FIG. 25B

FIG. 27

COMPOSITIONS AND METHODS FOR TREATING A COVID-19 INFECTION

CROSS-REFERENCE TO RELATED APPLICATIONS

This application claims the benefit of U.S. Provisional Application No. 63/051,481, filed Jul. 14, 2020, which is expressly incorporated herein by reference.

STATEMENT REGARDING FEDERALLY SPONSORED RESEARCH OR DEVELOPMENT

This invention was made with government support under grant numbers GM103712 and AI072726 awarded by the National Institutes of Health. The government has certain rights in the invention.

FIELD

The present disclosure relates to the field of treatment of a COVID-19 infection.

BACKGROUND

Severe acute respiratory syndrome coronavirus 2 (SARS-CoV-2), which causes COVID-19, is a coronavirus closely related to SARS-CoV and Middle East Respiratory Syndrome (MERS) coronaviruses (A. C. Walls et al. (2020)). COVID-19 can manifest in adults as a severe interstitial pneumonia with hyperinflammation while severe respiratory manifestations are rare in children (L. Cristiani et al. (2020); M. Z. Tay, et al. (2020); N. Vabret et al. (2020)). Recently, however, multisystem inflammatory syndrome in children (MIS-C) has been recognized in patients that either tested positive for COVID-19 (by PCR or serology) or had epidemiological links to COVID-19 (S. Riphagen, et al. (2020); L. Verdoni et al. (2020); Z. Belhadjer et al. (2020)). These children present with a constellation of symptoms including hypotension, multiorgan involvement, and elevated inflammatory markers. After initial reports in UK (S. Riphagen, et al. (2020)), many cases have now been reported in Europe (L. Verdoni et al. (2020); Z. Belhadjer et al. (2020)), and New York (USA CDC). However, no such cases have been reported in China, Japan, or South Korea, which have also been severely impacted by the COVID-19 pandemic (ECDC). What is needed are compositions and methods for treating a COVID-19 infection, including MIS-C. The compositions and methods disclosed herein address these and other needs.

DESCRIPTION OF DRAWINGS

In FIG. 1B, the segment $S_{680}PPRAR_{685}$ (SEQ ID NO:119) including the PRRA (SEQ ID NO:2) insert and highly conserved cleavage site R685 is shown in van der Waals representation (black labels) and nearby CDR residues of the TCRV β domain are labeled in white. See additional information in FIG. 5.

FIG. 2(A-D) shows sequence and structural properties of the insert "PRRA" motif. FIG. 2A shows sequence alignment of SARS-CoV-2 and multiple SARS-CoV and Bat SARS-like CoV strains (A. C. Walls et al. (2020)) near the insertion PRRA (SEQ ID NO:2). FIG. 2B shows structural alignment of SARS-CoV-2 and SARS-CoV at the same region. The PRRARS (SEQ ID NO:6) motif is shown. FIG. 2C shows sequence similarity between neurotoxin motifs and the close neighborhood of the PRRA insert, reported earlier (J. P. Changeux, et al. (2020)) as well as HIV-1 gp120 SAg motif (L. Bracci, et al. (1997)) in the last row. FIG. 2D shows SARS-CoV-2 S trimer composed of S1 subunits only. The protomers are displayed in van der Waals format. The sequences in FIG. 2 are

Figure 1B:
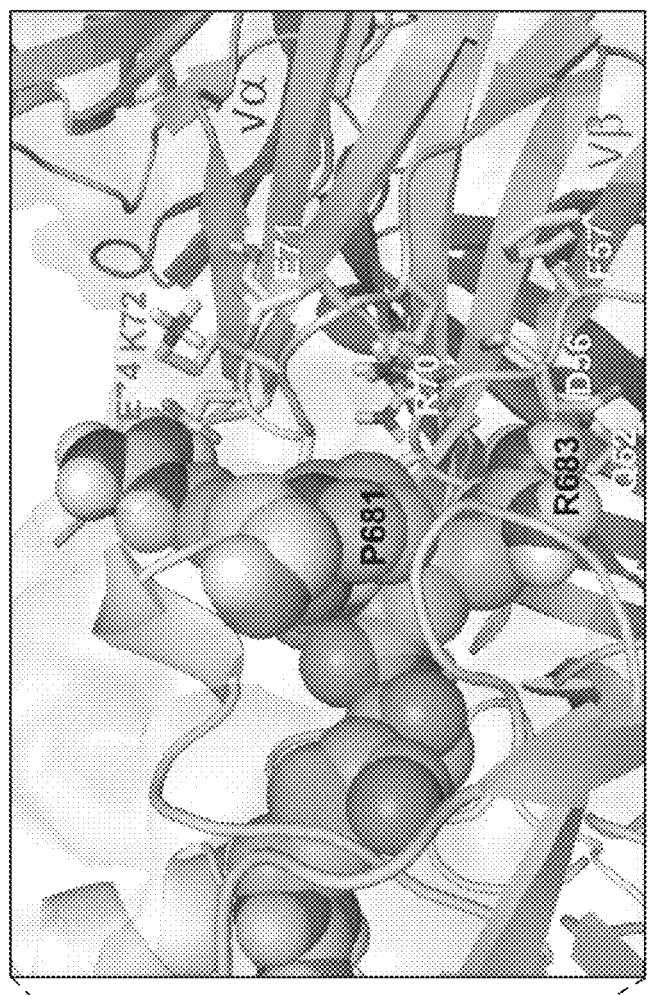
In FIG. 1B, for better visualization, the spike trimer is oriented such that its receptor binding domains (RBDs) are at the bottom. TCR α- and β-chains are shown.

|                   |                    |
|-------------------|--------------------|
| CASYQTQTNSPRRARSVASQSI, | (SEQ ID NO: 43) |
| CASYQTQTNS,       | (SEQ ID NO: 44)    |
| RSVASQSI,         | (SEQ ID NO: 45)    |
| CASYHTVSSL,       | (SEQ ID NO: 46)    |
| RSTSQKSI,         | (SEQ ID NO: 47)    |
| YQTQTNSPRRAR,     | (SEQ ID NO: 48)    |
| CDGFCSSRGKR,      | (SEQ ID NO: 49)    |
| CDAFCSSRGKV,      | (SEQ ID NO: 50)    |
| CDIFTNSRGKR,      | (SEQ ID NO: 51)    |
| CDAFCSIRGKR, and  | (SEQ ID NO: 52)    |
| FNISTSIRGKV.      | (SEQ ID NO: 53)    |

FIG. 3(A-E) shows that the "PRRA" insert in SARS-CoV-2 spike exhibits sequence and structure properties similar to those of bacterial superantigen SEB. FIG. 3A shows alignment of the superantigenic sequence of SEB (G. Arad et al. (2011)) against a homologous sequence of SARS-CoV-2 spike near the PRRA insert and corresponding SARS-CoV segment. Alignments are displayed for both forward (left) and reverse (right) ordering of the SEB sequence. Note the similarity between the former two, while the third (SARS-CoV) shows similarities to SARS-CoV-2, but not SEB, sequence. FIG. 3B shows structure of the superantigenic peptide (T150-D161) observed in the crystal structure of SEB (A. C. Papageorgiou, et al. (1998)) (PDB: 3SEB). FIG. 3C shows structural model for SARS-CoV-2 S palindromic motif E661-R685. FIG. 3D shows homologous region in SARS-CoV S exhibits totally distinctive structural features: a salt bridge, K152-E159 (in SEB) or R685-E661 (SARS-CoV-2), is absent in SARS-CoV spike; the former two are poly-basic (with three lysines and three arginines in the respective motifs), whereas SARS-CoV spike counterpart has one basic residue (R667) only; and the former two possess a scaffolding ASN, which is absent on SARS1. FIG.

3E shows structural alignment of CD28, the receptor binding SEB, onto TCRVβ domain, in support of the adaptability of the putative SAg site to accommodate spike-TCRβ or SEB-CD28 interactions. The sequences in FIG. 3 are YNKKKATVQELD (SEQ ID NO:54), TNSPRRARSVASQ (SEQ ID NO:55), SLLRSTSQK (SEQ ID NO:56), DLEQVTAKKKNY (SEQ ID NO:57), ECDIPIGAG-ICASYQTQTNSPRRAR (SEQ ID NO:58), and ECDIPI-GAGICASYHTVSLLR (SEQ ID NO:59).

FIG. 4(A-D) shows that the interfacial interactions between SARS-CoV-2 spike and αβTCR are further stabilized by the association of an ICAM-like motif with TCRVα domain. FIG. 4A shows interface between SARS-CoV-2 spike and TCR variable domains. The PRRARS (SEQ ID NO:6) insert is highlighted in dark grey; The mutation site D839 identified in recent study (B. Korber et al., (2020)) is displayed; SARS-CoV-2 counterpart of CD54-like motif identified for SARS-CoV spike (Y. Li et al., (2004)) is displayed. Residues involved in close interfacial contacts are shown in sticks, with nitrogen and oxygen atoms. Interactions between atom pairs separated by less than 2.5 Å are indicated by black dashed lines. FIG. 4B shows a close-up view of the interactions between the PRRARS (SEQ ID NO:6) insert/motif and TCR Vβ. FIG. 4C shows same for the D839 mutation site. FIG. 4D shows interactions between selected residues on ICAM-1-like motif (labeled) TCRVα CDRs.

Figure 1A:
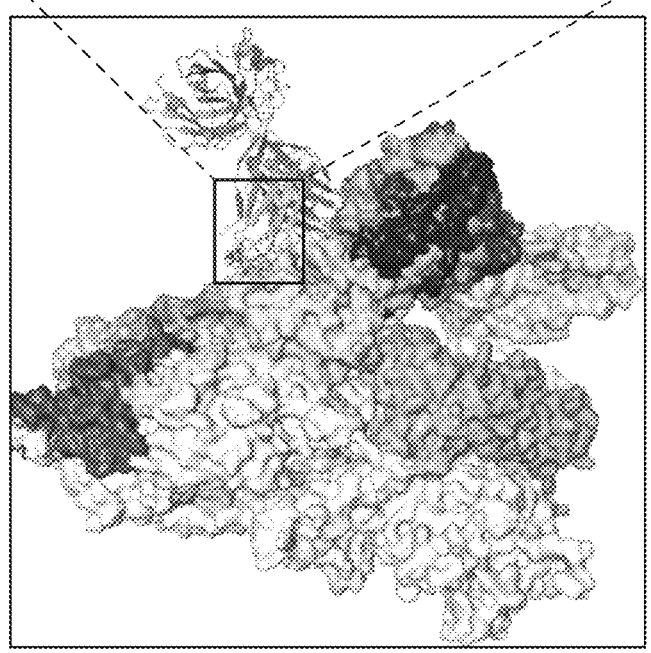
FIG. 1(A-B) shows binding of TCR to SARS-CoV-2 spike trimer near the "PRRA" insert region. Overall (FIG. 1A) and closeup (FIG. 1B) views of the complex and interfacial interactions.

FIG. 5(A-H) shows top-ranking binary complexes of SARS-CoV-2 spike with the T cell receptor (TCR) predicted by ClusPro. FIGS. 5A-5B show binding of TCR near the "PRRA" insert region. FIGS. 5C-5D show binding of TCR near the RBD of a subunit. The spike trimer subunits, the PRRA insert region (E661 to R685) and TCR α- and β-chains are shown. FIGS. 5E-5F show binding of TCR near the "PRRA" insert region of monomer 2 and monomer 1 in the respective panels A and B, showing that the PRRA insert and its close vicinity presents a high-affinity binding site for TCR. FIGS. 5G-5H show binding of TCR near the RBD of a subunit, indicating that the RBD is an alternative high-affinity site. The spike trimer subunits are shown. See more details for the interaction between the PRRA insert region and TCR in FIG. 1.

Figure 6B:
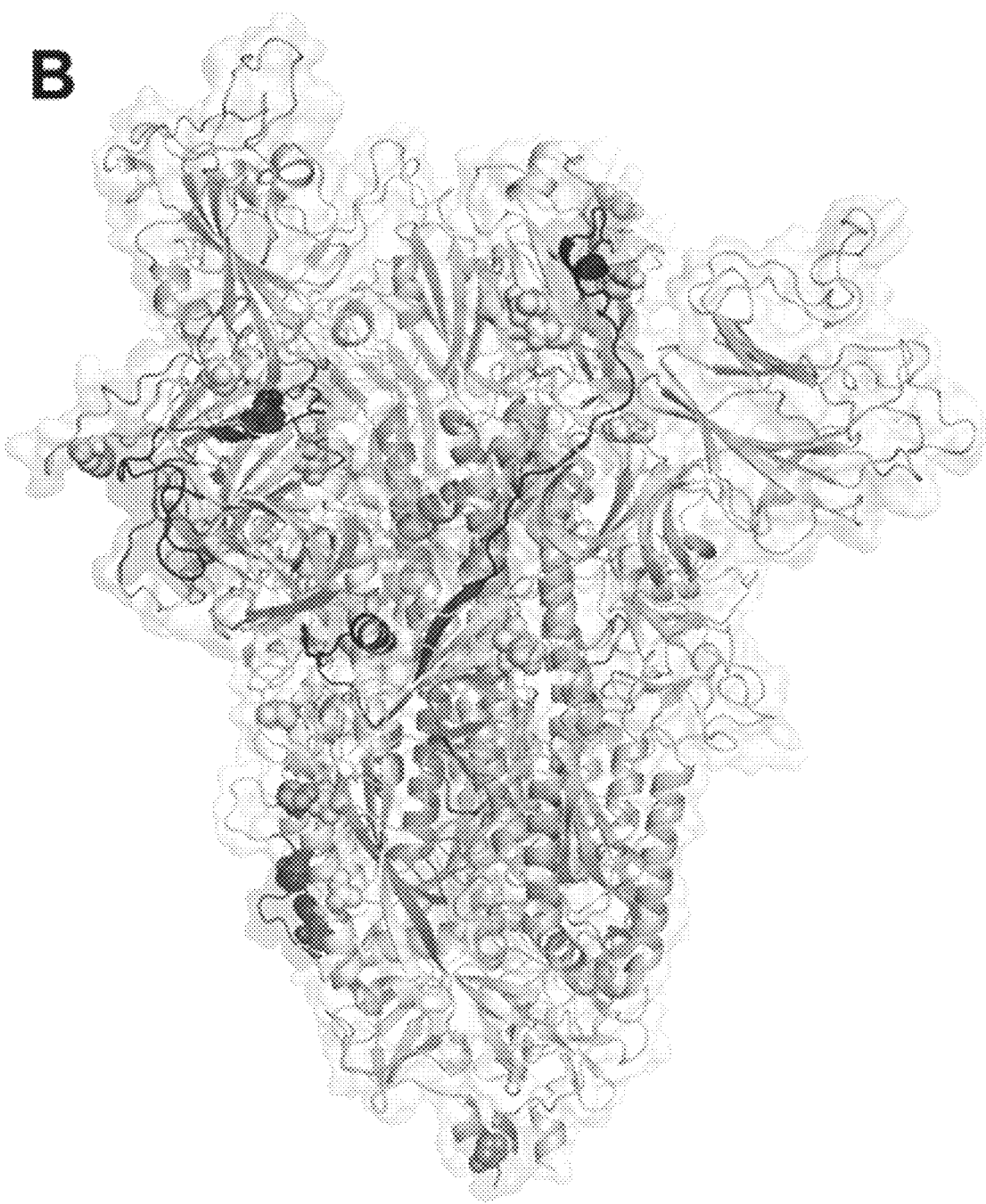

FIG. 6(A-B) shows motifs associated with superantigen, toxin, cytokine, and membrane surface proteins predicted for SARS-CoV spike and mapped onto SARS-CoV-2 spike sequence and structure. FIG. 6A shows sequence alignment of these motifs on SARS-CoV (upper rows) and SARS-CoV-2 spikes (lower rows), corresponding residue numbers (3rd column) and sequence identity (4th/last column). Superantigenic and toxic-like motifs are group 2 and 4. Residues that interact with TCR Vα are marked in bold. FIG. 6B shows predicted motifs mapped onto the trimeric structure of SARS-CoV-2 spike. The motifs are colored black (superantigenic and toxic-like). Mutation sites reported in recent work (Zhan, et al. (2020), Korber, B. et al. (2020)) are shown in spheres. The sequences in FIG. 6 are (SEQ ID NO: 60)
VIPFKDGIYFAATEKSNVVRGWVFGSTM, (SEQ ID NO: 61)
VLPFNDGVYFASTEKSNIIRGWIFGTTL, (SEQ ID NO: 62)
QTHTMIFDNAFNCTFEYISDAFSLDVS, (SEQ ID NO: 63)
ESEFRVYSSANNCTFEYVSQPFLMDLE, (SEQ ID NO: 64)
NITNFRAILTAFXSPAQDIWGTSA, (SEQ ID NO: 65)
NITRFQTLLALHRSYLTPGDSSSGWTAGA, (SEQ ID NO: 66)
YDENGTITDAVDCSQNPLAEKLKC, (SEQ ID NO: 67)
YNENGTITDAVDCALDPLSETKC, (SEQ ID NO: 68)
LKCSVKSFEIDKGIYQTSNFRVVPSGDVVRFPNITNLCPFGEVFNATK
FPSVY, (SEQ ID NO: 69)
TKCTLSKFTVEKGIYQTSNFRVQPTESIVRFPNITNLCPFGEVFNATR
FASVY, (SEQ ID NO: 70)
GCLIGAEHVDTSYECDIPIG, (SEQ ID NO: 71)
GCLIGAEHVNNSYECDIPIG, (SEQ ID NO: 72)
NTREVFAQVKQMYKTPTLKYFGGFNFSQILP, (SEQ ID NO: 73)
NTQEVFAQVKQIYKTPPIKDFGGFNFSQILP, (SEQ ID NO: 74)
EAEVQIDRLITGRLQSLQTYVTQQLIRAAEIRASANLAATKMSECVLG
QSKRVDFCGFPQAAPHGVVFLHVTYVPS, (SEQ ID NO: 75)
EAEVQIDRLITGRLQSLQTYVTQQLIRAAEIRASANLAATKMSECVLG
QSKRVDFCGFPQSAPHGVVFLHBTYVPA, (SEQ ID NO: 76)
LQPELDSFKEELDKYFKNHTSPDVDLGDISGINASVVNIQKEIDRLNE
VAKNLNESL,
and (SEQ ID NO: 77)
LQPELDSFKEELDKYFKNHTSPDVDLGDISGINASVVNIQKEIDRLNE
VAKNLNESL.

FIG. 7(A-B) shows modeled ternary complex formed by SARS CoV-2 spike, WWII and αβTCR. FIG. 7A shows side view of the complex. The trimeric spike subunits are shown in the same style and color as in FIG. 5, as well as TCRα and TCRβ. The TCR retains a similar pose as in FIG. 5B, now rotated by 180° along the z-axis. WWII is displayed in ribbon diagram. FIG. 7B shows top view of the interfacial contacts. Note that three spike residues reported to mutate in recent strains observed in European and western counties (Zhan, et al. (2020), Korber, B. et al. (2020)) (D614G, A831V and D839Y/N/E) are within 3-5 Å from either MCHII or TCR Vβ.

FIGS. 8(A-D) shows in silico mutagenesis analysis of SARS-CoV-2 spike protein residue D839Y/N/E. FIG. 8A shows a close-up view of the interaction between the wild type residue D839 in the spike and N30 of TCR Vβ. FIGS. 8B-8D show results obtained upon mutation to asparagine, glutamic acid, and tyrosine. The spike and TCR Vβ are shown. The mutation site is highlighted. Atomic interactions are indicated by black dashed lines along with their distances in Angstroms.

Figures 9C, 9D:
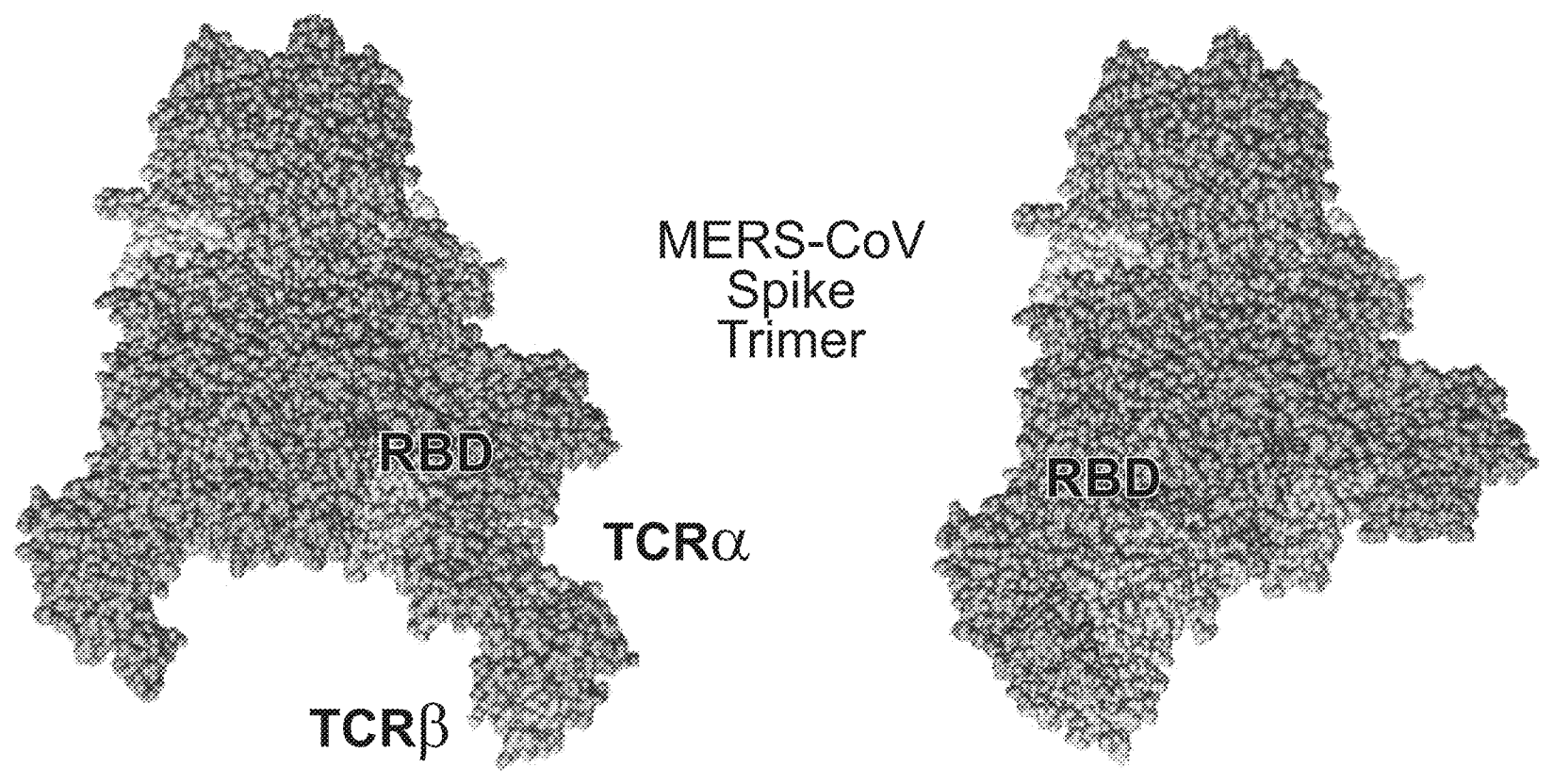

FIGS. 9(A-D) shows complex conformers formed upon binding of TCR onto SARS-CoV spike (FIGS. 9(A-B)) and MERS-CoV spike (FIGS. 9(C-D)), representative of the most probable clusters predicted by docking simulations. In FIGS. 9A-9B, top two TCR binding poses predicted for SARS-CoV spike: one within the RBDs and the other within S2 subunits near the C-terminal domains. In FIGS. 9C-9D, top two TCR binding poses predicted for MERS-CoV: one between the RBDs in the down conformation and the other on the RBD of the up conformation. The cleavage region in SARS-CoV (E647 to R667) and MERS-CoV (D726 to R751) are shown. TCR α- and β-chains are shown. Docking simulations were performed using ClusPro.

FIGS. 10(A-C) shows neurotoxin-like sequences in SARS-CoV-2 S RBD and their ability to bind TCRs. FIG. 10A shows comparison of bioactive/neurotoxin-like and ICAM-1 like segments identified for SARS1 S and their SARS-CoV-2 S counterparts. FIG. 10B shows loci of two neurotoxin-like regions and one ICAM-1 region (see FIG. 4) conserved between the two CoVs, shown on one monomer of SARS-CoV-2 S. FIG. 10C shows binding poses of TCR on SARS-CoV-2 (left) and SARS1 (right) S proteins, making contacts with the indicated conserved neurotoxin motif.

Figure 11:
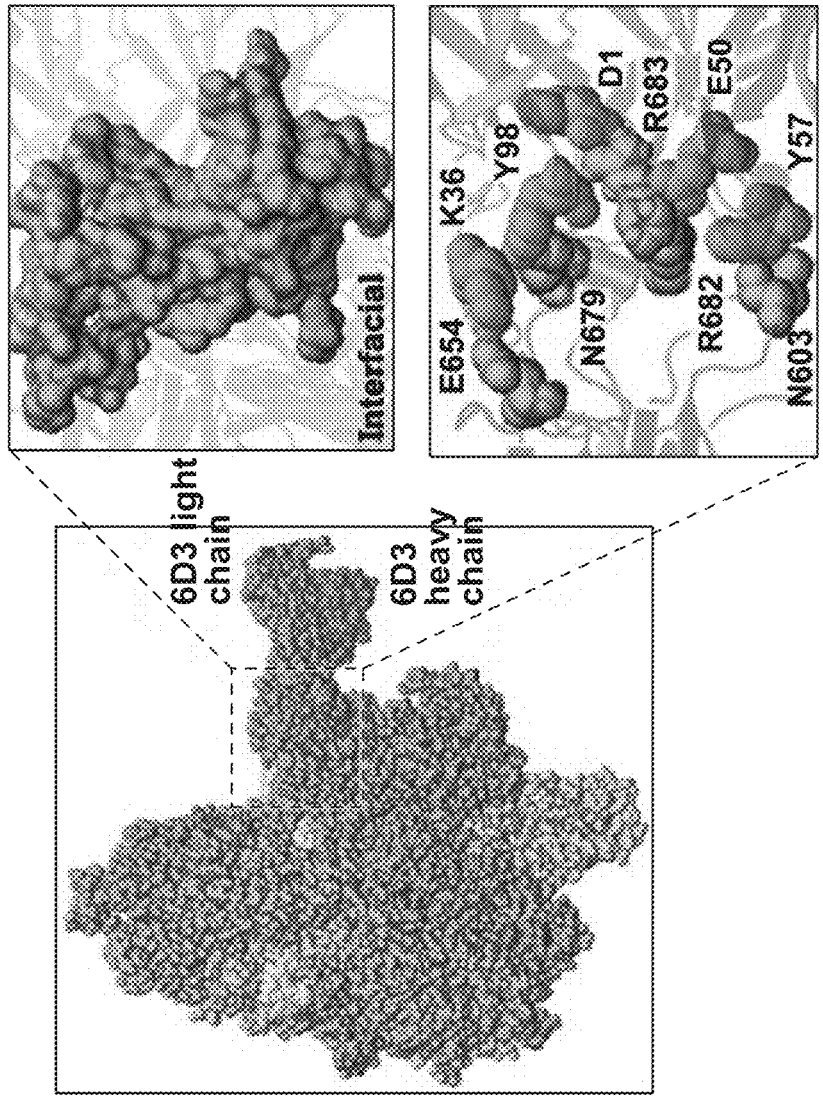

FIG. 11 shows that Fab 6D3 can bind to the TMPRSS2 cleavage site as well as the superantigen motif of SARS-CoV-2.

Figure 12A:
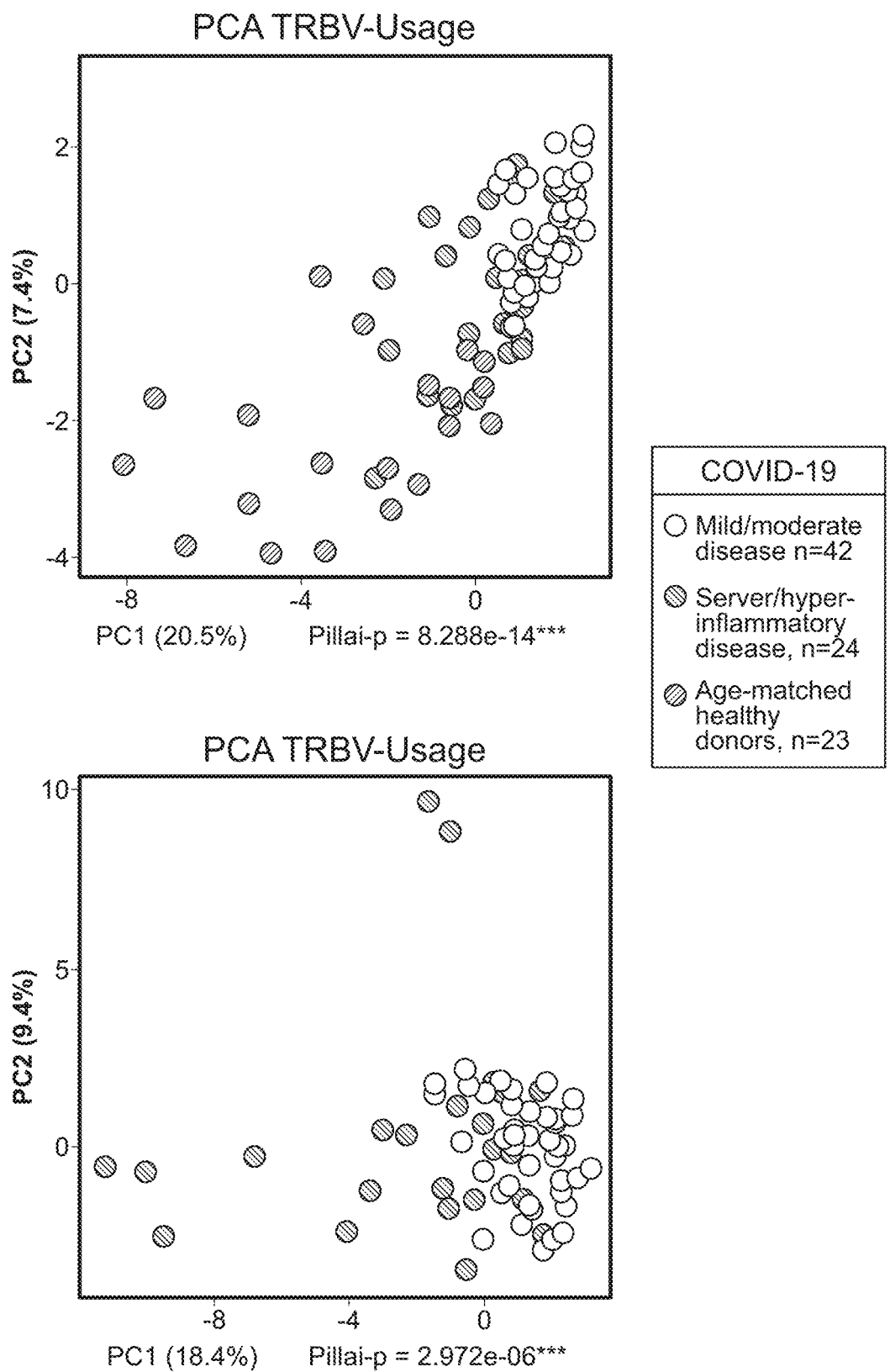
Figure 12B:
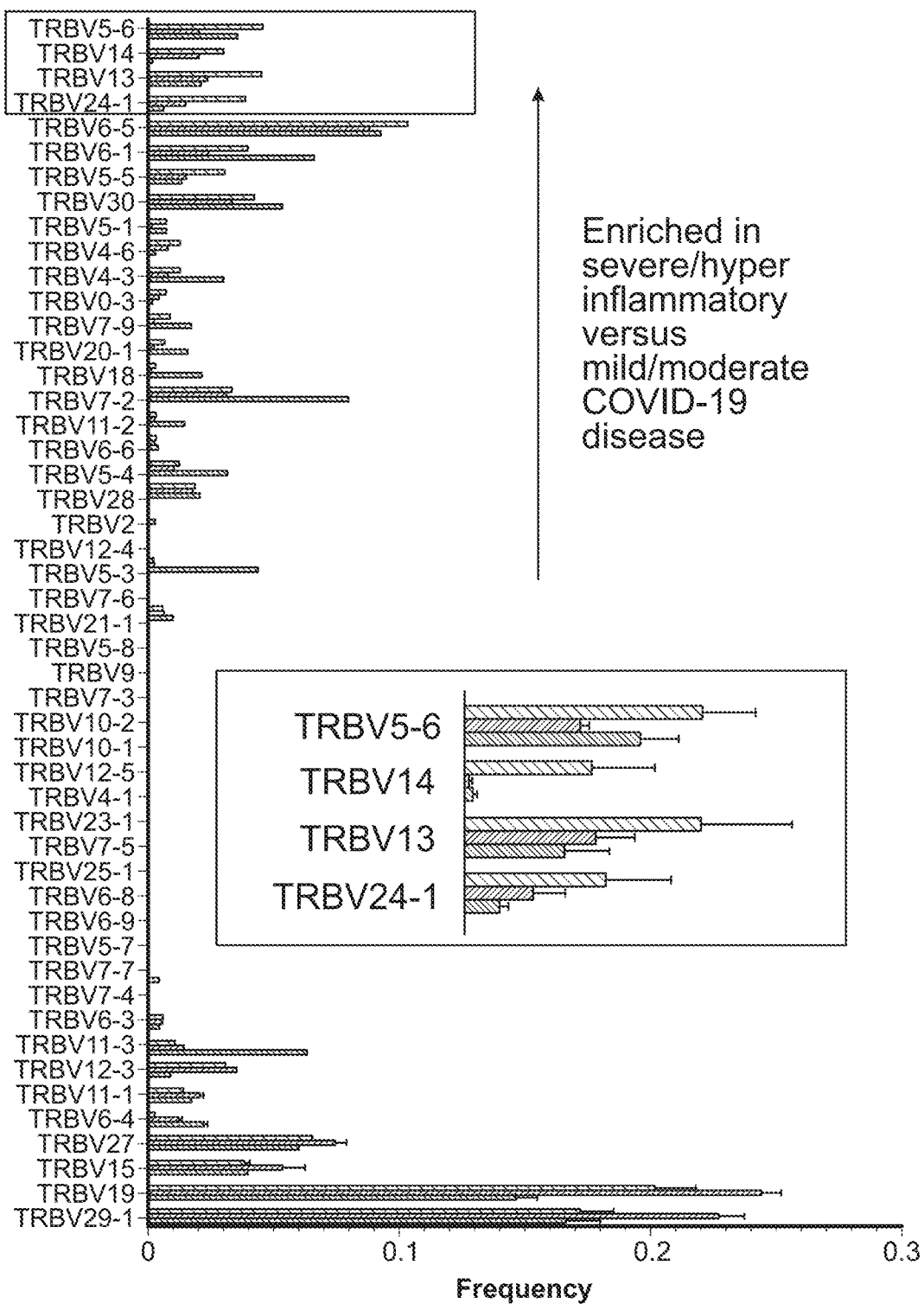
Figure 12C:
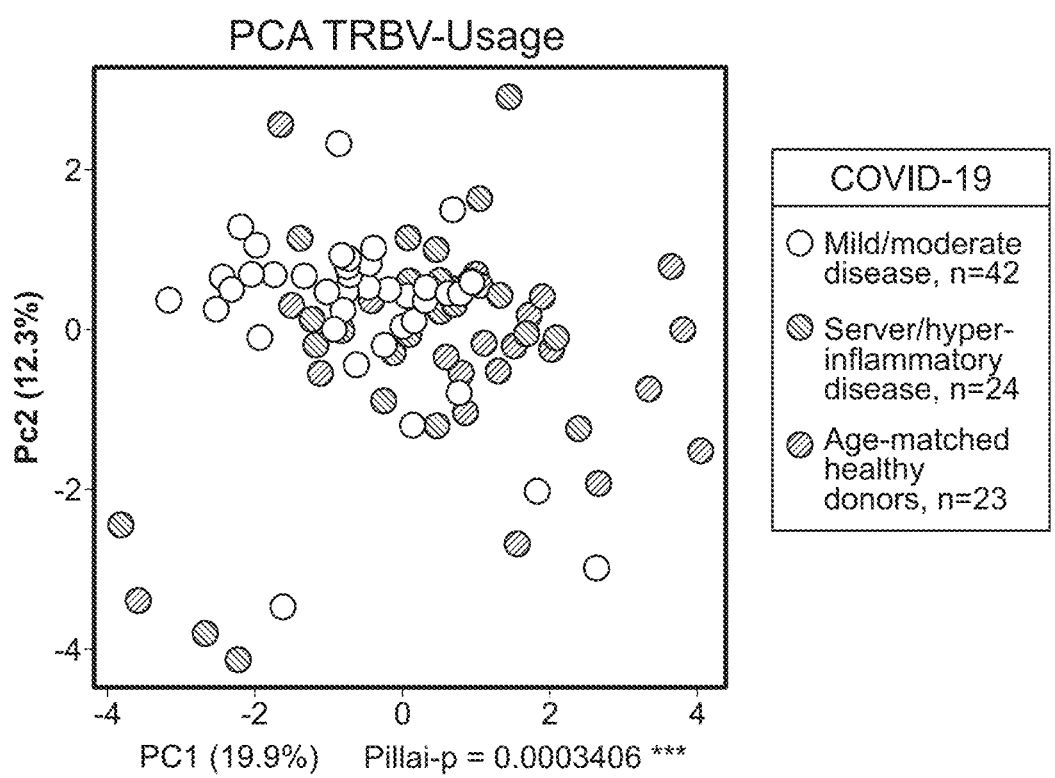

FIGS. 12(A-C) shows skewing of TRBV-usage in severe/hyperinflammatory COVID-19 patients. 24 repertoires of severe/hyperinflammatory COVID-19 cases versus 42 repertoires of mild/moderate COVID-19 cases were analyzed with and without 23 repertoires of age-matched healthy donors (age-matched to severe/hyperinflammatory COVID-19 group). FIG. 12A shows principal component analysis (PCA) of TRBV-Usage. Principal components 1 and 2 are shown, percentage of axis contributions are given in parentheses. Statistical analysis was performed using MANOVA Pillai-Bartlett test. FIG. 12B shows TRBV-Usage. The fraction of individual TRBV genes per repertoire is shown as mean±SEM. TRBV genes are sorted to enriched fractions in severe/hyperinflammatory versus mild/moderate COVID-19 disease in ascending order from bottom to top. The top TRBVs enriched in severe/hyperinflammatory COVID-19 patients (TRBV5-6, TRBV14, TRBV13 and TRBV24-1) are enlarged in the inset. FIG. 12C shows PCA of TRBJ-Usage as described in FIG. 12A. See also FIG. 14.

FIG. 13 shows position of SARS-CoV-2 S cross-reactive epitopes identified (Mateus J, et al. (2020)) in people who have not been exposed to SARS-CoV-2, which overlap with the neurotoxin-like fragment 299-355 identified here to have a strong affinity to bind TCRs. The positions of eight cross-reactive epitopes (15-mers each, with the starting amino acid shown in each case) that were recognized by CD4+ T cells are indicated. In each case the corresponding reactivity strength (SFC/$10^6$ cells) and the number of donors (out of a total of 16) who showed this type of 'memory' response (presumably due to earlier human coronavirus infections) are written. Two of the epitopes were found in the docking simulations to bind TCRs (see FIG. 10). Note that this is one of three neurotoxin-like regions on SARS-CoV-2 spike (see 3, 5, and 7 in FIGS. 6 and 3, 5, and 7 in FIG. 10A). The other two regions also contained epitopes that were cross-reactive, but this one was distinguished by its high frequency (fraction of donors) and high strength (SFC). The sequence in FIG. 13 is (SEQ ID NO: 78)
TKCTLKSFTVEKGIYQTSNFRVQPTESIVRFPNITNLCPFGEVFNATR

FASVY

Figure 14:
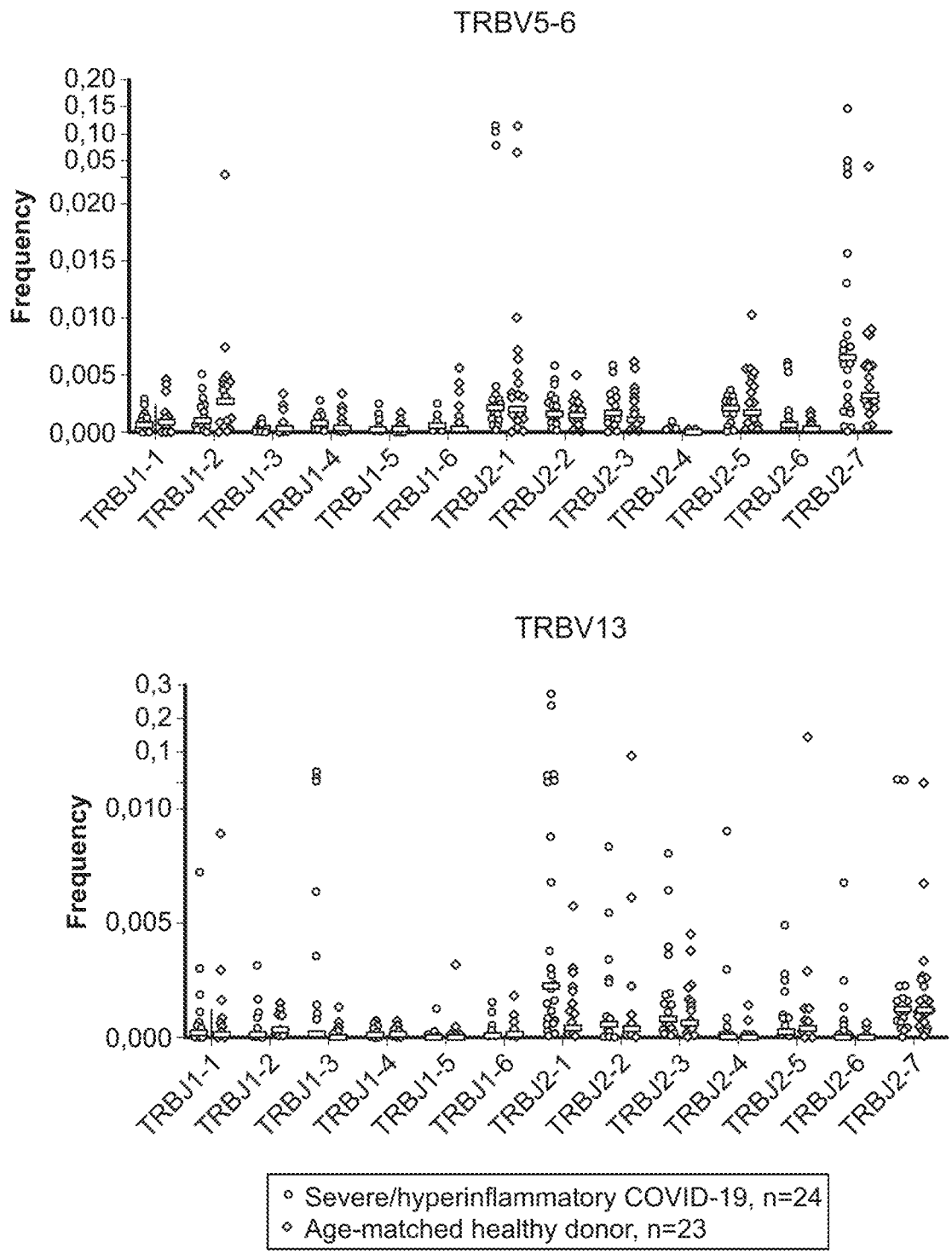

FIG. 14 shows TRBJ-Usage of TRBV genes enriched in hyperinflammatory COVID-19. 24 Repertoires of severe/hyperinflammatory COVID-19 cases versus 23 repertoires of age-matched healthy donors were analyzed. The fraction of individual TRBVJ gene combinations of TRBV5-6, TRBV13, TRBV14 and TRBV24-1 and all 13 different TRBJ genes per repertoire is shown, lines indicating median with interquartile range.

Figures 15A, 15B, 15C:
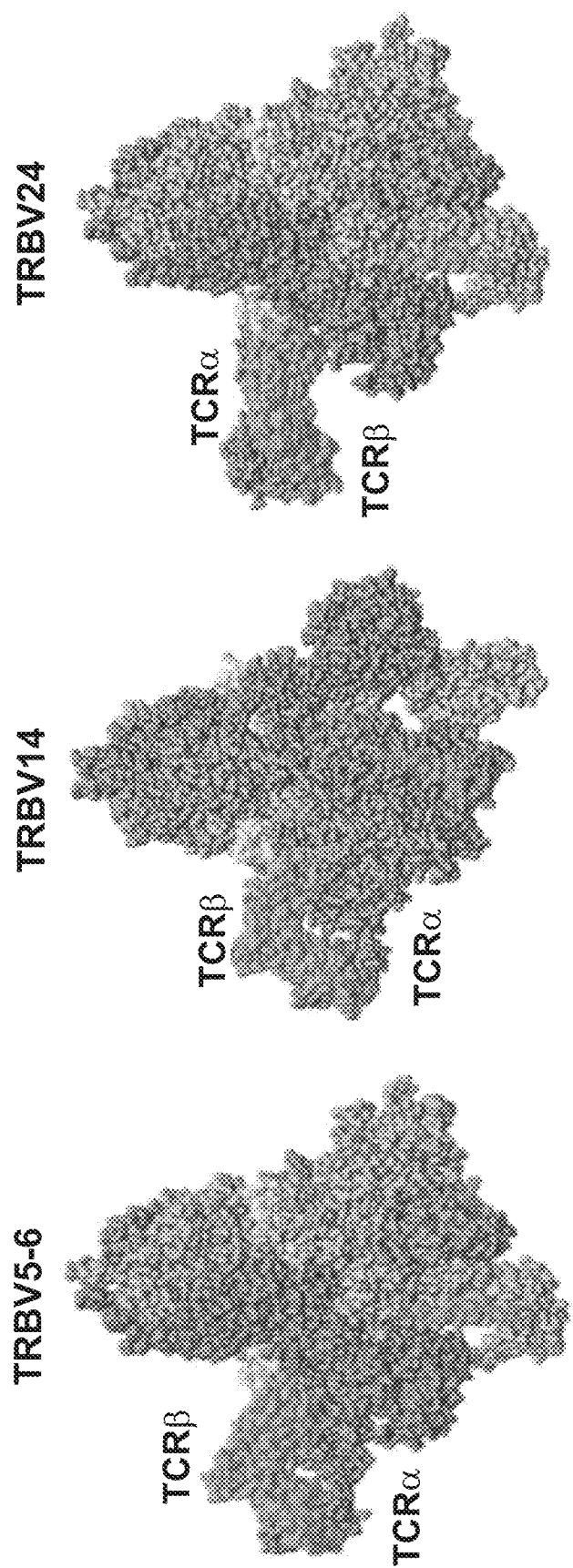

FIGS. 15(A-F) shows binding of TCRs (with Vβ chains identical to those overrepresented in the TCR repertoire of patients with severe COVID-19) to the putative SAg site and complexation with MHC II. FIGS. 15(A-C) shows that complexes predicted between SARS-CoV-2 spike SAg-like region and αβTCRs corresponding to the genes (FIG. 15A) TCRBVS-6; (FIG. 15B) TCRBV14; and (FIG. 15C) TCRBV24-1. The spike subunits, the Sag-like region (E661 to R685), and the neurotoxin motif (299-351) region, and the TCR α- and β-chains are shown. FIG. 15D shows sequence alignment of the Vβ domain of the TCRs shown in FIG. 1 (TCRB) and in FIGS. 15(A-C), generated by Clustal Omega (Sievers F, et al. (2011)). The βTCR paratopes that bind to the Sag-like site on spike are indicated. Note that there is an additional segment, which also includes residues making interfacial contacts with the Sag region of the spike, despite its sequence heterogeneity. FIG. 15(E-F) shows ternary complexes with WWII predicted for the overrepresented TCRs, illustrated for two cases. The sequences in FIG. 15 include (SEQ ID NO: 79)
MVDGGITQSPKYLFRKEGQNVTLSCEQNLNHDAMYWYRQDPGQGLRLI

YYSQIVNDFQKGDIAEGYSVSREKKESFPLTVTSAQKNPTAFYLCASS

SRSSYEQYFGPGTRLTVTEDL, (SEQ ID NO: 80)
MAGVTQSPTHLIKTRGQQVTLRCSPKSGHDTVSWYQQALGQGPQFIFQ

YYEEEERQRGNFPDRFSGHQFPNYSSELNVNALLLGDSALYLCASSLG

EGRVDGYTFGSGRLTVVEDL, (SEQ ID NO: 81)
EAGVTQFPSHSVIEKGQTVTLRCDPISGHDNLYWYRRVMGKEIKFLLH

FVKESKQDESGMPNNRFLAERTGGTYSTLKVQPAELEDSGVYFCASSQ

DRDTQYFGPGTRLTVLEDL,
and (SEQ ID NO: 82)
ADVTQTPRNRITKTGKRIMLECSQTKGHDRMYWYRQDPGLGLRLIYYS

FDVKDINKGEISDGYSVSRQAQAKFSLSLESAIPNQTALYFCATSDES

YGYTFGSGTRLTVVEDL.

Figure 16A:
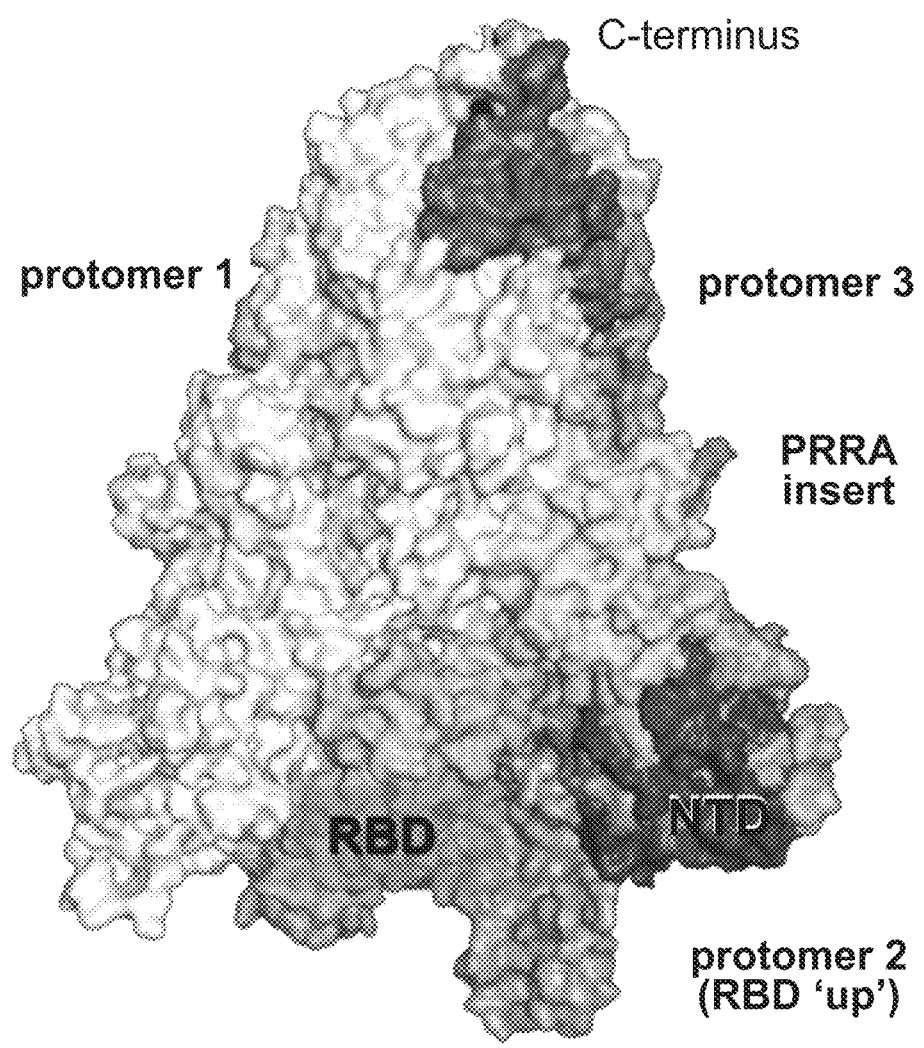
Figure 16C:
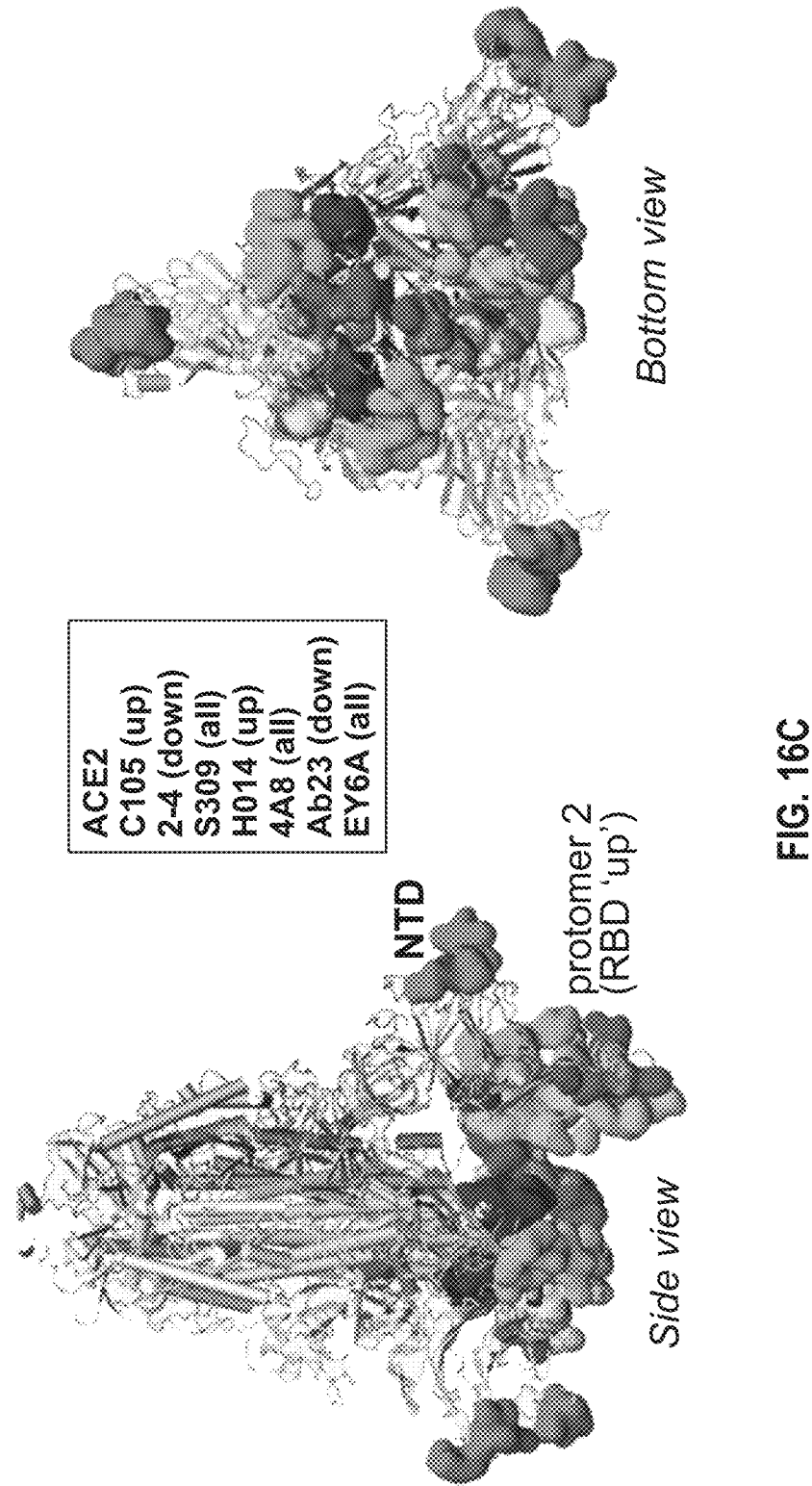

FIGS. 16(A-C) shows SARS-CoV-2 Spike (S) glycoprotein structure, sequence alignment against other CoVs, and interaction sites observed in cryo-EM studies with neutralizing antibodies. FIG. 16A shows SARS-CoV-2 S trimer in the pre-fusion state. Protomers 1 and 2, protomer 3 from N-terminal domain, NTD; residue 1-305 to C-terminus, except for the $_{681}$PRRA$_{684}$ (SEQ ID NO:2) insert. The insert is modeled using SWISS-MODEL (Waterhouse et al., 2018). Each protomer's RBD (residues 331-524) can assume up or down conformations in the respective receptor-bound and -unbound states. FIG. 16B shows sequence alignment of SARS-CoV-2 near the S1/S2 cleavage site against multiple bat and pangolin SARS-related strains, and other HCoVs, adjusted following previous studies (Coutard et al., 2020; Zhou et al., 2020b). Viruses belonging to the same lineage are shown by the same color shade; and HCoVs that encode furin-like cleavage sites are highlighted in bold fonts. Note that the polybasic insert PRRA (SEQ ID NO:2) of SARS-CoV-2 S is not found in closely related SARS-like CoVs but exists in MERS and HCoVs HKU1 and OC43. FIG. 16C shows side (left) and bottom (right) views of receptor (ACE2)- and antibody-binding sites observed in cryo-EM structures resolved for the S protein complexed with the ACE2 and/or various Abs. The S trimer is shown in cartoons with protomer in RBD-up conformation, and protomers in RBD-down conformation. Binding sites for ACE2 and antibodies C105 (Barnes et al., 2020), 2-4 (Liu et al., 2020), 5309 (Pinto et al., 2020), H014 (Lv et al., 2020b), 4A8 (Chi et al., 2020), Ab23 (Cao et al., 2020b), and EY6A (Zhou et al., 2020a) are shown in space-filling surfaces in different colors (see the code in the inset). See Table 4 for additional information. The sequences in FIG. 16 include CASYQTQT (SEQ ID NO:83), NSPR-RARSVASQSI (SEQ ID NO:84), CASYHTVS (SEQ ID NO:85), RSVSSQAI (SEQ ID NO:86), VGTNSI (SEQ ID NO:87), CASYHTAS (SEQ ID NO:88), RNTGQKSI (SEQ ID NO:89), RSTSQKAI (SEQ ID NO:90), RSTGQKAI (SEQ ID NO:91), CIDYALPS (SEQ ID NO:92), SRRKRR-GISSPYR (SEQ ID NO:93), CVDYSK (SEQ ID NO:94), NRRSRGAITTGY (SEQ ID NO:95), NRRSRGAITTGY (SEQ ID NO:96), CALPDTPSTLTPRSVRSVPGEMR (SEQ ID NO:97), CADGSIIAVQP (SEQ ID NO:98), RNVSYDSV (SEQ ID NO:99), CADGSLIPVRP (SEQ ID NO:100), RNSSDNGI (SEQ ID NO:101), and RSVASQSI (SEQ ID NO:45).

Figure 20A:
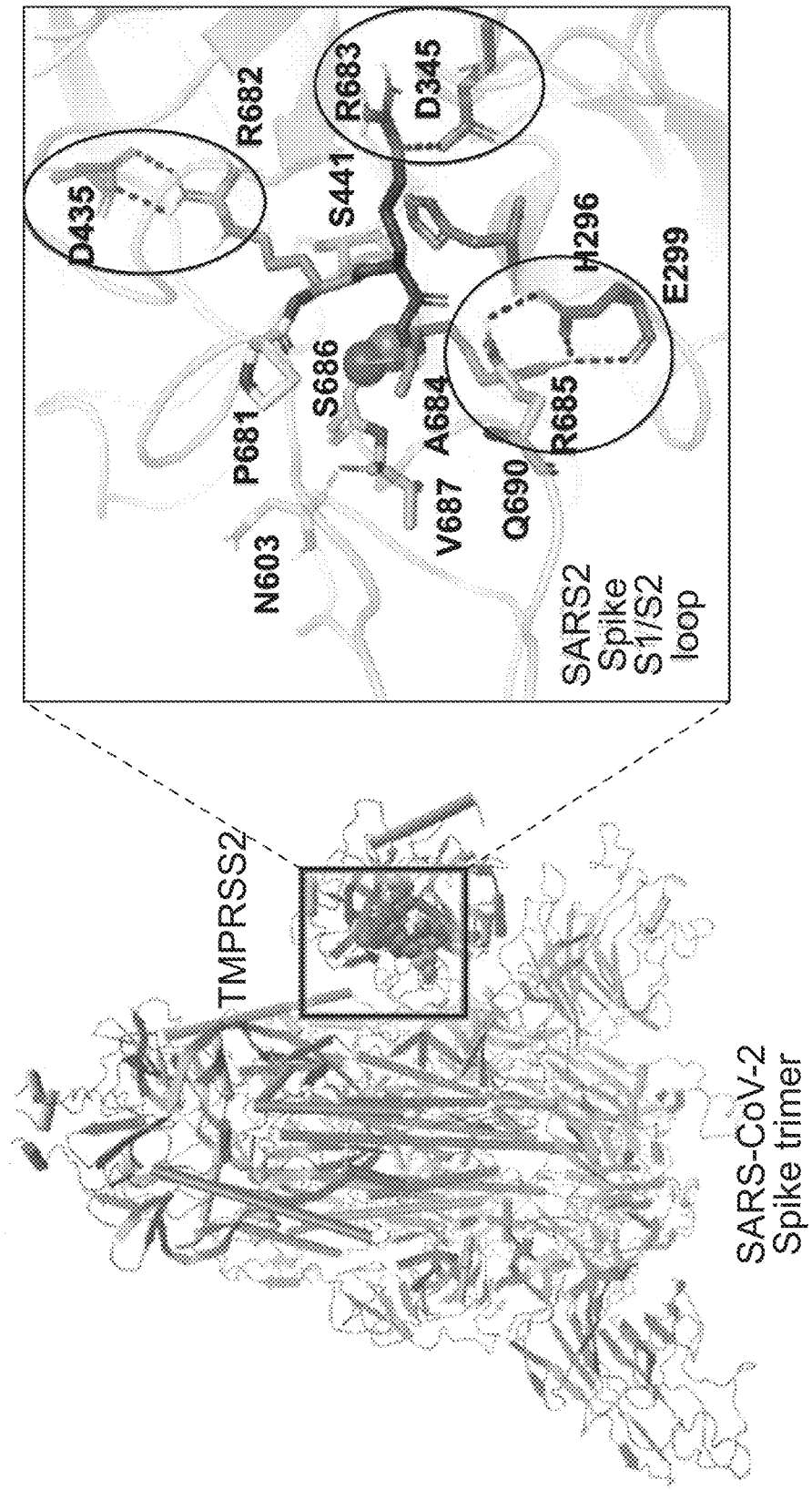
Figure 20B:
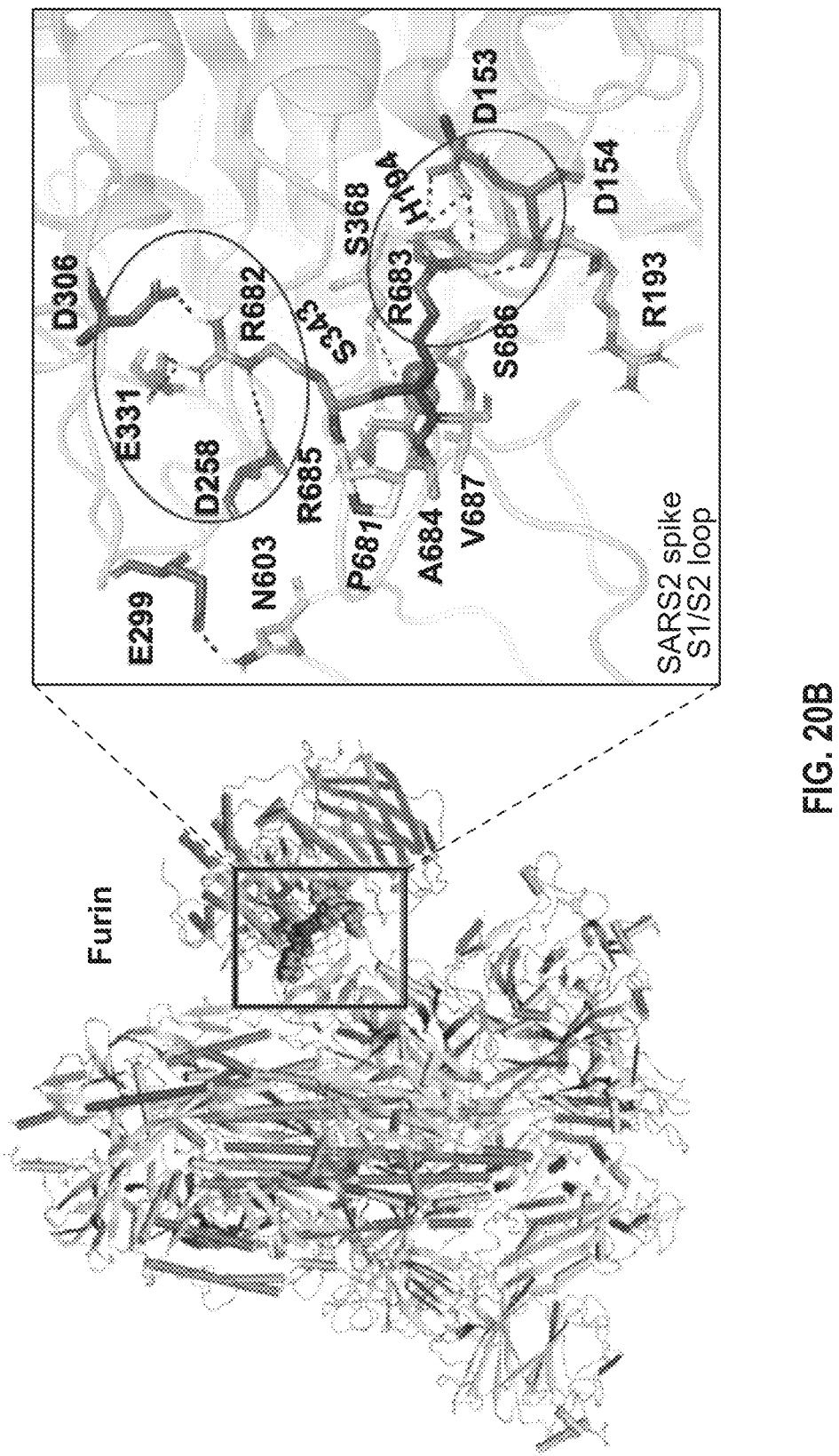

FIGS. 17(A-E) shows that SEB-associated mAb 6D3 binds the furin-cleavage site of SARS-CoV-2 S protein, interfering with the S1/S2 cleavage by furin or TMPRSS2. FIG. 17A shows binding pose of three SEB-neutralizing Abs (mAbs 6D3, 14G8, and 20B1) onto SEB. The diagram is generated by superposing the crystal structures (PDB IDs 4RGN and 4RGM) resolved for the complexes (Dutta et al., 2015). SEB is shown with its Sag motif $_{150}$TNKKKATVQELD$_{161}$ (SEQ ID NO:116) highlighted. FIG. 17B shows close-up view of the tight interaction between the acidic residues E50, D52, and D55 of the 6D3 heavy chain and four basic residues of SEB. In FIGS. 17(C-E), FIG. 17C shows interface between 6D3 and SEB Sag motif. Heavy and light chains of 6D3 are indicated, respectively. Overall (FIG. 17D) and close-up (FIG. 17E) views of the complex model for S protein and anti-SEB mAb 6D3. The interfacial interactions engage the arginines in the PRRA insert. SARS-CoV-2 S interfacial residues include I210-Q218, N603-Q607, E654-Y660 and A688-I693, and the SAg motif residues Y674, T678-R683. 6D3 interfacial residues include A24-K33, E50, D52, S54, D55, Y57, N59, K74-T77, and A100-A104 in the heavy chain, and D1, I2, Q27, N31-F38, Y55, W56, and D97-Y100 in the light chain. The Spike-6D3 complex is generated in silico using the S structure modeled with one RBD up (PDB: 6VSB).

FIGS. 18(A-B) shows that glycosylation of SARS-CoV-2 spike at N603 does not block mAb 6D3 binding and may even assist in binding the mAb. FIG. 18A shows computationally-modeled SARS-CoV-2 glycosylated spike. The three monomers of the spike protein are shown in surface representations, with their SAg region (residues 661 to 685) indicated. High-mannose N-glycans are shown in colored (small) spheres. FIG. 18B shows structural alignment of computationally modeled 6D3-spike protein complex onto the glycosylated spike. No spatial clash was observed. The inset shows a closeup view.

FIGS. 19(A-D) shows that monoclonal antibody 6D3 prevents SARS-CoV-2 infection. 6D3 or isotype control antibodies (at indicated concentrations) were incubated with virus (100 PFU/well) for 1 hour at room temperature before addition to Vero-E6 cells ($5\times10^3$ cells/well). 48 hours post infection cells were fixed and stained for dsRNA or SARS-CoV-2 spike protein. FIG. 19A shows quantification of the percentage of infected cells per well by dsRNA staining. FIG. 19B shows representative fluorescence images of 6D3-mediated inhibition of virus infection (dsRNA). FIG. 19C shows quantification of the percentage of infected cells per well by spike staining. FIG. 19D shows representative fluorescence images of 6D3-mediated inhibition of virus infection (spike). Data were analyzed by t test (6D3 vs. isotype control) with multiple testing correction (FDR). Data is presented as mean+/−standard error of the mean. n=3 technical replicates. Data are representative of three independent experiments. *$p<0.05$, <0.01, *$p<0.001$. See also FIG. 21 for detailed results as a function of 6D3 concentration.

FIGS. 20(A-B) shows binding poses of human proteases TMPRSS2 and furin to SARS-CoV-2 S protein. FIGS. 20(A-B) shows structural models for the SARS-CoV-2 S protein complexed with TMPRSS2 (FIG. 20A), and furin (FIG. 20B), obtained from docking simulations followed by refinements. An overview (left) and a zoomed in view (right) are shown in each case. The arginines in the S1/S2 loop P$_{681}$RRARS$_{686}$ (SEQ ID NO:6) are shown, and their interaction partner (acidic residues) in the proteases are shown. Spheres (right panels) highlight the R68515686 peptide bond. TMPRSS2 catalytic triad residues are 5441, H296 and D345. Their counterparts in furin are 5368, H194 and D153. Note the short distance between the carbonyl carbon of R685 and the hydroxyl oxygen of 5441 of TMPRSS2 (3.5 Å) or S368 of furin (3.1 Å). Black dashed lines show interfacial polar contacts and salt bridges, and those including the S1/S2 loop arginines are highlighted by ellipses.

FIGS. 21(A-B) shows that monoclonal antibody 6D3 prevents SARS-CoV-2 infection, related to FIG. 19. 6D3 or isotype control antibodies (at indicated concentrations) were incubated with virus (100 PFU/well) for 1 hour at room temperature before addition to Vero-E6 cells ($5\times10^3$ cells/well). 48 hours post infection cells were fixed and stained for dsRNA or SARS-CoV-2 spike protein. FIG. 21A shows representative fluorescence images of 6D3 mediated inhibition of virus infection as measured by dsRNA staining. FIG. 21B shows representative fluorescence images of 6D3 mediated inhibition of virus infection as measured by SARS-CoV-2 spike staining.

FIGS. 22(A-B) shows binding of TMPRSS2 to the SARS-CoV-2 Spike (S) protein yields an ensemble of conformers including one where the protease binds to the PRRA (SEQ ID NO:2) insert, Related to FIG. 20A. FIG. 22A shows overlay of models generated by the protein docking software ClusPro (Kozakov et al., 2017). FIG. 22B shows Model 1 where TMPRSS2 catalytic residues are positioned in close proximity of the S1/S2 cleavage site. Three basic residues, R682, R683, and R685 from the S protein, are shown as van der Waals (vdW) balls; the acidic residues of TMPRSS2 which form salt bridges with these three basic residues are displayed in vdW balls with catalytic residue D345 and catalytic serine residue S441. Model 1, found to be most favorable energetically, is shown in FIG. 20A.

FIG. 23 shows structural models generated for SARS-CoV-2 S protein complexed with furin, related to FIG. 20B. Six models, labeled Model 1 to Model 6, representative of clusters formed by top-ranking conformers are displayed. In all models, the catalytic residues (D153, H194 and 5368) of furin are in close proximity to the cleavage site 685RS686 of spike. Note that furin has multiple acidic residues that form intermolecular salt bridges in multiple poses: D153, D154, E236, D258, D264, D306, and E331, and the close proximity of the S1/S2 site is highly favorable, both energetically and entropically. Model 5, found to be most favorable energetically, is shown in FIG. 20B.

Figure 24:
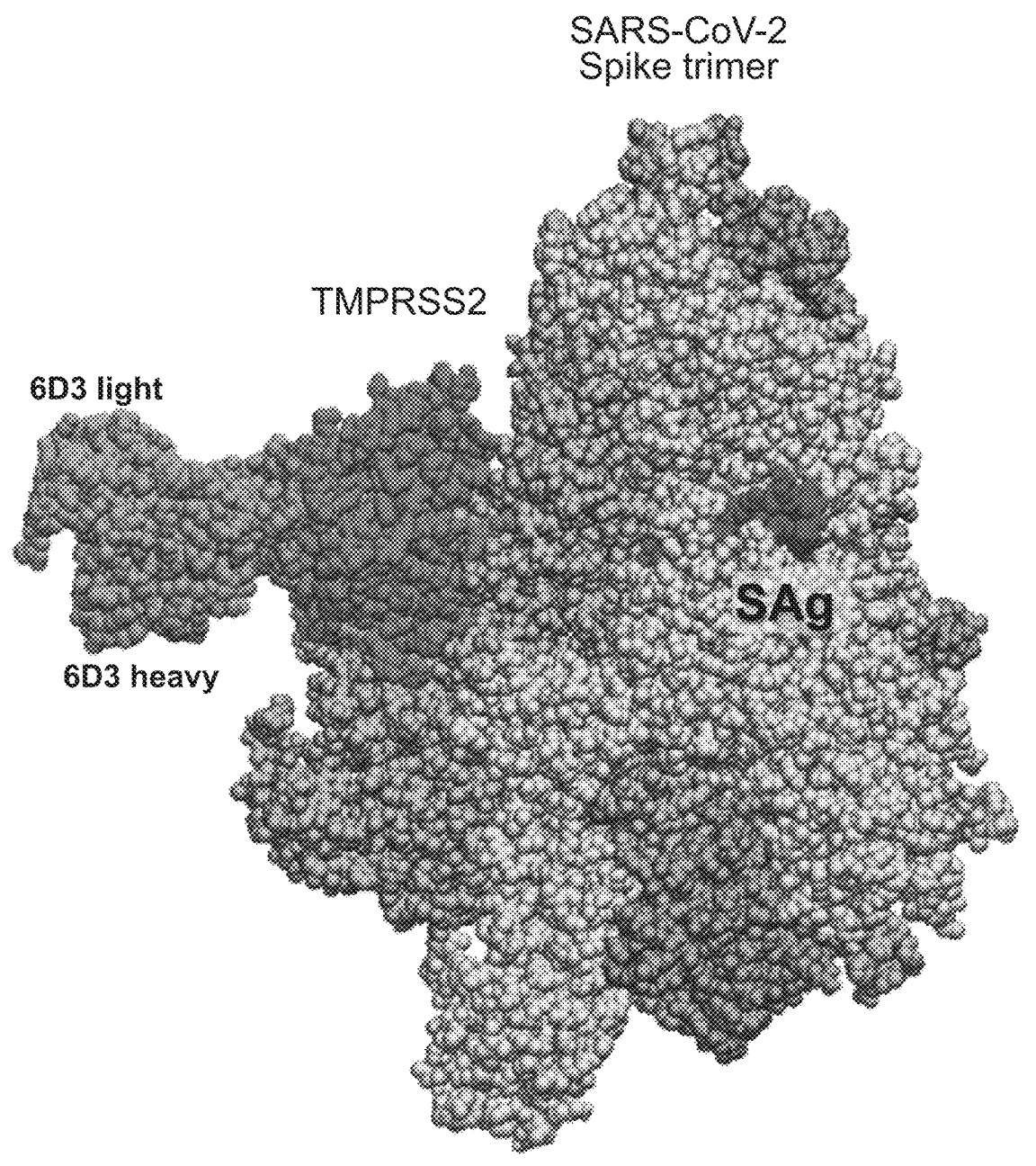

FIG. 24 shows that antibody 6D3 and TMPRSS2 compete for the same binding site on SARS-CoV-2 spike protein, Related to FIG. 17 and FIG. 20. The figure shows the overlay of the structural models generated for spike-TM-PRSS2 and spike-6D3 complexes, which illustrates how TMPRSS2 spatially overlaps with the variable domains (not seen, eclipsed by TMPRSS2) of 6D3. The diagram is generated by superposing the S protein of the complexes predicted in silico. Similar results were found for the spike-furin complex (not shown). The three S subunits are shown, with the SAg region.

Figure 25C:
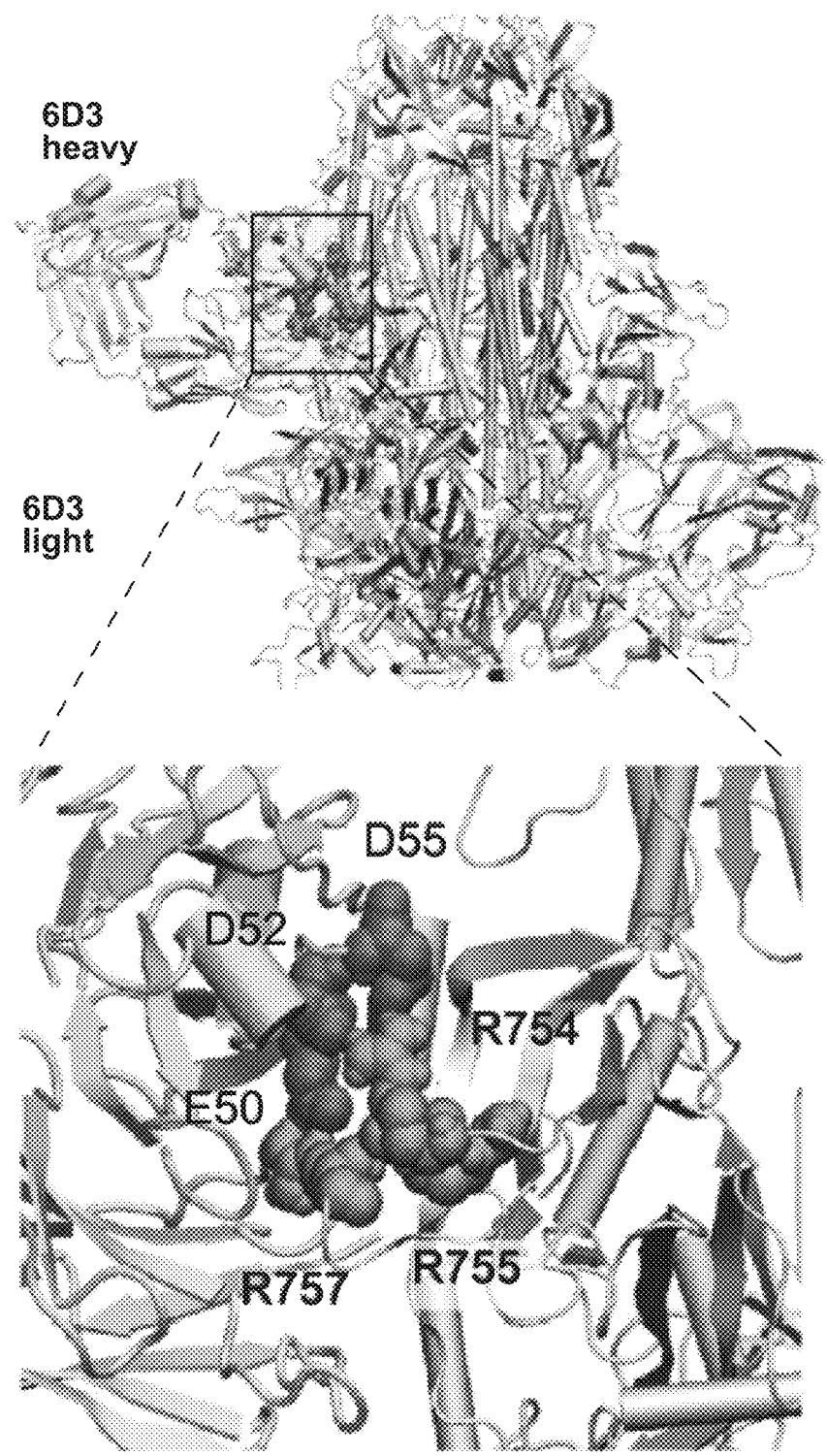

FIGS. 25(A-C) shows that polyacidic residues in the CDR2 of the mAbs 6D3 heavy chain play a major role in blocking the furin-like cleavage site of SARS-CoV-2 S protein. FIG. 25A shows multiple sequence alignment of the VH domain of anti-SEB Abs (6D3, 14G8 and 20B1) and anti-SARS-CoV-2 S Abs (see the names on the left column). The residue ranges of the three CDRs are: CDR1 (residues 25 to 32), CDR2 (51 to 58), and CDR3 (100 to 116) (Chi et al., 2020). FIG. 25B shows overall and close-up views of the complex and interfacial interaction of the Spike protein complexed with 6D3 antibody. Note that three acidic residues from CDR2 interact with the basic residues R682, R683 and R685 of the S protein. The complex in FIG. 25B is generated in silico using SARS-CoV-2 S structure with all three RBDs in the down conformer (PDB id: 6VXX). FIG. 25C is same as FIG. 25B, repeated for human cold virus HCoV-OC43 S protein. The complex in FIG. 25C is generated in silico using HCoV-OC43 S structure with all three RBDs in the down conformer (PDB id: 6NZK). HCoV-OC43 encodes a S1/S2 furin-like cleavage site at $_{754}$RRAR↑G$_{758}$ (SEQ ID NO:120). Note that three acidic residues from CDR2 interact with R754, R755 and R757 in hCoV-OC43 S protein. The residues belonging to the Abs are labelled in lightface, those of the S protein in boldface in both FIGS. 25B and 25C. The sequences in FIG. 25 include (SEQ ID NO: 102)
QVQLQQSGAELVKPGASVKLSCKASGYTFTSHWMHWVKQRPGQGLEWI

GEIDPSDSYINYNQIFEGKATLTVDKSSTTAYLQLSSLTSEDSAVYYC

ARTAGLLAPMDYWGQ, (SEQ ID NO: 103)
EVQLVESGAEVKKPGASVKVSCKVSGYTLTELSMHWVRQAPGKGLEWM

GGFDPEDGETMYAQKFQGRVTMEDTSTDTAYMELSSLRSEDTAVYYCA

TSTAVAGTPDLFDYYYGMDVWGQ, (SEQ ID NO: 104)
QVQLVQSGAEVKKPGASVKVSCKASGYPFTSYGISWVRQAPGQGLEWM

GWISTYNGNTNYAQKFQGRVTMTTDTSTTTGYMELRRLRSDDTAVYYC

ARDYTRGAWXFGESLIGGFDNWGQ, (SEQ ID NO: 105)
QVQLVESGGGLIQPGGSLRLSCAASGFTVSSNYMSWVRQAPGKGLEWV

SVIYSGGSTYYADSVKGRFTISRDNSKNTLYLQMNSLRAEDTAVYYCA

RGEGWELPYDYWGQ, (SEQ ID NO: 106)
QVQLVQSGAEVKKPGASVKVSCKASGYTFTGYYMHWVRQAPGQGLEWM

GWINPNSGGTNYTQMFQGRVTMTRDTSISTAYMEVSRLRSDDTAVYYC

ARDRSWAVVYYYMDVWGK, (SEQ ID NO: 107)
QVQLVQSGSELKKPGASVKVSCKASGYTFTSYAMNWVRQAPGQGLEWM

GWINTNTGNPTYAQGFTGRFVFSLDTSVSTAYLQISSLKAEDTAVYYC

ARPQGGSSWYRDYYYGMDVWGQ, (SEQ ID NO: 108)
EVQLVESGGGVVQPGRSLRLSCAASAFTFSSYDMHWVRQAPGKGLEWV

AVISYDGSNKYYADSVKGRFTISRDNSKNTLYLQMNSLRAEDTAVYYC

AKDGGKLWVYYFDYWGQ, (SEQ ID NO: 109)
EVQLVQSGAEVKKPGATVKISCKVSGYSFSNYYIHWVKQAPGKSLEWI

GYIDPFNGGTSDNLKFKGAATLTADTSTDTAYMELSSLRSEDTAVYYC

ARSEYDPYYVMDYWGQ, (SEQ ID NO: 110)
QIQLVQSGPELKKPGETVRISCKASGYIFTIAGIQWVQKMPGRGLRWI

GWINTHSGVPEYAEEFKGRFAFSLETSARTAYLQISNLKDEDTATYFC

ARIYYGNNGGVMDYWGQ,
and (SEQ ID NO: 111)
EVNLIESGGDLVKPGGSLKLSCATSGFTFSAYGLSWVRQTPERRLEWV

ASISGGGSVYYPDSVKGRFTISRDTAGDILFLQMNSLRSEDSAIYYCV

RDLYGDYVGRYAYWGQ.

Figure 26B:
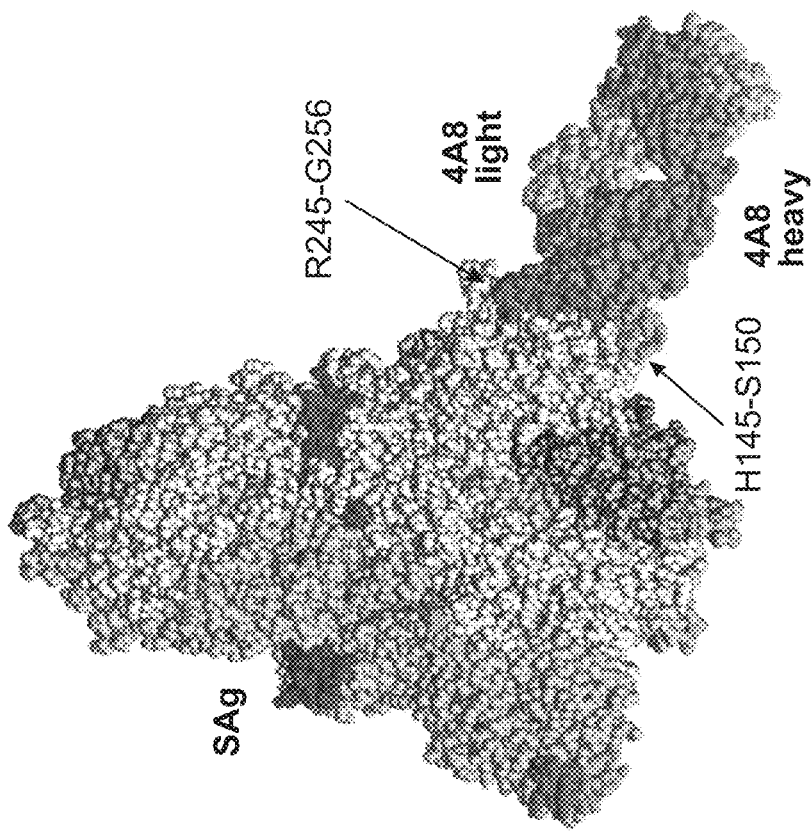
Figure 26A:
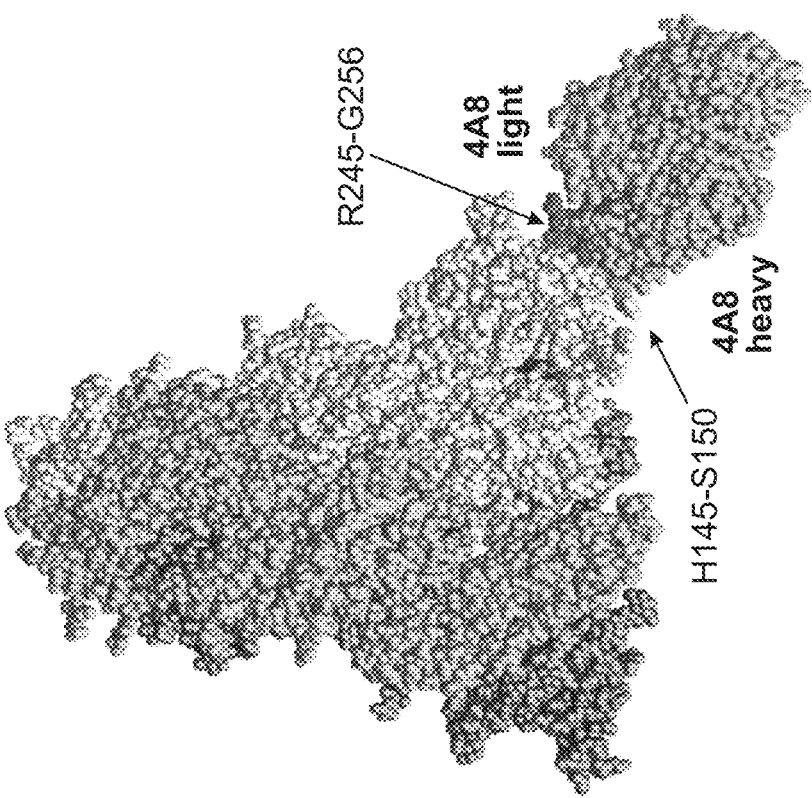
Figures 26C, 26D:
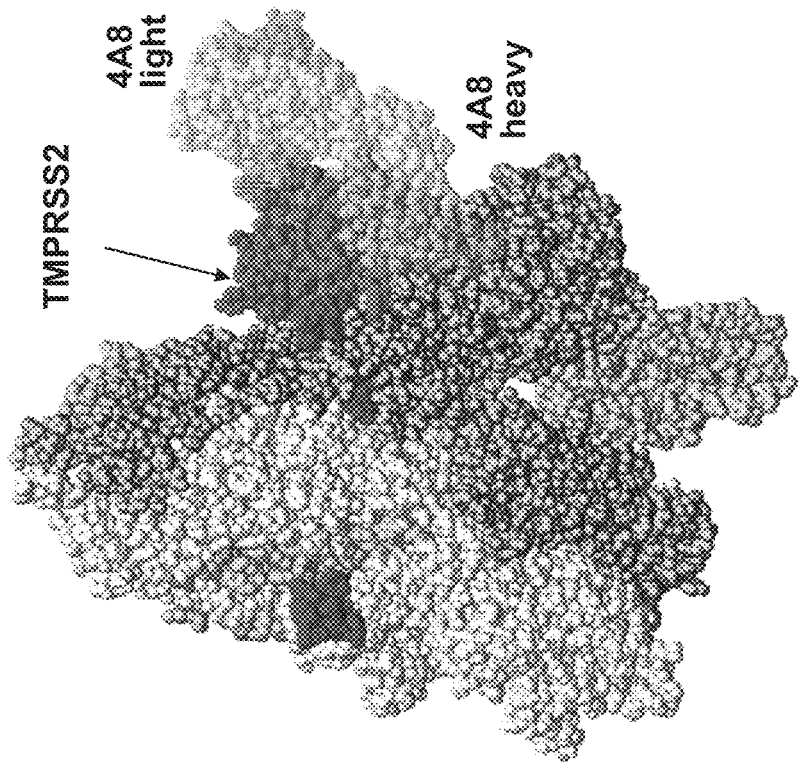

FIGS. 26(A-D) shows examination of binding characteristics of SARS-CoV-2-neutralizing mAbs 4A8, related to FIG. 20 and FIG. 25. FIG. 26A shows Cryo-EM structure (PDB: 7C2L) (Chi et al., 2020); FIGS. 26(B-C) shows energetically most favorable conformers predicted for the S protein-4A8 complex. The former resembles the cryo-EM structure, involving the same segment, R245-G256, at the binding epitope of S. In the latter case, the viral SAg-like region which also overlaps with the S1/S2 cleavage site, serves as the 4A8-binding epitope. FIG. 26D shows competition between 4A8 and TMRPSS2 for binding to the S1/S2 cleavage site, based on the overlap between the binding poses of these two substrates. The diagram is generated by superposing the S protein of the two complexes predicted in silico.

Figure 27:
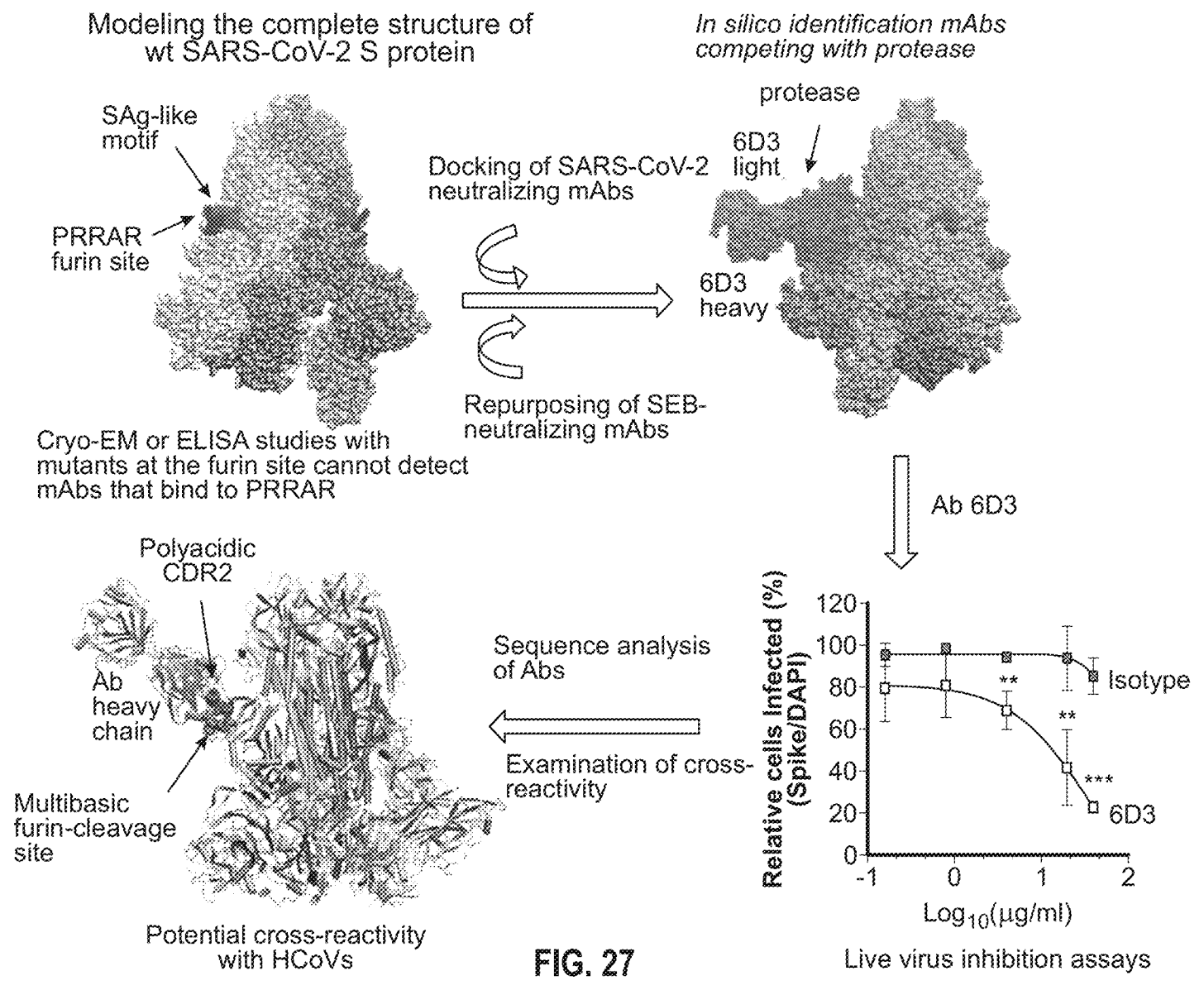

FIG. 27 shows that anti-SEB mAb, 6D3, to cross-react with the SARS-CoV-2 spike. Live virus assays demonstrated that 6D3 effectively blocks SARS-CoV-2 viral entry. 6D3 binds the S1/S2 site, interfering with the proteolytic activity of TMPRSS2/furin. An acidic residue cluster at 6D3 VH enables strong binding to the polybasic S1/S2 site.

SUMMARY

Provided herein are methods of treating a COVID-19 infection in a subject, comprising administering to the subject an effective amount of a composition that reduces the superantigen character of SARS-CoV-2 Spike protein. In some embodiments, the compositions are mimetic peptides of the superantigen region. In some embodiments, the compositions are humanized antibodies such as humanized mAb 6D3 that bind to the superantigen region.

Accordingly, provided herein are methods of treating a COVID-19 infection in a subject, comprising administering to the subject an effective amount of one or more of a humanized mAb 6D3, a humanized mAb 14G8, and a functional fragment thereof. In some embodiments, the humanized mAb 6D3 comprises one or more of a $V_H$ CDR amino acid sequence selected from the group consisting of SEQ ID NO:14, SEQ ID NO:15 and SEQ ID NO:16. In some embodiments, the humanized mAb 6D3 comprises one or more of a $V_L$ CDR amino acid sequence selected from the group consisting of SEQ ID NO:18, SEQ ID NO:19 and SEQ ID NO:20. In some embodiments, the humanized mAb 6D3 comprises (a) a $V_H$ domain having an amino acid sequence comprising SEQ ID NO:13, and (b) a $V_L$ domain having an amino acid sequence comprising SEQ ID NO:17. In some embodiments, the humanized mAb 14G8 comprises one or more of a $V_H$ CDR amino acid sequence selected from the group consisting of SEQ ID NO:36, SEQ ID NO:37 and SEQ ID NO:38. In some embodiments, the humanized mAb 14G8 comprises one or more of a $V_L$ CDR amino acid sequence selected from the group consisting of SEQ ID NO:40, SEQ ID NO:41 and SEQ ID NO:42. In some embodiments, the humanized mAb 14G8 comprises (a) a $V_H$ domain having an amino acid sequence comprising SEQ ID NO:35, and (b) a $V_L$ domain having an amino acid sequence comprising SEQ ID NO:39.

Also included herein are methods of treating a COVID-19 infection in a subject, comprising administering to the subject an effective amount of one or more SARS-CoV-2 superantigenic (SAg) peptides, wherein the one or more peptides comprise SEQ ID NO:2 or SEQ ID NO:3. In some embodiments, the one or more peptides comprise SEQ ID NO:4. In some embodiments, the one or more peptides comprise SEQ ID NO:5. In some embodiments, the one or more peptides comprise SEQ ID NO:6. In some embodiments, the one or more peptides comprise SEQ ID NO:7. In some embodiments, the one or more peptides comprise SEQ ID NO:8. In some embodiments, the one or more peptides comprise SEQ ID NO:9. In some embodiments, the one or more peptides comprise SEQ ID NO:10. In some embodiments, the one or more peptides comprise SEQ ID NO:11. In some embodiments, the one or more peptides comprise SEQ ID NO:12.

In some embodiments of the above-described methods, the subject is a human. The human can be of any age, but in some embodiments, the human is a child and the treatment results in an amelioration of a multisystem inflammatory syndrome. In some embodiments, the treatment results in an amelioration of a pneumonia.

DETAILED DESCRIPTION

Disclosed herein is the surprising discovery that SARS-CoV-2 encodes a superantigen (SAg) motif near the S1/S2 cleavage site of its Spike protein. This region is highly similar in structure to the SEB SAg motif that interacts with both the TCR and CD28 (G. Arad et al. (2011)) and mediates toxic shock syndrome (TSS). Superantigens are highly potent T cell activators that can bind to MHC class II (MHCII) molecules and/or to TCRs of both CD4+ and CD8+ T cells. The ability of SAgs to bypass the antigen specificity of the TCRs results in broad activation of T cells and a cytokine storm, leading to toxic shock (H. Li, et al. (1999), T. Krakauer (2019)). Notably SAgs do not bind the major (antigenic) peptide binding groove of MHCII, but instead bind other regions as well as the αβTCRs, directly. While early studies showed that bacterial SAgs activate T cells by binding the β-chain of dimeric TCRs at their variable domain (V) (M. T. Scherer, et al. (1993), Y. W. Choi et al. (1989), J. D. Fraser, T. Proft (2008)), more recent studies revealed that they can bind to either α- or β-chains, or both (M. Saline et al. (2010)). As a SAg, SEB enables large-scale T cell activation and proliferation (T. Krakauer (2019)), resulting in massive production of pro-inflammatory cytokines including IFNγ, TNFα and IL-2 from T cells as well as IL-1 and TNFα from antigen presenting cells (APCs) (T. Krakauer (2019)). This cytokine storm leads to multi-organ tissue damage similar to what is now observed in MIS-C.

Accordingly, included in the present invention are methods of treating a COVID-19 infection in a subject, comprising administering to the subject an effective amount of a composition that that prevents the SARS-CoV-2 Spike protein from acting as a SAg. Included herein are compositions and methods for reducing an amount of SARS-CoV-2 Spike protein binding to a T cell receptor, an MHC molecule and/or CD28. In some embodiments, the compositions and methods include or employ a 6D3 antibody, mAb 6D3. In some embodiments, the compositions and methods include or employ a SARS-CoV-2 SAg peptide.

Terms used throughout this application are to be construed with ordinary and typical meaning to those of ordinary skill in the art. However, Applicants desire that the following terms be given the particular definition as provided below.

Terminology

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "administering" refers to an administration that is oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

The term "antibody" is used in the broadest sense, and specifically covers monoclonal antibodies (including full length monoclonal antibodies), polyclonal antibodies, and multispecific antibodies (e.g., bispecific antibodies). Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain ($V_H$) followed by a number of constant domains. Each light chain has a variable domain at one end ($V_L$) and a constant domain at its other end. In some embodiments, the antibody is a human antibody. In some embodiments, the antibody is a humanized antibody.

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example a "functional fragment" refers to a fragment of mAb 6D3 that reduces binding of a SARS-CoV-2 Spike protein SAg region to a T cell receptor (TCR), an MHC molecule and/or CD28. As used herein, "functional fragment" with respect to antibodies, refers to Fv, F(ab) and $F(ab')_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define an target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for target binding. The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art.

As used herein, the word "child" refers to a human between the ages of 1 day and 16 years. In some embodiments, the child is between the ages of 1 and 16 years, 3 and 13 years, 5 and 11 years, or 6 and 10 years. In some embodiments, the child is 1, 2, 3, 4, 5, 6, 7, 8, 9, 10, 11, 12, 13, 14, 15 or 16 years old.

A "composition" is intended to include a combination of active agent and another compound or composition, inert (for example, a detectable agent or label) or active, such as an adjuvant.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purpose. A control can be "positive" or "negative."

"COVID-19" refers herein to a disease or disorder caused in whole or in part by a severe acute respiratory syndrome coronavirus 2 (SARS-CoV-2).

As used herein, a "COVID-19 infection symptom" includes, but is not limited to, pneumonia, interstitial pneumonia, interstitial pneumonia with hyperinflammation, multisystem inflammatory syndrome in children (MIS-C), hypotension, sepsis, septic shock, multiple organ disfunction syndrome (MODS), and respiratory failure, dyspnea, respiratory frequency≥30/min, blood oxygen saturation (SpO2) ≤93%, PaO2/FiO2 ratio or P/F [the ratio between the blood pressure of the oxygen (partial pressure of oxygen, PaO2) and the percentage of oxygen supplied (fraction of inspired oxygen, FiO2)]<300, and/or lung infiltrates >50% within 24 to 48 hours. In some embodiments, the COVID-19 infection symptom is MIS-C.

"Effective amount" encompasses, without limitation, an amount that can ameliorate, reverse, mitigate, and/or lessen a symptom or sign of a medical condition or disorder (e.g., a COVID-19 infection). Unless dictated otherwise, explicitly or by context, an "effective amount" is not limited to a minimal amount sufficient to reverse, mitigate, and/or lessen a condition. The severity of a disease or disorder, as well as the ability of a treatment to reverse, mitigate, and/or lessen the disease or disorder can be measured, without implying any limitation, by a biomarker or by a clinical parameter. In some instances, an amelioration, reversal, mitigation, and/or lessening is achieved following administration of multiple dosages of the composition to the subject over a period of days, weeks, or years. The effective amount will vary depending on the compound, such as a mAb 6D3 or COVID-19 SAg peptide, the disorder or conditions and its severity, the route of administration, time of administration, rate of excretion, drug combination, judgment of the treating physician, dosage form, and the age, weight, general health, sex and/or diet of the subject to be treated. In the context of the present methods, an effective amount or dose of a mAb 6D3 antibody or COVID-19 SAg peptide includes an amount that is sufficient to reverse, mitigate, and/or lessen a COVID-19 infection symptom. In some embodiments, an effective amount or dose of a mAb 6D3 or COVID-19 SAg peptide is an amount sufficient to ameliorate a COVID-19 infection symptom. In some embodiments, an effective amount or dose of a mAb 6D3 or COVID-19 SAg peptide is an amount sufficient to ameliorate a pneumonia. In some embodiments, an effective amount or dose of a mAb 6D3 or COVID-19 SAg peptide is an amount sufficient to ameliorate an interstitial pneumonia. In some embodiments, an effective amount or dose of a mAb 6D3 or COVID-19 SAg peptide is an amount sufficient to ameliorate hyperinflammation. In some embodiments, an effective amount or dose of a mAb 6D3 or COVID-19 SAg peptide is an amount sufficient to ameliorate a multisystem inflammatory syndrome in children (MIS-C).

"Homologs" are defined herein as two polynucleotides or two polypeptides that have identity or homology. Homologs include allelic variants, orthologs, and paralogs having the same relevant function (e.g., ability to bind to a COVID-19 SAg or ability to block binding of a COVID-19 SAg to a T cell receptor, a major histocompatibility (MHC) molecule and/or CD28). In some embodiments, homologs have about 99%, 98%, 97%, 96%, 95%, 94%, 93%, 92, 91% or 90% homology. In other embodiments, homologs have about 80% or about 85% homology.

"Humanized" forms of non-human (e.g. murine) antibodies are chimeric immunoglobulins, immunoglobulin chains or fragments thereof (such as Fv, Fab, Fab', F(ab')$_2$ or other target-binding subsequences of antibodies) which contain minimal sequence derived from non-human immunoglobulin. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody may also comprise at least a portion of an immunoglobulin constant region (Fc), typically that of a human immunoglobulin.

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. Neither N-nor C-terminal extensions nor insertions shall be construed as reducing identity or homology. A polynucleotide or polynucleotide region (or a polypeptide or polypeptide region) that has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art. In one embodiment, default parameters are used for alignment. In one embodiment a BLAST program is used with default parameters. In one embodiment, BLAST programs BLASTN and BLASTP are used with the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

The term "isolated" means separated from constituents, cellular and otherwise, in which the polynucleotide, peptide, polypeptide, protein, antibody, or fragments thereof, are normally associated with in nature.

The term "monoclonal antibody" or "mAb" as used herein refers to an antibody obtained from a substantially homogeneous population of antibodies, i.e., the individual antibodies within the population are identical except for possible naturally occurring mutations that may be present in a small subset of the antibody molecules.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. In some instances, the terms "treat", "treating", "treatment" and grammatical variations thereof, include partially or completely reducing the severity of a COVID-19 infection, partially or completely reducing a multisystem inflammatory syndrome, or partially or completely reducing a pneumonia associated with a COVID-19 infection as compared with prior to treatment of the subject or as compared with the incidence of such symptom in a general or study population.

Compositions and Methods

As noted above, it is disclosed herein that SARS-CoV-2 encodes a superantigen (SAg) motif near the S1/S2 cleavage site of its Spike protein. As used herein, "Spike protein" or "S protein" refers to a polypeptide that mediates binding of a SARS-CoV virus to a cell and/or membrane fusion of the virus to a cell. The Spike protein contains an extracellular domain (EC) with two subunits, a receptor-binding subunit (S1) and a membrane-fusion subunit (S2). S1 contains two domains, an N-terminal domain (S1-NTD) and receptor binding domain (RBD), which play a key role in receptor recognition and binding. During host-virus membrane fusion, Spike protein is usually cleaved at the S1/S2 boundary by host proteases, releasing the spike fusion peptide, which is necessary for virus entry.

In some embodiments, the Spike protein is that identified in a publicly available database as follows: UniProtKB P0DTC2. In some embodiments, the Spike protein comprises the sequence of SEQ ID NO: 1, or a polypeptide sequence having at or greater than about 80%, about 85%, about 90%, about 95%, or about 98% homology with SEQ ID NO: 1, or a polypeptide comprising a portion of SEQ ID NO: 1. In some embodiments, the Spike protein is an isoform of SEQ ID NO:1. In some embodiments, the Spike protein is a ortholog of SEQ ID NO:1. The Spike protein of SEQ ID NO: 1 may represent an immature or pre-processed form of mature Spike protein, and accordingly, included herein are mature or processed portions of the Spike protein in SEQ ID NO: 1. In other embodiments, the Spike protein comprises the sequence of SEQ ID NO:1 modified by one or more of the following mutations: D614G, A831V and D839Y/N/E.

Accordingly, included herein are methods of treating a COVID-19 infection in a subject, comprising administering to the subject an effective amount of a composition that that reduces binding of a SARS-CoV-2 Spike protein SAg region to a T cell receptor (TCR), an MHC molecule and/or CD28. In some embodiments, binding to a TCR alpha chain is reduced. In other embodiments, binding to a TCR beta chain is reduced. In some embodiments, the MHC molecule is an MHC Class II. In some embodiments, the reduction in binding is about 100%, about 95%, about 90%, about 85%, about 80%, about 75%, about 70%, about 65%, about 60%, about 55%, or about 50% as compared to a control.

One SAg region of the SARS-CoV-2 Spike protein comprises amino acids PRRA (SEQ ID NO:2), which correspond or correlate with amino acid positions 681 to 684 of SEQ ID NO:1. In some embodiments, the SAg region comprises 4, 5, 6, 7, 8, 9, 10, 11, 12, 13, 14, 15, 16, 17, 18, 19 or 20 amino acids and includes amino acids that correspond or correlate with positions 681 to 684 of SEQ ID NO:1. Another SAg region of the SARS-CoV-2 Spike protein comprises amino acids YNENGTITDAVD-CALDPLSETKC (SEQ ID NO:3), which correspond or correlate with amino acid positions 279 to 301 of SEQ ID NO:1.

In some embodiments, the SAg region comprises amino acids TNSPRRAR (SEQ ID NO:4), which correspond or correlate with amino acid positions 678 to 685 of SEQ ID NO:1. In some embodiments, the SAg region comprises amino acids YQTQTNSPRRAR (SEQ ID NO:5), which correspond or correlate with amino acid positions 674 to 685 of SEQ ID NO:1. In some embodiments, the SAg region comprises amino acids PRRARS (SEQ ID NO:6), which correspond or correlate with amino acid positions 681 to 686 of SEQ ID NO:1. In some embodiments, the SAg region comprises amino acids PRRASVASQ (SEQ ID NO:7), which correspond or correlate with amino acid positions 681 to 690 of SEQ ID NO:1. In some embodiments, the SAg region comprises amino acids PRRASVASQSI (SEQ ID NO:8), which correspond or correlate with amino acid positions 681 to 692 of SEQ ID NO:1. In some embodiments, the SAg region comprises amino acids TNSPRRASVASQ (SEQ ID NO:9), which correspond or correlate with amino acid positions 678 to 690 of SEQ ID NO:1. In some embodiments, the SAg region comprises amino acids QTNSPRRARSVAS (SEQ ID NO:10), which correspond or correlate with amino acid positions 677 to 689 of SEQ ID NO:1. In some embodiments, the SAg region comprises amino acids ECDIPIGAGICASYQTQTNSPRRARSV (SEQ ID NO:11), which correspond or correlate with amino acid positions 661 to 687 of SEQ ID NO:1. In some embodiments, the SAg region comprises amino acids ECDIPIGAGICASYQTQTNSPRRAR (SEQ ID NO:12), which correspond or correlate with amino acid positions 661 to 685 of SEQ ID NO: 1. In some embodiments, the SAg region comprises amino acids YNENGTITDAVDCALDPLSETKC (SEQ ID NO:3), which correspond or correlate with amino acid positions 279 to 301 of SEQ ID NO:1.

The present invention also includes compositions such as peptide mimetics of the SARS-CoV-2 SAg region and methods for using those compositions in treating a COVID-19 infection in a subject. As used herein, the term "peptide mimetic" refers to an amino acid sequence that comprises or corresponds to a SARS-CoV-2 Spike protein SAg region. Accordingly, included herein are SARS-CoV-2 SAg peptides comprising amino acids PRRA (SEQ ID NO:2), which correspond or correlate with amino acid positions 681 to 684 of SEQ ID NO:1. In some embodiments, the SARS-CoV-2 SAg peptide comprises 4, 5, 6, 7, 8, 9, 10, 11, 12, 13, 14, 15, 16, 17, 18, 19 or 20 amino acids and includes amino acids that correspond or correlate with positions 681 to 684 of SEQ ID NO:1.

In some embodiments, the SARS-CoV-2 SAg peptide comprises amino acids TNSPRRAR (SEQ ID NO:4), which correspond or correlate with amino acid positions 678 to 685 of SEQ ID NO:1. In some embodiments, the SARS-CoV-2 SAg peptide comprises amino acids YQTQTNSPRRAR (SEQ ID NO:5), which correspond or correlate with amino acid positions 674 to 685 of SEQ ID NO:1. In some embodiments, the SARS-CoV-2 SAg peptide comprises amino acids PRRARS (SEQ ID NO:6), which correspond or correlate with amino acid positions 681 to 686 of SEQ ID NO:1. In some embodiments, the SARS-CoV-2 SAg peptide comprises amino acids PRRASVASQ (SEQ ID NO:7), which correspond or correlate with amino acid positions 681 to 690 of SEQ ID NO:1. In some embodiments, the SARS-CoV-2 SAg peptide comprises amino acids PRRASVASQSI (SEQ ID NO:8), which correspond or correlate with amino acid positions 681 to 692 of SEQ ID NO:1. In some embodiments, the SARS-CoV-2 SAg peptide comprises amino acids TNSPRRASVASQ (SEQ ID NO:9), which correspond or correlate with amino acid positions 678 to 690 of SEQ ID NO:1. In some embodiments, the SAg peptide comprises amino acids QTNSPRRARSVAS (SEQ ID NO:10), which correspond or correlate with amino acid positions 677 to 689 of SEQ ID NO:1. In some embodiments, the SAg peptide comprises amino acids ECDIPIGAGICASYQTQTNSPRRARSV (SEQ ID NO:11), which correspond or correlate with amino acid positions 661 to 687 of SEQ ID NO:1. In some embodiments, the SARS-CoV-2 SAg peptide comprises amino acids ECDIPIGAGICASYQTQTNSPRRAR (SEQ ID NO:12), which correspond or correlate with amino acid positions 661 to 685 of SEQ ID NO:1. In some embodiments, the SARS-CoV-2 SAg peptide comprises amino acids YNENGTITDAVDCALDPLSETKC (SEQ ID NO:3), which correspond or correlate with amino acid positions 279 to 301 of SEQ ID NO:1.

It should be understood that the present invention includes methods of administering an effective amount of one or more SARS-CoV-2 SAg peptides for treating a COVID-19 infection in a subject. Provided are methods of treating a COVID-19 infection in a subject, comprising administering to the subject an effective amount of one or more SARS-CoV-2 superantigenic (SAg) peptides, wherein the one or more peptides are selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12. In some embodiments, the method of treating a COVID-19 infection in a subject, comprises administering to the subject an effective amount of a peptide comprising SEQ ID NO:2. In some embodiments, the method of treating a COVID-19 infection in a subject, comprises administering to the subject an effective amount of a peptide comprising SEQ ID NO:3. In some embodiments, the method of treating a COVID-19 infection in a subject, comprises administering to the subject an effective amount of a peptide comprising SEQ ID NO:4. In some embodiments, the method of treating a COVID-19 infection in a subject, comprises administering to the subject an effective amount of a peptide comprising SEQ ID NO:5. In some embodiments, the method of treating a COVID-19 infection in a subject, comprises administering to the subject an effective amount of a peptide comprising SEQ ID NO:6. In some embodiments, the method of treating a COVID-19 infection in a subject, comprises administering to the subject an effective amount of a peptide comprising SEQ ID NO:7. In some embodiments, the method of treating a COVID-19 infection in a subject, comprises administering to the subject an effective amount of a peptide comprising SEQ ID NO:8. In some embodiments, the method of treating a COVID-19 infection in a subject, comprises administering to the subject an effective amount of a peptide comprising SEQ ID NO:9. In some embodiments, the method of treating a COVID-19 infection in a subject, comprises administering to the subject an effective amount of a peptide comprising SEQ ID NO:10. In some embodiments, the method of treating a COVID-19 infection in a subject, comprises administering to the subject an effective amount of a peptide comprising SEQ ID NO:11. In some embodiments, the method of treating a COVID-19 infection in a subject, comprises administering to the subject an effective amount of a peptide comprising SEQ ID NO:12.

Also included in the present invention are methods of treating a COVID-19 infection in a subject, comprising administering to the subject an effective amount of one or more of an mAb 6D3, an mAb 20B1, an mAb 14G8, a functional fragment thereof, or a humanized form thereof. These methods can be used separately or in conjunction with the methods of administering one or more SARS-CoV-2 SAg peptides also described herein.

The term "mAb 6D3" refers to a 6D3 antibody as described in Patent Application Publication US 2014/0234325 (U.S. application Ser. No. 14/346,981) and/or Patent Application Publication US 2016/0039914 (U.S. application Ser. No. 14/774,283), each of which is incorporated by reference herein in its entirety. In some embodiments, the mAb 6D3 comprises a $V_H$ amino acid sequence of SEQ ID NO:13. In some embodiments, the mAb 6D3 comprises a $V_L$ amino acid sequence of SEQ ID NO:17. In some embodiments, the mAb 6D3 comprises a CDR amino acid sequence of one or more of SEQ ID NO:14 ($V_H$ CDR1), SEQ ID NO:15 ($V_H$ CDR2) and SEQ ID NO:16 ($V_H$ CDR3). In some embodiments, the mAb 6D3 comprises a CDR amino acid sequence of one or more of SEQ ID NO:18 ($V_L$ CDR1), SEQ ID NO:19 ($V_L$ CDR2) and SEQ ID NO:20 ($V_L$ CDR3). In some embodiments, the mAb 6D3 comprises a CDR3 amino acid sequence of SEQ ID NO:16 and a CDR3 amino acid sequence of SEQ ID NO:20.

In some embodiments, the mAb 6D3 is humanized. A "humanized mAb 6D3" refers to a chimeric antibody that comprises two or more CDR amino acid sequences of an mAb 6D3 and one or more human antibody sequences. In some embodiments, the humanized mAb 6D3 comprises human framework regions. In some embodiments, the humanized mAb 6D3 further comprises a human Fc region. In some embodiments, the humanized mAb 6D3 comprises two or more murine CDRs selected from the group consisting of SEQ ID NO:14 ($V_H$ CDR1), SEQ ID NO:15 ($V_H$ CDR2), SEQ ID NO:16 ($V_H$ CDR3), SEQ ID NO:18 ($V_L$ CDR1), SEQ ID NO:19 ($V_L$ CDR2) and SEQ ID NO:20 ($V_L$ CDR3). In some embodiments, the humanized mAb 6D3 comprises three or more murine CDRs selected from the group consisting of SEQ ID NO:14 ($V_H$ CDR1), SEQ ID NO:15 ($V_H$ CDR2), SEQ ID NO:16 ($V_H$ CDR3), SEQ ID NO:18 ($V_L$ CDR1), SEQ ID NO:19 ($V_L$ CDR2) and SEQ ID NO:20 ($V_L$ CDR3). In some embodiments, the humanized mAb 6D3 comprises four or more murine CDRs selected from the group consisting of SEQ ID NO:14 ($V_H$ CDR1), SEQ ID NO:15 ($V_H$ CDR2), SEQ ID NO:16 ($V_H$ CDR3), SEQ ID NO:18 ($V_L$ CDR1), SEQ ID NO:19 ($V_L$ CDR2) and SEQ ID NO:20 ($V_L$ CDR3). In some embodiments, the humanized mAb 6D3 comprises five or more murine CDRs selected from the group consisting of SEQ ID NO:14 ($V_H$ CDR1), SEQ ID NO:15 ($V_H$ CDR2), SEQ ID NO:16 ($V_H$ CDR3), SEQ ID NO:18 ($V_L$ CDR1), SEQ ID NO:19 ($V_L$ CDR2) and SEQ ID NO:20 ($V_L$ CDR3). In some embodiments, the humanized mAb 6D3 comprises all of SEQ ID NO:14 ($V_H$ CDR1), SEQ ID NO:15 ($V_H$ CDR2), SEQ ID NO:16 ($V_H$ CDR3), SEQ ID NO:18 ($V_L$ CDR1), SEQ ID NO:19 ($V_L$ CDR2) and SEQ ID NO:20 ($V_L$ CDR3).

The term "mAb 20B1" refers to a 20B1 antibody as described in Patent Application Publication US 2014/0234325 (U.S. application Ser. No. 14/346,981) and/or Patent Application Publication US 2016/0039914 (U.S. application Ser. No. 14/774,283). In some embodiments, the mAb 20B1 comprises a $V_H$ amino acid sequence of SEQ ID NO:21. In some embodiments, the mAb 20B1 comprises a $V_L$ amino acid sequence of SEQ ID NO:25. In some embodiments, the mAb 20B1 comprises a CDR amino acid sequence of one or more of SEQ ID NO:22 or SEQ ID NO:29 ($V_H$ CDR1), SEQ ID NO:23 or SEQ ID NO:30 ($V_H$ CDR2) and SEQ ID NO:24 or SEQ ID NO:31 ($V_H$ CDR3). In some embodiments, the mAb 20B1 comprises a CDR amino acid sequence of one or more of SEQ ID NO:26 or SEQ ID NO:32 ($V_L$ CDR1), SEQ ID NO:27 or SEQ ID NO:33 ($V_L$ CDR2) and SEQ ID NO:28 or SEQ ID NO:34 ($V_L$ CDR3). In some embodiments, the mAb 20B1 comprises a CDR3 amino acid sequence of SEQ ID NO:24 or SEQ ID NO:31 and a CDR3 amino acid sequence of SEQ ID NO:28 or SEQ ID NO:34.

In some embodiments, the mAb 20B1 is humanized. A "humanized mAb 20B1" refers to a chimeric antibody that comprises two or more CDR amino acid sequences of an mAb 20B1 and one or more human antibody sequences. In some embodiments, the humanized mAb 20B1 comprises human framework regions. In some embodiments, the humanized mAb 20B1 further comprises a human Fc region. In some embodiments, the humanized mAb 20B1 comprises two or more murine CDRs selected from the group consisting of SEQ ID NO:22 or SEQ ID NO:29 ($V_H$ CDR1), SEQ ID NO:23 or SEQ ID NO:30 ($V_H$ CDR2), SEQ ID NO:24 or SEQ ID NO:31 ($V_H$ CDR3), SEQ ID NO:26 or SEQ ID NO:32 ($V_L$ CDR1), SEQ ID NO:27 or SEQ ID NO:33 ($V_L$ CDR2) and SEQ ID NO:28 or SEQ ID NO:34 ($V_L$ CDR3). In some embodiments, the humanized mAb 20B1 comprises three or more murine CDRs selected from the group consisting of SEQ ID NO:22 or SEQ ID NO:29 ($V_H$ CDR1), SEQ ID NO:23 or SEQ ID NO:30 ($V_H$ CDR2), SEQ ID NO:24 or SEQ ID NO:31 ($V_H$ CDR3), SEQ ID NO:26 or SEQ ID NO:32 ($V_L$ CDR1), SEQ ID NO:27 or SEQ ID NO:33 ($V_L$ CDR2) and SEQ ID NO:28 or SEQ ID NO:34 ($V_L$ CDR3). In some embodiments, the humanized mAb 20B1 comprises four or more murine CDRs selected from the group consisting of SEQ ID NO:22 or SEQ ID NO:29 ($V_H$ CDR1), SEQ ID NO:23 or SEQ ID NO:30 ($V_H$ CDR2), SEQ ID NO:24 or SEQ ID NO:31 ($V_H$ CDR3), SEQ ID NO:26 or SEQ ID NO:32 ($V_L$ CDR1), SEQ ID NO:27 or SEQ ID NO:33 ($V_L$ CDR2) and SEQ ID NO:28 or SEQ ID NO:34 ($V_L$ CDR3). In some embodiments, the humanized mAb 20B1 comprises five or more murine CDRs selected from the group consisting of SEQ ID NO:22 or SEQ ID NO:29 ($V_H$ CDR1), SEQ ID NO:23 or SEQ ID NO:30 ($V_H$ CDR2), SEQ ID NO:24 or SEQ ID NO:31 ($V_H$ CDR3), SEQ ID NO:26 or SEQ ID NO:32 ($V_L$ CDR1), SEQ ID NO:27 or SEQ ID NO:33 ($V_L$ CDR2) and SEQ ID NO:28 or SEQ ID NO:34 ($V_L$ CDR3). In some embodiments, the humanized mAb 20B1 comprises six murine CDRs selected from the group consisting of SEQ ID NO:22 or SEQ ID NO:29 ($V_H$ CDR1), SEQ ID NO:23 or SEQ ID NO:30 ($V_H$ CDR2), SEQ ID NO:24 or SEQ ID NO:31 ($V_H$ CDR3), SEQ ID NO:26 or SEQ ID NO:32 ($V_L$ CDR1), SEQ ID NO:27 or SEQ ID NO:33 ($V_L$ CDR2) and SEQ ID NO:28 or SEQ ID NO:34 ($V_L$ CDR3).

The term "mAb 14G8" refers to a 14G8 antibody as described in Patent Application Publication US 2014/0234325 (U.S. application Ser. No. 14/346,981) and/or Patent Application Publication US 2016/0039914 (U.S. application Ser. No. 14/774,283). In some embodiments, the mAb 14G8 comprises a $V_H$ amino acid sequence of SEQ ID NO:35. In some embodiments, the mAb 14G8 comprises a $V_L$ amino acid sequence of SEQ ID NO:39. In some embodiments, the mAb 14G8 comprises a CDR amino acid sequence of one or more of SEQ ID NO:36 ($V_H$ CDR1), SEQ ID NO:37 ($V_H$ CDR2) and SEQ ID NO:38 ($V_H$ CDR3). In some embodiments, the mAb 14G8 comprises a CDR amino acid sequence of one or more of SEQ ID NO:40 ($V_L$ CDR1), SEQ ID NO:41 ($V_L$ CDR2) and SEQ ID NO:42 ($V_L$ CDR3). In some embodiments, the mAb 14G8 comprises a CDR3 amino acid sequence of SEQ ID NO:38 and a CDR3 amino acid sequence of SEQ ID NO:42.

In some embodiments, the mAb 14G8 is humanized. A "humanized mAb 14G8" refers to a chimeric antibody that comprises two or more CDR amino acid sequences of an mAb 14G8 and one or more human antibody sequences. In some embodiments, the humanized mAb 14G8 comprises human framework regions. In some embodiments, the humanized mAb 14G8 further comprises a human Fc region. In some embodiments, the humanized mAb 14G8 comprises two or more murine CDRs selected from the group consisting of SEQ ID NO:36 ($V_H$ CDR1), SEQ ID NO:37 ($V_H$ CDR2), SEQ ID NO:38 ($V_H$ CDR3), SEQ ID NO:40 ($V_L$ CDR1), SEQ ID NO:41 (V_L CDR2), and SEQ ID NO:42 (V_L CDR3). In some embodiments, the humanized mAb 14G8 comprises three or more murine CDRs selected from the group consisting of SEQ ID NO:36 (V_H CDR1), SEQ ID NO:37 (V_H CDR2), SEQ ID NO:38 (V_H CDR3), SEQ ID NO:40 (V_L CDR1), SEQ ID NO:41 (V_L CDR2), and SEQ ID NO:42 (V_L CDR3). In some embodiments, the humanized mAb 14G8 comprises four or more murine CDRs selected from the group consisting of SEQ ID NO:36 (V_H CDR1), SEQ ID NO:37 (V_H CDR2), SEQ ID NO:38 (V_H CDR3), SEQ ID NO:40 (V_L CDR1), SEQ ID NO:41 (V_L CDR2), and SEQ ID NO:42 (V_L CDR3). In some embodiments, the humanized mAb 14G8 comprises five or more murine CDRs selected from the group consisting of SEQ ID NO:36 (V_H CDR1), SEQ ID NO:37 (V_H CDR2), SEQ ID NO:38 (V_H CDR3), SEQ ID NO:40 (V_L CDR1), SEQ ID NO:41 (V_L CDR2), and SEQ ID NO:42 (V_L CDR3). In some embodiments, the humanized mAb 14G8 comprises all of SEQ ID NO:36 (V_H CDR1), SEQ ID NO:37 (V_H CDR2), SEQ ID NO:38 (V_H CDR3), SEQ ID NO:40 (V_L CDR1), SEQ ID NO:41 (V_L CDR2), and SEQ ID NO:42 (V_L CDR3).

In one aspect, the disclosed methods can be employed 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 years; 12, 11, 10, 9, 8, 7, 6, 5, 4, 3, 2, or 1 months; 30, 29, 28, 27, 26, 25, 24, 23, 22, 21, 20, 19, 18, 17, 16, 15, 14, 13, 12, 11, 10, 9, 8, 7, 6, 5, 4, or 3 days; 60, 48, 36, 30, 24, 18, 15, 12, 10, 9, 8, 7, 6, 5, 4, 3, or 2 hours prior to the onset of a COVID-19 symptom; or 1, 2, 3, 4, 5, 6, 7, 8, 9, 10, 15, 20, 25, 30, 35, 40, 45, 50, 55, 60, 75, 90, 105, 120 minutes; 3, 4, 5, 6, 7, 8, 9, 10, 11, 12, 15, 18, 24, 30, 36, 48, 60 hours; 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days; 4, 5, 6, 7, 8, 9, 10, 11, 12 or more months; 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 years after the onset of COVID-19 symptom. In some embodiments, the disclosed methods can be employed prior to or following the administering of another anti-SARS-CoV-2 agent.

A SARS-CoV-2 SAg peptide and/or a humanized mAb 6D3 described herein can be administered to the subject via any route including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

Dosing frequency for a SARS-CoV-2 SAg peptide and/or a humanized mAb 6D3 of any preceding aspects, includes, but is not limited to, at least once every year, once every two years, once every three years, once every four years, once every five years, once every six years, once every seven years, once every eight years, once every nine years, once every ten year, at least once every two months, once every three months, once every four months, once every five months, once every six months, once every seven months, once every eight months, once every nine months, once every ten months, once every eleven months, at least once every month, once every three weeks, once every two weeks, once a week, twice a week, three times a week, four times a week, five times a week, six times a week, daily, twice a day, three times a day, four times a day, or five times a day. Administration can also be continuous and adjusted to maintaining a level of the compound within any desired and specified range.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Materials and Methods

Viruses. SARS-CoV-2 (PODTC2) and SARS-CoV (CVHSA P59594) spike models were generated using SWISS-MODEL (L. Bordoli, T. Schwede, (Springer, 2011)), based on the resolved spike glycoprotein structures of SARS-CoV-2 (D. Wrapp et al. (2020)) (PDB: 6VSB) and SARS-CoV (W. Song, et al. (2018)) (PDB: 6ACD). The missing loops in the crystal structures were built using libraries of backbone fragments (Y. Zhang, J. Skolnick, (2005)) or by constraint space de novo reconstruction of these backbone segments (M. C. Peitsch (1995)). Two mutants associated with European Covid-19 patients (B. Korber et al. (2020)) were constructed using CHARMM-GUI (S. Jo, T. Kim, et al. (2008)): one is the main strain mutant D614G and the other contains four mutations including Q239K, A831V, D614G and D839Y. These two SARS-CoV-2 spike mutants together with the SARS-CoV-2 (PODTC2) originally taken from Wuhan were used to investigate the binding to αβTCR, and MHCII (PDB: 2XN9) (M. Saline et al. (2010)) using ClusPro (D. Kozakov et al. (2017)) and PRODIGY (L. C. Xue, et al. (2016)).

Generation of a binary complex between SARS-CoV-2 spike and T cell receptor (TCR). SARS-CoV-2 spike model in the prefusion state was generated using SwissModel (Bordoli, L. & Schwede, T. (Springer, 2011)) based on the resolved cryo-EM structure (Protein Data Bank (PDB): 6VSB (Wrapp, D. et al. (2020)) for the spike glycoprotein where one of the receptor binding domains (RBDs) is in the up conformation. The structure of the T cell receptor (TCR) containing both TCRα and TCRβ chains was taken from the crystal structure of the ternary complex between human TCR, staphylococcal enterotoxin H (SEH) and human major histocompatibility complex class II (MHCII) molecule (Saline, M. et al. (2010)). Using protein-protein docking software ClusPro (Kozakov, D. et al. (2017)), a series of binary complexes were constructed in silico for SARS-CoV-2 spike and TCR. 30 clusters of conformations were obtained for spike-TCR binary complexes, upon clustering 1000 models generated by ClusPro. The clusters were rank-ordered by cluster size, as recommended (Kozakov, D. et al. (2017)). All models were analyzed which found that the majority (>90%) showed that TCR bound to spike via its constant domain. Given that the constant domain is proximal to the cell membrane and TCR employs the variable domain for binding superantigens and/or antigen/MHC complexes (Saline, M. et al. (2010)), restraints were then added to the docking simulations to prevent the binding of TCR constant domain and filter out those conformers where the variable domain would bind to the spike. This led to 27 clusters (based on a set of 666 models) from ClusPro. Interestingly, 45% of models showed the binding of TCR near the region of "PRRA" insert and 46% of models showed the binding of TCR within multiple RBDs. Thus, two hot spots were identified for TCR binding within SARS-CoV-2 spike: one is near "PRRA" insert and the other within the RBD. Representative members belonging to the top-ranking clusters are presented in FIG. 5.

SARS-CoV-2 spike model in the prefusion state was generated using SwissModel (A. Waterhouse et al. (2018)) based on the resolved cryo-EM structure (Protein Data Bank (PDB): 6VSB) (Wrapp, D. et al. (2020)) for the S glycoprotein where one of the receptor binding domains (RBDs) is in the up conformation and the other two in the down conformation. The structure of the T cell receptor (TCR) containing both α- and β-chains was taken from the crystal structure (PDB: 2XN9) of the ternary complex resolved for human TCR, staphylococcal enterotoxin H (SEH) and human major histocompatibility complex class II (MHCII) molecule (Saline, M. et al. (2010)). Using protein-protein docking software ClusPro (Kozakov, D. et al. (2017)), a series of binary complexes were constructed in silico for SARS-CoV-2 spike and TCR. 30 clusters of conformations were obtained for spike-TCR binary complexes, upon clustering the 1000 models generated by ClusPro. The clusters were rank-ordered by cluster size, as recommended (Kozakov, D. et al. (2017)). We analyzed all models and found that a large fraction showed that TCR bound to spike via its constant domain. Given that the constant domain is proximal to the cell membrane and TCR employs the variable domain for binding superantigens (SAgs) and/or antigen/MHC complexes (Saline, M. et al. (2010)), restraints to the docking simulations were then added to filter out those conformers where the variable domain would bind to the spike. This led to 27 clusters (based on a set of 666 models) from ClusPro. Interestingly, in 45% of the generated models, the TCR was observed to bind to a spike epitope that contained the "PRRA" insert; and in 46% of models we observed an interaction between the TCR and one or two of the three RBDs.

Thus, two hot spots were identified for TCR binding within the SARS-CoV-2 spike: one overlapping with the "PRRA" insert and the other on the RBD surface. Representative members belonging to the top-ranking clusters are presented in FIG. 5. FIGS. 5E and 5F illustrate two cases where the TCR α- or β-chain tightly binds to the PRRA (SEQ ID NO:2) insert region (of monomers 2 (dark red) and monomer 1 (gray), respectively); and FIGS. 5G-5H illustrate two cases where the TCR binds to RBDs.

Generation of a binary complex between SARS-CoV spike and TCR. Further, SARS-CoV (SARS1) spike model in the prefusion state was generated using SwissModel (A. Waterhouse et al. (2018)) based on the cryo-EM structure resolved for SARS-CoV spike (PDB: 6ACD) (W. Song, et al. (2018)) where one of the RBDs is in the up conformation, and the other two in the down conformation. Following the same approach as we did for SARS-CoV-2 spike, a series of binary complexes were constructed in silico for SARS-CoV spike and TCR using ClusPro (Kozakov, D. et al. (2017)). Using the same filtering procedure, this led to 30 clusters (based on 686 models), among which 38% showed the binding of TCR to multiple RBDs (see FIG. 9A) similar to the behavior observed in (FIGS. 5G-5H) for SARS-CoV-2. Differently, 48% of the models showed the binding of TCR to two S2 subunits near the C-terminal domain of the trimers (see FIG. 9B). No significant binding of TCR near the S1/S2 cleavage site RS668 of the SARS-CoV spike was observed.

Note that the residues $S_{664}LLRS_{668}$ (SEQ ID NO:117) of SARS-CoV spike, which are sequentially aligned to SARS-COV-2 spike T678SPRRARS686 (SEQ ID NO:118) containing the "PRRA" insert (see FIG. 3A), lack the polybasic character of their counterpart SARS-COV-2. The lack of TCR binding to this region is consistent with the absence of this motif in SARS-CoV, which serves as a strong attractor in SARS-COV-2.

Generation of a binary complex between MERS-CoV spike and TCR. MERS-CoV spike model was generated using SwissModel (A. Waterhouse et al. (2018)) based on the cryo-EM structure resolved for MERS-CoV spike (W. Song, et al. (2018)) (PDB: 5X5F) in which one of RBDs is in the up conformation. 30 clusters (based on 588 models) were predicted by ClusPro (Kozakov, D. et al. (2017)). 56% of models led to TCR binding to the RBDs. Two representative poses from these most populated clusters are shown in FIGS. 9C-9D, which are comparable to those observed in SARS-CoV-2 spike (FIGS. 5G-5H) and SARS-CoV spike (FIG. 9A). Simulations also indicated that TCR binds near the S1/S2 cleavage site region of MERS-CoV spike (segment D726-R751; counterpart of SARS-CoV-2 E661-R685 at the C-terminus of subunit S1). Note that at this region the PRRA (SEQ ID NO:2) insert of SARS-CoV-2 spike is replaced by MERS-CoV spike sequence PRSV. The region near PRSV shows a tendency to bind TCR but it is weaker than that of SARS-CoV-2 spike due to the lack of the critical residues (e.g. N679 and R683 in SARS-CoV-2 spike) that are involved in the interface the spike makes with the TCR. The lack of polybasic residues at this sequence motif, as well as counterparts of N679 and R683 of SARS-CoV-2 spike renders this structural region less attractive to TCRs, indicating that MERS-CoV did not harbor a superantigen-like motif near its S1/S2 cleavage site.

Examination of neurotoxin-like and other bioactive segments on SARS-CoV-2 spike. FIG. 6 displays nine SARS-CoV segments that have been identified to be bioactive, neurotoxin-like or ICAM-like. In each case the 2nd row is the SARS-CoV-2 segment, identified by Li et al, 2004 and the 1st row is its SARS-CoV-2 spike counterpart. The last row lists their percent sequence identity. Note that the neurotoxin-like sequence #5, residues 299-351, contains several fragments (15-mers) that were recently shown (Mateus J, et al. (2020)) to stimulate T cell reactivity (illustrated in FIG. 13).

Generation of a ternary complex between SARS-CoV-2 spike, TCR, and MHCII. Structure of the human MHCII was taken from the crystal structure of the ternary complex (Saline, M. et al. (2010)) (PDB: 2XN9) between human TCR, SEH and MHCII. First, docking simulations were performed to generate binary complexes between MHCII and SARS-CoV-2 spike. Six representative MHCII-spike binary complexes were selected to explore further docking of TCR to form a ternary complex. All predicted ternary complex models of MHCII-Spike-TCR were analyzed. Tertiary MHCII-Spike-TCR complex models were selected following three filtering criteria: (1) TCR either binds near "PRRA" insert region or the RBD; (2) the binding regions involve homologous superantigen or toxin binding motifs predicted for SARS-CoV (FIG. 6); (3) MHCII and TCR are in close proximity. These filters led to the MHCII-Spike-TCR complex model illustrated in FIG. 7A. The SARS-CoV-2 spike binding region harbors three residues that have been recently reported to have mutated in new strains from Europe and USA (49, 50) (FIG. 7B): D614G, A831V and D839Y/N/E). While the possible occurrence of other potential tertiary complexes was not excluded, especially those involving the RBDs, the complex shown in FIG. 7 uniquely satisfied all three aforementioned criteria.

In silico mutagenesis of D839 of SARS-CoV-2 spike. D839 of the SARS-CoV-2 spike were mutated in silico to asparagine, glutamic acid and tyrosine in line with the aforementioned mutant D839Y/N/E observed in a new strain from Europe. To this aim, PyMOL mutagenesis tool (DeLano, W. L. (2002)) was used and the change in local conformation and energetics were evaluated in the complex formed with TCR. The most probable rotamers were selected and energetically minimized in the presence of the bound TCR (conformation shown in FIG. 1) using OpenMM (Eastman, P. et al. (2017)). These were further subjected to short (1 ns) molecular dynamics (MD) simulations for equilibration and energy minimization under the AMBER14 ff14SB forcefield (J. A. Maier et al (2015)). Five independent runs were carried out for each mutant (Y, N, or E, at the position 839) as well as the wild type (D839) spike, to assess the statistical significance of the results for each case. Binding affinities ($\Delta G$) and dissociation constants ($K_d$) were obtained for (i) the full complex (with the intact spike and entire TCR as interactors) or (ii) a single spike subunit and TCRV$\beta$ with the D839Y/N/E mutation on spike at 37° C. using PRODIGY server (Vangone, A. & Bonvin, A. M. (2015), Xue, L. C., et al. (2016)). The results are presented in Table 3.

Analysis of NGS immunosequencing data from COVID-19 patients. Blood collection from 38 patients (42 samples) with mild/moderate COVID-19, and 8 patients (24 samples) with severe/hyperinflammatory COVID-19 was performed under institutional review board approval number 2020-039. The patients and controls, and their immune repertoires, were part of a previously published cohort (Schultheiss C, et al. (2020)). For details of NGS data acquisition, please refer to the earlier work (Schultheiss C, et al. (2020)). Only productive TRB rearrangements were used and all repertoires were normalized to 20,000 reads. For the analyses, we used R version 3.5.1 for plotting of TRBV and TRBJ gene usage as previously described (Simnica D, et al. (2019), Simnica D, et al. (2019)). Differences in principal component analysis were studied by Pillai-Bartlett test of MANOVA. To study TRBJ gene diversity, J genes were extracted if they were part of rearrangements containing TRBV rearrangements expanded in patients with hyperinflammatory COVID-19. Frequencies of J gene families were summarized per repertoire and plotted separately for each rearrangement. See FIG. 14.

Generation of complexes between SARS-CoV-2 spike, SAg-specific TCRs and MHC II. Four TCR V$\beta$ genes (TRBV5-6, TRBV14, TRBV13 and TRBV24-1) were found to be overrepresented in severe/hyperinflammatory COVID-19 patients (FIG. 12). The binding properties of the $\beta$TCRs encoded by those genes were investigated. To this aim, the amino acid sequences corresponding to these respective genes were extracted from the UniProtKB (The UniProt Consortium (2016)), and were used in FASTA format to search for the corresponding structures, if any, in the Protein Data Bank (PDB) (Berman H M, et al. (2000)), using SwissModel (Waterhouse A, et al. (2018)). Structural data was found in the PDB for TCRV$\beta$ chains of three of the genes, TRBV5-6 (UniProt id: A0A599), TRBV14 (A0A5B0), and TRBV24-1 (A0A075B6N3). The respective PDB structures have PDB ids: 6ULR (Sim M J W, et al. (2020)), 2ESV (Hoare H L, et al. (2006)), and 6EH6 (Holland C J, et al. (2018)). These structures contain both $\alpha$- and $\beta$-chains and their V$\beta$ domains have 95-100% sequence identity with the V$\beta$ chains encoded by the respective TRVB genes. These PDB structures were used in docking simulations using the software ClusPro (Kozakov D, et al. (2017)) to examine their binding properties with respect to the SARS-CoV-2 spike. 30 clusters (obtained upon grouping 700 models) were generated for each of the TCRs complexed with the spike, and in each case there were 3 or more clusters where the TCR was bound to the SAg. FIG. 15 panels A-C display representative conformers from these clusters. FIG. 15D displays the multiple sequence alignment generated for the TCR V$\beta$ chains (with a few residues of the constant domain succeeding the CDR3). The binding paratopes are indicated by color-coded bars above the alignment. Simulations using the same protocol as the one adopted for generating FIG. 15 showed that ternary complexes with WWII were also energetically favorable for all three cases. FIGS. 15E and 15F illustrate the ternary complexes with MHCII for the TCRs corresponding to TRBV5-6 and TRBV14.

TABLE 3

Binding affinities between the $\alpha\beta$TCR and SARS-CoV-2 spike, for the wild type and mutant (D839Y/N/E) S glycoproteins

| | Aspartic Acid (D) $\Delta G$ (kcal mol$^{-1}$) | Tyrosine (Y) $\Delta G$ (kcal mol$^{-1}$) | Glutamic Acid (E) $\Delta G$ (kcal mol$^{-1}$) | Asparagine (N) $\Delta G$ (kcal mol$^{-1}$) |
|---|---|---|---|---|
| Full complex | −18.4 ± 0.2 | −19.3 ± 0.7 | −19.0 ± 1.3 | −19.0 ± 0.5 |
| S subunit - TCR V$\beta$ | −13.3 ± 0.3 | −14.5 ± 0.3 | −13.7 ± 0.6 | −13.9 ± 0.5 |

*Binding affinities ($\Delta G$) were obtained at 37° C. using PRODIGY server.

Example 2. Introduction

MIS-C manifests as persistent fever and hyperinflammation with multi organ system involvement including cardiac, gastrointestinal, renal, hematologic, dermatologic and neurologic symptoms (S. Riphagen, et al. (2020); L. Verdoni et al. (2020); Z. Belhadjer et al. (2020)) which are highly reminiscent of toxic shock syndrome (TSS) (D. E. Low (2013), A. Cook, et al. (2020)) (Table 1), rather than Kawasaki disease due to marked demographic, clinical, and laboratory differences (L. Verdoni et al. (2020)). The similarities to TSS and the association of MIS-C with COVID-19 indicate that SARS-CoV-2 can possess superantigenic fragments that induce an inflammatory cascade and contribute to the hyperinflammation and cytokine storm features observed in severe adult COVID-19 cases (M. Z. Tay, et al. (2020), N. Vabret et al. (2020)). The question is: does SARS-CoV-2 S possess superantigenic fragments that can elicit such reactions upon binding proteins involved in the host cell cytotoxic adaptive immune response? Such a reaction was not observed in the SARS-CoV pandemic of 2003 (shortly SARS1). What is unique to SARS-CoV-2, and how recent mutations in SARS-CoV-2 S promotes such an increased virulence?

TABLE 1

Similarities between clinical and laboratory features of MIS-C and pediatric TSS

| Clinical Features | MIS-C[a] | Pediatric TSS[b] |
|---|---|---|
| High fever | + | + |
| Skin rash | + | + |

TABLE 1-continued

Similarities between clinical and laboratory features of MIS-C and pediatric TSS

| Clinical Features | MIS-C[a] | Pediatric TSS[b] |
|---|---|---|
| Conjunctivitis | + | + |
| Oral mucosal involvement | + | + |
| Myalgia | + | + |
| Hypotension | + | + |
| Myocardial involvement (dysfunction) | + | + |
| Gastro-intestinal symptoms (vomiting, diarrhea, abdominal pain) | + | + |
| Renal involvement | + | + |
| CNS symptoms, altered mental state | + | + |
| Headache | + | + |
| High CRP | + | + |
| High Ferritin | + | + |
| High IL-6 | + | + |
| High D-dimers | + | + |
| High Procalcitonin | + | + |
| Lymphopenia | + | + |
| Reduced Platelet count | + | + |
| Increased Neutrophil count | + | + |
| Increased AST and ALST | + | + |
| High Pro-BNP | + | NA |
| High Troponin | + | NA |
| Isolation of TSS inducing bacteria (*Staphylococcus* or *Streptococcus*) | − | + |

[a]taken from refs (S. Riphagen, et al. (2020); L. Verdoni et al. (2020); Z. Belhadjer et al. (2020));
[b]taken from refs (8-11).
+ represents association with reported cases; NA: not available.

TSS can be caused by two types of superantigens (SAgs): bacterial or viral. Bacterial SAgs have been broadly studied. They include proteins secreted by *Staphylococcus aureus* and *Streptococcus pyogenes* that induce inflammatory cytokine gene induction and toxic shock. Typical examples are TSS toxin 1 (TSST1), and staphylococcal enterotoxins B (SEB) and H (SEH). They are highly potent T cell activators that can bind to MHC class II (MHCII) molecules and/or to TCRs of both CD4+ and CD8+ T cells. The ability of SAgs to bypass the antigen specificity of the TCRs results in broad activation of T cells and a cytokine storm, leading to toxic shock (H. Li, et al. (1999), T. Krakauer (2019)). Notably SAgs do not bind the major (antigenic) peptide binding groove of MHCII, but instead bind other regions as well as the αβTCRs, directly. While early studies showed that bacterial SAgs activate T cells by binding the β-chain of dimeric TCRs at their variable domain (V) (M. T. Scherer, et al. (1993), Y. W. Choi et al. (1989), J. D. Fraser, T. Proft (2008)), more recent studies revealed that they can bind to either α- or β-chains, or both (M. Saline et al. (2010)). The question is then, does SARS-CoV-2 S possess any superantigenic fragments/domains that can bind to the αβTCRs?

Here, computational modelling was used to determine whether the SARS-CoV-2 S possesses SAg activity. An insert present in SARS-CoV-2 S was found, which is absent from SARS1 and MERS, mediates high affinity, non-specific binding to the TCR. Notably, a motif of ~20 amino acids enclosing this insert unique to SARS-CoV-2 among beta coronaviruses has sequence and structure features highly similar to those of the SEB toxin. Furthermore, this analysis shows that a SARS-CoV-2 S mutation detected in a European strain can enhance TCR binding, indicating such mutations can account for geographical differences in MIS-C occurrence.

Example 3. SARS-CoV-2 Spike Harbors a High Affinity Site for TCR β-Chain Binding, which Contains an Insertion, $P_{681}RRA_{684}$ (SEQ ID NO:2), Unique to SARS2

First, whether SARS-CoV-2 S binds to the αβTCR was examined. To this aim, a SARS-CoV-2 S structural model was constructed based on the cryo-EM structure resolved for the spike glycoprotein (D. Wrapp et al. (2020)), and the X-ray structure of αβTCR resolved in a ternary complex was used with SEH and MHCII (M. Saline et al. (2010)), and a series of structural models were generated for possible SARS-CoV-2 S glycoprotein—TCR complex formation using ClusPro (D. Kozakov et al. (2017)). These simulations revealed two most probable TCR binding sites on each monomer of the S trimer: one on the receptor binding domain (RBD; residues R319-K529), and the other near the S1/S2 cleavage site between the subunits S1 and S2. The former was also shared by SARS1 and MERS-CoV S, while the latter was unique (or strongly preferred) in SARS-CoV-2 S, as de-scribed in detail in the FIG. 5 and FIG. 9. These simulations led to the binding pose presented in FIG. 1A as one of the most probable mechanisms of complex formation, as described in detail in FIG. 5. Therein, the TCR binds at the interface between the S1 and S2 subunits of the spike protein, near the S1/S2 cleavage site. A closeup view of the interface between the spike and TCRVβ domain (FIG. 1B) reveals several strong interatomic interactions, involving residues 5680-R683 on the spike, and R70-E74 and [Q52, D56] on the respective CDRs 3 and 2 on Vβ.

Figures 2A, 2B:
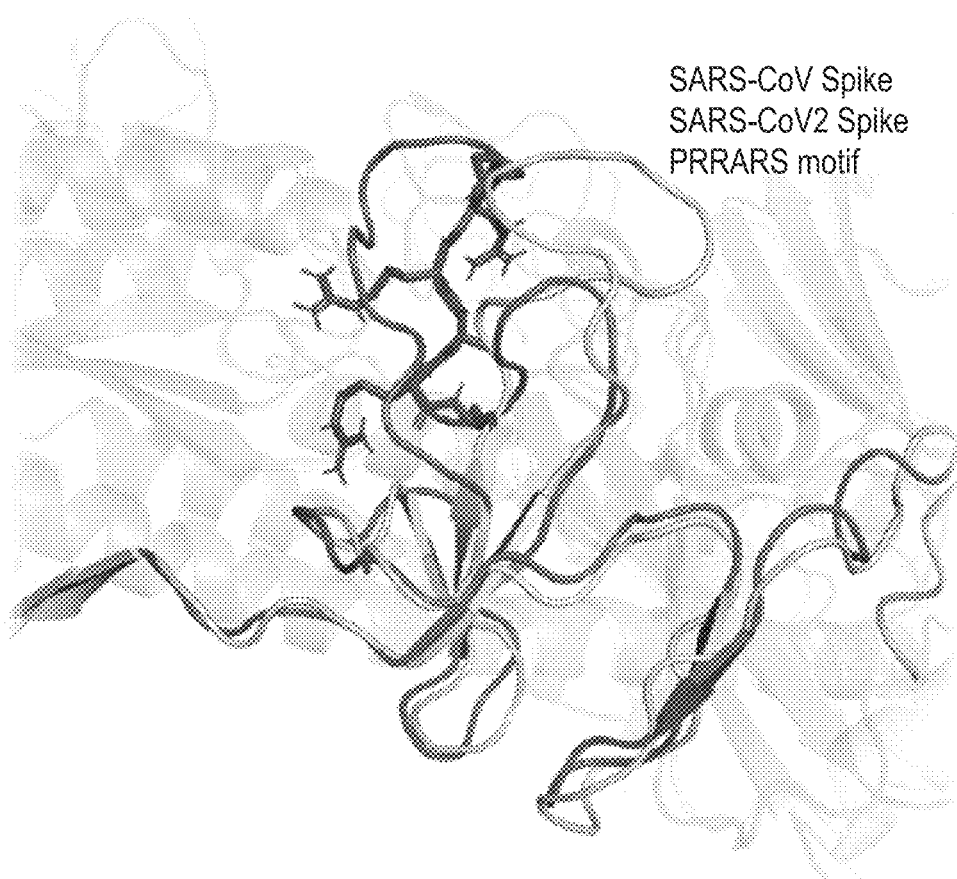
FIGS. 2A-2B show that SARS-CoV-2 encodes both a cleavage site (1) and neurotoxin motifs (J. P. Changeux, et al. (2020)) near the insertion PRRA (SEQ ID NO:2) that distinguishes it from SARS-CoV.

The TCRVβ-binding epitope on SARS-CoV-2 S is centered around a sequence motif, $P_{681}RRA_{684}$ (SEQ ID NO:2) (or shortly PRRA, hereafter), and its sequential and spatial neighbors. Comparison of SARS-CoV-2 S to other beta-coronavirus spike protein sequences showed (20) that SARS-CoV-2 is distinguished by the existence of this four-residue insertion, PRRA, preceding the furin cleavage site (R685-5686 peptide bond) between the subunits S1 and S2 of each protomer (FIG. 2A). Structural comparison of the trimeric S proteins between SARS-CoV and SARS-CoV-2 further shows their close structural similarity in general (except for the RBD which is engaged in specific interfacial interactions (D. Wrapp et al. (2020)), but the two spikes significantly differ near the PRRARS motif unique to SARS-CoV-2, which is exposed to the extracellular medium (FIG. 2B).

Notably the exposure of this motif and its close sequential neighbors is further accentuated in the S1 trimeric form (FIG. 2D) shed after cleavage by the human proteases (TMPRSS2 or furin) to enable the activation of the fusion trimer (composed of three S2 subunits).

Example 4. Further Examination of the Motif Near PRRA Reveals Close Structural Similarity to the SEB Superantigen as Well as Sequence Similarities to Neurotoxins and a Viral SAg The insertion PRRA (SEQ ID NO:2) together with the sequentially preceding seven amino acids and succeeding Arg (fully conserved among β-coronaviruses) have been pointed out to form a motif, $Y_{674}QTQTNSPRRAR_{685}$ (SEQ ID NO:48), homologous to that of neurotoxins from *Ophiophagus* (cobra) and *Bungarus* genera, as well as neurotoxin-like regions from three RABV strains (J. P. Changeux, et al. (2020)) (FIG. 2C). Further, the same segment bears close similarity to HIV-1 glycoprotein gp120 superantigenic motif F164-V164.

This close sequence similarity to both bacterial and viral SAgs, in support of the potential superantigenic character of the amino acid stretch Y674-R685 of SARS-CoV-2 S led to further analyze its local sequence and structural properties. This analysis led to an interesting sequence similarity between the partially overlapping fragment T678-Q690 of the spike and the SEB superantigenic peptide $Y_{150}$NKKKATVQELD$_{161}$ (SEQ ID NO:112) (FIG. 3A). This dodecapeptide sequence within the SEB shows strong conservation among a broad range of staphylococcal and streptococcal SAgs (G. Arad et al. (2011), A. Popugailo, et al. (2019)). The sequentially aligned segment of SARS1 (S664-K672) bears minimal similarity to the SEB SAg (FIG. 3A left). What is even more interesting is that SARS-Cov-2 motif showed a palindromic behavior with respect to the superantigenic SEB sequence in the sense that a broader stretch, from E661 to R685, can be aligned to the superantigen peptide in the reverse direction as well (FIG. 3A right). This brings to the attention that the versatility and high propensity of the SARS-CoV-2 S TCRVβ-binding site residues to potentially act as a superantigenic fragment.

Significantly, the structures of the two peptides exhibit a remarkable similarity (FIGS. 3B-3C), including a salt bridge stabilizing each structural motif (E159-K152 in SEB and E661-R685 in SARS-CoV-2 S), the relative orientations of three positively charged residues (K152-K153-K154 in SEB and R682-R683-R685 in SARS-CoV-2 S), and an asparagine (N151 in SEB, N679 in SARS-CoV-2) completes this motif. All three features are absent in SARS1 S (FIG. 3D). A β-hairpin that apparently serves as a scaffold is conserved in all three spikes, and we observe a pair of cysteines that may potentially form a disulfide bond in SARS-Cov-2 and SARS1 spikes (C648-C657 and C662-C671, respectively).

This analysis overall indicates that the segment $T_{678}$NSPRRAR$_{685}$ (SEQ ID NO:4) forms a putatively superantigenic core, consistently aligned against various bacterial or viral SAgs (FIGS. 2C and 3A-3C) with or without the participation of the adjoining amino acids. However, combined broader sequence and structure analysis in FIG. 3A (right) and FIGS. 3B-3C, reveals an even more compelling feature: this putative SAg core is structurally consolidated by spatial proximity to a conserved acidic segment, $E_{661}$CD$_{663}$, which forms a highly stable salt bridge with the polybasic segment PRRAR (SEQ ID NO:114) of SARS-CoV-2 S, much in the same way as to the salt bridge observed in SEB (but not in SARS1 S) complemented by an asparagine shared between SARS-CoV-2 S and SEB (but not SARS1 S), and the SAg character can be conferred by this type of structural scaffolding.

The SEB superantigen peptide $Y_{150}$NKKKATVQELD$_{161}$ (SEQ ID NO:112) has been reported to bind CD28 (G. Arad et al. (2011)), a T cell receptor that provides co-stimulatory signals required for T cell activation and survival. CD28 and TCRV domains share the same (immunoglobulin) fold (FIG. 3E), and the binding mechanism shown in FIG. 1B can be adopted with minor rearrangements to interactions with other Ig-fold molecules including neutralizing antibodies.

Finally, because of the homologous superantigenic segment of SEB binding CD28, the potential binding of SARS-CoV-2 spike E661-R685 onto CD28 was also tested, considering the possibility that the target of SARS2 spike superantigenic segment is CD28. The simulations indicated that the same segment can equally bind to CD28, further supporting the strong propensity of the fragment to stimulate T cell activation.

Example 5. An ICAM-1 Like Motif Shared Between SARS1 and SARS-CoV-2 Spikes Interacts with TCRVα to Further Stabilize the S-TCR Complex The existence of potential superantigenic, toxic or intercellular-adhesion molecule (ICAM)-like sequence fragments in SARS1 was thoroughly examined by Li et al. following the 2003 pandemic (Y. Li et al. (2004)). This led to the identification of the nine sequence stretches including three *Botulinum* neurotoxin type D or G precursors, and two motifs that have a high similarity with the intercellular adhesion molecule 1 (ICAM-1). Comparative analysis with SARS-CoV-2 spike sequence revealed that seven of these sequence motifs are conserved between SARS-CoV and SARS-CoV-2 (with >68% sequence identity) (FIG. 6). Among them, $Y_{279}$NENGTITDAVDCALDPLSETKC$_{301}$ (SEQ ID NO:67), an ICAM-1 (CD54)-like motif, also participates in the association between the SARS-CoV-2 spike and the bound αβTCR (see FIG. 4).

Figure 4A:
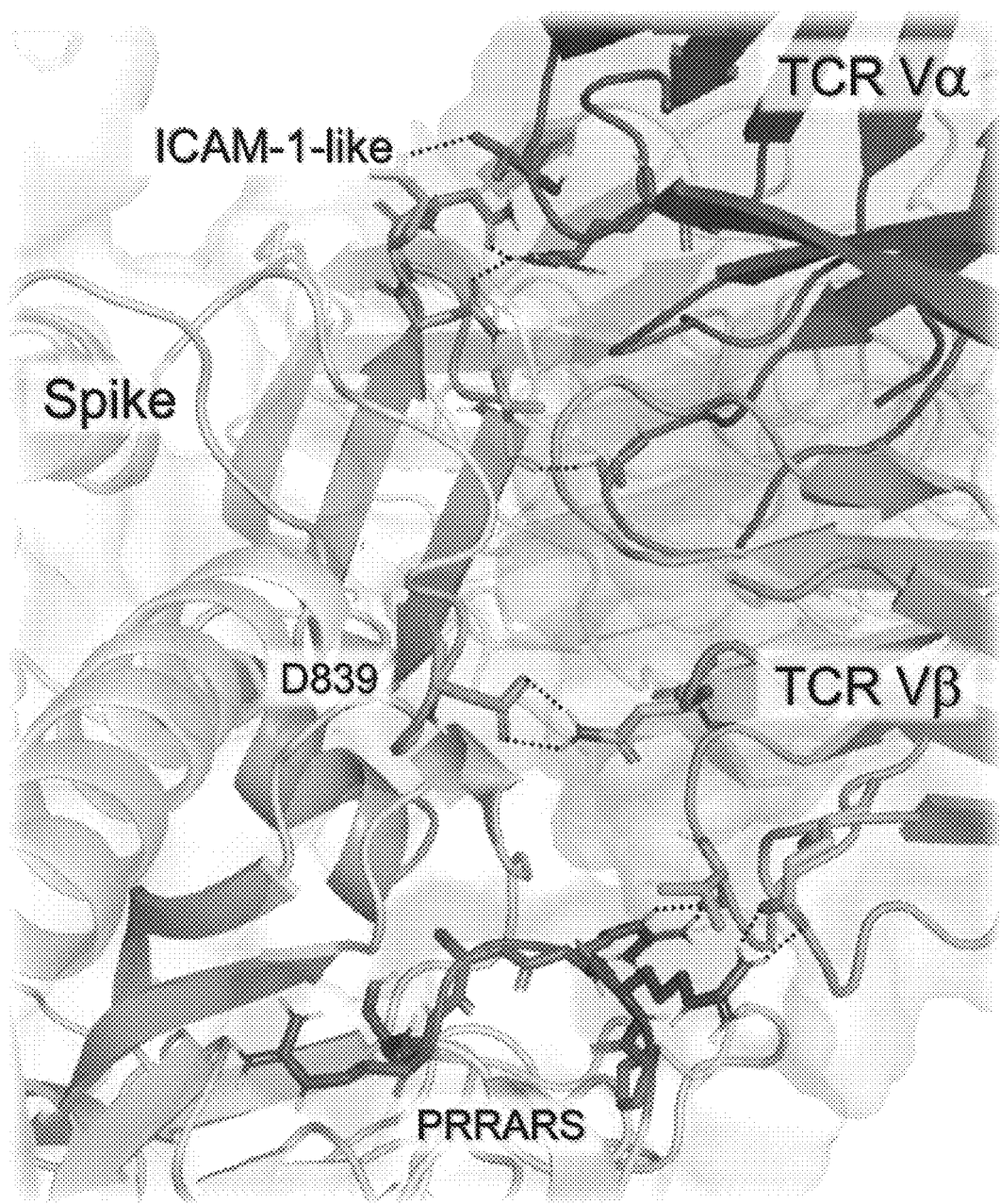
Figure 4B:
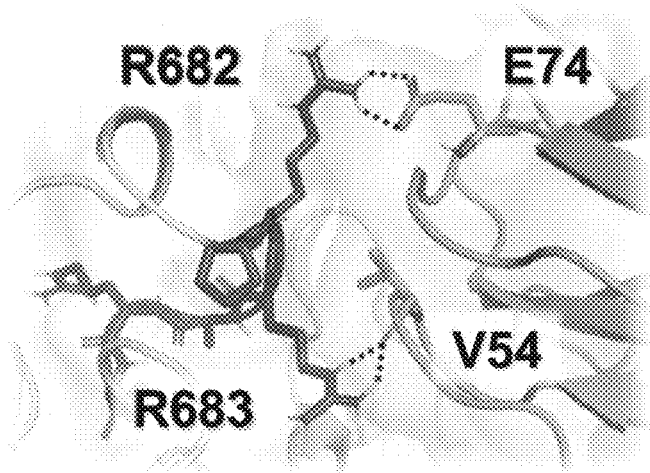
Figure 4C:
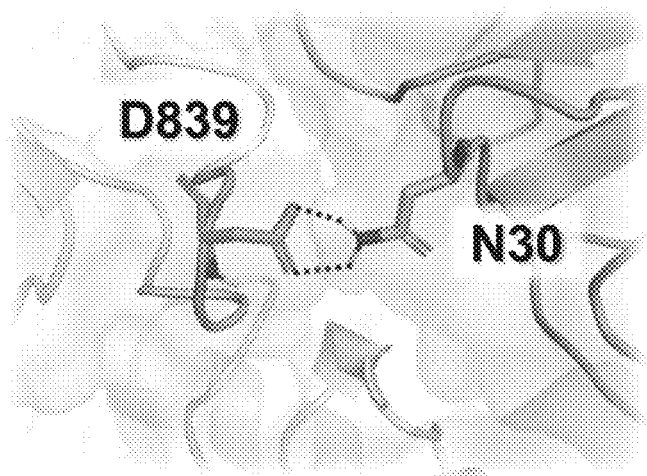
Figure 4D:
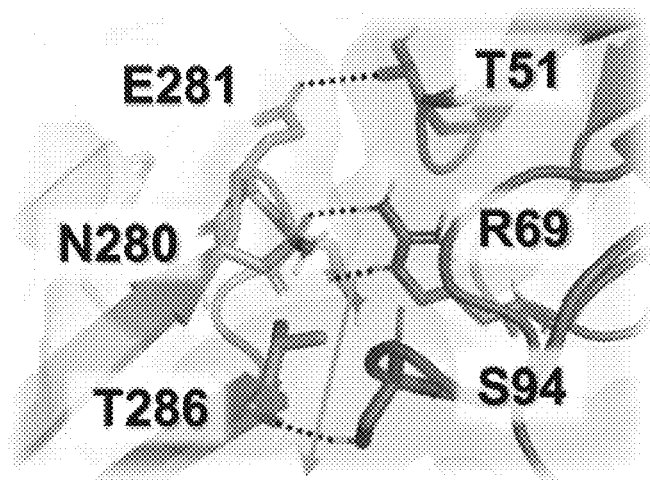
Figure 5A:
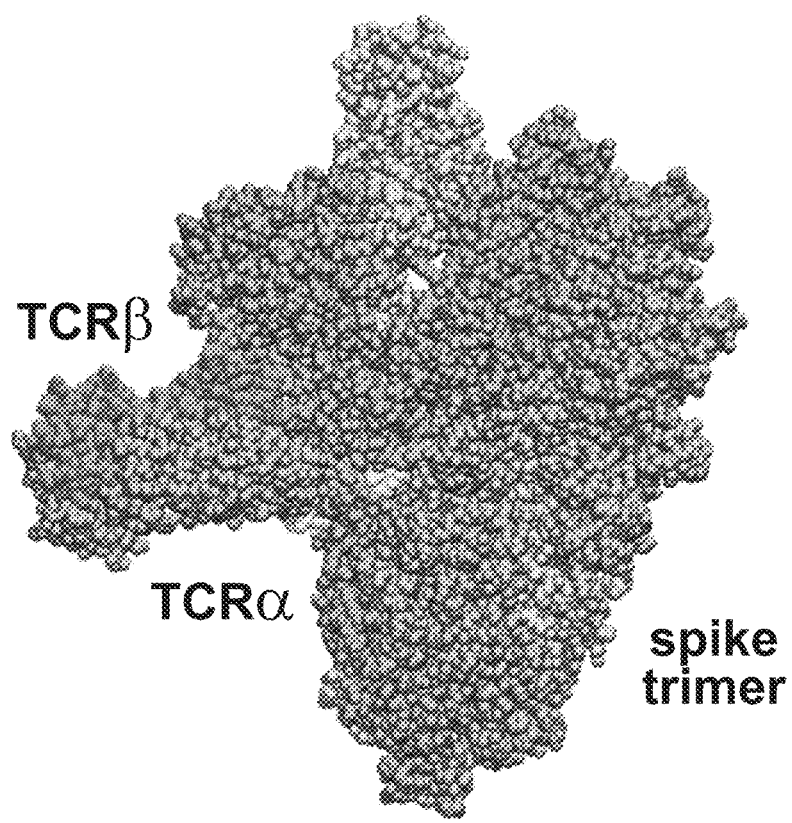
Figure 5B:
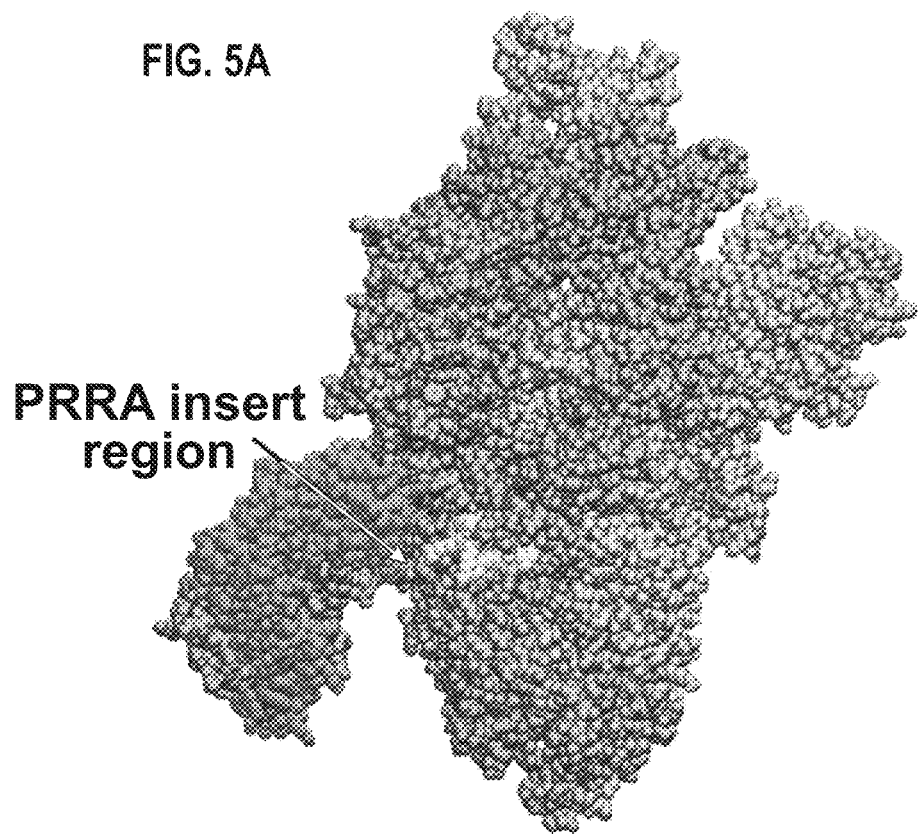
Figure 5C:
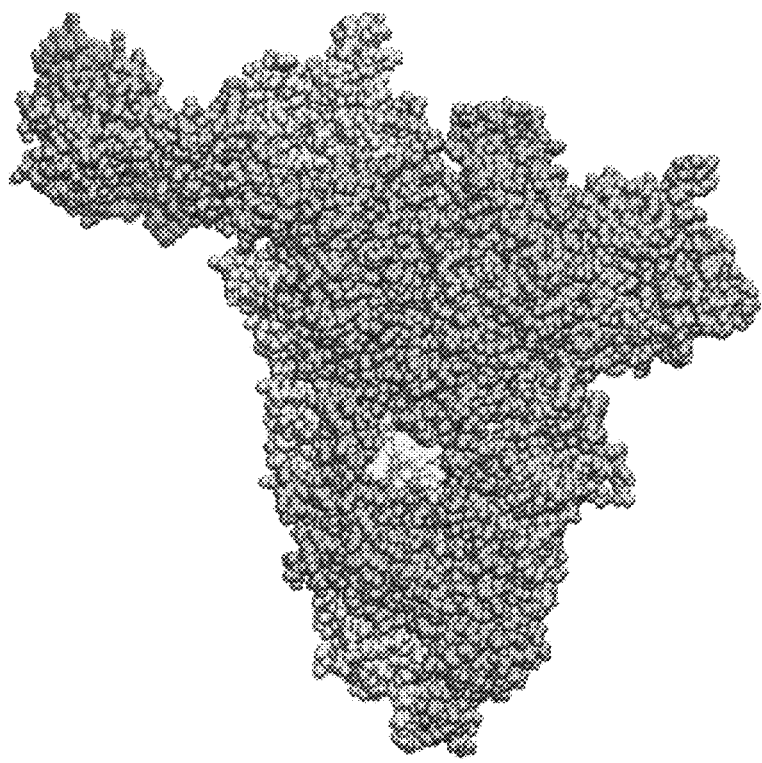
Figure 5D:
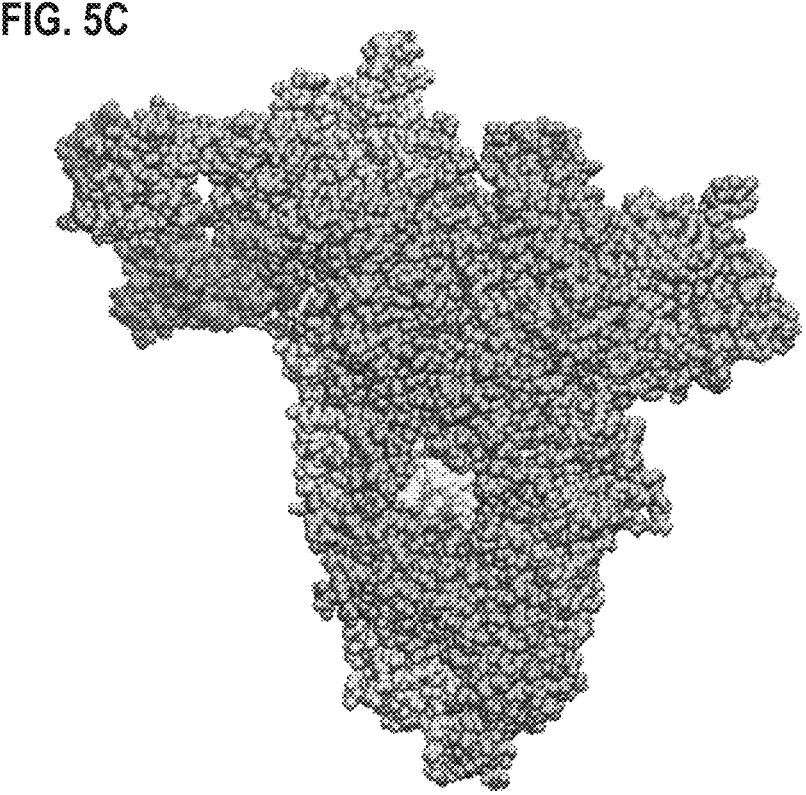

ICAM-1 involvement is critical to mediating immune and inflammatory responses. The observed interaction of the ICAM-1-like motif of SARS-CoV-2 S with TCRVα, in tandem with the interaction of the above discussed putative SAg motif (around the insert PRRA) with TCRVα, is to further strengthen the association of the virus with the T cell and the ensuing activation. Precisely, N280-E281-N282 and T286 belonging to the ICAM-like fragment closely interact with the TCRVα CDRs; mainly T286 (spike) makes close contacts with S94 (CDR3), E281 (spike) forms a hydrogen bond with T51 (CDR2), and N280 and N282 (spike) closely associate with R69 (FIG. 4D).

Figure 8A:
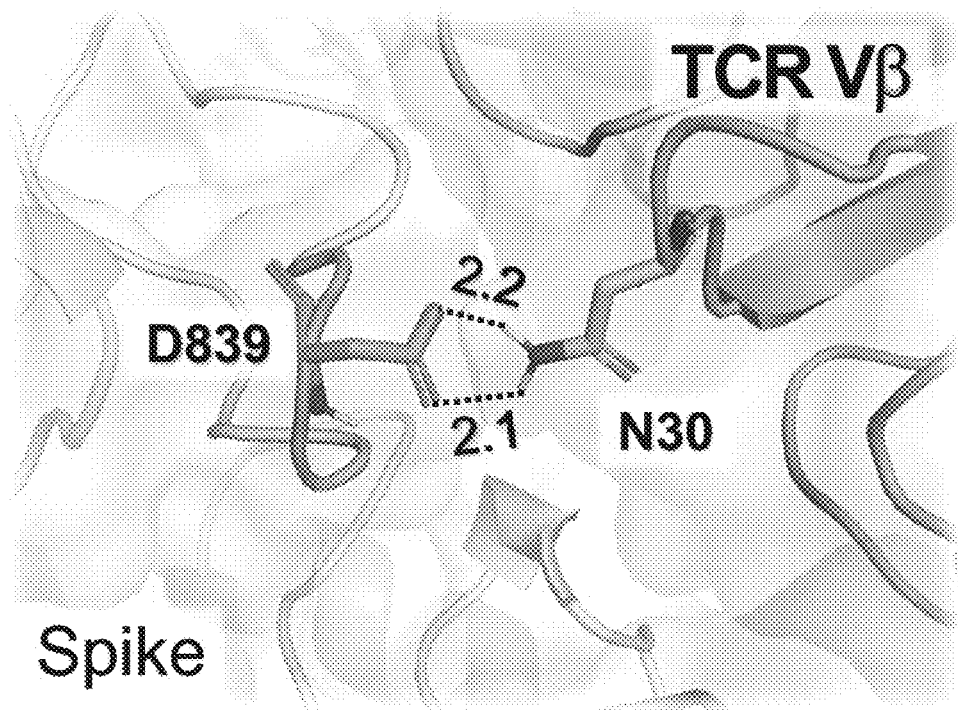
Figure 8B:
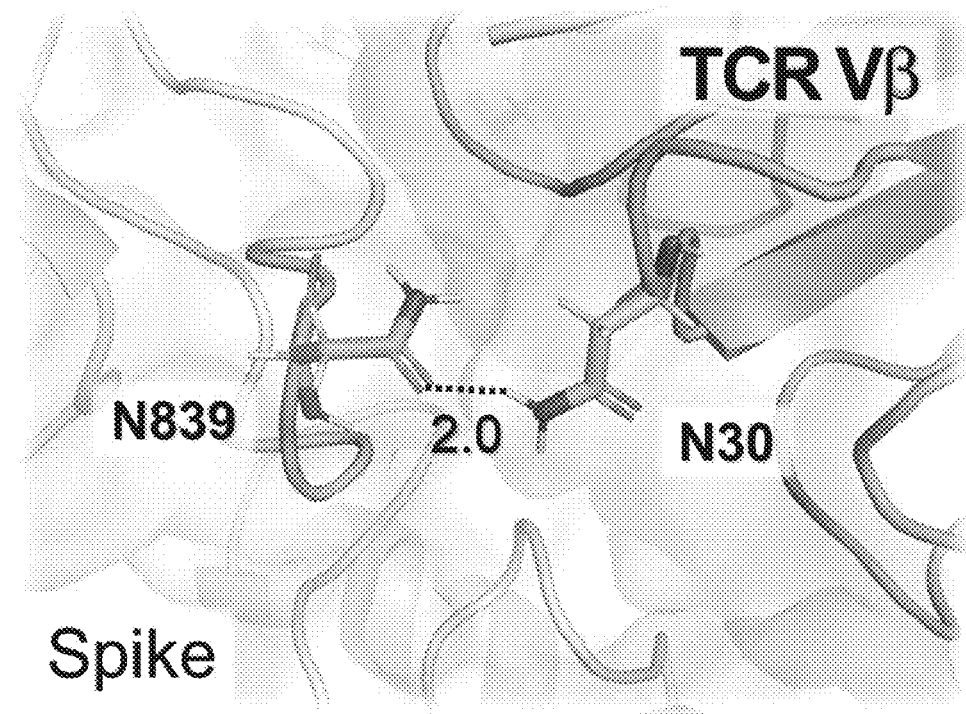
Figure 8C:
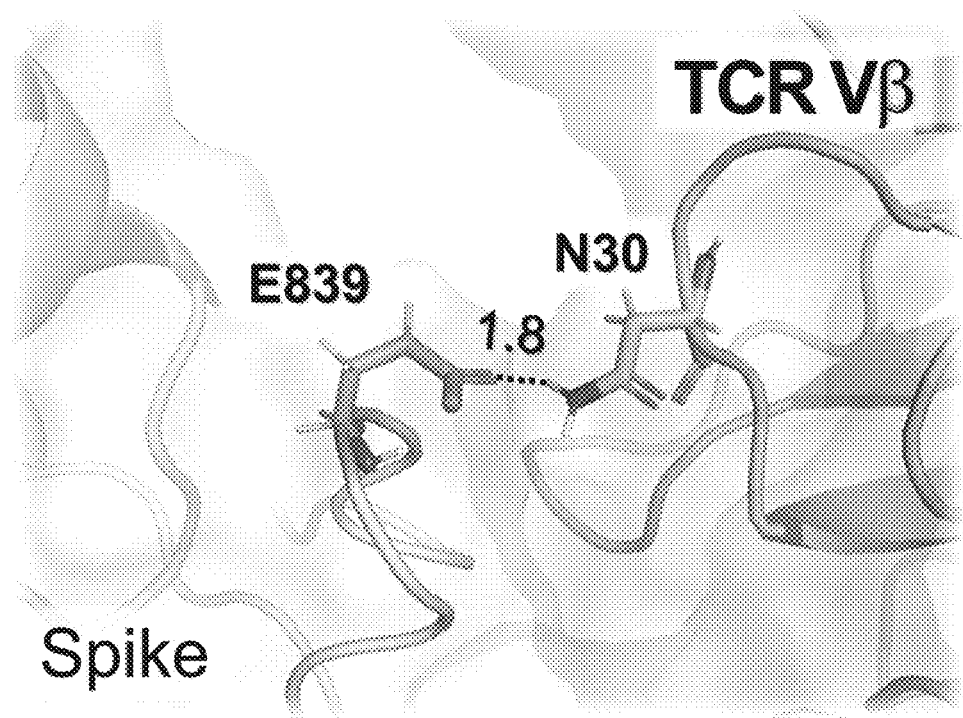
Figure 8D:
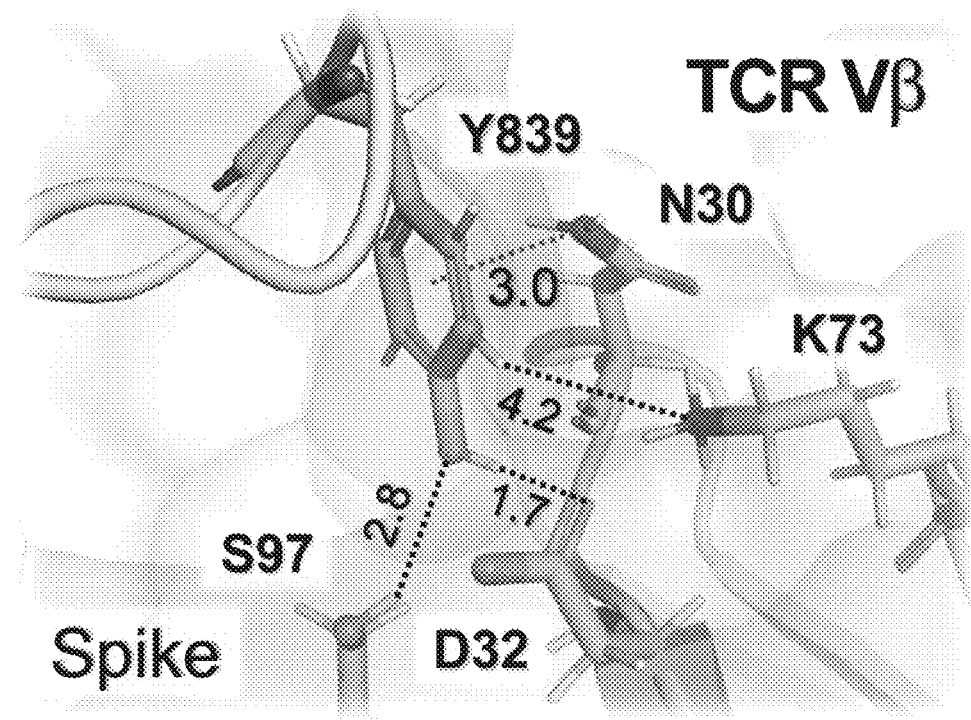

Example 6. A Rare Mutation, D839Y/E, Recently Observed in a SARS2 Strain from Europe Contributes to Stabilizing the Interaction with TCR The SARS-CoV-2 spike binding region harbors three residues that have been recently reported to have mutated in new strains from Europe and USA (S. H. Zhan, et al. (2020), B. Korber et al. (2020)): D614G, A831V and D839Y/N/E). The former two may potentially interact with MHCII; while the latter (D839, European strain) is located close to TCRVβ and strongly interacts with N30; (FIGS. 4A and 4C, and FIGS. 7 and 8A). Its substitution by glutamate in the mutant D839E increases the strength of the intermolecular (and thereby virus-T cell) association (FIG. 8C). Even stronger interactions between spike and TCRVβ are observed upon replacing D839 with a tyrosine as illustrated in FIG. 8D: The interfacial interactions in this case are further stabilized by a hydrogen bond between Y839 and D32; an aromatic (polar-π) interaction between Y839 and N30; as well as electrostatic interactions with K73 and S97. Quantitative evaluation of the change in binding affinity between the spike and TCR upon mutating D839 to Y, E and N yields $\Delta\Delta G_{D\to Y}$=−2.2 kcal mol$^{-1}$, $\Delta\Delta G_{D\to E}$=−2.1 kcal mol$^{-1}$, and $\Delta\Delta G_{D\to N}$=−1.3 kcal mol$^{-1}$ respectively (see Table 2 for details). Thus, the D839Y/N/E mutations strengthen/support the above described association between the superantigenic PRRA-containing segment and the TCRVβ. The change in binding affinity between the spike and TCR upon mutating D839 to tyrosine is $\Delta\Delta G_{D\to Y}$=−0.9±0.7 kcal/mol, indicating approximately 4-fold increase in binding affinity upon substituting the aspartic acid by a tyrosine at this position. The same qualitative effect is valid, but to a weaker extent in the mutations to asparagine or glutamic acid. See Table 3 therein for details on the method and results.

TABLE 2

Binding affinities predicted for the interactions between the αβTCR
and SARS-CoV-2 spike before/after the point mutation D839Y/N/E.

| | Aspartic Acid (D) | | Tyrosine (Y) | | Glutamic Acid (E) | | Asparagine (N) | |
|---|---|---|---|---|---|---|---|---|
| | ΔG (kcal mol$^{-1}$) | $K_d$ (nM) | ΔG (kcal mol$^{-1}$) | $K_d$ (nM) | ΔG (kcal mol$^{-1}$) | $K_d$ (nM) | ΔG (kcal mol$^{-1}$) | $K_d$ (nM) |
| Full complex | −11.0 | 18 | −13.2 | 0.46 | −13.1 | 0.56 | −12.3 | 2.3 |
| S subunit - TCR Vβ | −8.8 | 580 | −10.3 | 53 | −10.1 | 80 | −9.5 | 190 |

\* Binding affinities (ΔG) and dissociation constants (Kd) were obtained at 37° C. using PRODIGY server (Vangone, A. & Bonvin, A. M. (2015), Xue, L. C., et al. (2016)).

Example 7. A Neurotoxin-Like Fragment at the RBD can Also Bind αβTCR Thus Further Enhancing the Immune Response Further examination of the SARS-CoV-2 S segments sequentially homologous to the neurotoxinlike sequences identified (S. H. Zhan, et al. (2020)) for SARS1 S (rows highlighted in green in FIGS. 7 and 10) pointed to two motifs conserved between the two CoVs: SARS-CoV-2 S residues 299-351 partially overlapping with the RBD and S2 subunit residues 777-807. The simulations in search of possible binding poses of TCR on the two CoVs indicated the RBD to be the 2nd highest affinity site (after the PRRA region) in SARS-CoV-2 S, and the 1st in SARS1 S. FIG. 10C illustrates such complexes. Thus, the exposure of a neurotoxin-like sequence on the RBD deserve attention as a possible source of CNS disorders in COVID-19 patients.

A recent study (Mateus J, et al. (2020)) detected significant T cell reactivity against 66 epitopes on the SARS-CoV-2 S glycoprotein in people who have not been exposed to the virus, inviting attention to memory response acquired upon exposure to human CoVs (HCoVs) such as common cold HCoV-OC43, -HKU1, -NL63, and -229E, which share sequence homology with SARS-CoV-2 genome. A total of 142 such cross-reactive epitopes were identified upon screening 474 peptides in the SARS-CoV-2 proteome (Mateus J, et al. (2020)).

The next experiment examined whether the neurotoxin-like regions identified here were among these cross-reactive epitopes. Notably, of the top-ranking four epitopes (ranked by T cell reactivity measured by spot-forming cells (SFC)/10$^6$ PBMCs), two (peptides 321-335 and 316-330) belong to the neurotoxin-like fragment T299-Y351, and one (236-250) to 234-262. In fact, the former was completely spanned by eight partially overlapping cross-reactive epitopes as illustrated in the FIG. 13, pointing to the distinctive ability of this region to trigger CD4$^+$ T cell response. These observations provide strong support to the predicted high affinity of this motif to bind TCR (FIG. 10C). Overall, this neurotoxin-like sequence T299-Y351 deserves attention as a source of CNS disorders in COVID-19 patients.

Among the 66 epitopes, we note 661-675, which lies within the SAg-like region E661-R685 (FIG. 3), albeit at low reactivity and frequency. The insert PRRA (SEQ ID NO:2) among the cross-reactive epitopes is absent. This insert is unique to SARS-CoV-2 S among all SARS-related l3CoVs, and cross-reactivity increases with sequence similarity to antigens/peptides to which the donors have been already exposed to. The sequence identity between SARS-CoV-2 and SARS1 is 40% in the portion 671-685 of the SAg-like region, and the percentage of cross-reactive peptides having 33-40% sequence identity is reported to be 1% (Mateus J, et al. (2020)). On the other hand, it is interesting to note that in a recent study (Sekine T, et al. (2020)) on epitopes that show strong T cell reactivity in convalescent patients who experienced severe COVID-19, an epitope (680-688) overlapping with the PRRA-containing part of SAg region is predicted to be one of the highest affinity epitopes binding to HLA.

Example 8. A Rare Mutation, D839Y/E, Recently Observed in a SARS2 Strain from Europe May Contribute to Stabilizing the Interaction with TCR The SARS-CoV-2 S binding region harbors three residues that have been recently reported to have mutated in new strains from Europe and USA (Korber B, et al. (2020), Zhan S H, Deverman B E, & Chan Y A (2020)): D614G, A831V and D839Y/N/E. The former two may potentially interact with MHCII based on a ternary model we generated for SARS-CoV-2 S, MHCII and TCR (FIG. 7), while the latter (D839) is close to TCRVβ and strongly interacts with N30 (FIGS. 4A and 4C, and FIG. 8). The substitution of D839 by tyrosine strengthens the interactions between the spike and TCRVβ. The interfacial interactions in the D839Y mutant are stabilized by a hydrogen bond between Y839 and D32, an aromatic (polar-it) interaction between Y839 and N30, as well as electrostatic interactions with K73 and S97. The change in binding affinity between the spike and TCR upon mutating D839 to tyrosine is $\Delta\Delta G_{D \rightarrow Y}=-0.9\pm0.7$ kcal/mol, indicating approximately 4-fold increase in binding affinity upon substituting the aspartic acid by a tyrosine at this position. The same qualitative effect is valid, but to a weaker extent in the mutations to asparagine or glutamic acid. See Table 3 therein for details on the method and results.

Example 9. TCR Repertoire Analysis Shows TCRVβ Skewing and Junctional Diversity Indicating SAg Effect in Patients with Severe and Hyperinflammatory COVID-19

SAg binding to specific TCR Vβ chains results in Vβ skewing, such that T cells with specific Vβ chains and diverse antigen specificity dominate the TCR repertoire(Li H, Llera A, Malchiodi E L, & Mariuzza R A (1999), Scherer M T (1993)). If the motif identified in SARS-CoV-2 S acts as a SAg, it can be reasoned that patients with mild/moderate COVID-19 disease courses and recovery without hyperinflammation show adaptive immune responses mediated by T cells recognizing SARS-CoV-2 epitopes in a CDR3-mediated fashion; whereas patients with severe/hyperinflammatory COVID-19 would show immune responses consistent with at least partial SAg recognition. NGS immunosequencing data from 38 patients (42 samples) with mild/moderate COVID-19 and 8 patients (24 samples) with severe, hyperinflammatory COVID-19, which were part of a previously studied cohort (Schultheiss C, et al. (2020)). Principal component analysis (PCA) of the TCR β-chain variable gene (TRBV) repertoires corresponding to the two groups revealed that patients with mild/moderate COVID-19 course clustered apart from those with severe/hyperinflammatory COVID-19 (FIG. 12A).

Differential gene usage analysis showed that several TRBV genes were overrepresented in the severe/hyperinflammatory COVID-19 patient group (FIG. 12B). In contrast, PCA of J gene distribution showed much less skewing, indicating a selective pressure was preferentially exerted on the V gene distribution (FIG. 12C). To further investigate J gene diversity specifically for the V genes overrepresented in the severe/hyperinflammatory COVID-19 cases, all J genes rearranged with TRBV5-6, TRBV13, TRBV14 and TRBV24-1 were extracted from the repertoires of severe/hyperinflammatory COVID-19 patients and compared to J genes extracted from the age-matched healthy donors. This analysis showed very diverse TRBJ gene distribution, showing CDR3 diversity in the respective expanded rearrangements (FIG. 14).

Together, these results show that patients with severe and hyperinflammatory COVID-19 show expansion of TCRs using distinct V genes, along with J gene/CDR3 diversity in these rearrangements, compatible with a SAg selection process.

Example 10. TCRs Corresponding to TRVB Genes Activated in Severe COVID-19 Patients can Bind to the SAg-Like Region of SARS-CoV-2 S Finally, next experiment studied structurally resolved TCRs that contained Vβ chains encoded by the genes TRBV5-6, TRBV13, TRBV14 and TRBV24-1 enriched in severe/hyperinflammatory COVID-19 patients. Whether these TCRs could bind the SAg-like region E661-R685 of the SARS-CoV-2 S similarly to the TCR in FIG. 1 was tested. The PDB search yielded αβTCR structures corresponding to TRBV5-6, TRBV14 and TRBV24-1, i.e. TCRs whose Vβ chains were 95-100% identical to the protein product of these three genes. As shown in, FIG. 15, all three were verified to bind the SAg-like site with high-affinity, and to make interfacial interactions closely resembling those illustrated in FIG. 1. The models and simulations herein also indicated energetically favorable ternary complex formation between these TCRs, MHCII and spike. Overall, these simulations showed that these TCRs enriched in severe/inflammatory COVID-19 patients can bind the SARS-CoV-2 S at its SAg-like region and form ternary complexes with MHCII.

Example 11. Discussion

An understanding of the immunopathology leading to severe manifestations of COVID-19, in both adults and children, is of critical importance for effective management and treatment of the disease. MIS-C shows remarkable similarity to pediatric TSS (S. Riphagen, et al. (2020), L. Verdoni et al. (2020), Z. Belhadjer et al., (2020), D. E. Low, (2013), A. Cook, et al. (2020)). Using in silico modeling and analysis, it was found that SARS-CoV-2 encodes a superantigen motif near its S1/S2 cleavage site. This region is highly similar in structure to the SEB SAg motif that interacts with both the TCR and CD28 (G. Arad et al. (2011)) and mediates TSS. SEB enables large-scale T cell activation and proliferation, resulting in massive production of pro-inflammatory cytokines including IFNγ, TNFα and IL-2 from T cells as well as IL-1 and TNFα from APCs (T. Krakauer (2019)). This cytokine storm leads to multi-organ tissue damage similar to what is now observed in MIS-C. We therefore propose that MIS-C observed in COVID-19 patients may be mediated by superantigen activity of the SARS-CoV-2 S protein. Furthermore, these findings show that the hyperinflammation observed in severe cases of COVID-19 in adults can also be driven by the SAg-like activity of the S protein. Indeed, SAgs induce an inflammatory cytokine signature similar to that which predicts severity and death in COVID-19, including IL-6, TNFα, IL-8 and IL-10 (Krakauer T (2019), Del Valle D M, et al. (2020)). Moreover, the analysis of the T cell immune response in COVID-19 patients shows that those with more severe and hyperinflammatory clinical courses exhibit TCRVβ skewing consistent with SAg activity.

To date, MIS-C is mostly observed in Europe and East Coast of North America, and has not been described in Asia, despite sizeable outbreaks of COVID-19 (S. Riphagen, et al. (2020); L. Verdoni et al. (2020); Z. Belhadjer et al. (2020)) (CDC and ECDC). It is shown herein that a mutation at D839 found in a European strain of SARS-CoV-2 enhances the binding affinity of the SAg motif to the TCR. This can explain the geographical skewing of MIS-C to areas where the European strain is endemic, and identification of other strain-specific mutations helps predict where future outbreak of MIS-C may occur.

A study of SARS1 immunogenicity, conducted with a cohort of 128 individuals who have recovered from SARS1 (Li C K, et al. (2008)), showed that the SARS1 spike 18-mer D649-L666 (DIPIGAGICASYHTVSLL, SEQ ID NO:113) is one of the peptides most frequently recognized by T cells, among the screened 1,843 peptides that span the whole SARS1 CoV proteome (Table III in Li et al (Li C K, et al. (2008))). This segment coincides with the SARS1 S region E647-R667 that is sequentially (and structurally) homologous to our SARS-CoV-2 spike SAg-like motif E661-R685 (FIG. 3A, bottom alignment). This provides a very strong support for the T cell stimulatory ability of the SAg motif, given that it shares 12/18 amino acids with that SARS1 18-mer. And the remaining amino acids (including the insert PRRA, not present in SARS1 S) would endow even stronger superantigenic properties by virtue of their close similarity to the aligned SEB fragment.

These findings indicate that immunomodulatory therapeutic options used for TSS can also be effective for MIS-C, including IVIG and steroids. Given structural similarities between SEB and the S protein SAg motif, cross-reactivity of these immunoglobins explains that at least in part the response of MIS-C cases to IVIG. Other FDA-approved anti-inflammatory drugs tested in models of SEB TSS can also be effective, including CTLA4-Ig which can inhibit CD28 co-stimulation (S. J. Whitfield et al. (2017)), and the mTOR inhibitor rapamycin (T. Krakauer, et al. (2010)), which is already in use for COVID-19. In addition, humanized monoclonal anti-SEB Abs have been described (E. A. Larkin, et al. (2010)) that can also be of therapeutic benefit in MIS-C patients. Notably, it has been shown in the mouse model of TSS that lethal SEB superantigen challenge can be prevented by short peptide mimetics of its superantigen motif (G. Arad et al. (2011)). Short peptide mimetics of SARS-CoV-2 spike superantigen region can be employed to prevent/attenuate inflammatory cytokine gene induction and toxic shock in MIS-C patients.

At present, the majority of antibody therapies under investigation are designed to target the SARS-CoV-2 receptor binding domains (RBDs) (M. Yuan et al., (2020), X. Chi et al. (2020)), and the simulations also indicated that RBD might potentially interact with TCRs. However, compared with RBDs, relatively fewer mutations are found in the SAg region of SARS-CoV-2; notably, the "PRRA" insert is unique to SARS-CoV-2 and retained among all of its isolates sequenced to date (S. H. Zhan, et al. (2020), B. Korber et al., (2020)). It is constructive to design antibodies or drugs targeting this SAg region, to not only block the cleavage essential to enabling viral entry (A. C. Walls et al. (2020), M. Hoffmann et al. (2020)) and modulate the SAg-induced inflammatory cytokine gene induction (T. Krakauer (2019)), but also block the cleavage essential to enabling viral entry (Walls A C, et al. (2020), Hoffmann M, et al. (2020)). Alternatively, combination therapies that target both the SAg-like region and the RBD can prove useful.

Fortunately, severe respiratory manifestations of COVID-19 in children as well as development of MIS-C are rare. This is due to trained immunity (L. Cristiani et al. (2020)) or cross-viral immunity to other coronavirus strains (A. Grifoni, et al. (2020)). T and B cells play an important role in the anti-viral response. CD4+ and CD8+ T cells from convalescent COVID-19 patients can recognize a range of SARS2 epitopes, and the S protein represents a major target (A. Grifoni, et al. (2020)). T cells from unexposed individuals can also respond to S protein epitopes from SARS-CoV-2, which supports the hypothesis of cross-viral immunity from other coronavirus strains (A. Grifoni, et al. (2020)). However, why only a fraction of infected children develop MIS-C is unclear. The present study shows that the mutation D839Y found in a European strain of SARS-CoV-2 enhances the binding affinity of the SAg motif to the TCR. This can explain the geographical skewing of MIS-C to areas where the European strain is endemic. A poor initial antibody response to the virus fails to neutralize the SAg, as recently shown in MIS-C patients (Weisberg S P, et al. (2020)), leading to immune enhancement following re-exposure. Certain HLA types are more permissive of binding SAg, and indeed HLA has been shown to play a role in COVID-19 susceptibility (Nguyen A, et al. (2020)). Of the nine cases initially reported in the UK, six were of Afro-Caribbean descent, which also suggests a potential genetic component to susceptibility (Riphagen S, et al. (2020)). In addition, approximately 80% of individuals over age 12 harbor anti-SEB antibodies (LeClaire R D & Bavari S (2001), McGann V G, Rollins J B, & Mason D W (1971)), which may provide protection against the SAg effects of SARS-CoV-2 S protein. The prevalence of preexisting anti-SEB antibodies can also contribute to the age distribution of severe COVID-19 cases in adults, as protective SEB titers fall in older adults after age 70.

Approximately a third or fewer of MIS-C patients tested positive for the SARS-CoV-2, but the majority (but not all) have serologic evidence of infection or a history of exposure to COVID-19 (S. Riphagen, et al. (2020); L. Verdoni et al. (2020); Z. Belhadjer et al. (2020)). This indicates that the SARS-CoV-2 SAg causes a delayed hyperinflammation response in certain children. SAgs have been implicated in autoimmunity by triggering self-reactive T cells (H. Li, et al. (1999)). Antibody-mediated enhancement upon re-exposure to the virus can also contribute to uncontrolled infection and inflammation (S. M. C. Tirado, K.-J. Yoon (2003)). Despite a negative nasopharyngeal PCR test, the virus can still be present in the gastrointestinal tract (Y. Xu et al. (2020)). MIS-C patients demonstrate unusually severe GI symptoms, abdominal pain, vomiting and diarrhea, in addition to severe myocardial dysfunction and cardiac shock (S. Riphagen, et al. (2020); L. Verdoni et al. (2020); Z. Belhadjer et al. (2020)) and such severe GI symptoms are also frequently associated with the SAg (A. Cook, et al. (2020)). In the case of SEB, cleavage and release of a specific fragment is responsible for induction of GI symptoms. The SARS-CoV-2 SAg-like structure shown herein can be similarly cleaved and underlie the GI symptoms observed in MIS-C patients.

It was also observed that a neurotoxin-like segment (T299-Y351) partially overlapping with the RBD exhibited a high affinity to bind TCRs. Notably, this region was recently observed to elicit strong and frequent T cell reactivity mediated by CD4+ T cells in donors who have not been exposed to SARS-CoV-2 (Mateus J, et al. (2020)). This invites attention to its ability to trigger neurotoxic immune response in individuals who have not been exposed to CoVs that contain sequentially homologous peptides.

In summary, disclosed herein are five major observations: (a) PRRAR and sequential neighbors interact with TCRVβ residues D56, R70 and E74 at the CDRs, and this association closely resembles that of SEB SAg with TCRVβ; (b) nearby D839 participates in this interaction and its mutation to tyrosine further strengthens the association with TCRVβ; (c) a sequence motif (N280-T286) typical of ICAM-1 further interacts with the TCRVα further stabilizing or enhancing the association between the viral spike and host cell TCR; and (d) a neurotoxin-like motif (T299-Y351) shows a high tendency to bind TCRs and trigger neurotoxic responses. This latter effect can be attenuated if the SARS-CoV-2-infected individual has been exposed HCoVs that contain homologous segments, as suggested (Mateus J, et al. (2020)) by a recent study; and (e) adult patients with severe/hyperinflammatory COVID-19 exhibit a skewed TCR Vβ repertoire distinguishing them from patients with mild/moderate COVID-19. Overall, these results from both computational modeling and NGS immunosequencing of TCRBs analysis of human samples indicate that strategies used for the treatment of SEB-mediated TSS or approaches to block the interaction of the S protein with TCRs can help reduce hyperinflammatory manifestations or (neuro)toxic effects of COVID-19 in both adults and children.

Example 12. A Monoclonal Antibody Against Staphylococcal Enterotoxin B Superantigen Inhibits SARS-CoV-2 Entry In Vitro Introduciton Severe acute respiratory syndrome coronavirus 2 (SARS-CoV-2) can cause severe interstitial pneumonia with hyperinflammation (Tay et al., 2020; Vabret et al., 2020), as well as many extrapulmonary manifestations (Gupta et al., 2020). A novel multisystem inflammatory syndrome (MIS), reported in both children (MIS-C) and adults (MIS-A), has been observed in patients that either tested positive for, or had epidemiological links to, COVID-19 (Belhadjer et al.; Cheung et al., 2020; Riphagen et al.; Verdoni et al.). MIS-C manifests as persistent fever and hyperinflammation with multi-organ involvement (Belhadjer et al.; Cheung et al., 2020; Riphagen et al.; Verdoni et al.). The clinical similarity between MIS-C/A and the toxic shock syndrome (TSS) caused by bacterial superantigens (SAgs) led to the hypothesis that SARS-CoV-2 might possess a SAg-like motif that triggers hyperinflammation (Cheng et al., 2020; Noval Rivas et al., 2020). Comparison with bacterial toxins indeed revealed a motif in the SARS-CoV-2 spike (S) protein, the sequence and structure of which highly resemble a segment of a bacterial SAg, staphylococcal enterotoxin B (SEB). SAg-like character of the S protein was further supported by T cell receptor (TCR) skewing typical of reaction to SAgs, which was observed in severe COVID-19 patients (Cheng et al., 2020).

The location of the SAg-like motif in the S protein is worthy of attention. SARS-CoV-2 S is a homotrimer, belonging to the family of human coronaviruses (HCoVs), which includes SARS-CoV and Middle East Respiratory Syndrome (MERS), as well as common cold HCoVs NL63, 229E, OC43 and HKU1 (Coutard et al., 2020; Cui et al., 2019; Forni et al., 2017). Each HCoV protomer is composed of two subunits, S1 and S2, playing different roles in viral infection. S1 contains the receptor-binding domain (RBD) that binds to the host cell receptor (human angiotensin converting enzyme 2 (ACE2) for SARS-CoV-2, SARS-CoV, and HCoV-NL63) (Benton et al., 2020; Hoffmann et al., 2020; Matsuyama et al., 2020; Shang et al., 2020; Walls et al., 2020; Wrapp et al., 2020; Yan et al., 2020); whereas S2 contains the fusion peptide required for viral entry (Coutard et al., 2020; Cui et al., 2019; Forni et al., 2017). The SAg-like motif (residues E661-R685) lies at the C-terminus of S1 (Cheng et al., 2020), at the boundary with S2. Membrane fusion requires two successive cleavages by host cell proteases, one at the S1/S2 interface (peptide bond R685↕S686), and the other at S2' (R815↕S816) (Coutard et al., 2020; Hoffmann et al., 2020; Matsuyama et al., 2020; Shang et al., 2020; Walls et al., 2020; Wrapp et al., 2020; Yan et al., 2020). Thus, the SAg-like region overlaps with the S1/S2 cleavage site of the S protein (FIGS. 16A-16B).

Another feature at the SAg-like region is a unique insertion, $_{681}PRRA_{684}$ (SEQ ID NO:2), immediately neighboring the cleavage site R685↕S686 (FIG. 16A). Loss of these four residues in a mutant ΔPRRA has been recently shown to attenuate SARS-CoV-2 pathogenesis (Johnson et al., 2021). SARS-CoV-2 is the only member of the SARS-family of β-coronaviruses (βCoVs) that has such an insertion (see nine such members sequentially aligned in FIG. 16B; top 9 rows), despite its high sequence similarity with other members of this genus (>80% sequence identity with SARS-CoV). MERS and common cold HKU1 and OC43 S proteins have a similar insertion at that position, despite their low (30-40%) overall sequence identity with respect to SARS-CoV-2 spike (FIG. 16B). The PRRA (SEQ ID NO:2) insert is highly flexible, and together with the adjacent arginine, the segment $_{681}PRRAR_{685}$ (SEQ ID NO:114) forms a highly reactive site. It plays a role in recognizing and binding the host cell proteases transmembrane protease serine 2 (TMPRSS2) and furin, whose cleavage activity is essential to S protein priming (Hoffmann et al., 2020; Shang et al., 2020; Walls et al., 2020; Wrapp et al., 2020). Recent studies further showed the role of S1/S2 site in potentiating infectivity upon binding to the host cell co-receptor neuropilin-1 (Cantuti-Castelvetri et al., 2020; Daly et al., 2020); and our simulations revealed its propensity to bind TCRs (Cheng et al., 2020).

This polybasic site, 681PRRAR685 (SEQ ID NO:114), can thus serve as a target for SARS-CoV-2 S-neutralizing antibodies (Abs). Most SARS-CoV-2 S Abs under investigation target the RBD (and some, the N-terminal domain, NTD) (Cao et al., 2020b; Chi et al., 2020; Hansen et al., 2020; Pinto et al., 2020; Renn et al., 2020; Shi et al., 2020; Yuan et al., 2020). FIG. 16C illustrates the S protein epitopes (colored surfaces) that have been observed by cryo-EM to bind mAbs and ACE2 molecules. The Abs bind various poses/sites depending on the up or down states of the RBDs and their specific sequences (see Table 4). However, these cryo-EM studies were conducted with variants where the polybasic segment $_{682}RRAR_{685}$ (SEQ ID NO:121) has been replaced by GSAS or SGAG (Barnes et al., 2020; Cao et al., 2020b; Chi et al., 2020; Liu et al., 2020; Lv et al., 2020b; Pinto et al., 2020; Zhou et al., 2020a; Zost et al., 2020). Therefore, the ability, if any, of wild type (wt) S protein to bind an Ab near the PRRA (SEQ ID NO:2) insert or the S1/S2 cleavage site can have eluded these experiments. Identification of alternative binding sites for neutralizing mAbs is now increasingly important with the need to design combination mAbs that target different sites, given the ability of newly emerging variants to potentially evade those Abs that target the RBD site (Andreano et al., 2020; Greaney et al., 2021; Kemp et al., 2020; McCarthy et al., 2020).

The present study focuses here on this polybasic site as a target for mAb binding. The recently detected sequence- and structure-similarity between the PRRA-insert-enclosing SAg-like motif and the bacterial toxin SEB indicated that previously generated anti-SEB monoclonal Abs (mAbs) can bind the viral SAg-like motif, and in particular the segment 682RRAR685 (SEQ ID NO:2), and can thus block access to the S1/S2 cleavage site. The in silico examination of the possible interactions of known anti-SEB mAbs (Dutta et al., 2015) with SARS-CoV-2 S revealed that SEB-specific mAb 6D3 has a high affinity for binding to the S1/S2 site. The models further show that the 6D3 binding site overlaps with those of TMPRSS2 and/or furin, indicating that 6D3 can impede viral entry. Experiments conducted with live viruses confirmed that 6D3 inhibited viral entry. Given that its binding site does not overlap with those of known Abs (FIG. 16C), 6D3 can be used in combination with other neutralizing Abs that target the RBD or other non-overlapping sites to increase efficacy.

Results

Anti-SEB antibody 6D3 is distinguished by its high affinity to bind SARS-CoV-2 S SAg-like region. As shown in the recent work (Cheng et al., 2020), the S residues E661-R685 that enclose the polybasic segment $_{681}PRRAR_{685}$ (SEQ ID NO:114) are sequentially and structurally similar to the segment T150-D161 of SEB. Given this strong similarity, it was examined if mAbs specific for SEB (Dutta et al., 2015; Varshney et al., 2011) can neutralize SARS-CoV-2 S. The close proximity (or adjacency) of the SAg-like region to the cleavage bond R685↕S686 further indicated that an anti-SEB mAb that cross-reacts with SARS-CoV-2 can have the added potential to block the cleavage site essential to viral entry, apart from its ability to attenuate the SAg-mediated hyperinflammatory cytokine storm (Krakauer, 2019).

Figures 17A, 17B:
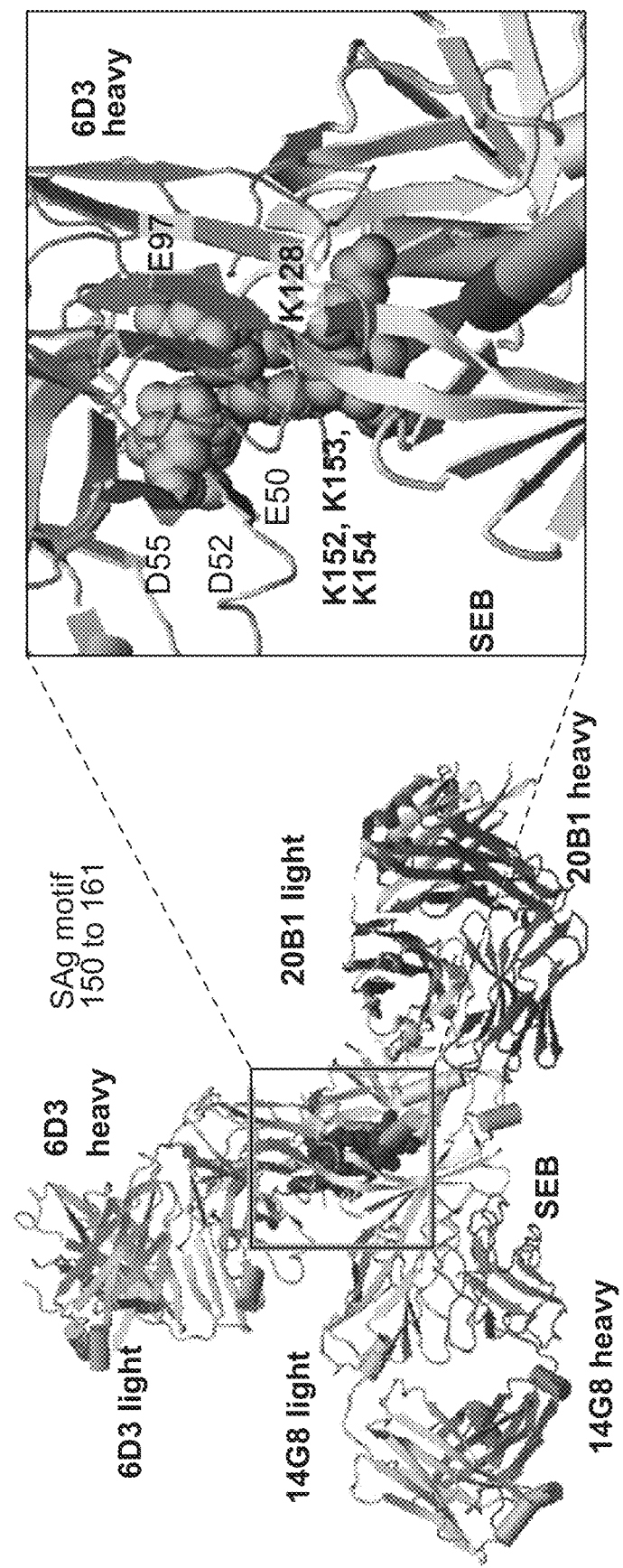
Figure 17C:
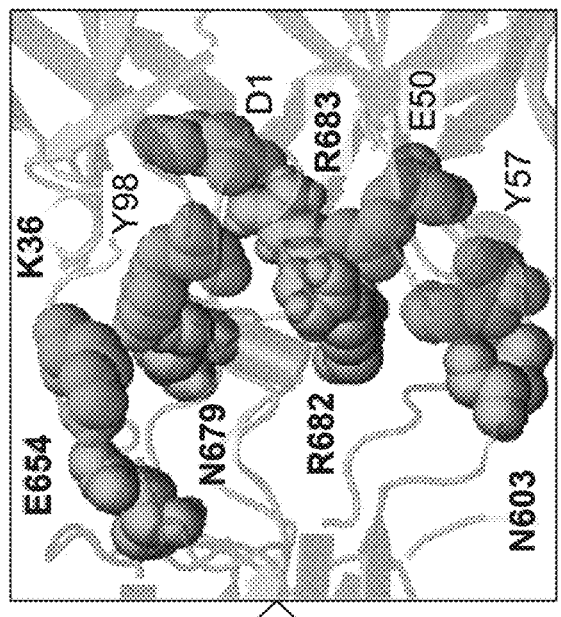
Figure 17D:
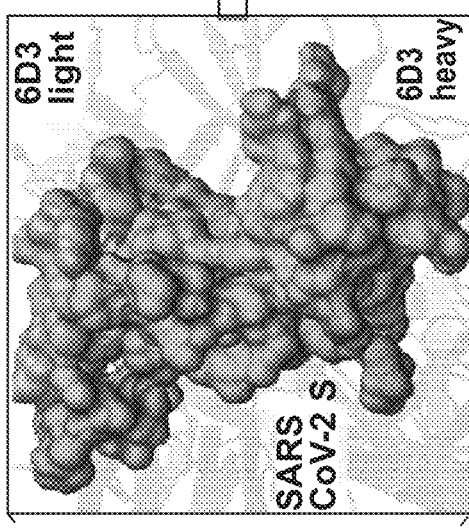

Three SEB-specific mAbs, 14G8, 6D3, and 20B1, have been generated as effective blockers of the SAg activity of SEB in an animal model of TSS (Varshney et al., 2011). Examination of their crystal structures shows that these mAbs bind different sites on SEB (Dutta et al., 2015), as illustrated in FIG. 17A. Notably, only 6D3 targets the SEB polybasic segment T150-D161 (shown in dark blue space-filling representation) that is the counterpart of the SARS-CoV-2 S SAg-like motif (Cheng et al., 2020). A closeup view shows the tight interaction between the acidic residues E50, D52 and D55 of 6D3 heavy chain and four basic residues of SEB (FIG. 17B).

Figure 17E:
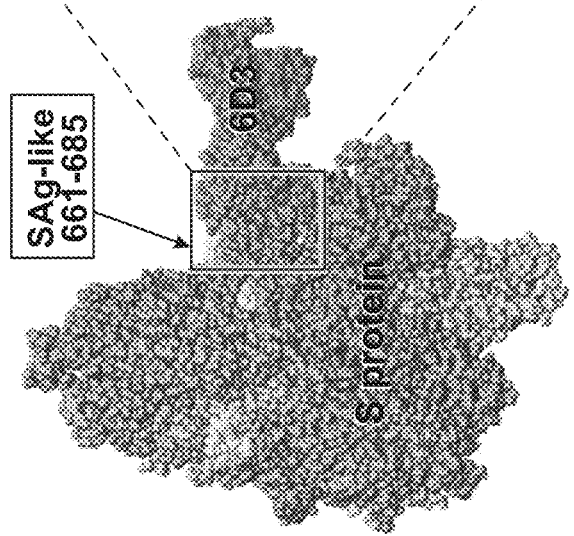

Among these three SEB mAbs, 6D3 was the only one able to bind to the SARS-CoV-2 S SAg motif (FIGS. 17C-17E), consistent with 6D3 binding to the precise SEB fragment that aligns with the spike SAg-like motif. The computational analysis indicated the 6D3 Ab to bind with an affinity of −14.2±2.3 kcal/mol (see Methods). Notably, acidic residues E50, D52 and D55 from the heavy chain of 6D3 were found to interact with polybasic insert PRRA (SEQ ID NO:2) in SARS-CoV-2 S, with R682 and R683 playing a central role. Yet, interfacial contacts were quite distributed, involving other SARS-CoV-2 S amino acids such as E654, N603 and N679 interacting with either the heavy or light chains of 6D3 (FIG. 17E).

Figure 18B:
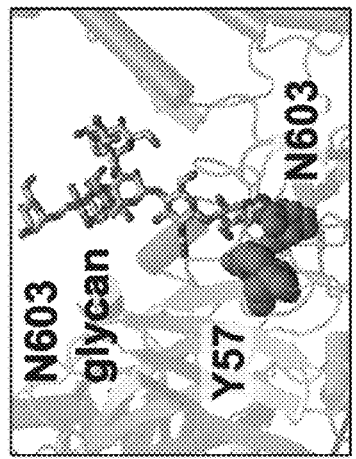
Figure 18A:
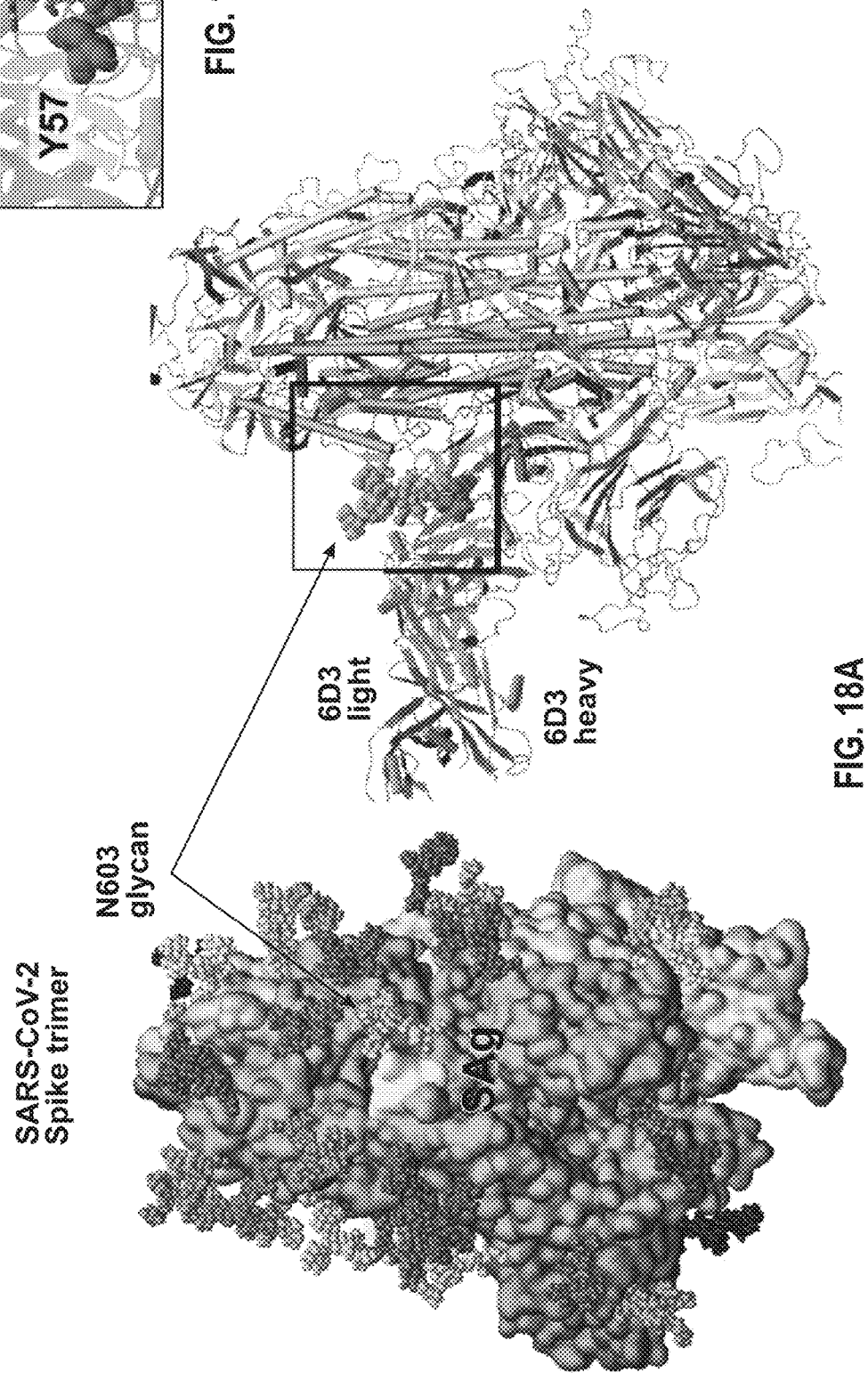

Among those 6D3-interacting S residues, N603 has been identified as an N-linked glycan site by site-specific glycan analysis of SARS-CoV-2 S (Watanabe et al., 2020) (FIG. 18A). To investigate if the glycan sequons can interfere with 6D3 binding, the spike-6D3 complex model was aligned against the glycosylated spike (Woo et al., 2020). No steric overlap was observed between 6D3 and glycan sequons as illustrated in FIG. 18B. Of note is that the N603-linked glycan even assists in the association of 6D3 with the specific binding epitope that overlaps with the SAg-like (and S1/S2 cleavage) site, rather than obstructing it. A tight interaction between N603 and Y57 on 6D3 heavy chain variable domain (VH) is observed, in addition to contacts between the glycan and 6D3 VH residues Y57-Y60 that further contribute to the stabilization of 6D3 binding. These results indicate that the anti-SEB mAb 6D3 shows high affinity binding to the SARS-CoV2 superantigen-like motif, therefore blocking its interaction with TCR, and attenuating the SAg-mediated T cell activation and cytokine release.

These results indicated that 6D3 can decrease the exposure of the cleavage site to the extracellular environment and interfere with SARS-CoV-2 viral entry upon competing with the host cell proteases TMPRSS2 and furin whose binding to the cleavage site, is essential to S protein priming for viral entry. Next, the investigation of the neutralizing effect of 6D3 was tested in live virus experiments.

Figure 19A:
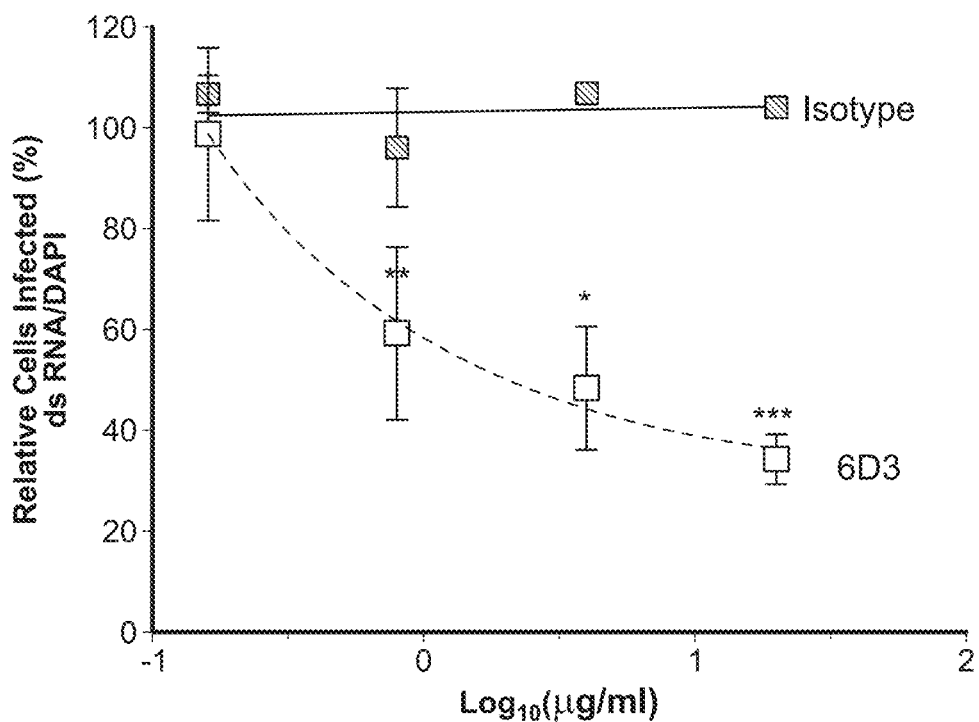
Figure 19B:
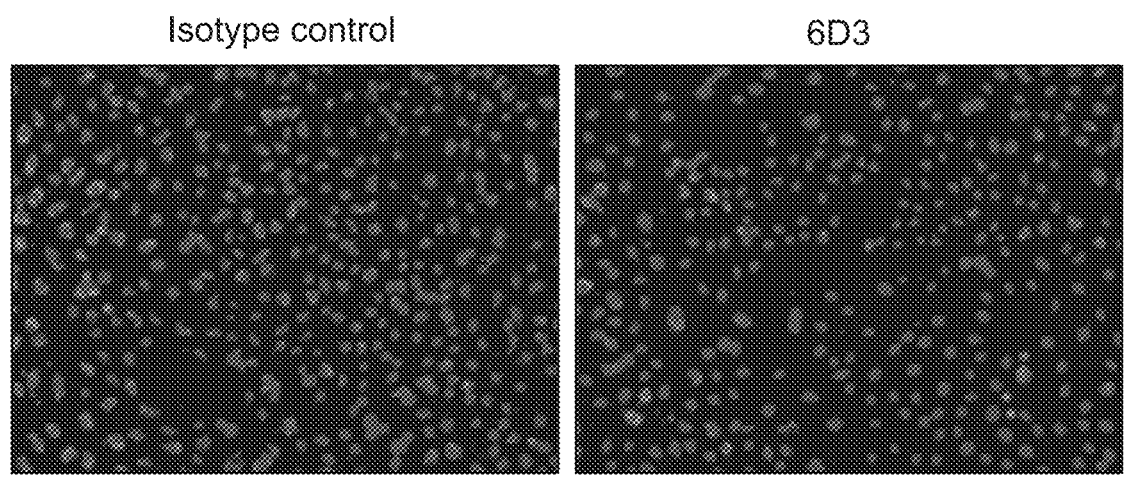
Figure 19C:
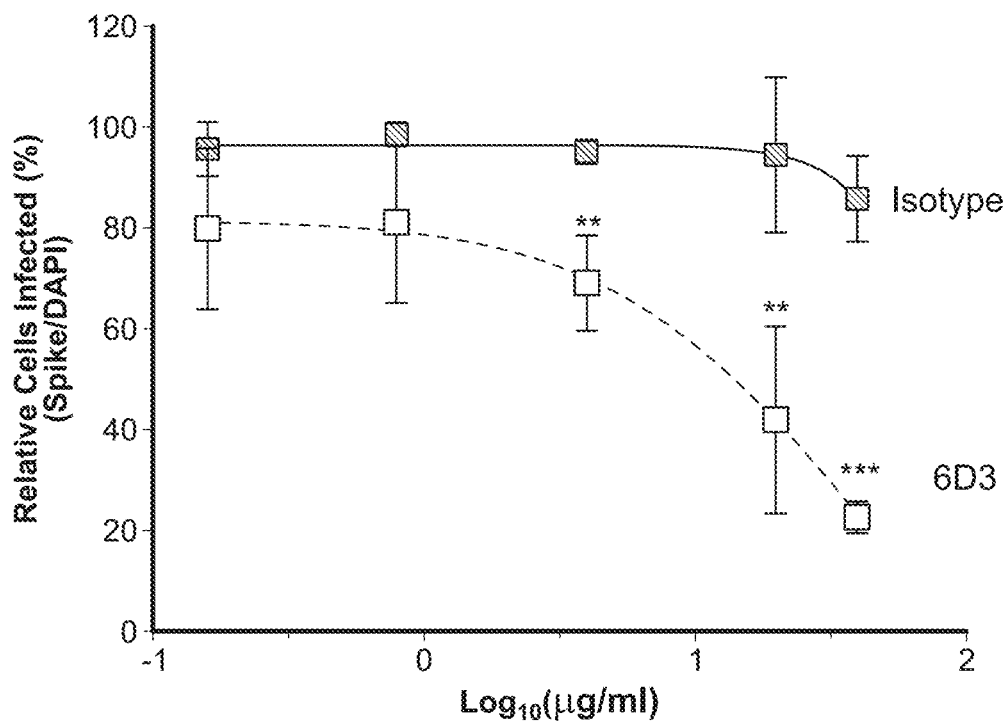
Figure 19D:
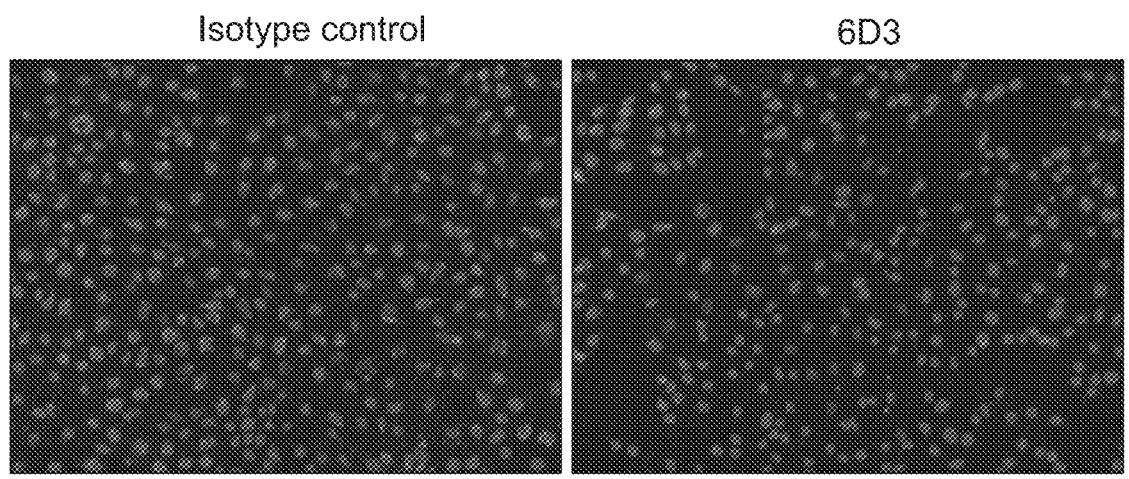
Figure 21A:
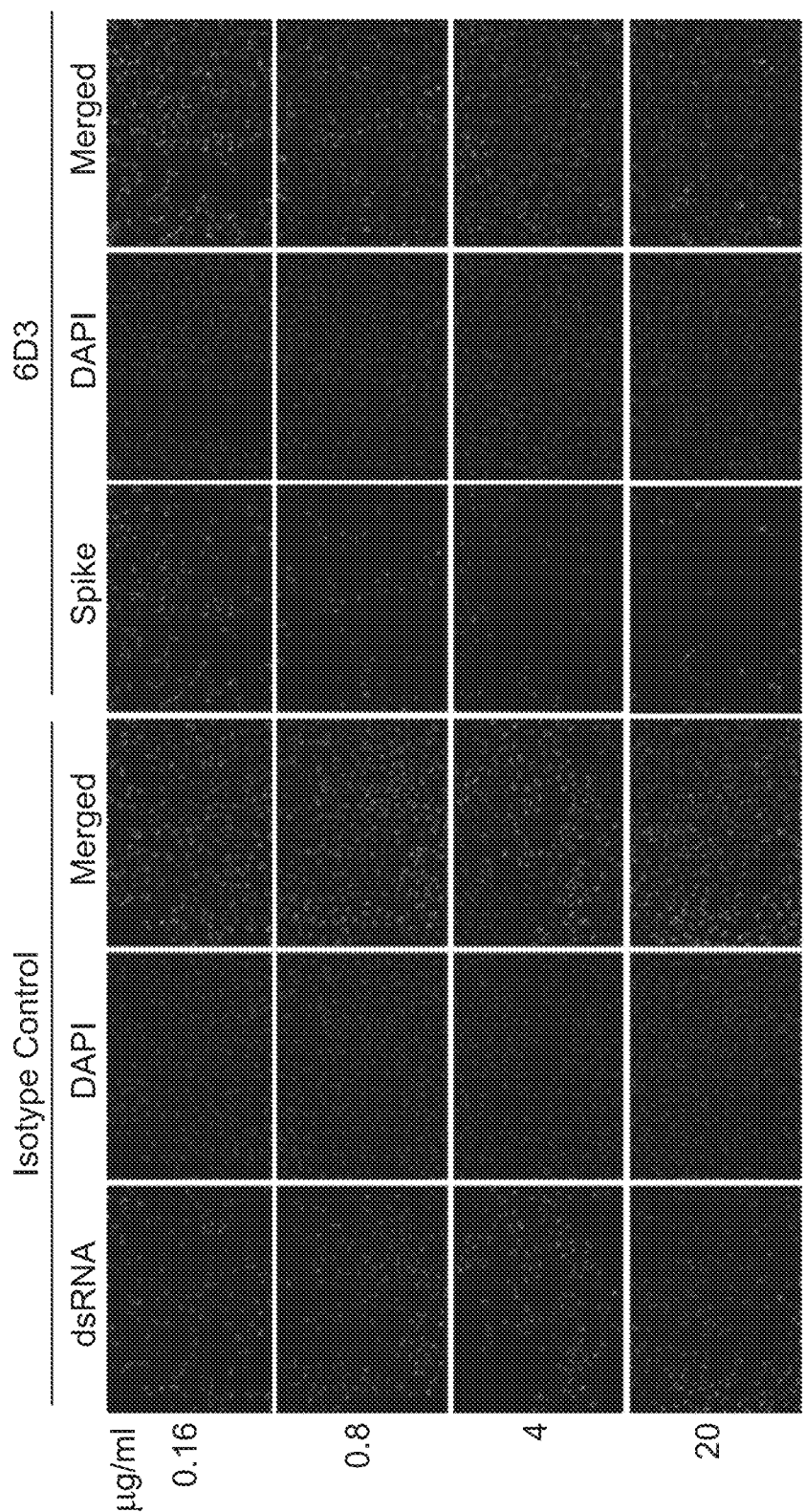
Figure 21B:
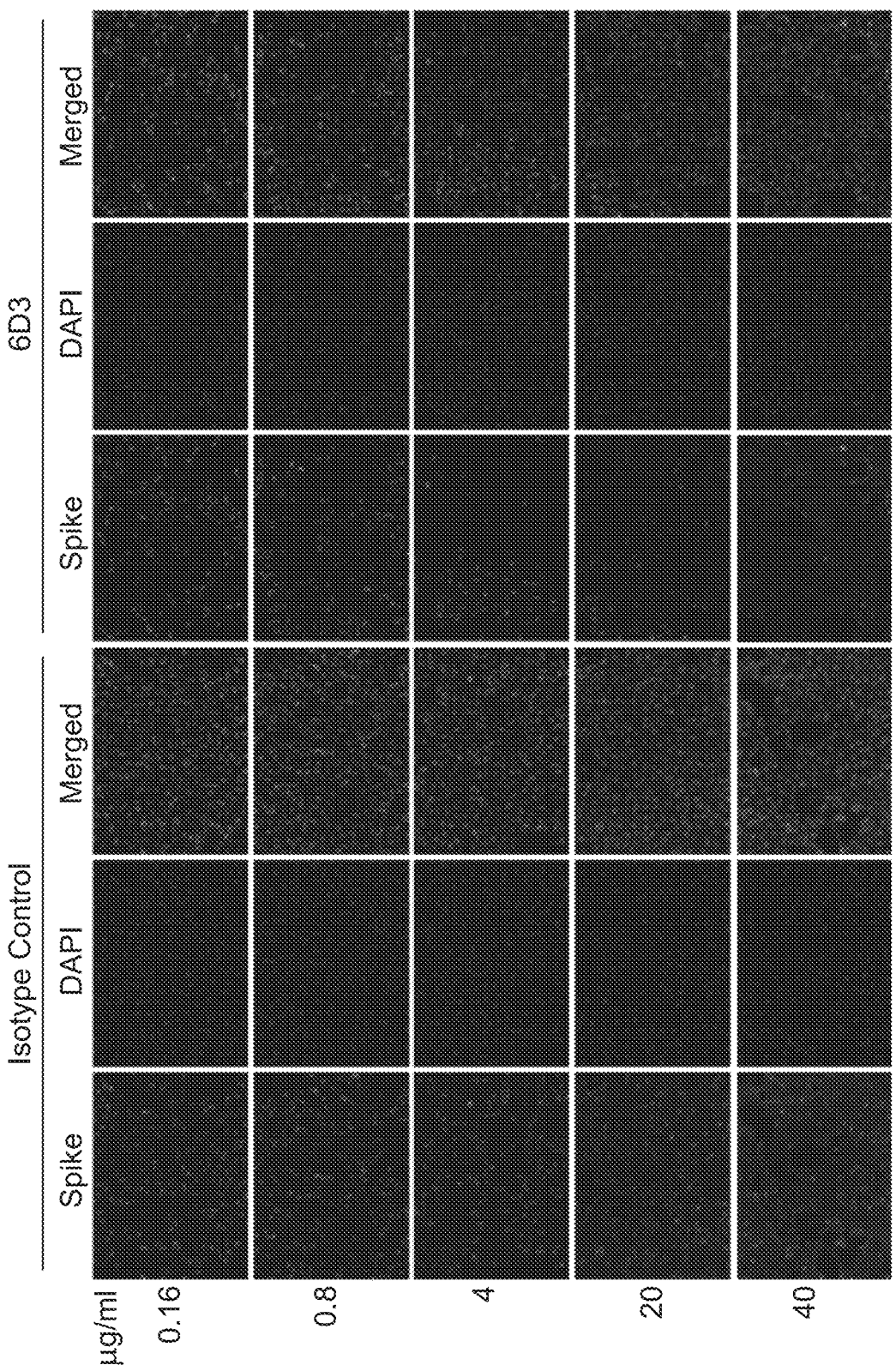

Anti-SEB antibody, 6D3, inhibits SARS-CoV-2 infection in live virus assays. Here, whether the SEB-specific mAb 6D3 possessed any neutralizing efficacy vis-à-vis SARS-CoV-2 viral entry was investigated. To this end, the ability of 6D3 to inhibit SARS-CoV-2 infection was tested in an in vitro cell culture infection system. Antibodies were incubated with SARS-CoV-2 for 1 hour and then added to plated Vero-E6 cells. At 48 hours post infection, viral infection was analyzed by immunofluorescence using antibodies against dsRNA or SARS-CoV-2 S protein. (FIG. 19 and FIG. 21). It was found that 6D3 significantly inhibited viral infection, as measured by the percentage of dsRNA positive cells, at concentrations of 0.8, 4 and 20 µg/ml of antibody, with an IC50 of 5.63 µg/ml (FIGS. 19A-19B and FIG. 21A). Furthermore, in an independent set of experiments, it was found that 6D3 significantly inhibited viral infection, as measured by the percentage of spike positive cells, at concentrations of 4, 20 and 40 µg/ml of antibody, while there was a trend for inhibition at 0.16 and 0.8 µg/ml of antibody (FIGS. 19C-19D and FIG. 21B).

These results indicate that 6D3, can also block viral entry in a concentration-dependent manner, in addition to its high affinity binding to the SARS-CoV2 superantigen-like motif and potentially blocking its interaction with TCRs. Toward assessing whether 6D3 competitively binds the S1/S2 site in the presence of the proteases, the spike-binding mechanisms and affinities of TMPRSS2 and furin was explored and presented next.

Figure 22B:
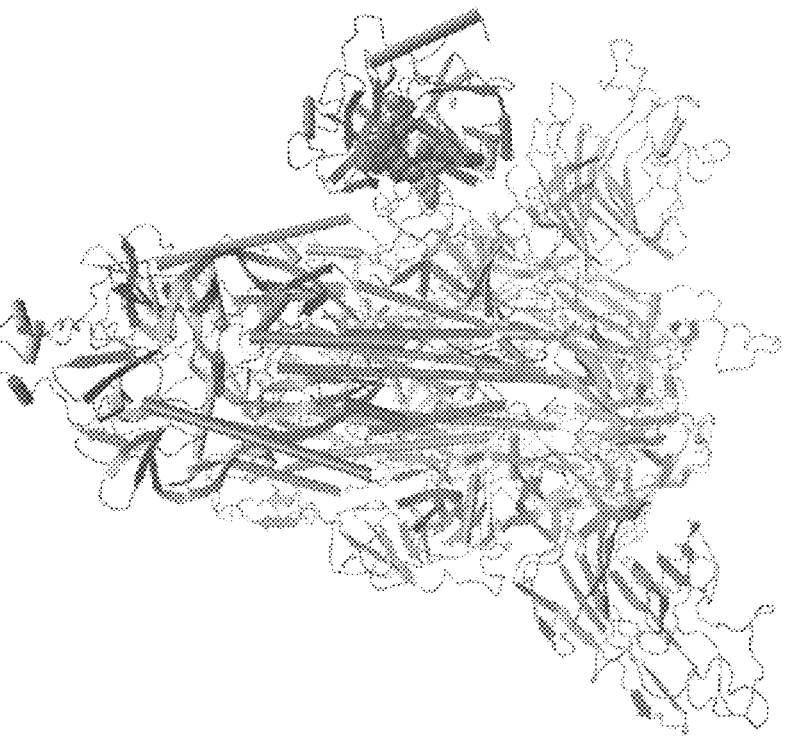
Figure 22A:
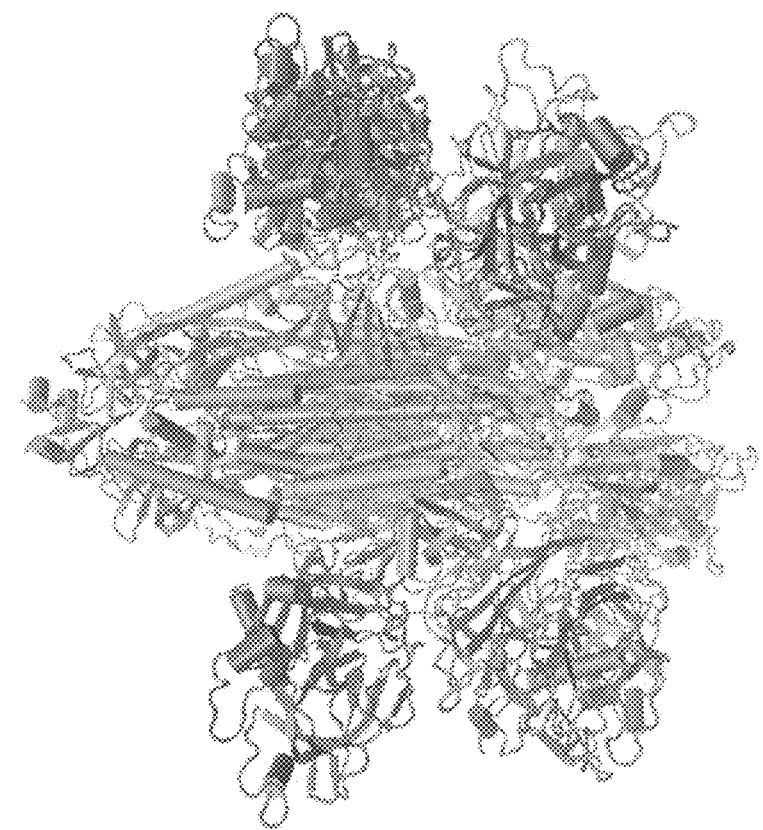
Figure 23:
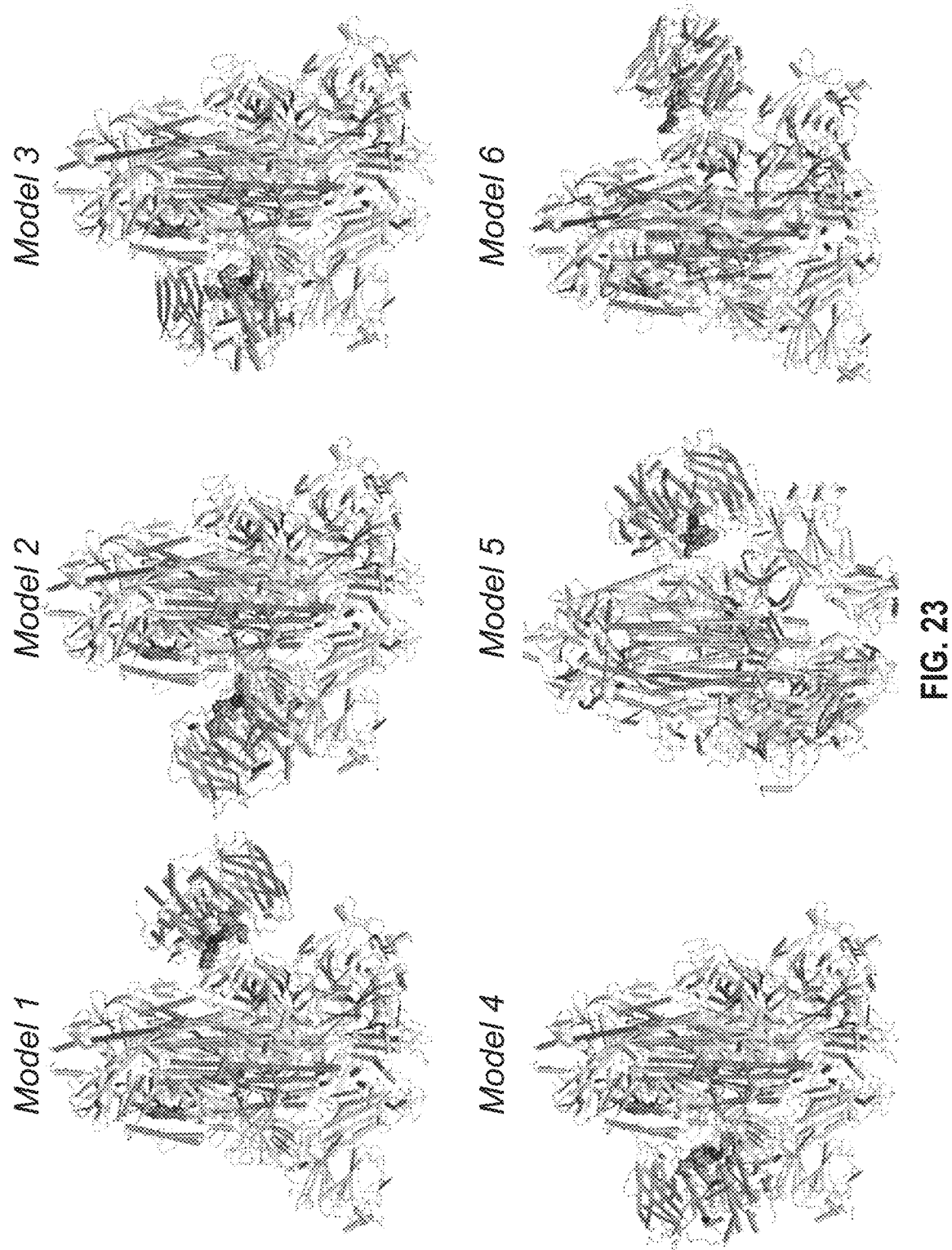

TMPRSS2 and/or furin bind to the S1/S2 site in close association with the PRRA (SEQ ID NO:2) insert. The protease-binding characteristics of the S1/S2 site were analyzed to assess whether Abs that targets the PRRA (SEQ ID NO:2) site can also hinder the access of proteases. The S1/S2 site, also known as furin-cleavage site, typically contains eight central residues including the polybasic segment (here $_{680}$SPRRAR↑SV$_{687}$, SEQ ID NO:115), flanked by solvent-accessible residues on both sides (Tian et al., 2012). The resulting structural models generated for the interactions of TMPRSS2 and furin with the S protein are presented in the respective FIGS. 20A an 20B, and more details are reported in the FIGS. 22 and 23. To generate these models, the available structural data was used (Dahms et al., 2016; Walls et al., 2020; Wrapp et al., 2020) for the proteins, as well as the docking software ClusPro (Kozakov et al., 2017) and protocols outlined in the STAR Methods. An ensemble of structural models were generated for each complex, and those conformers satisfying the criteria for S1/S2 cleavage, mainly positioning of catalytic residues within 3-7 Å atom-atom distance from the cleavage site, were selected for further refinement and energetic evaluation using PRODIGY (Xue et al., 2016).

TMPRSS2 catalytic residues (H296, D345 and S441) were observed to bind near $_{681}$PRRARS$_{686}$ (SEQ ID NO:6) in 7.5% of the generated models (FIG. 22B); their binding affinities varied from −14.1 to −11.3 kcal/mol with an average of −12.7±2.0 kcal/mol. FIG. 20A displays the most energetically-favorable model where the three arginines in $_{681}$PRRARS$_{686}$ (SEQ ID NO:6) penetrate in the catalytic cavity (FIG. 20A, right): R682 forms a salt bridge with TMPRSS2 residue D435; R683 with catalytic aspartate D345, and R685 with TMPRSS2 E299, positioning the scissile bond (spheres) near catalytic residues S441 and H296.

In the case of furin binding, 70% of the structural models showed the catalytic residues (D153, H194 and S368) stabilized in close proximity of $_{681}$PRRARS$_{686}$ (SEQ ID NO:6) (see FIG. 23), indicating that binding of furin to the cleavage site was entropically more favorable than that of TMPRSS2. The binding affinities varied from −16.4 to −11.8 kcal/mol with an average of −14.1±2.3 kcal/mol. The best pose with the catalytic residues facing the S1/S2 site, shown in FIG. 20B (and FIG. 23A), reveals the insertion of R682 and R683 into negatively charged pockets of furin to enable the cleavage of the SARS-CoV-2 S.

Overall, the analysis shows that TMPRSS2 or furin engage in tight intermolecular interactions, in which the basic residues R682 and R683 reach out to the catalytic site of either protease. Binding of either enzyme is accommodated by changes in the local conformations near the cleavage region. However, this analysis also shows that furin binds with higher potency and probability, compared to TMPRSS2. Most importantly, 6D3 and the proteases compete for the same binding site (FIG. 24). Comparison with the binding affinity of 6D3 evaluated above shows that 6D3 has a spike-binding affinity comparable to that of furin, and stronger than TMPRSS2, indicating that it can effectively compete with those proteases, in agreement with the experimentally observed efficacy in reducing viral entry.

An acidic residue cluster at VH CDR2 is the hallmark of Abs targeting the furin-like cleavage site. The study pointed to the distinctive ability 6D3 to bind to the S1/S2 cleavage site while other mAbs (in Table 4) did not show such a binding propensity. Which sequence/structure features distinguish 6D3 from others was investigated. Abs target viruses mainly through their three complementarity determining regions (CDR1-3) in the variable domains, especially in the heavy chains (Li et al., 2020). FIG. 25A compares the sequences of the VH chains of the SARS-CoV-2 S-associated mAbs, and three mAbs associated with SEB. CDR3s exhibit large sequence variation, in accord with their role in conferring specificity. However, the alignment reveals a unique feature that distinguishes 6D3 and another mAb, 4A8, from all other mAbs: mainly a poly-acidic cluster at their CDR2. Specifically, the 6D3 CDR2 possesses three acidic residues E50, D52, and D55, already noted above to enable binding to the precise cleavage-site on the S protein. Likewise, mAb 4A8 has four acidic residues D52, E54, D55 and D57 (FIG. 25A). 4A8 is known to bind the NTD of the spike (Chi et al., 2020; McCarthy et al., 2020) (FIG. 26A). The docking simulations also indicated that the particular S epitope and 4A8 paratope observed in the cryo-EM structure of the spike-4A8 complex were selected as the most favorable binding pose (FIG. 26B). However, the SAg-like motif E661-R685 was also found to be favorable, albeit with a weaker binding affinity (FIG. 26C) and could compete with human proteases for binding the same site (FIG. 26D). These simulations indicated a binding affinity of −13.4±2.4 kcal/mol for the NTD (experimentally observed and computationally most probable) site, consistent with the equilibrium dissociation constant ($K_d$=2.14 nM, or corresponding $\Delta G$=−12.3 kcal/mol) measured by biolayer interferometry for the spike-4A8 complex (Chi et al., 2020).

A poly-acidic CDR2 at the VH chain thus emerges as a hallmark of the mAbs that target the polybasic furin-like cleavage site. As shown in FIG. 25B, these acidic residues facilitate Ab-spike complexation through salt bridges formed with the basic residues (R682, R683 and R685) in $_{680}$SPRRARSV$_{687}$ (SEQ ID NO:115), the central component of typical furin-cleavage sites (Tian et al., 2012), thus attenuating, if not blocking, access of proteases.

As shown in FIG. 16B, the polybasic insertion of SARS-CoV-2 is not shared by other SARS-family βCoVs, but found in common cold HCoVs HKU1 and OC43, and in MERS. Present findings strongly show that mAbs 6D3 can also target these other HCoVs that encode a furin-cleavage site. The binding properties of 6D3 to a structural model for HCoV-OC43 S was investigated based on the 0C43 cryo-EM structure (PDB: 6NZK) (Tortorici et al., 2019). The highest affinity binding pose predicted by our simulations are presented in FIG. 25C, indicating that 6D3 binds the S1/S2 cleavage site of HCoV-OC43 S. Again, poly-acidic residues in CDR2 play a primary role in binding to the cleavage site of HCoV-OC43 S. These findings underscore the effectiveness and cross-reactivity of 6D3 that target the furin-cleavage site between the S protein of SARS-CoV-2 and other selected HCoVs.

Discussion

A new strategy for combatting SARS-CoV-2: repurposing of antibodies that target the S1/S2 cleavage site. SARS-CoV-2 S is the main determinant of cell entry and the major target of neutralizing Abs (Cao et al., 2020b; Chi et al., 2020; Hansen et al., 2020; Pinto et al., 2020; Renn et al., 2020; Shi et al., 2020; Yuan et al., 2020). The majority of COVID-19 Ab therapies under investigation are designed to target the S protein RBD, while other potential neutralizing epitopes have also been found (Cao et al., 2020b; Chi et al., 2020; Hansen et al., 2020; Liu et al., 2020; Pinto et al., 2020; Renn et al., 2020; Shi et al., 2020; Yuan et al., 2020). Given the high glycosylation and antigenic variability of SARS-CoV-2 S (Graham et al., 2019), a combination of mAbs that target multiple sites and multiple conformations of SARS-CoV-2 S, is likely the most effective strategy. Besides blocking ACE2 binding, distinct neutralizing mechanisms have been proposed, including Ab-dependent cell cytotoxicity and phagocytosis (Pinto et al., 2020) and restraining the structural changes of SARS-CoV-2 Spike (Chi et al., 2020).

Proteolytic cleavage of SARS-CoV-2 S is the second critical step, succeeding ACE2 binding, in the life cycle of SARS-CoV-2. TMPRSS2 and furin inhibitors have been found to block cell entry of SARS-CoV-2 (Bestle et al., 2020; Hoffmann et al., 2020). The critical role of the furin-cleavage site in SARS-CoV-2 infectivity and Ab activity is also demonstrated in a recent study where the deletion ΔPRRA reduced SARS-CoV-2 viral replication in a human respiratory and attenuated infectivity (Johnson et al., 2021). Unlike TMPRSS2, furin is a ubiquitous proprotein convertase and is required for normal development and function (Thomas, 2002) and its inhibition is not a viable strategy. But, design or repurposing of Abs that block the S1/S2 site is an attractive alternative solution that avoids effects on the (other) activities of TMPRSS2 and furin.

It is well known that the SARS-CoV-2 spike is heavily glycosylated, and the possible interference of glycans with Ab binding is a plausible consideration (Casalino et al., 2020). Notably, 6D3-binding did not give rise to steric clash with the N-linked glycan sequons near the S1/S2 site (e.g. N603, or N657N658 as reported (Watanabe et al., 2020)). In addition SARS-CoV-2 S was predicted to be 0-glycosylated at 5673, T678 and 5686 near the S1/S2 cleavage site (Andersen et al., 2020), yet to be confirmed by experiments (Shajahan et al., 2020; Watanabe et al., 2020). 6D3 can target directly the S1/S2 site of SARS-CoV-2 S (as the host proteases do) without any shielding effect by glycans. On the contrary, the glycosylation near N603 can even assist in promoting its binding near the PRRA (SEQ ID NO:2) site. The modulating role of glycans on the structure and dynamics of the S glycoprotein has been pointed out to be a feature that could be harnessed in anti-SARS-CoV-2 vaccine development (Casalino et al., 2020).

The ability of the polybasic insert to bind antibodies may have escaped prior cryo-EM studies with mutant S protein. It has been a challenge to resolve The S1/S2 loop in cryo-EM studies of HCoV S proteins. First, pre-activation of HCoV S during protein preparation results in a mixture of cleaved and uncleaved spikes (Cai et al., 2020). Second, local conformational changes near the S1/S2 region may differ between cleaved and intact structures, as observed in influenza viruses (Steinhauer, 1999). Third, multiple conformations, if not a disordered state, may exist near that region, as indicated by microseconds simulations and ab initio modeling (Lemmin et al., 2020). Therefore, most of cryo-EM studies of SARS-CoV-2 S protein complexed with Abs have resorted to variants where the 682RRAR685 (SEQ ID NO:121) segment has been replaced by GSAS or SGAG (Barnes et al., 2020; Cao et al., 2020b; Chi et al., 2020; Liu et al., 2020; Lv et al., 2020b; Pinto et al., 2020; Zhou et al., 2020a; Zost et al., 2020) (Table 4). These ‘mutant spikes’ may have precluded the discovery of binding of Abs to the S1/S2 site. Molecular modeling and simulations provided insights into the interactions at this region, including those with proteases and other receptors (Cheng et al., 2020; Jaimes et al., 2020; Lemmin et al., 2020). Such modeling studies was utilized (FIGS. 17C-17E, 18, 20 and 25), and performed live-virus experiments (FIG. 19 and FIG. 21) to investigate the Abs that possibly interfere with the binding of TMPRSS2 and furin. An antibody (6D3) that can block the S1/S2 cleavage site in SARS-CoV-2 S protein was identified. It is noted that, due to the conformational variability of the S1/S2 loop, the actual binding site of 6D3 on SARS-CoV-2 S can be different from that predicted by computational models, and there can be multiple binding sites on S, as predicted for the Ab 4A8 (FIG. 26).

6D3 is a repurposable anti-SEB mAb that targets the S1/S2 site and inhibits viral infection. 6D3 is an Ab originally discovered for neutralizing the superantigenic bacterial toxin SEB. it's the present study indicates its use as repurposable mAb against SARS-CoV-2 S protein, by virtue of its ability to bind a sequence motif shared between SEB and S protein. The recent study revealed the high similarity between SARS-CoV-2 S amino acids E661-R685 and SEB amino acids T150-D161, which can contribute to hyperinflammation and MIS-C/A pathogenesis through a SAg-induced immune activation (Cheng et al., 2020). This hypothesis was supported by the clinical and laboratory features observed in MIS-C and severe COVID-19 patients, which were similar to those of toxic shock syndrome (TSS) caused by bacterial toxins such as SEB (Cheng et al., 2020; Noval Rivas et al., 2020). Adult patients with severe Covid-19 (Cheng et al., 2020) as well as children with the multisystem inflammatory syndrome (MIS-C) (Porritt et al., 2020) displayed TCR skewing typical of SAg-induced immune responses. Among the three mAbs discovered against SEB, 6D3 was the only one specific to the region of interest (FIGS. 17A-17B), and computations and experiments indicated that this anti-SEB mAb can bind to the SARS-CoV-2 S protein.

Another feature was the fact that this SAg-like segment (that binds 6D3) overlapped with the furin-like cleavage site characteristic of SARS-CoV-2 (and MERS and HCOVs HKU1 and OC43; see FIG. 16B). Furin-cleavage sites usually involve ~20 residues, eight of which play a central role (Tian et al., 2012). In the case of SARS-CoV-2, the segment $_{680}$SPRRAR↑SV$_{687}$ (SEQ ID NO:115) of the S protein forms this central component. Simulations indeed showed strong interactions (salt bridges) formed between 6D3 VH CDR2 (distinguished by a stretch of acidic residues) and the polybasic $_{682}$RRAR$_{685}$ (SEQ ID NO:121) (FIGS. 17C-17E and 25B), and in vitro assays confirmed that 6D3 inhibited viral entry (FIG. 19 and FIG. 21).

By binding the viral spike protein, SARS-CoV-2 specific antibodies in the blood or mucosal surface could prevent the virus from binding to and infecting target cells. The antibody neutralization assay that we performed in cell culture simulates this scenario, where the specific mAb 6D3 incubated with SARS-CoV-2 binds and neutralizes the virus's ability to attach to the cell receptor and to initiate infection in vitro. Thus, mAb 6D3 can have a differentiating dual role in not only inhibiting viral entry but also blocking the SARS-CoV-2 superantigen-like motif-induced T cell activation, cytokine storm, and hyperinflammation. The next experimental steps assessing the in vivo effect of mAb 6D3 in relevant mouse models of SARS-CoV-2 infection are currently underway.

mAbs with a cluster of acidic residues at their VII CDR2 can mitigate viral infections caused by CoVs that contain furin-like cleavage sites. HCoVs include three highly pathogenic viruses, SARS-CoV-2, SARS-CoV and MERS, and four circulating endemic viruses (HCoV-NL63, HCoV-229E, HCoV-OC43 and HKU1) which cause mild to moderate upper respiratory diseases (Coutard et al., 2020; Cui et al., 2019; Forni et al., 2017). Many individuals who have not been exposed to SARS-CoV-2 possess SARS-CoV-2 Spike reactive T cells, due to cross-reaction of immune responses generated against other HCoV strains (Grifoni et al., 2020; Mateus et al., 2020). Cross-reactive antibodies between human βCoV strains have also been identified, including those between SARS and SARS-CoV-2 (Huang et al., 2020; Lv et al., 2020a). Indeed, SARS monoclonal antibody 5309 can potently neutralize both SARS and SARS-CoV-2(Pinto et al., 2020). Furthermore, the effectiveness of IVIG (Belhadjer et al.; Riphagen et al.; Verdoni et al.), may, in part, be due to the presence of cross-reactive antibodies against other HCoV stains. These findings show designing wide spectrum Abs with cross-reactivity among HCoVs. The two Abs (6D3 and 4A8) identified in this study to present the suitable paratope for binding the PRRAR or similar polybasic inserts can block the S1/S2 cleavage site in HCoVs that encode furin-like cleavage sites (FIG. 25), providing additional benefit beyond those applicable to the current pandemic. The hallmark poly-acidic residues in the CDR2 of VH can be exploited as a benchmark to sort out mAbs that can target the SARS-CoV-2 furin cleavage site.

Alternative strategies targeting the S1/S2 site in the light of these repurposable mAbs. Based on the scaffold of 6D3 heavy chain, mini-proteins can be designed to target SARS-CoV-2, MERS, HCoV-OC43 or HKU1, to block CoV entry. Notably, designed de novo mini-proteins have been shown to block ACE2 binding, based on the scaffold of ACE2 (Cao et al., 2020a). Very recently, neuropilin-1 (NRP1) has been identified as a host factor for SARS-CoV-2 infection, bound to the 681RRAR685 (SEQ ID NO:121) segment (Daly et al., 2020). Remarkably, blockade of this interaction by RNAi or mAb against NRP1 significantly reduced in vitro SARS-CoV-2 cellular entry (Cantuti-Castelvetri et al., 2020; Daly et al., 2020). 6D3 can block the binding of NRP1. At present, no clinical treatments or prevention strategies are available for HCoVs (Cui et al., 2019). The present work leads to an improved understanding of coronavirus immunity, facilitating future studies to understand mechanisms of antibody recognition and neutralization, and help screen SARS-CoV-2 Abs for treatment of COVID-19. These findings also show designing therapeutic approaches using a combination of 6D3 and known neutralizing mAbs that bind the RBD, for treating severe COVID-19 and MIS-C/A patients and/or combatting the spread of the newly emerging variants.

Method Details

In vitro viral inhibition assays. SARS-CoV-2 viral assays were performed in UCLA BSL3 high containment facility, following previous procedure(Garcia et al., 2020). SARS-CoV-2 Isolate USA-WA1/2020 was obtained from BEI Resources of National Institute of Allergy and Infectious Diseases (NIAID). Mouse Fab 6D3 (IgG2b) was generated as(Varshney et al., 2011). Vero-E6 cells were plated in 96-well plates ($5\times10^3$ cells/well). 6D3 IgG2b or mouse IgG2b isotype control (Bio X Cell) were incubated with virus (100 PFU/well) for 1 hour at room temperature prior to addition to Vero-E6 cells. After 48 hours post-infection the cells were fixed with methanol for 30-60 minutes in −20° C. Cells were washed 3 times with PBS and permeabilized using blocking buffer (0.3% Triton X-100, 2% BSA, 5% Goat Serum, 5% Donkey Serum in 1×PBS) for 1 hour at room temperature. Subsequently, cells were incubated with mouse anti-dsRNA antibody (Absolute Antibody, 1:200) or anti-SARS-CoV-2 spike antibody (Sino Biological, 1:200) at 4° C. overnight. Cells were then washed 3 times with PBS and incubated with fluorescence conjugated secondary antibody: Goat anti-mouse IgG Secondary Antibody, Alexa Fluor 555 (Fisher Scientific, 1:1000) for 1 hour at room temperature. Nuclei were stained with DAPI (4',6-Diamidino-2-Phenylindole, Dihydrochloride) (Life Technologies) at a dilution of 1:5000 in PBS for 10 minutes. Cells were analyzed by fluorescence microscopy. Images were obtained using a Biorevo BZ-X710 (Keyence) microscope and software.

Structural data for SARS-CoV-2, human TMPRSS2 and furin. SARS-CoV-2 (residues A27-D1146; UniProt ID:

P0DTC2) spike models were generated using SWISS-MODEL (Waterhouse et al., 2018), based on the resolved SARS-CoV-2 Spike glycoprotein structures of SARS-CoV-2 in different conformational states (PDBs: 6VSB (Wrapp et al., 2020) and 6VXX (Walls et al., 2020)). The missing loops in the crystal structures, were built using the well-established libraries of backbone fragments (Zhang and Skolnick, 2005) and constraint space de novo reconstruction of the backbone segments (Peitsch, 1995). The catalytic domain of human TMPRSS2 (residues N146-D491; UniProt ID: O15393) was constructed using SWISS-MODEL (Waterhouse et al., 2018), based on the crystal structure of serine protease hepsin (PDB: 5CE1). A crystal structure of human furin (Y110-A408; P09958) was used as is (PDB: 5JMO) (Dahms et al., 2016).

Generation and assessment of SARS-CoV-2 Spike and protease complex models. To investigate priming of the S1/S2 site of SARS-CoV-2 Spike, protein-protein docking analysis was performed for TMPRSS2 or furin with SARS-CoV-2 Spike in the pre-fusion state. Using docking software ClusPro (Kozakov et al., 2017), a series of SARS-CoV-2 Spike and protease complexes were constructed in silico. SARS-CoV-2 Spike was set as receptor and protease as ligand. Residues in the proximity of the cleavage site from SARS-CoV-2 Spike (T676 to V687) were set as attractor sites of receptor, and the catalytic residues from TMPRSS2 (H296, D345 and S441) or furin (D153, H194 and S368) were set as attractor sites for ligand. For each complex, 30 clusters of conformations were obtained, upon clustering ~800 models generated by ClusPro. The clusters were rank-ordered by cluster size (Kozakov et al., 2017) as recommended, and representative members from top-ranking clusters were further examined and refined Mainly, protein-protein binding free energies were calculated using PRODIGY (Xue et al., 2016); and mutagenesis and sculpting wizards in PyMOL 2.3.0 (Open Source version) (DeLano, 2002) were used to interactively refine rotamers and interactions, respectively.

Monoclonal antibodies binding to SARS-CoV-2 Spike. SEB-associated monoclonal antibodies 14G8, 6D3 and 20B1 were taken from the crystal structures of SEB bound to two neutralizing Abs, 14G8 and 6D3 (PDB: 4RGN), and one neutralizing Ab, 20B1 (PDB: 4RGM). SARS-CoV-2 S-associated neutralizing Abs were taken from the crystal structures listed in Table 4. Ab-binding poses were predicted using protein-protein docking module in ClusPro (Kozakov et al., 2017) where SARS-CoV-2 spike was set as the receptor and 6D3 as the ligand. Computations repeated with the antibody mode of ClusPro confirmed the S1/S2 cleavage site to be most favorable binding site for mAb 6D3. All docking simulations were performed using ClusPro default parameters.

TABLE 4

Antibody-bound complexes resolved by cryo-EM for SARS-CoV-2 spike mutants

| Binding domain (conformation) | Mechanism of action | SARS-CoV-2 Ab (PDB IDs)[a] | Mutation at "RRAR" | Epitope on SARS2 spike[b] | Reference |
|---|---|---|---|---|---|
| RBD (up) | sterically hinders ACE2 binding | C105 (6XCN, 6XCM) | SGAG | D405, T415, G416, K417, Y421, Y453, F456, R457, K458, N460, Y473, A475, G476, F486, N487, G502, Y505 | Barnes et al., 2020 |
| RBD (down) | blocks ACE2-binding interface of RBD | 2-4 (6XEY) | GSAS | Y449, Y453, L455, F456, V483, E484, G485, F486, Y489, F490, L492, Q493, S494 | Liu et al., 2020 |
| RBD (up/down) distinct from ACE2 binding sites | Ab-dependent cell cytotoxicity and phagocytosis | S309 (6WPT, 6WPS) | SGAG | N334, L335, P337, G339, E340, N343, A344, T345, R346, K356, R357, S359, N360, C361, L441, N343 glycan | Pinto et al., 2020 |
| RBD (up) | blocks ACE2 binding and attachment to host cell | H014 (7CAI, 7CAC, 7CAB, 7CAK, 7CAH) | GSAS | Y369, A372, S373, F374, S375, T376, F377, K378, C379, Y380, V382, S383, P384, T385, D405, V407, R408, A411, P412, Q414, N437, V503 | Lv et al., 2020b |
| NTD (up/down) | restrains S protein structural changes | 4A8 (7C2L) | GSAS | Y144, Y145, H146, K147, K150, W152, H245, R246, S247, Y248, L249 | Chi et al., 2020 |

TABLE 4-continued

Antibody-bound complexes resolved by cryo-EM for SARS-CoV-2 spike mutants

| Binding domain (conformation) | Mechanism of action | SARS-CoV-2 Ab (PDB IDs)[a] | Mutation at "RRAR" | Epitope on SARS2 spike[b] | Reference |
|---|---|---|---|---|---|
| RBD/NTD (down) | blocks ACE2 binding | Ab23 (7BYR) | GSAS | G446, Y449, E484, G485, F486, Y489, F490, L492, Q493, S494, G496, Q498 N501, Y505, N165 glycan | Cao et al., 2020b |
| RBD | blocks the RBD | EY6A (6ZDH) | GSAS | Y369, F374, S375, T376, F377, K378, C379, Y380, G381, V382, S383, P384, T385, K386, D389, L390, F392, P412, G413, D427, D428, F429, T430 | Zhou et al., 2020a |

[a]PDB IDs of the cryo-EM structures containing the indicated Ab are given in parentheses.
[b]Epitope residues of SARS-CoV-2 within 4 Å distance of the antibody based on the first PDB ID listed in column 3.

Model refinement and binding affinity calculations. Selective protease-Spike and mAb-Spike complexes were further refined using the refinement protocol implemented in the webserver HADDOCK 2.4 (Van Zundert et al., 2016). Refinement was performed by MD energy minimization following the protocol and default parameters provided by the webserver. Binding free energies were evaluated using the inter-residue contact-based method accessible in the webserver PRODIGY (Xue et al., 2016). The standard deviations of binding free energy were estimated based on multiple binding poses taken from docking simulations and model refinement.

Sequence alignment. Multiple sequence alignment of the variable heavy chain domain of anti-SEB Abs (6D3, 14G8 and 20B1) and anti-SARS-CoV-2 S Abs were generated by Clustal Omega (Sievers et al., 2011).

Quantification and statistical analysis. For viral inhibition assays: Quantification of immunofluorescence images was performed manually, blinded to the conditions. Five images per well were quantified and the average calculated. n=3 technical replicates (wells) per condition. Data is presented as mean+/−standard error of the mean and is representative of three independent experiments. Data were analyzed by t test (6D3 vs. isotype control) with multiple testing correction (Benjamini, Krieger and Yekutieli FDR test) using GraphPad Prism software. No methods were used to test the assumptions of the statistical approach. Statistical analysis details are found in the methods description, results and figure captions.

TABLE 5

Key resources table

| REAGENT or RESOURCE | SOURCE | IDENTIFIER |
|---|---|---|
| Antibodies | | |
| 6D3 IgG2b | Stony Brook University, New York | N/A |
| InVivoMab mouse IgG2b isotype control | BioXcell | Cat#BE0086 |
| mouse anti-dsRNA [J2] antibody | Absolute Antibody | Cat#Ab01299-2.0 |
| Goat anti-Mouse IgG (H + L) Cross-Adsorbed Secondary Antibody, Alexa Fluor 555 | Thermo Fisher Scientific | Cat#A21422 |
| Bacterial and Virus Strains | | |
| SARS-CoV-2 | BEI Resources of National Institute of Allergy and Infectious Diseases (NIAID) | Isolate USA-WA1/2020 |
| Chemicals, Peptides, and Recombinant Proteins | | |
| DAPI (4',6-Diamidino-2-Phenylindole, Dihydrochloride) | Life Technologies | Cat#D1306 |

TABLE 5-continued

Key resources table

| REAGENT or RESOURCE | SOURCE | IDENTIFIER |
|---|---|---|
| Penicillin-Streptomycin (10,000 U/mL) | Gibco | Cat#15140122 |
| Deposited Data | | |
| Antibody-Spike complexes see Table 4 | Protein Data Bank (PDB) | N/A |
| SARS-CoV-2 Spike with one chain in up state | (Wrapp et al., 2020) | PDB: 6VSB |
| SARS-CoV-2 Spike in down state | (Walls et al., 2020) | PDB: 6VXX |
| HCoV-OC43 Spike in down state | (Tortorici et al., 2019) | PDB: 6NZK |
| Furin | (Dahms et al., 2016) | PDB: 5JMO |
| SARS-CoV-2 glycosylated Spike protein model | (Woo et al., 2020) | charmm-gui.org/?doc=archive&lib=covid19 |
| Antibodies 6D3 and 14G8 bound to SEB | (Dutta et al., 2015) | PDB: 4RGN |
| Antibody 20B1 bound to SEB | (Dutta et al., 2015) | PDB: 4RGM |
| Human TMPRSS2 homology model | This paper | zenodo.org/record/4667694#.YGz7DOhKhPZ |
| SARS-CoV-2 Spike bound to TMPRSS2 | This paper | zenodo.org/record/4667694#.YGzUgOhKhPY |
| SARS-CoV-2 Spike bound to furin | This paper | zenodo.org/record/4667694#.YGzUgOhKhPY |
| Ab 6D3 bound to SARS-CoV-2 Spike in one up state | This paper | zenodo.org/record/4667694#.YGzUgOhKhPY |
| Ab 6D3 bound to SARS-CoV-2 Spike in down state | This paper | zenodo.org/record/4667694#.YGzUgOhKhPY |
| Ab 6D3 bound to HCoV-OC43 Spike in down state | This paper | zenodo.org/record/4667694#.YGzUgOhKhPY |
| Experimental Models: Cell Lines | | |
| Vero-E6 | ATCC | Cat#CRL-1586 |
| Software and Algorithms | | |
| ClusPro | (Kozakov et al., 2017) | cluspro.bu.edu/ |
| SWISS-MODEL | (Waterhouse et al., 2018) | swissmodel.expasy.org/interactive |
| PRODIGY | (Xue et al., 2016) | bianca.science.uu.nl//prodigy/ |
| PyMOL | (DeLano, 2002) | pymol.org/2/ |
| HADDOCK 2.4 | (Van Zundert et al., 2016) | bianca.science.uu.nl/haddock2.4/ |
| Clustal Omega | (Sievers et al., 2011) | www.ebi.ac.uk/Tools/msa/clustalo/ |
| Prism | GraphPad | www.graphpad.com/scientific-software/prism/ |
| BZ-X700 Analysis Software | Keyence | keyence.com/landing/microscope/lp_fluorescence.jsp |
| Other | | |
| Eagle's Minimum Essential Medium (MEM) | Corning | Cat#10009CV |
| Regular Fetal Bovine Serum | Corning | Cat#35010CV |
| Goat Serum | Cell Signaling | Cat#5425S |
| Normal Donkey Serum | Jackson ImmunoResearch | Cat#017-000-121 |
| BZ-X710 Fluorescence Microscope | Keyence | Model#BZ-X710 |

REFERENCES

1. A. C. Walls et al., Structure, Function, and Antigenicity of the SARS-CoV-2 Spike Glycoprotein. Cell 180, 281-292 (2020).
2. L. Cristiani et al., Will children reveal their secret? The coronavirus dilemma. Eur. Respir. J., in press (2020).
3. M. Z. Tay, C. M. Poh, L. Rénia, P. A. MacAry, L. F. P. Ng, The trinity of COVID-19: immunity, inflammation and intervention. Nat. Rev. Immunol., in press (2020).
4. N. Vabret et al., Immunology of COVID-19: current state of the science. Immunity, in press (2020).
5. S. Riphagen, X. Gomez, C. Gonzalez-Martinez, N. Wilkinson, P. Theocharis, Hyperinflammatory shock in children during COVID-19 pandemic. Lancet, in press (2020).
6. L. Verdoni et al., An outbreak of severe Kawasaki-like disease at the Italian epicentre of the SARS-CoV-2 epidemic: an observational cohort study. Lancet, in press (2020).
7. Z. Belhadjer et al., Acute heart failure in multisystem inflammatory syndrome in children (MIS-C) in the context of global SARS-CoV-2 pandemic. Circulation, in press (2020).

8. D. E. Low, Toxic shock syndrome: major advances in pathogenesis, but not treatment. Crit. Care Clin. 29, 651-675 (2013).
9. A. Cook, S. Janse, J. Watson, G. Erdem, Manifestations of Toxic Shock Syndrome in Children, Columbus, Ohio, USA, 2010-2017. Emerg. Infect. Dis. 26, 1077-1083 (2020).
10. A. E. Young, K. L. Thornton, Toxic shock syndrome in burns: diagnosis and management. Arch. Dis. Child. Educ. Pract. 92, ep97-ep100 (2007).
11. Y. Matsuda et al., Early and definitive diagnosis of toxic shock syndrome by detection of marked expansion of T-cell-receptor Vβ2-positive T cells. Emerg. Infect. Dis. 9, 387 (2003).
12. H. Li, A. Llera, E. L. Malchiodi, R. A. Mariuzza, The structural basis of T cell activation by superantigens. Annu. Rev. Immunol. 17, 435-466 (1999).
13. T. Krakauer, Staphylococcal superantigens: pyrogenic toxins induce toxic shock. Toxins 11, 178 (2019).
14. M. T. Scherer, L. Ignatowicz, G. M. Winslow, J. W. Kappler, P. Marrack, Superantigens: bacterial and viral proteins that manipulate the immune system. Annu. Rev. Cell Biol. 9, 101-128 (1993).
15. Y. W. Choi et al., Interaction of *Staphylococcus aureus* toxin "superantigens" with human T cells. Proc. Natl. Acad. Sci. U.S.A. 86, 8941-8945 (1989).
16. J. D. Fraser, T. Proft, The bacterial superantigen and superantigen-like proteins. Immunol. Rev. 225, 226-243 (2008).
17. M. Saline et al., The structure of superantigen complexed with TCR and MHC reveals novel insights into superantigenic T cell activation. Nat. Commun. 1, 119 (2010).
18. D. Wrapp et al., Cryo-EM structure of the 2019-nCoV spike in the prefusion conformation. Science 367, 1260-1263 (2020).
19. D. Kozakov et al., The ClusPro web server for protein-protein docking. Nat. Protoc. 12, 255 (2017).
20. M. Hoffmann et al., SARS-CoV-2 Cell Entry Depends on ACE2 and TMPRSS2 and Is Blocked by a Clinically Proven Protease Inhibitor. Cell 181, 271-280 (2020).
21. J. P. Changeux, Z. Amoura, F. Rey, M. Miyara, A nicotinic hypothesis for Covid-19 with preventive and therapeutic implications. Qeios doi:10.32388/FXGQSB. (2020).
22. L. Bracci, S. K. Ballas, A. Spreafico, P. Neri, Molecular mimicry between the rabies virus glycoprotein and human immunodeficiency virus-1 GP120: cross-reacting antibodies induced by rabies vaccination. Blood, Am. J. Hematol. 90, 3623-3628 (1997).
23. G. Arad et al., Binding of superantigen toxins into the CD28 homodimer interface is essential for induction of cytokine genes that mediate lethal shock. PLoS Biol. 9, e1001149 (2011).
24. A. Popugailo, Z. Rotfogel, E. Supper, D. Hillman, R. Kaempfer, Staphylococcal and streptococcal superantigens trigger B7/CD28 costimulatory receptor engagement to hyperinduce inflammatory cytokines. Front Immunol. 10, 942 (2019).
25. A. C. Papageorgiou, H. S. Tranter, K. R. Acharya, Crystal structure of microbial superantigen staphylococcal enterotoxin B at 1.5 A resolution: implications for superantigen recognition by MHC class II molecules and T-cell receptors. J. Mol. Biol. 277, 61-79 (1998).
26. Y. Li et al., Structure-based preliminary analysis of immunity and virulence of SARS coronavirus. Viral Immunol. 17, 528-534 (2004).
27. S. H. Zhan, B. E. Deverman, Y. A. Chan, SARS-CoV-2 is well adapted for humans. What does this mean for re-emergence? bioRxiv, 2020.2005.2001.073262 (2020).
28. B. Korber et al., Spike mutation pipeline reveals the emergence of a more transmissible form of SARS-CoV-2. bioRxiv, 2020.2004.2029.069054 (2020).
29. J.-I. Nishi et al., B cell epitope mapping of the bacterial superantigen staphylococcal enterotoxin B: the dominant epitope region recognized by intravenous IgG. J. Immunol. 158, 247-254 (1997).
30. S. J. Whitfield et al., Interference of the T cell and antigen-presenting cell costimulatory pathway using CTLA4-Ig (abatacept) prevents Staphylococcal enterotoxin B pathology. J. Immunol. 198, 3989-3998 (2017).
31. T. Krakauer, M. Buckley, H. J. Issaq, S. D. Fox, Rapamycin protects mice from staphylococcal enterotoxin B-induced toxic shock and blocks cytokine release in vitro and in vivo. Antimicrob. Agents Chemother. 54, 1125-1131 (2010).
32. E. A. Larkin, B. G. Stiles, R. G. Ulrich, Inhibition of toxic shock by human monoclonal antibodies against staphylococcal enterotoxin B. PLoS One 5, e13253 (2010).
33. M. Yuan et al., A highly conserved cryptic epitope in the receptor binding domains of SARS-CoV-2 and SARS-CoV. Science 368, 630-633 (2020).
34. X. Chi et al., A potent neutralizing human antibody reveals the N-terminal domain of the Spike protein of SARS-CoV-2 as a site of vulnerability. bioRxiv, 2020.2005.2008.083964 (2020).
35. A. Grifoni, Weiskopf, D., Ramirez, S. I., Mateus, J., Dan, J. M., Moderbacher, R. C. R., S. A., Sutherland, A., Premkumar, L., Jadi, R. S., Marrama, D., de Silva, A. M., Frazier, A., A. Carlin, Greenbaum, J. A., Peters, B., Krammer, F., Smith, D. M., Crotty, S., Sette, A., Targets of T cell responses to SARS-CoV-2 coronavirus in humans with COVID-19 disease and unexposed individuals. Cell in press (2020).
36. A. Nguyen et al., Human leukocyte antigen susceptibility map for SARS-CoV-2. J. Virol., JVI.00510-00520 (2020).
37. S. M. C. Tirado, K.-J. Yoon, Antibody-dependent enhancement of virus infection and disease. Viral Immunol. 16, 69-86 (2003).
38. Y. Xu et al., Characteristics of pediatric SARS-CoV-2 infection and potential evidence for persistent fecal viral shedding. Nat. Med. 26, 502-505 (2020).
39. L. Bordoli, T. Schwede, "Automated protein structure modeling with SWISS-MODEL Workspace and the Protein Model Portal" in Homology Modeling. (Springer, 2011), pp. 107-136.
40. W. Song, M. Gui, X. Wang, Y. Xiang, Cryo-EM structure of the SARS coronavirus spike glycoprotein in complex with its host cell receptor ACE2. PLoS Pathog. 14, e1007236 (2018).
41. Y. Zhang, J. Skolnick, The protein structure prediction problem could be solved using the current PDB library. Proc. Natl. Acad. Sci. U.S.A. 102, 1029-1034 (2005).
42. M. C. Peitsch, Protein modeling by E-mail. Bio/technology 13, 658-660 (1995).
43. S. Jo, T. Kim, V. G. Iyer, W. Im, CHARMM-GUI: a web-based graphical user interface for CHARMM. J Comput. Chem. 29, 1859-1865 (2008).
44. L. C. Xue, J. P. Rodrigues, P. L. Kastritis, A. M. Bonvin, A. Vangone, PRODIGY: a web server for predicting the binding affinity of protein-protein complexes. Bioinformatics 32, 3676-3678 (2016).

45. Bordoli, L. & Schwede, T. in Homology Modeling 107-136 (Springer, 2011).
46. Wrapp, D. et al. Cryo-EM structure of the 2019-nCoV spike in the prefusion conformation. Science (New York, N.Y.) 367, 1260-1263, doi:10.1126/science.abb2507 (2020).
47. Saline, M. et al. The structure of superantigen complexed with TCR and MHC reveals novel insights into superantigenic T cell activation. Nat. Commun 1, 119, doi: 10.1038/ncomms1117 (2010).
48. Kozakov, D. et al. The ClusPro web server for protein-protein docking. Nat. Protocols 12, 255 (2017).
49. Zhan, S. H., Deverman, B. E. & Chan, Y. A. SARS-CoV-2 is well adapted for humans. What does this mean for re-emergence? bioRxiv, 2020.2005.2001.073262, doi: 10.1101/2020.05.01.073262 (2020).
50. Korber, B. et al. Spike mutation pipeline reveals the emergence of a more transmissible form of SARS-CoV-2. bioRxiv, 2020.2004.2029.069054, doi:10.1101/ 2020.04.29.069054 (2020).
51. DeLano, W. L. Pymol: An open-source molecular graphics tool. CCP4 Newsletter on protein crystallography 40, 82-92 (2002).
52. Eastman, P. et al. OpenMM 7: Rapid development of high performance algorithms for molecular dynamics. PLoS computational biology 13, e1005659 (2017).
53. Vangone, A. & Bonvin, A. M. Contacts-based prediction of binding affinity in protein-protein complexes. elife 4, e07454 (2015).
54. Xue, L. C., Rodrigues, J. P., Kastritis, P. L., Bonvin, A. M. & Vangone, A. PRODIGY: a web server for predicting the binding affinity of protein-protein complexes. Bioinformatics 32, 3676-3678 (2016).
55. A. Waterhouse et al., SWISS-MODEL: homology modelling of protein structures and complexes. Nucleic Acids Res 46, W296-W303 (2018).
56. W. Song, M. Gui, X. Wang, Y. Xiang, Cryo-EM structure of the SARS coronavirus spike glycoprotein in complex with its host cell receptor ACE2. PLoS Pathog. 14, e1007236 (2018).
57. Y. Yuan et al., Cryo-EM structures of MERS-CoV and SARS-CoV spike glycoproteins reveal the dynamic receptor binding domains. Nature communications 8, 15092 (2017).
58. Y. Li et al., Structure-based preliminary analysis of immunity and virulence of SARS coronavirus. Viral Immunol. 17, 528-534 (2004).
59. W. L. DeLano, Pymol: An open-source molecular graphics tool. CCP4 Newsletter On Protein Crystallography 40, 82-92 (2002).
60. J. A. Maier et al., ff14SB: Improving the Accuracy of Protein Side Chain and Backbone Parameters from ff99SB. J. Chem. Theory Comput. 11, 3696-3713 (2015).
61. Mateus J, et al. (2020) Selective and cross-reactive SARS-CoV-2 T cell epitopes in unexposed humans. Science.
62. Schultheiss C, et al. (2020) Next-Generation Sequencing of T and B Cell Receptor Repertoires from COVID-19 Patients Showed Signatures Associated with Severity of Disease. Immunity 53:442-455.
63. Simnica D, et al. (2019) T cell receptor next-generation sequencing reveals cancer-associated repertoire metrics and reconstitution after chemotherapy in patients with hematological and solid tumors. Oncoimmunology 8(11): e1644110.
64. Simnica D, et al. (2019) High-Throughput Immunogenetics Reveals a Lack of Physiological T Cell Clusters in Patients With Autoimmune Cytopenias. Frontiers in Immunology 10(1897).
65. Berman H M, et al. (2000) The protein data bank. *Nucleic acids research* 28(1):235-242.
66. Sim M J W, et al. (2020) High-affinity oligoclonal TCRs define effective adoptive T cell therapy targeting mutant KRAS-G12D. Proceedings of the National Academy of Sciences of the United States of America 117(23):12826-12835.
67. Hoare H L, et al. (2006) Structural basis for a major histocompatibility complex class Ib-restricted T cell response. Nature Immunology 7(3):256-264.
68. Holland C J, et al. (2018) In Silico and Structural Analyses Demonstrate That Intrinsic Protein Motions Guide T Cell Receptor Complementarity Determining Region Loop Flexibility. Frontiers in immunology 9:674.
69. The UniProt Consortium (2016) UniProt: the universal protein knowledgebase. Nucleic Acids Research 45(D1): D158-D169.
70. Sievers F, et al. (2011) Fast, scalable generation of high-quality protein multiple sequence alignments using Clustal Omega. Mol Syst Biol 7(1):539.
71. Andersen, K. G., Rambaut, A., Lipkin, W. I., Holmes, E. C., and Garry, R. F. (2020). The proximal origin of SARS-CoV-2. Nat Med 26, 450-452.
72. Andreano, E., Piccini, G., Licastro, D., Casalino, L., Johnson, N. V., Paciello, I., Monego, S. D., Pantano, E., Manganaro, N., Manenti, A., et al. (2020). SARS-CoV-2 escape in vitro from a highly neutralizing COVID-19 convalescent plasma. bioRxiv.
73. Barnes, C. O., West, A. P., Huey-Tubman, K., Hoffmann, M. A., Sharaf, N. G., Hoffman, P. R., Koranda, N., Gristick, H. B., Gaebler, C., and Muecksch, F. (2020). Structures of human antibodies bound to SARS-CoV-2 spike reveal common epitopes and recurrent features of antibodies. Cell 182, 828-842.
74. Belhadjer, Z., Méot, M., Bajolle, F., Khraiche, D., Legendre, A., Abakka, S., Auriau, J., Grimaud, M., Oualha, M., Beghetti, M., et al. (2020). Acute heart failure in multisystem inflammatory syndrome in children (MIS-C) in the context of global SARS-CoV-2 pandemic. Circulation 142, 429-436.
75. Benton, D. J., Wrobel, A. G., Xu, P., Roustan, C., Martin, S. R., Rosenthal, P. B., Skehel, J. J., and Gamblin, S. J. (2020). Receptor binding and priming of the spike protein of SARS-CoV-2 for membrane fusion. Nature, in press.
76. Bestle, D., Heindl, M. R., Limburg, H., Van Lam van, T., Pilgram, O., Moulton, H., Stein, D. A., Hardes, K., Eickmann, M., Dolnik, O., et al. (2020). TMPRSS2 and furin are both essential for proteolytic activation of SARS-CoV-2 in human airway cells. Life Sci Alliance 3, e202000786.
77. Cai, Y., Zhang, J., Xiao, T., Peng, H., Sterling, S. M., Walsh, R. M., Jr., Rawson, S., Rits-Volloch, S., and Chen, B. (2020). Distinct conformational states of SARS-CoV-2 spike protein. Science 369, 1586-1592.
78. Cantuti-Castelvetri, L., Ojha, R., Pedro, L. D., Djannatian, M., Franz, J., Kuivanen, S., van der Meer, F., Kallio, K., Kaya, T., and Anastasina, M. (2020). Neuropilin-1 facilitates SARS-CoV-2 cell entry and infectivity. Science 370, 856-860.
79. Cao, L., Goreshnik, I., Coventry, B., Case, J. B., Miller, L., Kozodoy, L., Chen, R. E., Carter, L., Walls, A. C., Park, Y.-J., et al. (2020a). De novo design of picomolar SARS-CoV-2 miniprotein inhibitors. Science 370, 426-431.

80. Cao, Y., Su, B., Guo, X., Sun, W., Deng, Y., Bao, L., Zhu, Q., Zhang, X., Zheng, Y., Geng, C., et al. (2020b). Potent neutralizing antibodies against SARS-CoV-2 identified by high-throughput single-cell sequencing of convalescent patients' B cells. Cell 182, 73-84.e16.

81. Casalino, L., Gaieb, Z., Goldsmith, J. A., Hjorth, C. K., Dommer, A. C., Harbison, A. M., Fogarty, C. A., Barros, E. P., Taylor, B. C., McLellan, J. S., et al. (2020). Beyond shielding: The roles of glycans in the SARS-CoV-2 Spike protein. ACS central science 6, 1722-1734.

82. Cheng, M. H., Zhang, S., Porritt, R. A., Arditi, M., and Bahar, I. (2020). Superantigenic character of an insert unique to SARS-CoV-2 spike supported by skewed TCR repertoire in patients with hyperinflammation. Proc Natl Acad Sci USA 117, 25254-25262.

83. Cheung, E. W., Zachariah, P., Gorelik, M., Boneparth, A., Kernie, S. G., Orange, J. S., and Milner, J. D. (2020). Multisystem inflammatory syndrome related to COVID-19 in previously healthy children and adolescents in New York city. JAMA 324, 294-296.

84. Chi, X., Yan, R., Zhang, J., Zhang, G., Zhang, Y., Hao, M., Zhang, Z., Fan, P., Dong, Y., Yang, Y., et al. (2020). A neutralizing human antibody binds to the N-terminal domain of the Spike protein of SARS-CoV-2. Science 369, 650-655.

85. Coutard, B., Valle, C., de Lamballerie, X., Canard, B., Seidah, N. G., and Decroly, E. (2020). The spike glycoprotein of the new coronavirus 2019-nCoV contains a furin-like cleavage site absent in CoV of the same Glade. Antiviral Res 176, 104742.

86. Cui, J., Li, F., and Shi, Z.-L. (2019). Origin and evolution of pathogenic coronaviruses. Nat Rev Microbiol 17, 181-192.

87. Dahms, S. O., Creemers, J. W., Schaub, Y., Bourenkov, G. P., Zogg, T., Brandstetter, H., and Than, M. E. (2016). The structure of a furin-antibody complex explains non-competitive inhibition by steric exclusion of substrate conformers. Sci Rep 6, 34303.

88. Daly, J. L., Simonetti, B., Klein, K., Chen, K.-E., Williamson, M. K., Antón-Plágaro, C., Shoemark, D. K., Simón-Gracia, L., Bauer, M., Hollandi, R., et al. (2020). Neuropilin-1 is a host factor for SARS-CoV-2 infection. Science 370, 861-865.

89. DeLano, W. L. (2002). Pymol: An open-source molecular graphics tool. CCP4 Newsletter on protein crystallography 40, 82-92.

90. Dutta, K., Varshney, A. K., Franklin, M. C., Goger, M., Wang, X., and Fries, B. C. (2015). Mechanisms mediating enhanced neutralization efficacy of staphylococcal enterotoxin B by combinations of monoclonal antibodies. J Biol Chem 290, 6715-6730.

91. Forni, D., Cagliani, R., Clerici, M., and Sironi, M. (2017). Molecular evolution of human coronavirus genomes. Trends Microbiol 25, 35-48.

92. Garcia, G., Sharma, A., Ramaiah, A., Sen, C., Kohn, D., Gomperts, B., Svendsen, C. N., Damoiseaux, R. D., and Arumugaswami, V. (2020). Antiviral Drug Screen of Kinase inhibitors Identifies Cellular Signaling Pathways Critical for SARS-CoV-2 Replication. bioRxiv, 2020.2006.2024.150326.

93. Graham, B. S., Gilman, M. S. A., and McLellan, J. S. (2019). Structure-Based Vaccine Antigen Design. Annu Rev Med 70, 91-104.

94. Greaney, A. J., Starr, T. N., Gilchuk, P., Zost, S. J., Binshtein, E., Loes, A. N., Hilton, S. K., Huddleston, J., Eguia, R., Crawford, K. H. D., et al. (2021). Complete Mapping of Mutations to the SARS-CoV-2 Spike Receptor-Binding Domain that Escape Antibody Recognition. Cell Host Microbe 29, 44-57.e49.

95. Grifoni, A., Weiskopf, D., Ramirez, S. I., Mateus, J., Dan, J. M., Moderbacher, C. R., Rawlings, S. A., Sutherland, A., Premkumar, L., Jadi, R. S., et al. (2020). Targets of T cell responses to SARS-CoV-2 coronavirus in humans with COVID-19 disease and unexposed individuals. Cell 181, 1489-1501 e1415.

96. Gupta, A., Madhavan, M. V., Sehgal, K., Nair, N., Mahajan, S., Sehrawat, T. S., Bikdeli, B., Ahluwalia, N., Ausiello, J. C., Wan, E. Y., et al. (2020). Extrapulmonary manifestations of COVID-19. Nat Med 26, 1017-1032.

97. Hansen, J., Baum, A., Pascal, K. E., Russo, V., Giordano, S., Wloga, E., Fulton, B. O., Yan, Y., Koon, K., Patel, K., et al. (2020). Studies in humanized mice and convalescent humans yield a SARS-CoV-2 antibody cocktail. Science 369, 1010-1014.

98. Hoffmann, M., Kleine-Weber, H., Schroeder, S., Kruger, N., Herrler, T., Erichsen, S., Schiergens, T. S., Herrler, G., Wu, N.-H., Nitsche, A., et al. (2020). SARS-CoV-2 cell entry depends on ACE2 and TMPRSS2 and is blocked by a clinically proven protease inhibitor. Cell 181, 271-280.

99. Huang, A. T., Garcia-Carreras, B., Hitchings, M. D. T., Yang, B., Katzelnick, L. C., Rattigan, S. M., Borgert, B. A., Moreno, C. A., Solomon, B. D., Trimmer-Smith, L., et al. (2020). A systematic review of antibody mediated immunity to coronaviruses: kinetics, correlates of protection, and association with severity. Nat Commun 11, 4704.

100. Jaimes, J. A., André, N. M., Chappie, J. S., Millet, J. K., and Whittaker, G. R. (2020). Phylogenetic analysis and structural modeling of SARS-CoV-2 spike protein reveals an evolutionary distinct and proteolytically sensitive activation loop. J Mol Biol 432, 3309-3325.

101. Johnson, B. A., Xie, X., Bailey, A. L., Kalveram, B., Lokugamage, K. G., Muruato, A., Zou, J., Zhang, X., Juelich, T., Smith, J. K., et al. (2021). Loss of furin cleavage site attenuates SARS-CoV-2 pathogenesis. Nature in press.

102. Kemp, S., Collier, D., Datir, R., Gayed, S., Jahun, A., Hosmillo, M., Ferreira, I., Rees-Spear, C., Mlcochova, P., Lumb, I. U., et al. (2020). Neutralising antibodies drive Spike mediated SARS-CoV-2 evasion. medRxiv, 2020.2012.2005.20241927.

103. Kozakov, D., Hall, D. R., Xia, B., Porter, K. A., Padhorny, D., Yueh, C., Beglov, D., and Vajda, S. (2017). The ClusPro web server for protein-protein docking. Nat Protoc 12, 255.

104. Krakauer, T. (2019). Staphylococcal superantigens: pyrogenic toxins induce toxic shock. Toxins 11, 178.

105. Lemmin, T., Kalbermatter, D., Harder, D., Plattet, P., and Fotiadis, D. (2020). Structures and dynamics of the novel S1/S2 protease cleavage site loop of the SARS-CoV-2 spike glycoprotein. J Struct Biol: X 4, 100038.

106. Li, W., Schafer, A., Kulkarni, S. S., Liu, X., Martinez, D. R., Chen, C., Sun, Z., Leist, S. R., Drelich, A., Zhang, L., et al. (2020). High potency of a bivalent human VH domain in SARS-CoV-2 animal models. Cell 183, 429-441.e416.

107. Liu, L., Wang, P., Nair, M. S., Yu, J., Rapp, M., Wang, Q., Luo, Y., Chan, J. F., Sahi, V., Figueroa, A., et al. (2020). Potent neutralizing antibodies directed to multiple epitopes on SARS-CoV-2 spike. Nature 584, 450-456.

108. Lv, H., Wu, N. C., Tsang, O. T., Yuan, M., Perera, R., Leung, W. S., So, R. T. Y., Chan, J. M. C., Yip, G. K., Chik, T. S. H., et al. (2020a). Cross-reactive Antibody Response between SARS-CoV-2 and SARS-CoV Infections. Cell Rep 31, 107725.

109. Lv, Z., Deng, Y.-Q., Ye, Q., Cao, L., Sun, C.-Y., Fan, C., Huang, W., Sun, S., Sun, Y., Zhu, L., et al. (2020b). Structural basis for neutralization of SARS-CoV-2 and SARS-CoV by a potent therapeutic antibody. Science 369, 1505-1509.

110. Mateus, J., Grifoni, A., Tarke, A., Sidney, J., Ramirez, S. I., Dan, J. M., Burger, Z. C., Rawlings, S. A., Smith, D. M., Phillips, E., et al. (2020). Selective and cross-reactive SARS-CoV-2 T cell epitopes in unexposed humans. Science 370, 89-94.

111. Matsuyama, S., Nao, N., Shirato, K., Kawase, M., Saito, S., Takayama, I., Nagata, N., Sekizuka, T., Katoh, H., Kato, F., et al. (2020). Enhanced isolation of SARS-CoV-2 by TMPRSS2-expressing cells. Proc Natl Acad Sci USA 117, 7001-7003.

112. McCarthy, K. R., Rennick, L. J., Nambulli, S., Robinson-McCarthy, L. R., Bain, W. G., Haidar, G., and Duprex, W. P. (2020). Natural deletions in the SARS-CoV-2 spike glycoprotein drive antibody escape. bioRxiv, 2020.2011.2019.389916.

113. Noval Rivas, M., Porritt, R. A., Cheng, M. H., Bahar, I., and Arditi, M. (2020). COVID-19-associated multisystem inflammatory syndrome in children (MIS-C): A novel disease that mimics toxic shock syndrome—the superantigen hypothesis. J Allergy Clin Immunol, S0091-6749 (0020)31414-31417.

114. Peitsch, M. C. (1995). Protein modeling by E-mail. Bio/technology 13, 658-660.

115. Pinto, D., Park, Y.-J., Beltramello, M., Walls, A. C., Tortorici, M. A., Bianchi, S., Jaconi, S., Culap, K., Zatta, F., De Marco, A., et al. (2020). Cross-neutralization of SARS-CoV-2 by a human monoclonal SARS-CoV antibody. Nature 583, 290-295.

116. Porritt, R. A., Paschold, L., Rivas, M. N., Cheng, M. H., Yonker, L. M., Chandnani, H., Lopez, M., Simnica, D., Schultheiß, C., Santiskulvong, C., et al. (2020). HLA Class I-associated expansion of TRBV11-2 T cells via a CDR3-independent mechanism in Multisystem Inflammatory Syndrome in Children (MIS-C). J Clin Invest, in press.

117. Renn, A., Fu, Y., Hu, X., Hall, M. D., and Simeonov, A. (2020). Fruitful neutralizing antibody pipeline brings hope to defeat SARS-Cov-2. Trends Pharmacol Sci 41, 815-829.

118. Riphagen, S., Gomez, X., Gonzalez-Martinez, C., Wilkinson, N., and Theocharis, P. (2020). Hyperinflammatory shock in children during COVID-19 pandemic. Lancet 395, 1607-1608.

119. Shajahan, A., Supekar, N. T., Gleinich, A. S., and Azadi, P. (2020). Deducing the N- and O-glycosylation profile of the spike protein of novel coronavirus SARS-CoV-2. Glycobiology, in press.

120. Shang, J., Wan, Y., Luo, C., Ye, G., Geng, Q., Auerbach, A., and Li, F. (2020). Cell entry mechanisms of SARS-CoV-2. Proc Natl Acad Sci USA 117, 11727-11734.

121. Shi, R., Shan, C., Duan, X., Chen, Z., Liu, P., Song, J., Song, T., Bi, X., Han, C., Wu, L., et al. (2020). A human neutralizing antibody targets the receptor-binding site of SARS-CoV-2. Nature 584, 120-124.

122. Sievers, F., Wilm, A., Dineen, D., Gibson, T. J., Karplus, K., Li, W., Lopez, R., McWilliam, H., Remmert, M., Riding, J., et al. (2011). Fast, scalable generation of high-quality protein multiple sequence alignments using Clustal Omega. Mol Syst Biol 7, 539-539.

123. Steinhauer, D. A. (1999). Role of hemagglutinin cleavage for the pathogenicity of influenza virus. Virology 258, 1-20.

124. Tay, M. Z., Poh, C. M., Rénia, L., MacAry, P. A., and Ng, L. F. P. (2020). The trinity of COVID-19: immunity, inflammation and intervention. Nat Rev Immunol 20, 363-374.

125. Thomas, G. (2002). Furin at the cutting edge: from protein traffic to embryogenesis and disease. Nat Rev Mol Cell Biol 3, 753-766.

126. Tian, S., Huajun, W., and Wu, J. (2012). Computational prediction of furin cleavage sites by a hybrid method and understanding mechanism underlying diseases. Sci Rep 2, 261-261.

127. Tortorici, M. A., Walls, A. C., Lang, Y., Wang, C., Li, Z., Koerhuis, D., Boons, G. J., Bosch, B. J., Rey, F. A., de Groot, R. J., et al. (2019). Structural basis for human coronavirus attachment to sialic acid receptors. Nature structural & molecular biology 26, 481-489.

128. Vabret, N., Britton, G. J., Gruber, C., Hegde, S., Kim, J., Kuksin, M., Levantovsky, R., Malle, L., Moreira, A., and Park, M. D. (2020). Immunology of COVID-19: current state of the science. Immunity 52, 910-941.

129. Van Zundert, G., Rodrigues, J., Trellet, M., Schmitz, C., Kastritis, P., Karaca, E., Melquiond, A., van Dijk, M., De Vries, S., and Bonvin, A. (2016). The HADDOCK2. 2 web server: user-friendly integrative modeling of biomolecular complexes. J Mol Biol 428, 720-725.

130. Varshney, A. K., Wang, X., Cook, E., Dutta, K., Scharff, M. D., Goger, M. J., and Fries, B. C. (2011). Generation, characterization, and epitope mapping of neutralizing and protective monoclonal antibodies against staphylococcal enterotoxin B-induced lethal shock. J Biol Chem 286, 9737-9747.

131. Verdoni, L., Mazza, A., Gervasoni, A., Martelli, L., Ruggeri, M., Ciuffreda, M., Bonanomi, E., and D'Antiga, L. (2020). An outbreak of severe Kawasaki-like disease at the Italian epicentre of the SARS-CoV-2 epidemic: an observational cohort study. Lancet 395, 1771-1778.

132. Walls, A. C., Park, Y.-J., Tortorici, M. A., Wall, A., McGuire, A. T., and Veesler, D. (2020). Structure, function, and antigenicity of the SARS-CoV-2 spike glycoprotein. Cell 180, 281-292.

133. Watanabe, Y., Allen, J. D., Wrapp, D., McLellan, J. S., and Crispin, M. (2020). Site-specific glycan analysis of the SARS-CoV-2 spike. Science 369, 330-333.

134. Waterhouse, A., Bertoni, M., Bienert, S., Studer, G., Tauriello, G., Gumienny, R., Heer, F. T., de Beer, T. A. P., Rempfer, C., and Bordoli, L. (2018). SWISS-MODEL: homology modelling of protein structures and complexes. Nucleic Acids Res 46, W296-W303.

135. Woo, H., Park, S.-J., Choi, Y. K., Park, T., Tanveer, M., Cao, Y., Kern, N. R., Lee, J., Yeom, M. S., Croll, T. I., et al. (2020). Developing a fully glycosylated full-Length SARS-CoV-2 spike protein model in a viral membrane. J Phys Chem B 124, 7128-7137.

136. Wrapp, D., Wang, N., Corbett, K. S., Goldsmith, J. A., Hsieh, C. L., Abiona, O., Graham, B. S., and McLellan, J. S. (2020). Cryo-EM structure of the 2019-nCoV spike in the prefusion conformation. Science 367, 1260-1263.

137. Xue, L. C., Rodrigues, J. P., Kastritis, P. L., Bonvin, A. M., and Vangone, A. (2016). PRODIGY: a web server for predicting the binding affinity of protein-protein complexes. Bioinformatics 32, 3676-3678.

138. Yan, R., Zhang, Y., Li, Y., Xia, L., Guo, Y., and Zhou, Q. (2020). Structural basis for the recognition of SARS-CoV-2 by full-length human ACE2. Science 367, 1444-1448.
139. Yuan, M., Wu, N. C., Zhu, X., Lee, C. D., So, R. T. Y., Lv, H., Mok, C. K. P., and Wilson, I. A. (2020). A highly conserved cryptic epitope in the receptor binding domains of SARS-CoV-2 and SARS-CoV. Science 368, 630-633.
140. Zhang, Y., and Skolnick, J. (2005). The protein structure prediction problem could be solved using the current PDB library. Proc Natl Acad Sci USA 102, 1029-1034.
141. Zhou, D., Duyvesteyn, H. M., Chen, C.-P., Huang, C.-G., Chen, T.-H., Shih, S.-R., Lin, Y.-C., Cheng, C.-Y., Cheng, S.-H., Huang, Y.-C., et al. (2020a). Structural basis for the neutralization of SARS-CoV-2 by an antibody from a convalescent patient. Nat Struct Mol Biol 27, 950-958.
142. Zhou, H., Chen, X., Hu, T., Li, J., Song, H., Liu, Y., Wang, P., Liu, D., Yang, J., and Holmes, E. C. (2020b). A novel bat coronavirus closely related to SARS-CoV-2 contains natural insertions at the S1/S2 cleavage site of the spike protein. Curr Biol 30, 2196-2203.
143. Zost, S. J., Gilchuk, P., Case, J. B., Binshtein, E., Chen, R. E., Nkolola, J. P., Schäfer, A., Reidy, J. X., Trivette, A., Nargi, R. S., et al. (2020). Potently neutralizing and protective human antibodies against SARS-CoV-2. Nature 584, 443-449.

What is claimed is:

1. A method of treating a COVID-19 infection in a subject, comprising administering to the subject an effective amount of one or more of a humanized mAb 6D3, a humanized mAb 14G8, and a functional fragment thereof.

2. The method of claim 1, wherein the humanized mAb 6D3 comprises one or more of a $V_H$ CDR amino acid sequence selected from the group consisting of SEQ ID NO:14, SEQ ID NO:15 and SEQ ID NO:16.

3. The method of claim 1, wherein the humanized mAb 6D3 comprises one or more of a $V_L$ CDR amino acid sequence selected from the group consisting of SEQ ID NO:18, SEQ ID NO:19 and SEQ ID NO:20.

4. The method of claim 1, wherein the humanized mAb 6D3 comprises (a) a $V_H$ domain having an amino acid sequence comprising SEQ ID NO:13, and (b) a $V_L$ domain having an amino acid sequence comprising SEQ ID NO:17.

5. The method of claim 1, wherein the humanized mAb 14G8 comprises one or more of a $V_H$ CDR amino acid sequence selected from the group consisting of SEQ ID NO:36, SEQ ID NO:37 and SEQ ID NO:38.

6. The method of claim 1, wherein the humanized mAb 14G8 comprises one or more of a $V_L$ CDR amino acid sequence selected from the group consisting of SEQ ID NO:40, SEQ ID NO:41 and SEQ ID NO:42.

7. The method of claim 1, wherein the humanized mAb 14G8 comprises (a) a $V_H$ domain having an amino acid sequence comprising SEQ ID NO:35, and (b) a $V_L$ domain having an amino acid sequence comprising SEQ ID NO:39.

8. The method of claim 1, wherein the subject is a human.

9. The method of claim 8, wherein the subject is a child and wherein the treatment results in an amelioration of a multisystem inflammatory syndrome.

10. The method of claim 8, wherein the treatment results in an amelioration of a pneumonia.

11. A method of treating a COVID-19 infection in a subject, comprising administering to the subject an effective amount of one or more SARS-CoV-2 superantigenic (SAg) peptides, wherein the one or more peptides comprise SEQ ID NO:2 or SEQ ID NO:3.

12. The method of claim 11, wherein the one or more peptides comprise SEQ ID NO:4.

13. The method of claim 11, wherein the one or more peptides comprise SEQ ID NO:5.

14. The method of claim 11, wherein the one or more peptides comprise SEQ ID NO:6.

15. The method of claim 11, wherein the one or more peptides comprise SEQ ID NO:7.

16. The method of claim 11, wherein the one or more peptides comprise SEQ ID NO:8.

17. The method of claim 11, wherein the one or more peptides comprise SEQ ID NO:9.

18. The method of claim 11, wherein the one or more peptides comprise SEQ ID NO:10.

19. The method of claim 11, wherein the one or more peptides comprise SEQ ID NO:11.

20. The method of claim 11, wherein the one or more peptides comprise SEQ ID NO:12.

21. The method of claim 11, wherein the subject is a human.

22. The method of claim 11, wherein the subject is a child and wherein the treatment results in an amelioration of a multisystem inflammatory syndrome.

23. The method of claim 11, wherein the treatment results in an amelioration of a pneumonia.

* * * * *

SEQUENCE LISTING

```
<160> NUMBER OF SEQ ID NOS: 121

<210> SEQ ID NO 1
<211> LENGTH: 1273
<212> TYPE: PRT
<213> ORGANISM: Artificial Sequence
<220> FEATURE:
<223> OTHER INFORMATION: Synthetic construct

<400> SEQUENCE: 1

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255
```

```
Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670
```

```
Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080
```

```
Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 2
<211> LENGTH: 4
<212> TYPE: PRT
<213> ORGANISM: Artificial Sequence
<220> FEATURE:
<223> OTHER INFORMATION: Synthetic construct

<400> SEQUENCE: 2

Pro Arg Arg Ala
1

<210> SEQ ID NO 3
<211> LENGTH: 23
<212> TYPE: PRT
<213> ORGANISM: Artificial Sequence
<220> FEATURE:
<223> OTHER INFORMATION: Synthetic construct

<400> SEQUENCE: 3

Tyr Asn Glu Asn Gly Thr Ile Thr Asp Ala Val Asp Cys Ala Leu Asp
1               5                   10                  15

Pro Leu Ser Glu Thr Lys Cys
            20

<210> SEQ ID NO 4
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 4

Thr Asn Ser Pro Arg Arg Ala Arg
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic construct

<400> SEQUENCE: 5

Tyr Gln Thr Gln Thr Asn Ser Pro Arg Arg Ala Arg
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Synthetic construct

<400> SEQUENCE: 6

Pro Arg Arg Ala Arg Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Pro Arg Arg Ala Ser Val Ala Ser Gln
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic construct

<400> SEQUENCE: 8

Pro Arg Arg Ala Ser Val Ala Ser Gln Ser Ile
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

Thr Asn Ser Pro Arg Arg Ala Ser Val Ala Ser Gln
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic construct
```

<400> SEQUENCE: 10

Gln Thr Asn Ser Pro Arg Arg Ala Arg Ser Val Ala Ser
1               5                   10

<210> SEQ ID NO 11
<211> LENGTH: 27
<212> TYPE: PRT
<213> ORGANISM: Artificial Sequence
<220> FEATURE:
<223> OTHER INFORMATION: Synthetic construct

<400> SEQUENCE: 11

Glu Cys Asp Ile Pro Ile Gly Ala Gly Ile Cys Ala Ser Tyr Gln Thr
1               5                   10                  15

Gln Thr Asn Ser Pro Arg Arg Ala Arg Ser Val
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic construct

<400> SEQUENCE: 12

Glu Cys Asp Ile Pro Ile Gly Ala Gly Ile Cys Ala Ser Tyr Gln Thr
1               5                   10                  15

Gln Thr Asn Ser Pro Arg Arg Ala Arg
            20                  25

<210> SEQ ID NO 13
<211> LENGTH: 119
<212> TYPE: PRT
<213> ORGANISM: Artificial Sequence
<220> FEATURE:
<223> OTHER INFORMATION: Synthetic construct

<400> SEQUENCE: 13

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser His
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Ile Asn Tyr Asn Gln Ile Phe
    50                  55                  60

Glu Gly Lys Ala Thr Leu Thr Val Asp Lys Ser Ser Thr Thr Ala Tyr
65                  70                  75                  80

Leu Gln Leu Ser Ser Leu Thr Ser Glu Asp Ser Ala Val Tyr Tyr Cys
                85                  90                  95

Ala Arg Thr Ala Gly Leu Leu Ala Pro Met Asp Tyr Trp Gly Gln Gly
            100                 105                 110

Thr Ser Val Thr Val Ser Ser
        115

<210> SEQ ID NO 14
<211> LENGTH: 8
<212> TYPE: PRT
<213> ORGANISM: Artificial Sequence
<220> FEATURE:
<223> OTHER INFORMATION: Synthetic construct

```
<400> SEQUENCE: 14

Gly Tyr Thr Phe Thr Ser His Trp
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic construct

<400> SEQUENCE: 15

Ile Asp Pro Ser Asp Ser Tyr Ile
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic construct

<400> SEQUENCE: 16

Ala Arg Thr Ala Gly Leu Leu Ala Pro Met Asp Tyr
1               5                   10

<210> SEQ ID NO 17
<211> LENGTH: 113
<212> TYPE: PRT
<213> ORGANISM: Artificial Sequence
<220> FEATURE:
<223> OTHER INFORMATION: Synthetic construct

<400> SEQUENCE: 17

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Phe Asn Ser
                20                  25                  30

Gly Asn Gln Lys Asn Phe Leu Thr Trp Tyr Gln Gln Ile Pro Gly Gln
            35                  40                  45

Pro Pro Lys Leu Leu Ile Tyr Trp Ala Ser Thr Arg Asp Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Thr Tyr Pro Leu Thr Phe Gly Val Gly Thr Lys Leu Glu Leu
            100                 105                 110

Lys

<210> SEQ ID NO 18
<211> LENGTH: 12
<212> TYPE: PRT
<213> ORGANISM: Artificial Sequence
<220> FEATURE:
<223> OTHER INFORMATION: Synthetic construct

<400> SEQUENCE: 18

Gln Ser Leu Phe Asn Ser Gly Asn Gln Lys Asn Phe
1               5                   10
```

```
<210> SEQ ID NO 19
<211> LENGTH: 3
<212> TYPE: PRT
<213> ORGANISM: Artificial Sequence
<220> FEATURE:
<223> OTHER INFORMATION: Synthetic construct

<400> SEQUENCE: 19

Trp Ala Ser
1

<210> SEQ ID NO 20
<211> LENGTH: 9
<212> TYPE: PRT
<213> ORGANISM: Artificial Sequence
<220> FEATURE:
<223> OTHER INFORMATION: Synthetic construct

<400> SEQUENCE: 20

Gln Asn Asp Tyr Thr Tyr Pro Leu Thr
1               5

<210> SEQ ID NO 21
<211> LENGTH: 121
<212> TYPE: PRT
<213> ORGANISM: Artificial Sequence
<220> FEATURE:
<223> OTHER INFORMATION: Synthetic construct

<400> SEQUENCE: 21

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Ile Phe Thr Ile Ala
            20                  25                  30

Gly Ile Gln Trp Val Gln Lys Met Pro Gly Arg Gly Leu Arg Trp Ile
        35                  40                  45

Gly Trp Ile Asn Thr His Ser Gly Val Pro Gly Tyr Ala Glu Glu Phe
    50                  55                  60

Lys Gly Arg Phe Ala Phe Ser Leu Glu Thr Ser Ala Arg Thr Ala Tyr
65                  70                  75                  80

Leu Gln Ile Ser Asn Leu Lys Asp Glu Asp Thr Ala Thr Tyr Phe Cys
                85                  90                  95

Ala Arg Ile Tyr Tyr Gly Asn Asn Gly Gly Val Met Asp Tyr Trp Gly
            100                 105                 110

Gln Gly Thr Ser Val Thr Val Ser Ser
        115                 120

<210> SEQ ID NO 22
<211> LENGTH: 8
<212> TYPE: PRT
<213> ORGANISM: Artificial Sequence
<220> FEATURE:
<223> OTHER INFORMATION: Synthetic construct

<400> SEQUENCE: 22

Gly Tyr Ile Phe Thr Ile Ala Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 23

Ile Asn Thr His Ser Gly Val Pro
1               5

<210> SEQ ID NO 24
<211> LENGTH: 13
<212> TYPE: PRT
<213> ORGANISM: Artificial Sequence
<220> FEATURE:
<223> OTHER INFORMATION: Synthetic construct

<400> SEQUENCE: 24

Arg Ile Tyr Tyr Gly Asn Asn Gly Gly Val Met Asp Tyr
1               5                   10

<210> SEQ ID NO 25
<211> LENGTH: 107
<212> TYPE: PRT
<213> ORGANISM: Artificial Sequence
<220> FEATURE:
<223> OTHER INFORMATION: Synthetic construct

<400> SEQUENCE: 25

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Asp Tyr
            20                  25                  30

Leu Thr Trp Leu Gln Gln Lys Pro Asp Gly Thr Ile Lys Arg Leu Ile
        35                  40                  45

Tyr Val Ala Ser Ser Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Asn Tyr Pro Trp
                85                  90                  95

Thr Phe Gly Gly Gly Thr Lys Leu Glu Ile Arg
            100                 105

<210> SEQ ID NO 26
<211> LENGTH: 6
<212> TYPE: PRT
<213> ORGANISM: Artificial Sequence
<220> FEATURE:
<223> OTHER INFORMATION: Synthetic construct

<400> SEQUENCE: 26

Gln Glu Ile Ser Asp Tyr
1               5

<210> SEQ ID NO 27
<211> LENGTH: 3
<212> TYPE: PRT
<213> ORGANISM: Artificial Sequence
<220> FEATURE:
<223> OTHER INFORMATION: Synthetic construct

<400> SEQUENCE: 27

Val Ala Ser
1
```

```
<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Leu Gln Tyr Ala Asn Tyr Pro Trp Thr
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic construct

<400> SEQUENCE: 29

Gly Tyr Ile Phe Thr Ile Ala Gly Ile Gln
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Synthetic construct

<400> SEQUENCE: 30

Trp Ile Asn Thr His Ser Gly Val Pro Glu Tyr Ala Glu Glu Phe Lys
1               5                   10                  15

Gly

<210> SEQ ID NO 31
<211> LENGTH: 12
<212> TYPE: PRT
<213> ORGANISM: Artificial Sequence
<220> FEATURE:
<223> OTHER INFORMATION: Synthetic construct

<400> SEQUENCE: 31

Ile Tyr Tyr Gly Asn Asn Gly Gly Val Met Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic construct

<400> SEQUENCE: 32

Arg Ala Ser Gln Glu Ile Ser Asp Tyr Leu Thr
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Synthetic construct

<400> SEQUENCE: 33

Val Ala Ser Ser Leu Asp Ser
1               5
```

```
<210> SEQ ID NO 34
<211> LENGTH: 9
<212> TYPE: PRT
<213> ORGANISM: Artificial Sequence
<220> FEATURE:
<223> OTHER INFORMATION: Synthetic construct

<400> SEQUENCE: 34

Leu Gln Tyr Ala Asn Tyr Pro Trp Thr
1               5

<210> SEQ ID NO 35
<211> LENGTH: 120
<212> TYPE: PRT
<213> ORGANISM: Artificial Sequence
<220> FEATURE:
<223> OTHER INFORMATION: Synthetic construct

<400> SEQUENCE: 35

Glu Val Gln Leu Leu Glu Ser Gly Gly Gly Leu Val Gln Pro Gly Gly
1               5                   10                  15

Ser Leu Lys Leu Ser Cys Ala Thr Ser Gly Phe Thr Phe Ser Ala Tyr
            20                  25                  30

Gly Leu Ser Trp Val Arg Gln Thr Pro Glu Arg Arg Leu Glu Trp Val
        35                  40                  45

Ala Ser Ile Ser Gly Gly Gly Ser Val Tyr Tyr Pro Asp Ser Val Lys
    50                  55                  60

Gly Arg Phe Thr Ile Ser Arg Asp Thr Ala Gly Asp Ile Leu Phe Leu
65                  70                  75                  80

Gln Met Asn Ser Leu Arg Ser Glu Asp Ser Ala Ile Tyr Tyr Cys Val
                85                  90                  95

Arg Asp Leu Tyr Gly Asp Tyr Val Gly Arg Tyr Ala Tyr Trp Gly Gln
            100                 105                 110

Gly Thr Leu Val Ile Val Ser Ala
        115                 120

<210> SEQ ID NO 36
<211> LENGTH: 8
<212> TYPE: PRT
<213> ORGANISM: Artificial Sequence
<220> FEATURE:
<223> OTHER INFORMATION: Synthetic construct

<400> SEQUENCE: 36

Gly Phe Thr Phe Ser Ala Tyr Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic construct

<400> SEQUENCE: 37

Ile Ser Gly Gly Gly Ser Val
1               5

<210> SEQ ID NO 38
<211> LENGTH: 14
<212> TYPE: PRT
<213> ORGANISM: Artificial Sequence
<220> FEATURE:
<223> OTHER INFORMATION: Synthetic construct
```

<400> SEQUENCE: 38

Val Arg Asp Leu Tyr Gly Asp Tyr Val Gly Arg Tyr Ala Tyr
1               5                   10

<210> SEQ ID NO 39
<211> LENGTH: 107
<212> TYPE: PRT
<213> ORGANISM: Artificial Sequence
<220> FEATURE:
<223> OTHER INFORMATION: Synthetic construct

<400> SEQUENCE: 39

Asp Thr Val Met Thr Gln Ser Pro Ala Thr Leu Ser Val Thr Pro Gly
1               5                   10                  15

Asp Arg Val Ser Leu Ser Cys Arg Ala Ser Gln Ser Ile Gly Asp Tyr
            20                  25                  30

Leu His Trp Tyr Gln Gln Lys Ser His Glu Ser Pro Arg Leu Leu Ile
        35                  40                  45

Asn Tyr Ala Ser Gln Ser Ile Ser Gly Ile Pro Ser Arg Phe Ser Gly
    50                  55                  60

Ser Gly Ser Gly Ser Asp Phe Thr Leu Ile Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Lys Leu Glu Ile Arg
            100                 105

<210> SEQ ID NO 40
<211> LENGTH: 6
<212> TYPE: PRT
<213> ORGANISM: Artificial Sequence
<220> FEATURE:
<223> OTHER INFORMATION: Synthetic construct

<400> SEQUENCE: 40

Gln Ser Ile Gly Asp Tyr
1               5

<210> SEQ ID NO 41
<211> LENGTH: 3
<212> TYPE: PRT
<213> ORGANISM: Artificial Sequence
<220> FEATURE:
<223> OTHER INFORMATION: Synthetic construct

<400> SEQUENCE: 41

Tyr Ala Ser
1

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

Gln Asn Gly His Ser Phe Pro Tyr Thr
1               5

```
<210> SEQ ID NO 43
<211> LENGTH: 22
<212> TYPE: PRT
<213> ORGANISM: Artificial Sequence
<220> FEATURE:
<223> OTHER INFORMATION: Synthetic construct

<400> SEQUENCE: 43

Cys Ala Ser Tyr Gln Thr Gln Thr Asn Ser Pro Arg Arg Ala Arg Ser
1               5                   10                  15

Val Ala Ser Gln Ser Ile
            20

<210> SEQ ID NO 44
<211> LENGTH: 10
<212> TYPE: PRT
<213> ORGANISM: Artificial Sequence
<220> FEATURE:
<223> OTHER INFORMATION: Synthetic construct

<400> SEQUENCE: 44

Cys Ala Ser Tyr Gln Thr Gln Thr Asn Ser
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Synthetic construct

<400> SEQUENCE: 45

Arg Ser Val Ala Ser Gln Ser Ile
1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic construct

<400> SEQUENCE: 46

Cys Ala Ser Tyr His Thr Val Ser Ser Leu
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Synthetic construct

<400> SEQUENCE: 47

Arg Ser Thr Ser Gln Lys Ser Ile
1               5

<210> SEQ ID NO 48
<211> LENGTH: 12
<212> TYPE: PRT
<213> ORGANISM: Artificial Sequence
<220> FEATURE:
<223> OTHER INFORMATION: Synthetic construct

<400> SEQUENCE: 48

Tyr Gln Thr Gln Thr Asn Ser Pro Arg Arg Ala Arg
1               5                   10
```

```
<210> SEQ ID NO 49
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 49

Cys Asp Gly Phe Cys Ser Ser Arg Gly Lys Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 50

Cys Asp Ala Phe Cys Ser Ser Arg Gly Lys Val
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 51

Cys Asp Ile Phe Thr Asn Ser Arg Gly Lys Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any naturally occurring amino acid

<400> SEQUENCE: 52

Cys Asp Ala Phe Cys Ser Ile Arg Gly Lys Arg
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be any naturally occurring amino acid
```

```
<400> SEQUENCE: 53

Phe Asn Ile Ser Thr Ser Ile Arg Gly Lys Val
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 54

Tyr Asn Lys Lys Lys Ala Thr Val Gln Glu Leu Asp
1               5                   10

<210> SEQ ID NO 55

<400> SEQUENCE: 55

000

<210> SEQ ID NO 56
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(7)
<223> OTHER INFORMATION: Xaa can be any naturally occurring amino acid

<400> SEQUENCE: 56

Ser Leu Leu Arg Ser Thr Ser Gln Lys
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(16)
<223> OTHER INFORMATION: Xaa can be any naturally occurring amino acid

<400> SEQUENCE: 57

Asp Leu Glu Gln Val Thr Ala Lys Lys Lys Asn Tyr
1               5                   10

<210> SEQ ID NO 58
<211> LENGTH: 25
<212> TYPE: PRT
<213> ORGANISM: Artificial Sequence
<220> FEATURE:
<223> OTHER INFORMATION: Synthetic construct

<400> SEQUENCE: 58

Glu Cys Asp Ile Pro Ile Gly Ala Gly Ile Cys Ala Ser Tyr Gln Thr
1               5                   10                  15

Gln Thr Asn Ser Pro Arg Arg Ala Arg
            20                  25
```

```
<210> SEQ ID NO 59
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (21)..(24)
<223> OTHER INFORMATION: Xaa can be any naturally occurring amino acid

<400> SEQUENCE: 59

Glu Cys Asp Ile Pro Ile Gly Ala Gly Ile Cys Ala Ser Tyr His Thr
1               5                   10                  15

Val Ser Leu Leu Arg
            20

<210> SEQ ID NO 60
<211> LENGTH: 28
<212> TYPE: PRT
<213> ORGANISM: Artificial Sequence
<220> FEATURE:
<223> OTHER INFORMATION: Synthetic construct

<400> SEQUENCE: 60

Val Ile Pro Phe Lys Asp Gly Ile Tyr Phe Ala Ala Thr Glu Lys Ser
1               5                   10                  15

Asn Val Val Arg Gly Trp Val Phe Gly Ser Thr Met
            20                  25

<210> SEQ ID NO 61
<211> LENGTH: 28
<212> TYPE: PRT
<213> ORGANISM: Artificial Sequence
<220> FEATURE:
<223> OTHER INFORMATION: Synthetic construct

<400> SEQUENCE: 61

Val Leu Pro Phe Asn Asp Gly Val Tyr Phe Ala Ser Thr Glu Lys Ser
1               5                   10                  15

Asn Ile Ile Arg Gly Trp Ile Phe Gly Thr Thr Leu
            20                  25

<210> SEQ ID NO 62
<211> LENGTH: 27
<212> TYPE: PRT
<213> ORGANISM: Artificial Sequence
<220> FEATURE:
<223> OTHER INFORMATION: Synthetic construct

<400> SEQUENCE: 62

Gln Thr His Thr Met Ile Phe Asp Asn Ala Phe Asn Cys Thr Phe Glu
1               5                   10                  15

Tyr Ile Ser Asp Ala Phe Ser Leu Asp Val Ser
            20                  25

<210> SEQ ID NO 63
<211> LENGTH: 27
<212> TYPE: PRT
<213> ORGANISM: Artificial Sequence
<220> FEATURE:
<223> OTHER INFORMATION: Synthetic construct
```

<400> SEQUENCE: 63

Glu Ser Glu Phe Arg Val Tyr Ser Ser Ala Asn Asn Cys Thr Phe Glu
1               5                   10                  15

Tyr Val Ser Gln Pro Phe Leu Met Asp Leu Glu
            20                  25

<210> SEQ ID NO 64
<211> LENGTH: 23
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid

<400> SEQUENCE: 64

Asn Ile Thr Asn Phe Arg Ala Ile Leu Thr Ala Phe Ser Pro Ala Gln
1               5                   10                  15

Asp Ile Trp Gly Thr Ser Ala
            20

<210> SEQ ID NO 65
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: Xaa can be any naturally occurring amino acid

<400> SEQUENCE: 65

Asn Ile Thr Arg Phe Gln Thr Leu Leu Ala Leu His Arg Ser Tyr Leu
1               5                   10                  15

Thr Pro Gly Asp Ser Ser Ser Gly Trp Thr Ala Gly Ala
            20                  25

<210> SEQ ID NO 66
<211> LENGTH: 24
<212> TYPE: PRT
<213> ORGANISM: Artificial Sequence
<220> FEATURE:
<223> OTHER INFORMATION: Synthetic construct

<400> SEQUENCE: 66

Tyr Asp Glu Asn Gly Thr Ile Thr Asp Ala Val Asp Cys Ser Gln Asn
1               5                   10                  15

Pro Leu Ala Glu Lys Leu Lys Cys
            20

<210> SEQ ID NO 67
<211> LENGTH: 23
<212> TYPE: PRT
<213> ORGANISM: Artificial Sequence
<220> FEATURE:
<223> OTHER INFORMATION: Synthetic construct

```
<400> SEQUENCE: 67

Tyr Asn Glu Asn Gly Thr Ile Thr Asp Ala Val Asp Cys Ala Leu Asp
1               5                   10                  15

Pro Leu Ser Glu Thr Lys Cys
            20

<210> SEQ ID NO 68
<211> LENGTH: 53
<212> TYPE: PRT
<213> ORGANISM: Artificial Sequence
<220> FEATURE:
<223> OTHER INFORMATION: Synthetic construct

<400> SEQUENCE: 68

Leu Lys Cys Ser Val Lys Ser Phe Glu Ile Asp Lys Gly Ile Tyr Gln
1               5                   10                  15

Thr Ser Asn Phe Arg Val Val Pro Ser Gly Asp Val Val Arg Phe Pro
            20                  25                  30

Asn Ile Thr Asn Leu Cys Pro Phe Gly Glu Val Phe Asn Ala Thr Lys
        35                  40                  45

Phe Pro Ser Val Tyr
    50

<210> SEQ ID NO 69
<211> LENGTH: 53
<212> TYPE: PRT
<213> ORGANISM: Artificial Sequence
<220> FEATURE:
<223> OTHER INFORMATION: Synthetic construct

<400> SEQUENCE: 69

Thr Lys Cys Thr Leu Ser Lys Phe Thr Val Glu Lys Gly Ile Tyr Gln
1               5                   10                  15

Thr Ser Asn Phe Arg Val Gln Pro Thr Glu Ser Ile Val Arg Phe Pro
            20                  25                  30

Asn Ile Thr Asn Leu Cys Pro Phe Gly Glu Val Phe Asn Ala Thr Arg
        35                  40                  45

Phe Ala Ser Val Tyr
    50

<210> SEQ ID NO 70
<211> LENGTH: 20
<212> TYPE: PRT
<213> ORGANISM: Artificial Sequence
<220> FEATURE:
<223> OTHER INFORMATION: Synthetic construct

<400> SEQUENCE: 70

Gly Cys Leu Ile Gly Ala Glu His Val Asp Thr Ser Tyr Glu Cys Asp
1               5                   10                  15

Ile Pro Ile Gly
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic construct
```

```
<400> SEQUENCE: 71

Gly Cys Leu Ile Gly Ala Glu His Val Asn Asn Ser Tyr Glu Cys Asp
1               5                   10                  15

Ile Pro Ile Gly
            20

<210> SEQ ID NO 72
<211> LENGTH: 31
<212> TYPE: PRT
<213> ORGANISM: Artificial Sequence
<220> FEATURE:
<223> OTHER INFORMATION: Synthetic construct

<400> SEQUENCE: 72

Asn Thr Arg Glu Val Phe Ala Gln Val Lys Gln Met Tyr Lys Thr Pro
1               5                   10                  15

Thr Leu Lys Tyr Phe Gly Gly Phe Asn Phe Ser Gln Ile Leu Pro
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: Synthetic construct

<400> SEQUENCE: 73

Asn Thr Gln Glu Val Phe Ala Gln Val Lys Gln Ile Tyr Lys Thr Pro
1               5                   10                  15

Pro Ile Lys Asp Phe Gly Gly Phe Asn Phe Ser Gln Ile Leu Pro
            20                  25                  30

<210> SEQ ID NO 74
<211> LENGTH: 76
<212> TYPE: PRT
<213> ORGANISM: Artificial Sequence
<220> FEATURE:
<223> OTHER INFORMATION: Synthetic construct

<400> SEQUENCE: 74

Glu Ala Glu Val Gln Ile Asp Arg Leu Ile Thr Gly Arg Leu Gln Ser
1               5                   10                  15

Leu Gln Thr Tyr Val Thr Gln Gln Leu Ile Arg Ala Ala Glu Ile Arg
            20                  25                  30

Ala Ser Ala Asn Leu Ala Ala Thr Lys Met Ser Glu Cys Val Leu Gly
            35                  40                  45

Gln Ser Lys Arg Val Asp Phe Cys Gly Phe Pro Gln Ala Ala Pro His
        50                  55                  60

Gly Val Val Phe Leu His Val Thr Tyr Val Pro Ser
65                  70                  75

<210> SEQ ID NO 75
<211> LENGTH: 76
<212> TYPE: PRT
<213> ORGANISM: Artificial Sequence
<220> FEATURE:
<223> OTHER INFORMATION: Synthetic construct
```

```
<400> SEQUENCE: 75

Glu Ala Glu Val Gln Ile Asp Arg Leu Ile Thr Gly Arg Leu Gln Ser
1               5                   10                  15

Leu Gln Thr Tyr Val Thr Gln Gln Leu Ile Arg Ala Ala Glu Ile Arg
                20                  25                  30

Ala Ser Ala Asn Leu Ala Ala Thr Lys Met Ser Glu Cys Val Leu Gly
            35                  40                  45

Gln Ser Lys Arg Val Asp Phe Cys Gly Phe Pro Gln Ser Ala Pro His
        50                  55                  60

Gly Val Val Phe Leu His Asx Thr Tyr Val Pro Ala
65                  70                  75

<210> SEQ ID NO 76
<211> LENGTH: 57
<212> TYPE: PRT
<213> ORGANISM: Artificial Sequence
<220> FEATURE:
<223> OTHER INFORMATION: Synthetic construct

<400> SEQUENCE: 76

Leu Gln Pro Glu Leu Asp Ser Phe Lys Glu Glu Leu Asp Lys Tyr Phe
1               5                   10                  15

Lys Asn His Thr Ser Pro Asp Val Asp Leu Gly Asp Ile Ser Gly Ile
                20                  25                  30

Asn Ala Ser Val Val Asn Ile Gln Lys Glu Ile Asp Arg Leu Asn Glu
            35                  40                  45

Val Ala Lys Asn Leu Asn Glu Ser Leu
        50                  55

<210> SEQ ID NO 77
<211> LENGTH: 57
<212> TYPE: PRT
<213> ORGANISM: Artificial Sequence
<220> FEATURE:
<223> OTHER INFORMATION: Synthetic construct

<400> SEQUENCE: 77

Leu Gln Pro Glu Leu Asp Ser Phe Lys Glu Glu Leu Asp Lys Tyr Phe
1               5                   10                  15

Lys Asn His Thr Ser Pro Asp Val Asp Leu Gly Asp Ile Ser Gly Ile
                20                  25                  30

Asn Ala Ser Val Val Asn Ile Gln Lys Glu Ile Asp Arg Leu Asn Glu
            35                  40                  45

Val Ala Lys Asn Leu Asn Glu Ser Leu
        50                  55

<210> SEQ ID NO 78
<211> LENGTH: 53
<212> TYPE: PRT
<213> ORGANISM: Artificial Sequence
<220> FEATURE:
<223> OTHER INFORMATION: Synthetic construct

<400> SEQUENCE: 78

Thr Lys Cys Thr Leu Lys Ser Phe Thr Val Glu Lys Gly Ile Tyr Gln
1               5                   10                  15

Thr Ser Asn Phe Arg Val Gln Pro Thr Glu Ser Ile Val Arg Phe Pro
                20                  25                  30
```

```
Asn Ile Thr Asn Leu Cys Pro Phe Gly Glu Val Phe Asn Ala Thr Arg
            35                  40                  45
Phe Ala Ser Val Tyr
     50

<210> SEQ ID NO 79
<211> LENGTH: 117
<212> TYPE: PRT
<213> ORGANISM: Artificial Sequence
<220> FEATURE:
<223> OTHER INFORMATION: Synthetic construct

<400> SEQUENCE: 79

Met Val Asp Gly Gly Ile Thr Gln Ser Pro Lys Tyr Leu Phe Arg Lys
1               5                   10                  15
Glu Gly Gln Asn Val Thr Leu Ser Cys Glu Gln Asn Leu Asn His Asp
            20                  25                  30
Ala Met Tyr Trp Tyr Arg Gln Asp Pro Gly Gln Gly Leu Arg Leu Ile
        35                  40                  45
Tyr Tyr Ser Gln Ile Val Asn Asp Phe Gln Lys Gly Asp Ile Ala Glu
    50                  55                  60
Gly Tyr Ser Val Ser Arg Glu Lys Lys Glu Ser Phe Pro Leu Thr Val
65                  70                  75                  80
Thr Ser Ala Gln Lys Asn Pro Thr Ala Phe Tyr Leu Cys Ala Ser Ser
                85                  90                  95
Ser Arg Ser Ser Tyr Glu Gln Tyr Phe Gly Pro Gly Thr Arg Leu Thr
            100                 105                 110
Val Thr Glu Asp Leu
        115

<210> SEQ ID NO 80
<211> LENGTH: 116
<212> TYPE: PRT
<213> ORGANISM: Artificial Sequence
<220> FEATURE:
<223> OTHER INFORMATION: Synthetic construct

<400> SEQUENCE: 80

Met Ala Gly Val Thr Gln Ser Pro Thr His Leu Ile Lys Thr Arg Gly
1               5                   10                  15
Gln Gln Val Thr Leu Arg Cys Ser Pro Lys Ser Gly His Asp Thr Val
            20                  25                  30
Ser Trp Tyr Gln Gln Ala Leu Gly Gln Gly Pro Gln Phe Ile Phe Gln
        35                  40                  45
Tyr Tyr Glu Glu Glu Glu Arg Gln Arg Gly Asn Phe Pro Asp Arg Phe
    50                  55                  60
Ser Gly His Gln Phe Pro Asn Tyr Ser Ser Glu Leu Asn Val Asn Ala
65                  70                  75                  80
Leu Leu Leu Gly Asp Ser Ala Leu Tyr Leu Cys Ala Ser Ser Leu Gly
                85                  90                  95
Glu Gly Arg Val Asp Gly Tyr Thr Phe Gly Ser Gly Arg Leu Thr Val
            100                 105                 110
Val Glu Asp Leu
        115

<210> SEQ ID NO 81
<211> LENGTH: 115
<212> TYPE: PRT
<213> ORGANISM: Artificial Sequence
```

<220> FEATURE:
<223> OTHER INFORMATION: Synthetic construct

<400> SEQUENCE: 81

Glu Ala Gly Val Thr Gln Phe Pro Ser His Ser Val Ile Glu Lys Gly
1               5                   10                  15

Gln Thr Val Thr Leu Arg Cys Asp Pro Ile Ser Gly His Asp Asn Leu
            20                  25                  30

Tyr Trp Tyr Arg Arg Val Met Gly Lys Glu Ile Lys Phe Leu Leu His
        35                  40                  45

Phe Val Lys Glu Ser Lys Gln Asp Glu Ser Gly Met Pro Asn Asn Arg
50                  55                  60

Phe Leu Ala Glu Arg Thr Gly Gly Thr Tyr Ser Thr Leu Lys Val Gln
65                  70                  75                  80

Pro Ala Glu Leu Glu Asp Ser Gly Val Tyr Phe Cys Ala Ser Ser Gln
                85                  90                  95

Asp Arg Asp Thr Gln Tyr Phe Gly Pro Gly Thr Arg Leu Thr Val Leu
            100                 105                 110

Glu Asp Leu
        115

<210> SEQ ID NO 82
<211> LENGTH: 113
<212> TYPE: PRT
<213> ORGANISM: Artificial Sequence
<220> FEATURE:
<223> OTHER INFORMATION: Synthetic construct

<400> SEQUENCE: 82

Ala Asp Val Thr Gln Thr Pro Arg Asn Arg Ile Thr Lys Thr Gly Lys
1               5                   10                  15

Arg Ile Met Leu Glu Cys Ser Gln Thr Lys Gly His Asp Arg Met Tyr
            20                  25                  30

Trp Tyr Arg Gln Asp Pro Gly Leu Gly Leu Arg Leu Ile Tyr Tyr Ser
        35                  40                  45

Phe Asp Val Lys Asp Ile Asn Lys Gly Glu Ile Ser Asp Gly Tyr Ser
50                  55                  60

Val Ser Arg Gln Ala Gln Ala Lys Phe Ser Leu Ser Leu Glu Ser Ala
65                  70                  75                  80

Ile Pro Asn Gln Thr Ala Leu Tyr Phe Cys Ala Thr Ser Asp Glu Ser
                85                  90                  95

Tyr Gly Tyr Thr Phe Gly Ser Gly Thr Arg Leu Thr Val Val Glu Asp
            100                 105                 110

Leu

<210> SEQ ID NO 83
<211> LENGTH: 8
<212> TYPE: PRT
<213> ORGANISM: Artificial Sequence
<220> FEATURE:
<223> OTHER INFORMATION: Synthetic construct

<400> SEQUENCE: 83

Cys Ala Ser Tyr Gln Thr Gln Thr
1               5

<210> SEQ ID NO 84
<211> LENGTH: 14
<212> TYPE: PRT
<213> ORGANISM: Artificial Sequence
<220> FEATURE:
<223> OTHER INFORMATION: Synthetic construct

<400> SEQUENCE: 84

Asn Ser Pro Arg Arg Ala Arg Ser Val Ala Ser Gln Ser Ile
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Synthetic construct

<400> SEQUENCE: 85

Cys Ala Ser Tyr His Thr Val Ser
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic construct

<400> SEQUENCE: 86

Arg Ser Val Ser Ser Gln Ala Ile
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic construct

<400> SEQUENCE: 87

Val Gly Thr Asn Ser Ile
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic construct

<400> SEQUENCE: 88

Cys Ala Ser Tyr His Thr Ala Ser
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic construct

<400> SEQUENCE: 89

Arg Asn Thr Gly Gln Lys Ser Ile
1               5

```
<210> SEQ ID NO 90
<211> LENGTH: 8
<212> TYPE: PRT
<213> ORGANISM: Artificial Sequence
<220> FEATURE:
<223> OTHER INFORMATION: Synthetic construct

<400> SEQUENCE: 90

Arg Ser Thr Ser Gln Lys Ala Ile
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic construct

<400> SEQUENCE: 91

Arg Ser Thr Gly Gln Lys Ala Ile
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic construct

<400> SEQUENCE: 92

Cys Ile Asp Tyr Ala Leu Pro Ser
1               5

<210> SEQ ID NO 93
<211> LENGTH: 13
<212> TYPE: PRT
<213> ORGANISM: Artificial Sequence
<220> FEATURE:
<223> OTHER INFORMATION: Synthetic construct

<400> SEQUENCE: 93

Ser Arg Arg Lys Arg Arg Gly Ile Ser Ser Pro Tyr Arg
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Synthetic construct

<400> SEQUENCE: 94

Cys Val Asp Tyr Ser Lys
1               5

<210> SEQ ID NO 95
<211> LENGTH: 12
<212> TYPE: PRT
<213> ORGANISM: Artificial Sequence
<220> FEATURE:
<223> OTHER INFORMATION: Synthetic construct

<400> SEQUENCE: 95

Asn Arg Arg Ser Arg Gly Ala Ile Thr Thr Gly Tyr
1               5                   10
```

```
<210> SEQ ID NO 96
<211> LENGTH: 12
<212> TYPE: PRT
<213> ORGANISM: Artificial Sequence
<220> FEATURE:
<223> OTHER INFORMATION: Synthetic construct

<400> SEQUENCE: 96

Asn Arg Arg Ser Arg Gly Ala Ile Thr Thr Gly Tyr
1               5                   10

<210> SEQ ID NO 97
<211> LENGTH: 23
<212> TYPE: PRT
<213> ORGANISM: Artificial Sequence
<220> FEATURE:
<223> OTHER INFORMATION: Synthetic construct

<400> SEQUENCE: 97

Cys Ala Leu Pro Asp Thr Pro Ser Thr Leu Thr Pro Arg Ser Val Arg
1               5                   10                  15

Ser Val Pro Gly Glu Met Arg
            20

<210> SEQ ID NO 98
<211> LENGTH: 11
<212> TYPE: PRT
<213> ORGANISM: Artificial Sequence
<220> FEATURE:
<223> OTHER INFORMATION: Synthetic construct

<400> SEQUENCE: 98

Cys Ala Asp Gly Ser Ile Ile Ala Val Gln Pro
1               5                   10

<210> SEQ ID NO 99
<211> LENGTH: 8
<212> TYPE: PRT
<213> ORGANISM: Artificial Sequence
<220> FEATURE:
<223> OTHER INFORMATION: Synthetic construct

<400> SEQUENCE: 99

Arg Asn Val Ser Tyr Asp Ser Val
1               5

<210> SEQ ID NO 100
<211> LENGTH: 11
<212> TYPE: PRT
<213> ORGANISM: Artificial Sequence
<220> FEATURE:
<223> OTHER INFORMATION: Synthetic construct

<400> SEQUENCE: 100

Cys Ala Asp Gly Ser Leu Ile Pro Val Arg Pro
1               5                   10

<210> SEQ ID NO 101
<211> LENGTH: 8
<212> TYPE: PRT
<213> ORGANISM: Artificial Sequence
<220> FEATURE:
<223> OTHER INFORMATION: Synthetic construct

<400> SEQUENCE: 101

Arg Asn Ser Ser Asp Asn Gly Ile
1               5
```

<210> SEQ ID NO 102
<211> LENGTH: 111
<212> TYPE: PRT
<213> ORGANISM: Artificial Sequence
<220> FEATURE:
<223> OTHER INFORMATION: Synthetic construct

<400> SEQUENCE: 102

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser His
                20                  25                  30

Trp Met His Trp Val Lys Gln Arg Pro Gly Gln Gly Leu Glu Trp Ile
            35                  40                  45

Gly Glu Ile Asp Pro Ser Asp Ser Tyr Ile Asn Tyr Asn Gln Ile Phe
        50                  55                  60

Glu Gly Lys Ala Thr Leu Thr Val Asp Lys Ser Ser Thr Thr Ala Tyr
65                  70                  75                  80

Leu Gln Leu Ser Ser Leu Thr Ser Glu Asp Ser Ala Val Tyr Tyr Cys
                85                  90                  95

Ala Arg Thr Ala Gly Leu Leu Ala Pro Met Asp Tyr Trp Gly Gln
                100                 105                 110

<210> SEQ ID NO 103
<211> LENGTH: 119
<212> TYPE: PRT
<213> ORGANISM: Artificial Sequence
<220> FEATURE:
<223> OTHER INFORMATION: Synthetic construct

<400> SEQUENCE: 103

Glu Val Gln Leu Val Glu Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Met Tyr Ala Gln Lys Phe
        50                  55                  60

Gln Gly Arg Val Thr Met Glu Asp Thr Ser Thr Asp Thr Ala Tyr Met
65                  70                  75                  80

Glu Leu Ser Ser Leu Arg Ser Glu Asp Thr Ala Val Tyr Tyr Cys Ala
                85                  90                  95

Thr Ser Thr Ala Val Ala Gly Thr Pro Asp Leu Phe Asp Tyr Tyr Tyr
                100                 105                 110

Gly Met Asp Val Trp Gly Gln
        115

<210> SEQ ID NO 104
<211> LENGTH: 120
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (106)..(106)
<223> OTHER INFORMATION: Xaa can be any naturally occurring amino acid

<400> SEQUENCE: 104

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr Asn Tyr Ala Gln Lys Phe
    50                  55                  60

Gln Gly Arg Val Thr Met Thr Thr Asp Thr Ser Thr Thr Thr Gly Tyr
65                  70                  75                  80

Met Glu Leu Arg Arg Leu Arg Ser Asp Asp Thr Ala Val Tyr Tyr Cys
                85                  90                  95

Ala Arg Asp Tyr Thr Arg Gly Ala Trp Xaa Phe Gly Glu Ser Leu Ile
            100                 105                 110

Gly Gly Phe Asp Asn Trp Gly Gln
        115                 120
```

<210> SEQ ID NO 105
<211> LENGTH: 110
<212> TYPE: PRT
<213> ORGANISM: Artificial Sequence
<220> FEATURE:
<223> OTHER INFORMATION: Synthetic construct

<400> SEQUENCE: 105

```
Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Glu Gly Trp Glu Leu Pro Tyr Asp Tyr Trp Gly Gln
            100                 105                 110
```

<210> SEQ ID NO 106
<211> LENGTH: 114
<212> TYPE: PRT
<213> ORGANISM: Artificial Sequence
<220> FEATURE:
<223> OTHER INFORMATION: Synthetic construct

<400> SEQUENCE: 106

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Thr Gln Met Phe
    50                  55                  60
```

```
Gln Gly Arg Val Thr Met Thr Arg Asp Thr Ser Ile Ser Thr Ala Tyr
65                  70                  75                  80

Met Glu Val Ser Arg Leu Arg Ser Asp Thr Ala Val Tyr Tyr Cys
                85                  90                  95

Ala Arg Asp Arg Ser Trp Ala Val Val Tyr Tyr Tyr Met Asp Val Trp
            100                 105                 110

Gly Lys
```

<210> SEQ ID NO 107
<211> LENGTH: 118
<212> TYPE: PRT
<213> ORGANISM: Artificial Sequence
<220> FEATURE:
<223> OTHER INFORMATION: Synthetic construct

<400> SEQUENCE: 107

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Pro Gln Gly Gly Ser Ser Trp Tyr Arg Asp Tyr Tyr Tyr Gly
            100                 105                 110

Met Asp Val Trp Gly Gln
        115
```

<210> SEQ ID NO 108
<211> LENGTH: 113
<212> TYPE: PRT
<213> ORGANISM: Artificial Sequence
<220> FEATURE:
<223> OTHER INFORMATION: Synthetic construct

<400> SEQUENCE: 108

```
Glu Val Gln Leu Val Glu Ser Gly Gly Gly Val Val Gln Pro Gly Arg
1               5                   10                  15

Ser Leu Arg Leu Ser Cys Ala Ala Ser Ala Phe Thr Phe Ser Ser Tyr
                20                  25                  30

Asp Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Lys Leu Trp Val Tyr Tyr Phe Asp Tyr Trp Gly
            100                 105                 110

Gln
```

```
<210> SEQ ID NO 109
<211> LENGTH: 112
<212> TYPE: PRT
<213> ORGANISM: Artificial Sequence
<220> FEATURE:
<223> OTHER INFORMATION: Synthetic construct

<400> SEQUENCE: 109
```

| Glu | Val | Gln | Leu | Val | Gln | Ser | Gly | Ala | Glu | Val | Lys | Lys | Pro | Gly | Ala |
|-----|-----|-----|-----|-----|-----|-----|-----|-----|-----|-----|-----|-----|-----|-----|-----|
| 1 | | | | 5 | | | | | 10 | | | | | 15 | |

| Thr | Val | Lys | Ile | Ser | Cys | Lys | Val | Ser | Gly | Tyr | Ser | Phe | Ser | Asn | Tyr |
| | | | 20 | | | | | 25 | | | | | 30 | | |

| Tyr | Ile | His | Trp | Val | Lys | Gln | Ala | Pro | Gly | Lys | Ser | Leu | Glu | Trp | Ile |
| | | 35 | | | | | 40 | | | | | 45 | | | |

| Gly | Tyr | Ile | Asp | Pro | Phe | Asn | Gly | Gly | Thr | Ser | Asp | Asn | Leu | Lys | Phe |
| 50 | | | | | 55 | | | | | 60 | | | | | |

| Lys | Gly | Ala | Ala | Thr | Leu | Thr | Ala | Asp | Thr | Ser | Thr | Asp | Thr | Ala | Tyr |
| 65 | | | | 70 | | | | | 75 | | | | | 80 | |

| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |

| Ala | Arg | Ser | Glu | Tyr | Asp | Pro | Tyr | Tyr | Val | Met | Asp | Tyr | Trp | Gly | Gln |
| | | | 100 | | | | | 105 | | | | | 110 | | |

```
<210> SEQ ID NO 110
<211> LENGTH: 113
<212> TYPE: PRT
<213> ORGANISM: Artificial Sequence
<220> FEATURE:
<223> OTHER INFORMATION: Synthetic construct

<400> SEQUENCE: 110
```

| Gln | Ile | Gln | Leu | Val | Gln | Ser | Gly | Pro | Glu | Leu | Lys | Lys | Pro | Gly | Glu |
|-----|-----|-----|-----|-----|-----|-----|-----|-----|-----|-----|-----|-----|-----|-----|-----|
| 1 | | | | 5 | | | | | 10 | | | | | 15 | |

| Thr | Val | Arg | Ile | Ser | Cys | Lys | Ala | Ser | Gly | Tyr | Ile | Phe | Thr | Ile | Ala |
| | | | 20 | | | | | 25 | | | | | 30 | | |

| Gly | Ile | Gln | Trp | Val | Gln | Lys | Met | Pro | Gly | Arg | Gly | Leu | Arg | Trp | Ile |
| | | 35 | | | | | 40 | | | | | 45 | | | |

| Gly | Trp | Ile | Asn | Thr | His | Ser | Gly | Val | Pro | Glu | Tyr | Ala | Glu | Glu | Phe |
| 50 | | | | | 55 | | | | | 60 | | | | | |

| Lys | Gly | Arg | Phe | Ala | Phe | Ser | Leu | Glu | Thr | Ser | Ala | Arg | Thr | Ala | Tyr |
| 65 | | | | 70 | | | | | 75 | | | | | 80 | |

| Leu | Gln | Ile | Ser | Asn | Leu | Lys | Asp | Glu | Asp | Thr | Ala | Thr | Tyr | Phe | Cys |
| | | | | 85 | | | | | 90 | | | | | 95 | |

| Ala | Arg | Ile | Tyr | Tyr | Gly | Asn | Asn | Gly | Gly | Val | Met | Asp | Tyr | Trp | Gly |
| | | | 100 | | | | | 105 | | | | | 110 | | |

| Gln |
|-----|

```
<210> SEQ ID NO 111
<211> LENGTH: 112
<212> TYPE: PRT
<213> ORGANISM: Artificial Sequence
<220> FEATURE:
<223> OTHER INFORMATION: Synthetic construct

<400> SEQUENCE: 111
```

| Glu | Val | Asn | Leu | Ile | Glu | Ser | Gly | Gly | Asp | Leu | Val | Lys | Pro | Gly | Gly |
|-----|-----|-----|-----|-----|-----|-----|-----|-----|-----|-----|-----|-----|-----|-----|-----|
| 1 | | | | 5 | | | | | 10 | | | | | 15 | |

| Ser | Leu | Lys | Leu | Ser | Cys | Ala | Thr | Ser | Gly | Phe | Thr | Phe | Ser | Ala | Tyr |
| | | | 20 | | | | | 25 | | | | | 30 | | |

-continued

```
Gly Leu Ser Trp Val Arg Gln Thr Pro Glu Arg Arg Leu Glu Trp Val
             35                  40                  45

Ala Ser Ile Ser Gly Gly Ser Val Tyr Tyr Pro Asp Ser Val Lys
 50                  55                  60

Gly Arg Phe Thr Ile Ser Arg Asp Thr Ala Gly Asp Ile Leu Phe Leu
 65                  70                  75                  80

Gln Met Asn Ser Leu Arg Ser Glu Asp Ser Ala Ile Tyr Tyr Cys Val
                 85                  90                  95

Arg Asp Leu Tyr Gly Asp Tyr Val Gly Arg Tyr Ala Tyr Trp Gly Gln
            100                 105                 110
```

<210> SEQ ID NO 112
<211> LENGTH: 12
<212> TYPE: PRT
<213> ORGANISM: Artificial Sequence
<220> FEATURE:
<223> OTHER INFORMATION: Synthetic construct

<400> SEQUENCE: 112

```
Tyr Asn Lys Lys Lys Ala Thr Val Gln Glu Leu Asp
 1               5                  10
```

<210> SEQ ID NO 113
<211> LENGTH: 18
<212> TYPE: PRT
<213> ORGANISM: Artificial Sequence
<220> FEATURE:
<223> OTHER INFORMATION: Synthetic construct

<400> SEQUENCE: 113

```
Asp Ile Pro Ile Gly Ala Gly Ile Cys Ala Ser Tyr His Thr Val Ser
 1               5                  10                  15

Leu Leu
```

<210> SEQ ID NO 114
<211> LENGTH: 5
<212> TYPE: PRT
<213> ORGANISM: Artificial Sequence
<220> FEATURE:
<223> OTHER INFORMATION: Synthetic construct

<400> SEQUENCE: 114

```
Pro Arg Arg Ala Arg
 1               5
```

<210> SEQ ID NO 115
<211> LENGTH: 8
<212> TYPE: PRT
<213> ORGANISM: Artificial Sequence
<220> FEATURE:
<223> OTHER INFORMATION: Synthetic construct

<400> SEQUENCE: 115

```
Ser Pro Arg Arg Ala Arg Ser Val
 1               5
```

<210> SEQ ID NO 116
<211> LENGTH: 12
<212> TYPE: PRT
<213> ORGANISM: Artificial Sequence
<220> FEATURE:
<223> OTHER INFORMATION: Synthetic construct

```
<400> SEQUENCE: 116

Thr Asn Lys Lys Lys Ala Thr Val Gln Glu Leu Asp
1               5                   10

<210> SEQ ID NO 117
<211> LENGTH: 5
<212> TYPE: PRT
<213> ORGANISM: Artificial Sequence
<220> FEATURE:
<223> OTHER INFORMATION: Synthetic construct

<400> SEQUENCE: 117

Ser Leu Leu Arg Ser
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic construct

<400> SEQUENCE: 118

Thr Ser Pro Arg Arg Ala Arg Ser
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic construct

<400> SEQUENCE: 119

Ser Pro Pro Arg Ala Arg
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic construct

<400> SEQUENCE: 120

Arg Arg Ala Arg Gly
1               5

<210> SEQ ID NO 121
<211> LENGTH: 4
<212> TYPE: PRT
<213> ORGANISM: Artificial Sequence
<220> FEATURE:
<223> OTHER INFORMATION: Synthetic construct

<400> SEQUENCE: 121

Arg Arg Ala Arg
1
```